United States Patent
Honda et al.

(10) Patent No.: US 11,167,018 B2
(45) Date of Patent: Nov. 9, 2021

(54) COMPOSITIONS AND METHODS FOR THE INDUCTION OF CD8+ T-CELLS

(71) Applicants: Keio University, Tokyo (JP); The University of Tokyo, Tokyo (JP)

(72) Inventors: Kenya Honda, Tokyo (JP); Takeshi Tanoue, Tokyo (JP); Masahira Hattori, Tokyo (JP); Yutaka Kawakami, Tokyo (JP)

(73) Assignees: Keio University, Tokyo (JP); The University of Tokyo, Tokyo (JP)

( * ) Notice: Subject to any disclaimer, the term of this patent is extended or adjusted under 35 U.S.C. 154(b) by 2 days.

(21) Appl. No.: 16/472,937

(22) PCT Filed: Dec. 22, 2017

(86) PCT No.: PCT/JP2017/046232
§ 371 (c)(1),
(2) Date: Jun. 24, 2019

(87) PCT Pub. No.: WO2018/117263
PCT Pub. Date: Jun. 28, 2018

(65) Prior Publication Data
US 2020/0093871 A1    Mar. 26, 2020

Related U.S. Application Data

(60) Provisional application No. 62/574,446, filed on Oct. 19, 2017, provisional application No. 62/491,062, (Continued)

(51) Int. Cl.
*A61K 39/02* (2006.01)
*A61P 35/00* (2006.01)
(Continued)

(52) U.S. Cl.
CPC ........ *A61K 39/0208* (2013.01); *A61K 9/0053* (2013.01); *A61K 9/19* (2013.01);
(Continued)

(58) Field of Classification Search
CPC ...... A61K 39/39; A61K 9/19; A61K 2035/11; A61K 2039/505; A61K 38/2013;
(Continued)

(56) References Cited

U.S. PATENT DOCUMENTS 10,576,136 B2    3/2020  Honda et al.
10,695,412 B2    6/2020  Honda et al.
(Continued)

FOREIGN PATENT DOCUMENTS

BR    112015018625-4 A2    9/2017
BR    112016011830-8 A2    9/2017
(Continued)

OTHER PUBLICATIONS

Genbank accession No. LN998073. Mar. 15, 2018.
(Continued)

*Primary Examiner* — Jana A Hines
(74) *Attorney, Agent, or Firm* — Wolf, Greenfield & Sacks, P.C.

(57) ABSTRACT

Provided herein are compositions and methods for the induction and/or proliferation of CD8+ T-cells. The disclosure also provides methods of treatment of diseases that can be treated by the induction and/or proliferation of CD8+ T-cells.

17 Claims, 84 Drawing Sheets

Specification includes a Sequence Listing.

Related U.S. Application Data filed on Apr. 27, 2017, provisional application No. 62/484,607, filed on Apr. 12, 2017, provisional application No. 62/438,793, filed on Dec. 23, 2016.

(51) Int. Cl.

| | | |
|---|---|---|
| *A61K 35/74* | (2015.01) | |
| *A61K 39/114* | (2006.01) | |
| *A61K 39/395* | (2006.01) | |
| *C07K 16/28* | (2006.01) | |
| *A61K 31/7036* | (2006.01) | |
| *A61K 35/12* | (2015.01) | |
| *A61K 9/00* | (2006.01) | |
| *A61K 9/19* | (2006.01) | |
| *A61K 35/742* | (2015.01) | |
| *A61K 39/08* | (2006.01) | |
| *C12N 1/20* | (2006.01) | |
| *C12Q 1/689* | (2018.01) | |
| *A61K 39/00* | (2006.01) | |
| *A61K 35/00* | (2006.01) | |

(52) U.S. Cl.
CPC .......... *A61K 31/7036* (2013.01); *A61K 35/12* (2013.01); *A61K 35/74* (2013.01); *A61K 35/742* (2013.01); *A61K 39/0216* (2013.01); *A61K 39/08* (2013.01); *A61K 39/114* (2013.01); *A61K 39/3955* (2013.01); *A61K 39/39558* (2013.01); *A61P 35/00* (2018.01); *C07K 16/2818* (2013.01); *C12N 1/20* (2013.01); *C12Q 1/689* (2013.01); *A61K 2035/11* (2013.01); *A61K 2035/115* (2013.01); *A61K 2039/505* (2013.01); *A61K 2039/52* (2013.01); *A61K 2039/542* (2013.01); *A61K 2039/585* (2013.01)

(58) Field of Classification Search
CPC ........ A61K 2039/542; A61K 2035/115; A61K 38/2086; A61K 2039/572; A61K 39/114; A61K 39/08; A61K 38/20; A61K 39/39558; A61K 2039/57; A61K 2039/82; C12N 1/20; C12N 15/09; A61P 35/00
See application file for complete search history.

(56) References Cited

U.S. PATENT DOCUMENTS

| | | | | |
|---|---|---|---|---|
| 2008/0193373 | A1* | 8/2008 | Stritzker | A61K 33/26 424/1.17 |
| 2009/0217401 | A1* | 8/2009 | Korman | A61K 51/10 800/18 |
| 2013/0017199 | A1* | 1/2013 | Langermann | A61P 33/02 424/134.1 |
| 2019/0343944 | A1 | 11/2019 | Honda et al. | |
| 2019/0381111 | A1 | 12/2019 | Honda et al. | |
| 2020/0254079 | A1 | 8/2020 | Honda et al. | |

FOREIGN PATENT DOCUMENTS

| | | | |
|---|---|---|---|
| BR | 112017025813-7 | A2 | 8/2018 |
| EP | 3012270 | | 4/2016 |
| RU | 2546251 | C2 | 4/2015 |
| WO | WO 2011/058535 | A1 | 5/2011 |
| WO | WO 2013/080561 | A1 | 6/2013 |
| WO | WO 2014/121298 | | 8/2014 |
| WO | WO 2014/121302 | A2 | 8/2014 |
| WO | WO-2014121298 | A2 * | 8/2014 ............ A61K 35/74 |
| WO | WO 2015/077794 | A1 | 5/2015 |
| WO | WO 2015/156419 | A1 | 10/2015 |
| WO | WO 2016/063263 | | 4/2016 |
| WO | WO 2016/196605 | A1 | 12/2016 |

OTHER PUBLICATIONS

Genbank accession No. KR822463. Mar. 15, 2018.
Genbank accession No. CP011531. Mar. 15, 2018.
Genbank accession No. NR112945. Mar. 15, 2018.
Genbank accession No. NZACWW00000000 Mar. 15, 2018.
Genbank accession No. AB331897. Mar. 15, 2018.
Genbank accession No. AB261128. Mar. 15, 2018.
Genbank accession No. NZCAEG00000000. Mar. 15, 2018.
Genbank accession No. AB470343. Mar. 15, 2018.
Genbank accession No. AB595134. Mar. 15, 2018.
Genbank accession No. HE974920. Mar. 15, 2018.
Genbank accession No. NR112933. Mar. 15, 2018.
Genbank accession No. AB490801. Mar. 15, 2018.
Genbank accession No. NZACWB00000000. Mar. 15, 2018.
Genbank accession No. AY608696. Mar. 15, 2018.
Genbank accession No. CR626927. Mar. 15, 2018.
Genbank accession No. AB247141. Mar. 15, 2018.
Genbank accession No. NR112935. Mar. 15, 2018.
Genbank accession No. AB249652. Mar. 15, 2018.
Genbank accession No. NR113076. Mar. 15, 2018.
Genbank accession No. AF13925. Mar. 15, 2018.
U.S. Appl. No. 16/421,557, filed May 24, 2019, Honda et al.
U.S. Appl. No. 16/421,578, filed May 24, 2019, Honda et al.
PCT/JP2017/046232, Apr. 3, 2018, International Search Report and Written Opinion.
Genbank accession No. AB247141. Hasegawa et al. Jan. 19, 2006.
Genbank accession No. AB249652. Tamura et al. Oct. 17, 2012.
Genbank accession No. AB261128. Sakamoto et al. Nov. 9, 2012.
Genbank accession No. AB490801. Watanabe et al. Aug. 6, 2010.
Genbank accession No. AB331897. Morotomi et al. Aug. 19, 2009.
Genbank accession No. AB470343. Sakamoto et al. Nov. 9, 2012.
Genbank accession No. AB595134. Sakamoto et al. Nov. 9, 2012.
Genbank accession No. AF139525. Gregg et al. Jun. 2, 1999.
Genbank accession No. AY608696. Song et al. Dec. 2, 2005.
Genbank accession No. CP011531. Russell et al. May 3, 2016.
Genbank accession No. CR626927. Cerdano-Tarraga et al. Feb. 6, 2015.
Genbank accession No. KR822463. Asao et al. Oct. 27, 2016.
Genbank accession No. LN998073. Ndongo et al. Feb. 6, 2016.
Genbank accession No. NR_112933. Sakamoto et al. Feb. 3, 2015.
Genbank accession No. NR_112935. Sakamoto et al. Feb. 3, 2015.
Genbank accession No. NR_112945. Sakamoto et al. Feb. 3, 2015.
Genbank accession No. NR_113076. Sakamoto et al. Feb. 3, 2015.
Genbank accession No. HE974920. Sjoberg et al. Jul. 1, 2013.
Genbank accession No. NZ_CAEG00000000. Apr. 8, 2017.
Genbank accession No. NZ_ACWB00000000. Apr. 17, 2017.
Genbank accession No. NZ_ACWW00000000. Jun. 19, 2017.
Li et al., Gut microbes in correlation with mood: case study in a closed experimental human life support system. Neurogastroenterol Motil. Aug. 2016;28(8):1233-40. doi: 10.1111/nmo.12822. Epub Mar. 29, 2016.
Perez-Cano et al., in vitro immunomodulatory activity of *Lactobacillus fermentum* CECT5716 and *Lactobacillus salivarius* CECT5713: two probiotic strains isolated from human breast milk. Immunobiology. Dec. 2010;215(12):996-1004. doi: 10.1016/j.imbio.2010.01.004. Epub Feb. 6, 2010.
Pitt et al., Fine-Tuning Cance Immunotherapy: Optimizing the Gut Microbiome. Cancer Res. Aug. 15, 2016;76(16):4602-7. doi: 10.1158/0008-5472.CAN-16-0448. Epub Jul. 29, 2016.
Sivan et al., Commensal Bifidobacterium promotes antitumor immunity and facilitates anti-PD-L1 efficacy. Science. Nov. 27, 2015;350(6264):1084-9. doi: 10.1126/science.aac4255. Epub Nov. 5, 2015.
Smelt et al., Probiotics can generate FoxP3 T-cell responses in the small intestine and simultaneously inducing CD4 and CD8 T cell activation in the large intestine. PLoS One. Jul. 4, 2013;8(7):e68952. doi: 10.1371/journal.pone.0068952.
Tanoue et al., A defined commensal consortium elicits CD8 T cells and anti-cancer immunity. Nature. Jan. 2019;565(7741):600-605. doi: 10.1038/s41586-019-0878-z. Epub Jan. 23, 2019.

(56) References Cited

OTHER PUBLICATIONS

Vetizou et al., Anticancer immunotherapy by CTLA-4 blockade relies on the gut microbiota. Science. Nov. 27, 2015;350(6264):1079-84. doi: 10.1126/science.aad1329. Epub Nov. 5, 2015.
EP 17884311.6, Oct. 14, 2020, Partial Supplementary European Search Report.
Third Party Observations for Application No. BR 112019013125-6, mailed Feb. 1, 2021. 11 pages.
Yarza et al., Update of the All-Species Living Tree Project based on 16S and 23S rRNA sequence analyses. Syst Appl Microbiol. Oct. 2010;33(6):291-9. doi: 10.1016/j.syapm.2010.08.001.

* cited by examiner

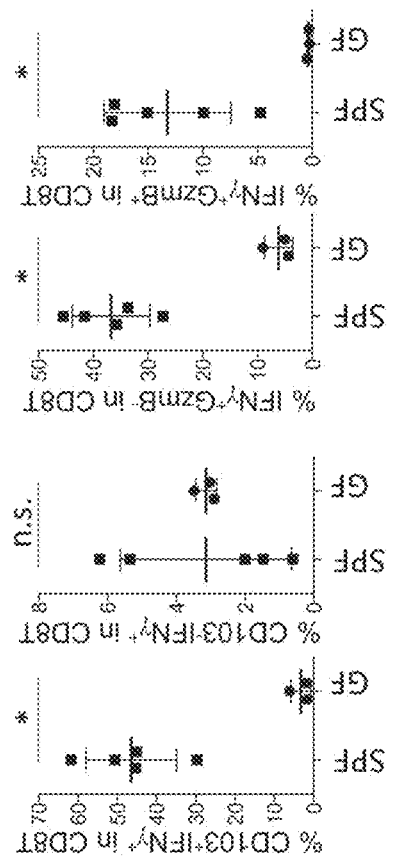
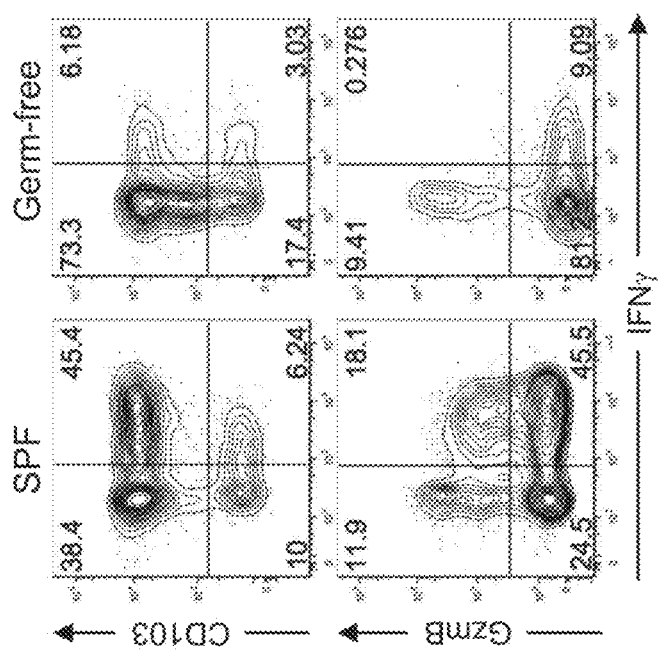
Fig. 2A
Fig. 2B

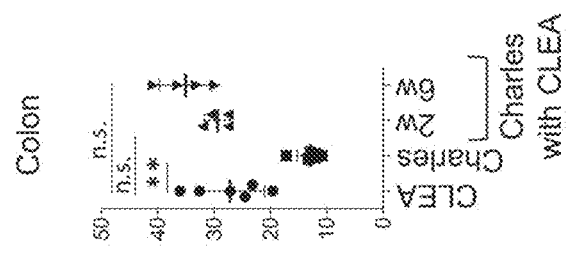
Fig. 4B
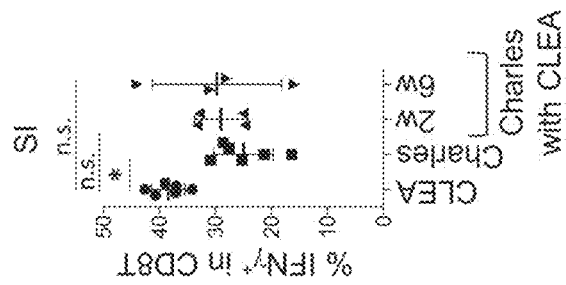
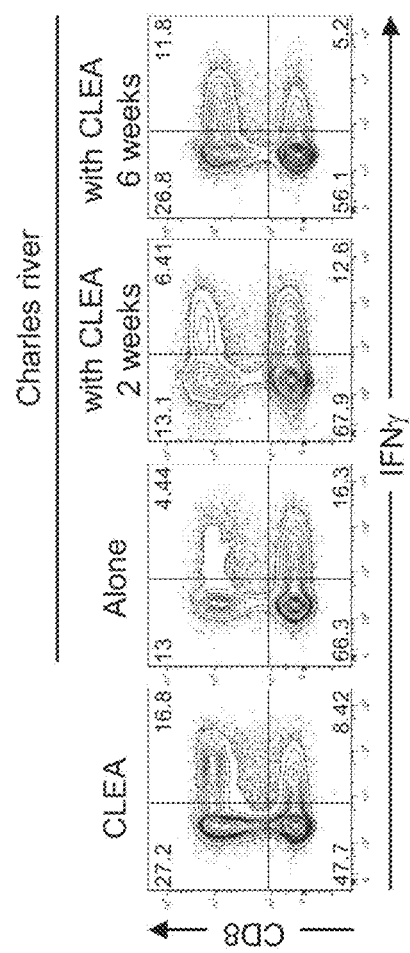
Fig. 4A

| ID | S_ab Score | Sequence Name | # |
|---|---|---|---|
| 1A1 | 1 | Clostridium innocuum | 26 |
| 1F3 | 0.99 | Ruminococcus sp. | 25 |
| 1E6 | 0.99 | Clostridium lavalense | 24 |
| 1G1 | 0.99 | Hungatella hathewayi | 23 |
| 3F2 | 0.79 | Lachnospiraceae bacterium HGA0140 | 22 |
| 1H8 | 0.99 | Bacteriodes sp. | 21 |
| 2E8 | 0.99 | Parabacteroides goldsteinii | 20 |
| 2D2 | 0.98 | Clostridium sp. | 19 |
| 2B11 | 0.99 | Bacteroides eggerthii | 18 |
| 1A2 | 0.99 | Bacteroides uniformis | 17 |
| 2A12 | 0.99 | Bacteroides fragilis | 16 |
| 2A3 | 0.99 | Bacteroides salyersiae | 15 |
| 1B4 | 1 | Anaerostipes caccae | 14 |
| 2C1 | 0.99 | Bacteroides clarus | 13 |
| 2B7 | 0.99 | Bacteroides cellulosilyticus | 12 |
| 2G9 | 0.99 | Parabacteroides distasonis | 11 |
| 1C1 | 0.99 | Eubacterum limosum | 10 |
| 1H9 | 0.97 | Parabacteroides gordonii | 9 |
| 1E7 | 0.97 | Alistipes sp. | 8 |
| 2F11 | 0.99 | Parabacteroides johnsonii | 7 |
| 2A6 | 0.99 | Paraprevotella xylaniphila | 6 |
| 2B1 | 1 | Subdoligranulum sp. | 5 |
| 2G1 | 0.99 | Bacteroides uniformis | 4 |
| 1B11 | 1 | Bacteroides dorei | 3 |
| 1A6 | 0.99 | Fusobacterium ulcerans | 2 |
| 2G5 | 0.99 | Phascolarctobacterium faecium | 1 |

- negatively correlated with IFNγ + CD8T
- positively correlated with IFNγ + CD8T
- detected in Chloro. B#5
- corresponding to isolated strains

Fig. 7B

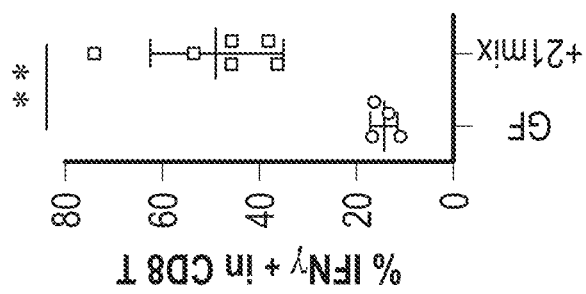
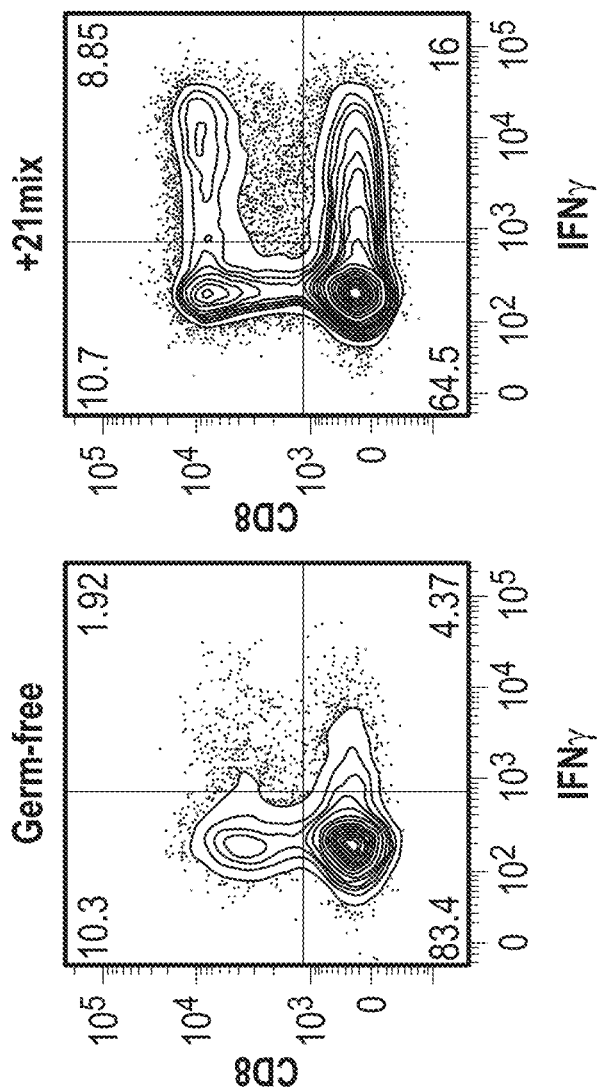
Fig. 8A
Fig. 8B

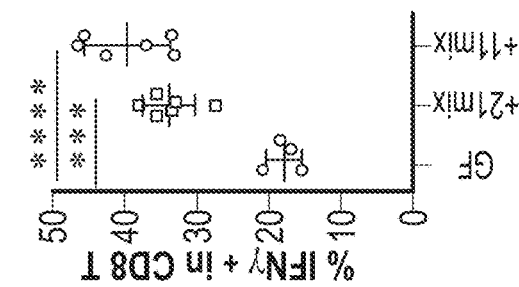
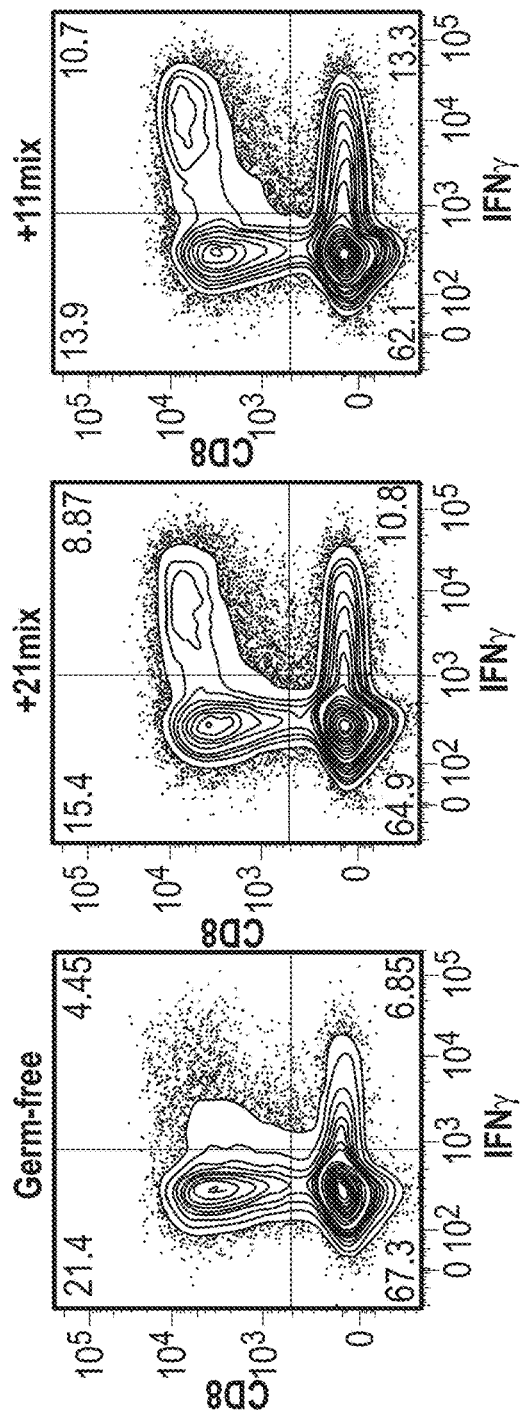
Fig. 10A
Fig. 10B

| | ID | S_ab score | Closest sequence | # |
|---|---|---|---|---|
| Detected in Chloro. B#5 | 81A1 | 1 | Clostridium innocuum | 26 |
| | 81F3 | 0.99 | Ruminococcus sp. | 25 |
| | 81E6 | 0.99 | Clostridium lavalense | 24 |
| | 81G1 | 0.99 | Hungatella hathewayi | 23 |
| | 83F2 | 0.79 | Lachnospiraceae bacterium HGA0140 | 22 |
| 10-mix | 81H8 | 0.99 | Bacteriodes sp. | 21 |
| | 82E8 | 0.99 | Parabacteroides goldsteinii | 20 |
| | 82D2 | 0.98 | Clostridium sp. | 19 |
| | 82B11 | 0.99 | Bacteroides eggerthii | 18 |
| | 81A2 | 0.99 | Bacteroides uniformis | 17 |
| | 82A12 | 0.99 | Bacteroides fragilis | 16 |
| | 82A3 | 0.99 | Bacteroides salyersiae | 15 |
| | 81B4 | 1 | Anaerostipes caccae | 14 |
| | 82C1 | 0.99 | Bacteroides clarus | 13 |
| | 82B7 | 0.99 | Bacteroides cellulosilyticus | 12 |
| 11-mix | 82G9 | 0.99 | Parabacteroides distasonis | 11 |
| | 81C1 | 0.99 | Eubacterum limosum | 10 |
| | 81H9 | 0.97 | Parabacteroides gordonii | 9 |
| | 81E7 | 0.97 | Alistipes sp. | 8 |
| | 82F11 | 0.99 | Parabacteroides johnsonii | 7 |
| | 82A6 | 0.99 | Paraprevotella xylaniphila | 6 |
| | 82B1 | 1 | Subdoligranulum sp. | 5 |
| | 82G1 | 0.99 | Bacteroides uniformis | 4 |
| | 81B11 | 1 | Bacteroides dorei | 3 |
| | 81A6 | 0.99 | Fusobacterium ulcerans | 2 |
| | 82G5 | 0.99 | Phascolarctobacterium faecium | 1 |

▦ negatively correlated with IFNγ + CD8T (10-Mix)

▨ positively correlated with IFNγ + CD8T (11-Mix)

▩ detected in Chloro. B#5

Fig. 11

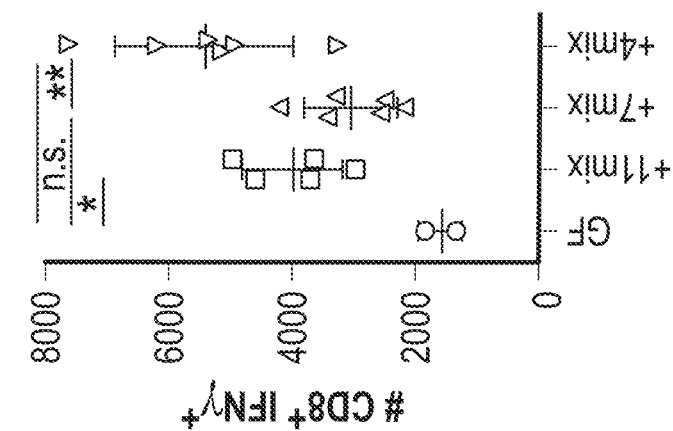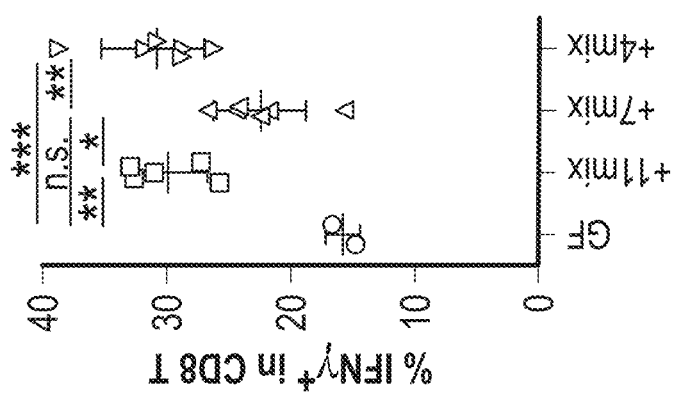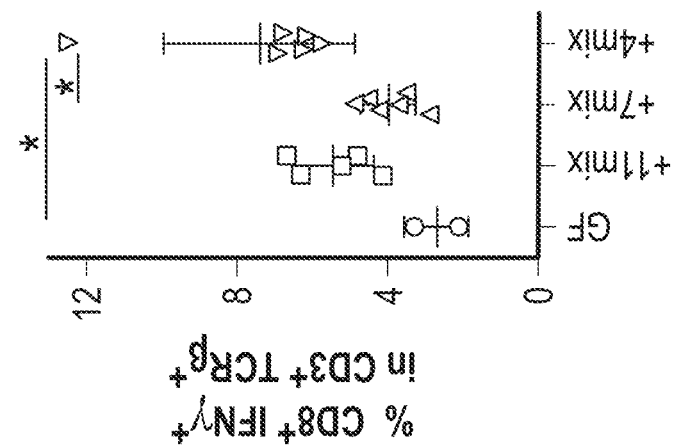
Fig. 14B

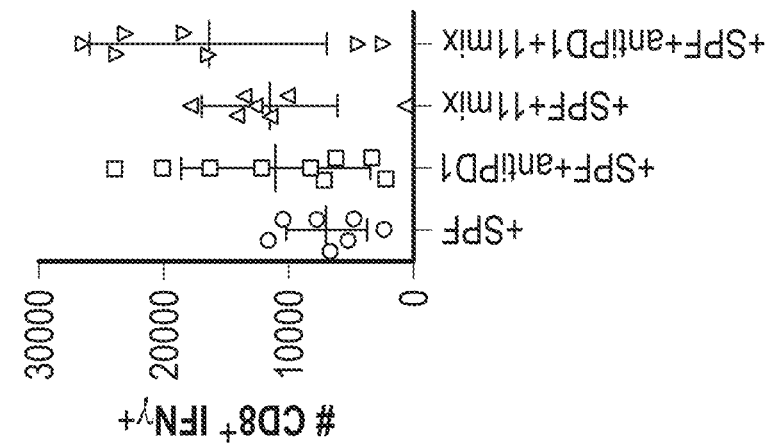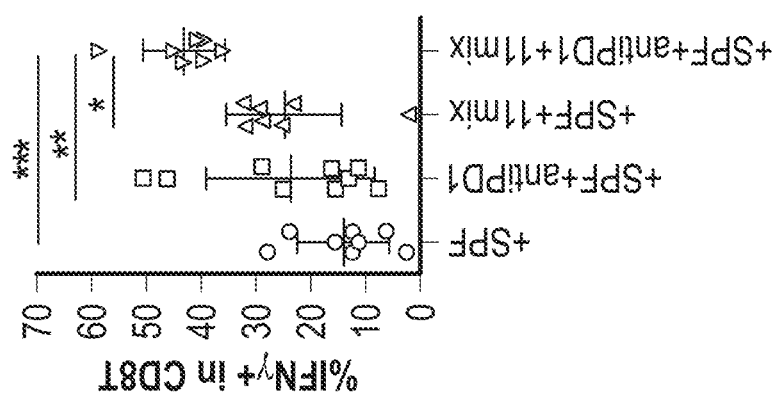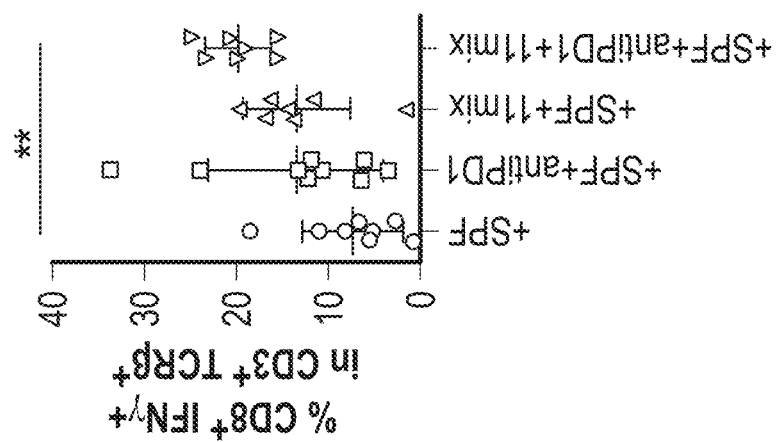
Fig. 16B

| ID | S_ab score | Selected 11 Strains | # |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides Sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2G9 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Bacteroides sp. | 8 |
| 2F11 | 0.989 | Parabacteroides johnsonii | 7 |
| 2A6 | 0.966 | Paraprevotella xylaniphila | 6 |
| 2B1 | 1 | Ruminococcaceae bacterium | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

Fig. 20

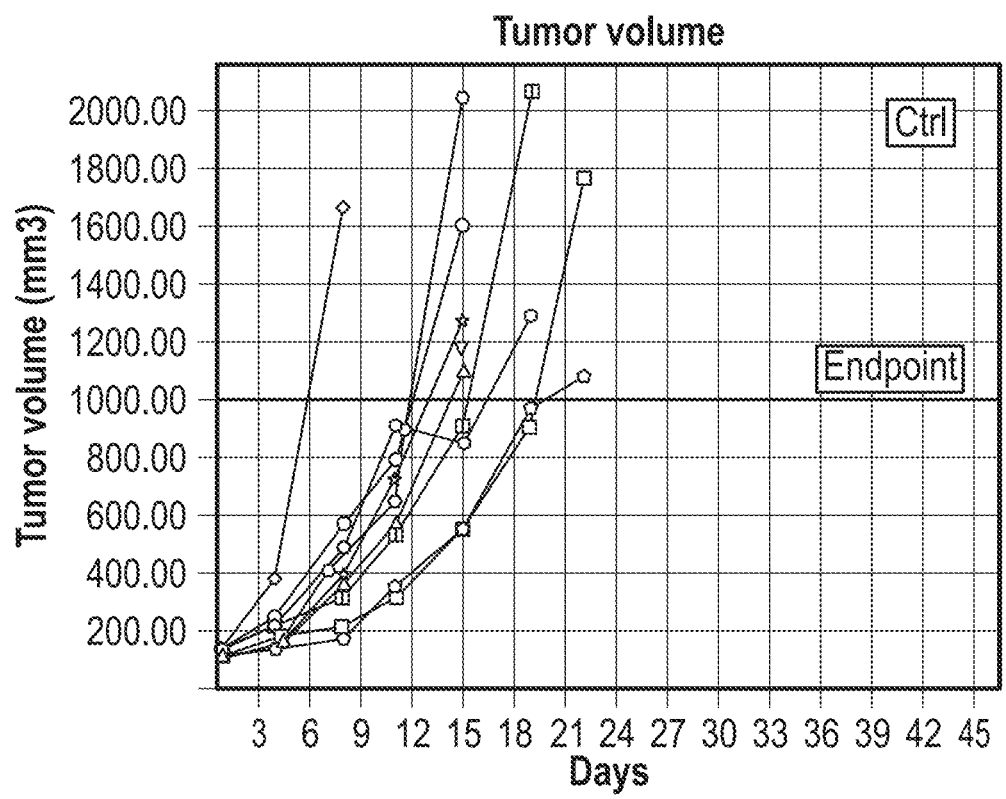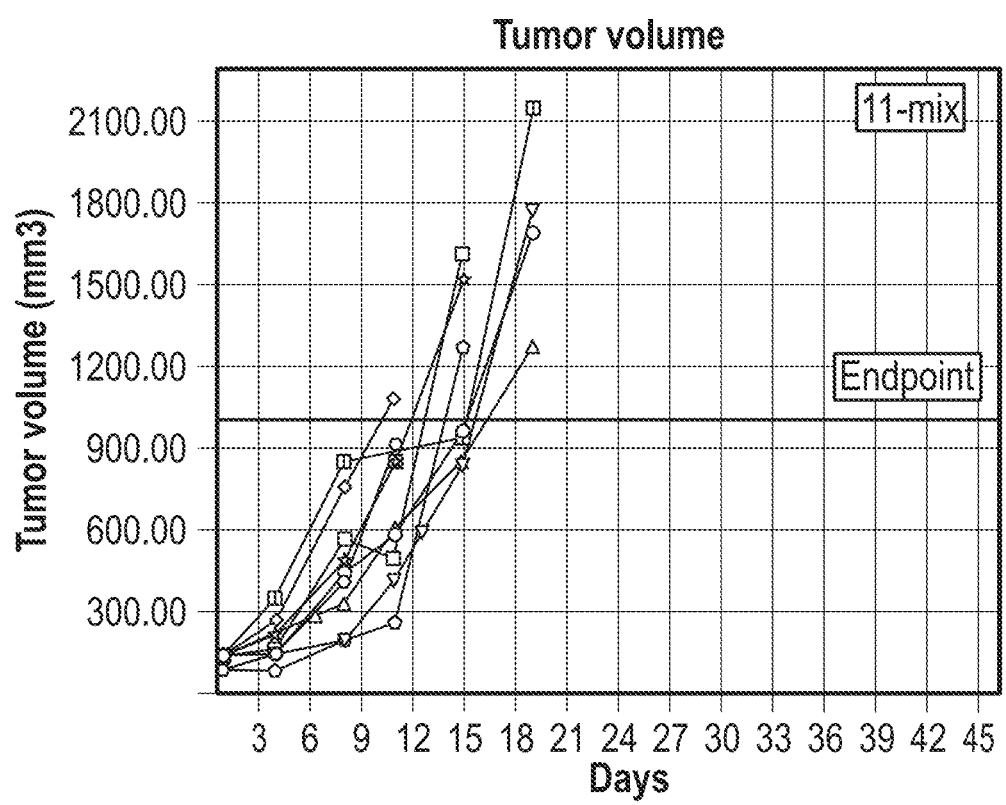
Fig. 27A

One mouse in SPF feces group (among 8 mice) died at day 6. % BW of 11mix group is significantly (P<0.05) higher than the other 2 groups at day 3-5.

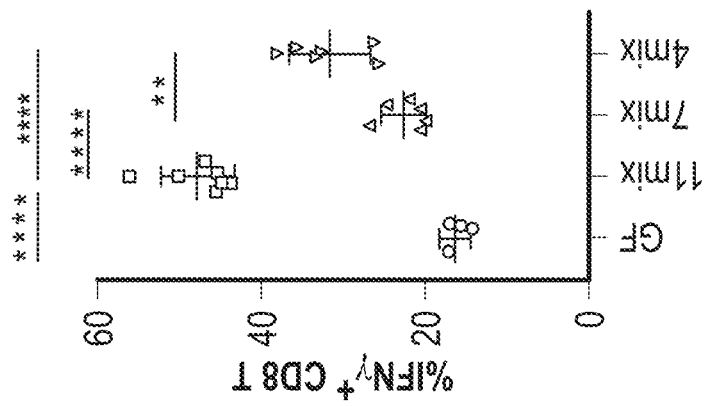
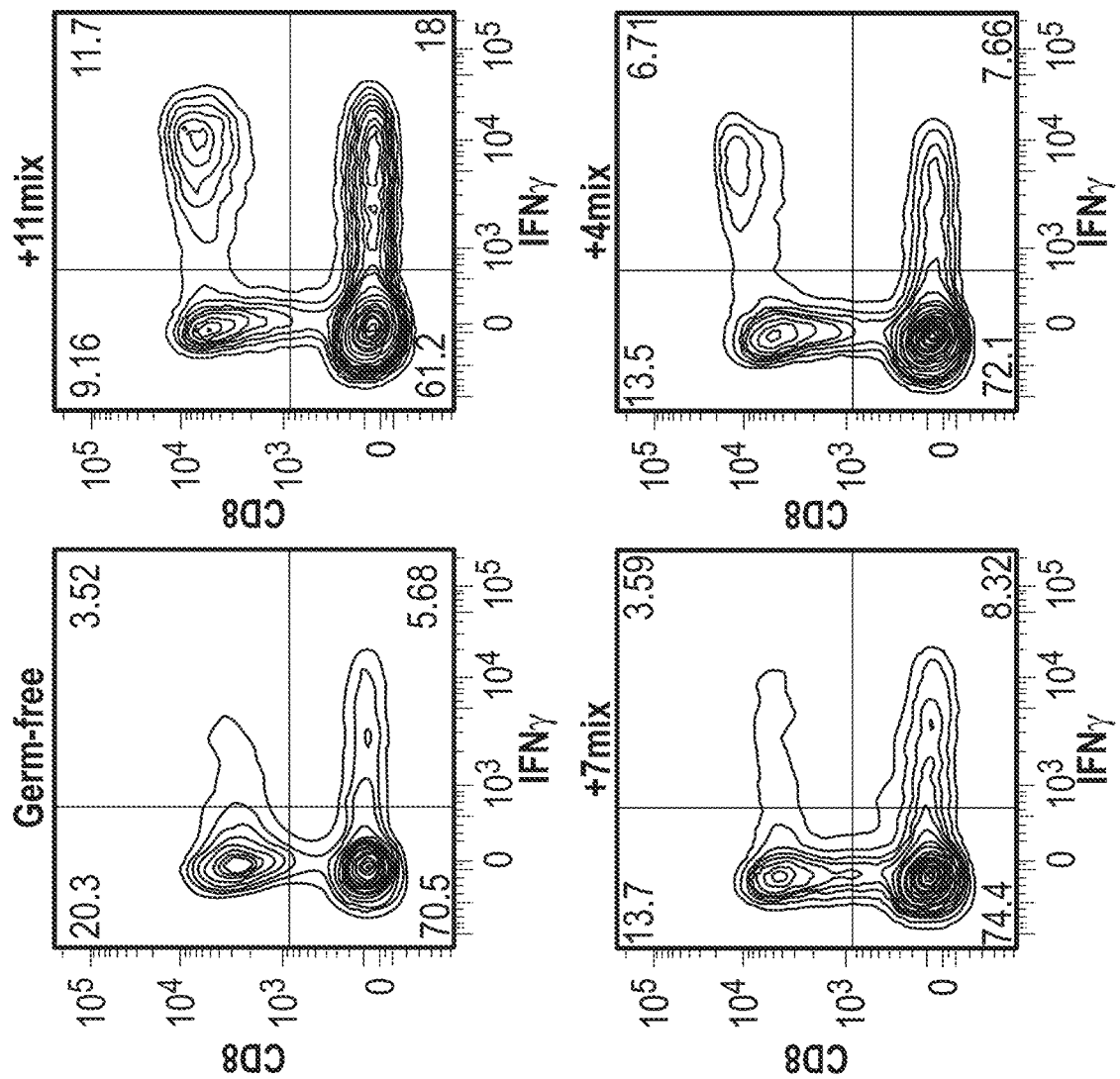
Fig. 47A
Fig. 47B

COMPOSITIONS AND METHODS FOR THE INDUCTION OF CD8+ T-CELLS

RELATED APPLICATIONS

This application is a national stage filing under 35 U.S.C. § 371 of International Patent Application PCT/JP2017/046232, filed Dec. 22, 2017, which claims priority under 35 U.S.C § 119(e) to U.S. Provisional Application Ser. No. 62/574,446, filed Oct. 19, 2017; U.S. Provisional Application Ser. No. 62/491,062, filed Apr. 27, 2017; U.S. Provisional Application Ser. No. 62/484,607, filed Apr. 12, 2017; and U.S. Provisional Application Ser. No. 62/438,793, filed Dec. 23, 2016. The entire contents of these applications are incorporated herein by reference in their entirety.

TECHNICAL FIELD

The disclosure relates to compositions and methods for the induction and/or proliferation of CD8+ T-cells. The disclosure also provides methods of treatment of diseases that can be treated by the induction and/or proliferation of CD8+ T-cells.

BACKGROUND ART

Animals, including humans, harbor a multitude of microbes (collectively referred to as the microbiota) in anatomical locations including the mouth, esophagus, stomach, small intestine, large intestine, caecum, vagina, skin, nasal cavities, ear, and lungs. The human microbiota is responsible for a multitude of critical processes, including the development of the immune system, metabolism of carbohydrates, proteins and xenobiotics, formation and regeneration of the epithelium, fat storage, production of hormones, production of vitamins, and protection from pathogen infections, among others (See e.g., LeBlanc et al. Curr. Opin. Biotechnol. (2013) 24(2):160-168; Hooper et al. Science (2012) 336(6086):1268-1273; Hughes et al. Am. J. Gastroenterol. (2013) 108(7):1066-1074). Modification of the human microbiota, which can be caused by a number of factors such as antibiotic use, excessive hygiene, diet, genetic background or combinations of the above, has been associated with a number of unwanted effects including the occurrence of infectious diseases (e.g., *C. difficile* infections), inflammatory, autoimmune and allergic diseases (e.g., ulcerative colitis, Crohn's disease, Type I diabetes, food allergies, asthma, rheumatoid arthritis) and metabolic diseases (e.g., Type II diabetes, metabolic syndrome, obesity, malnutrition), and cancer, among others. For instance, modifications of the microbiota can lead to a loss of tolerance against harmless food antigens or commensal bacterial antigens, subsequent excessive inflammatory responses, metabolic dysregulation, and damage to the intestinal tissue, which compromises its ability to serve as a barrier between the gut lumen and the systemic circulation.

Manipulation of the immune response is of great importance in the treatment of cancer and in vaccination. Cancer therapies that target the immune system have attained improvements in survival rates. However, a large percentage of patients do not respond to cancer immunotherapies. Similarly, large population subsets (e.g., the elderly) cannot mount strong immune responses to vaccines.

Approaches for countering the harmful effects of microbiota modifications on health are limited, despite the role that such modifications play in promoting human pathology. Interventions known to modulate the microbiota include antibiotics, prebiotics, probiotics and fecal transplants, each of which has limitations and potential adverse effects. Additional approaches to counter the detrimental effects of microbiome modification on human health are clearly needed. Furthermore, approaches for promoting stronger immune responses to cancer and to vaccines are also needed.

SUMMARY OF INVENTION

The inventors joined the Innovative Advanced Research and Development Support Project Incubation Type of Japan Agency for Medical Research and Development (AMED) in 2016, whose Research and Development Subject entitled "Creating New Drugs Using Intestinal Bacterial Strain Cocktail" (AMED-LEAP Research Program), and obtained the present invention as the result of the AMED-LEAP Research Program.

The disclosure relates to compositions of bacterial strains and methods for the induction and/or proliferation of CD8+ T-cells by administering these compositions. The disclosure also provides compositions and methods for the treatment of diseases that can be treated by the induction and/or proliferation of CD8+ T-cells. Diseases that can be treated by the induction and/or proliferation of CD8+ T-cells include infectious diseases and cancers.

As disclosed herein, for the first-time compositions of human-derived bacterial strains are provided which activate the immune system through the induction of interferon gamma producing CD8+ T cells (also referred to herein as IFNγ+CD8+ T cells, CD8+IFNγ+ T cells, CD8+ T cells or CD8 positive T-cells). While microbialbased compositions for inducing proliferation or accumulation of regulatory T-cells (WO2011/152566), and composition for inducing Th17 cells (WO2015/156419) were previously reported, this disclosure is the first report on microbial species which induce IFNγ+CD8+ T-cells. IFNγ+CD8+ T-cells play important roles in the immune system, in particular the surveillance of infections (e.g., viral infections) and cancer cell development. The compositions provided herein can therefore be used in, for instance, the treatment of infectious diseases and cancer immunotherapy.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdo-* ligranulum sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii,* and *Bacteroides* sp. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii,* and *Bacteroides* sp. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis.*

In one aspect, the disclosure provides compositions comprising a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis.*

In one aspect, the disclosure provides compositions comprising a purified bacterial mixture essentially consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis.*

In one aspect, the disclosure provides compositions comprising a purified bacterial mixture comprising one or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae* bacterium cv2, *Gemminger formicilis, Paraprevotella xylaniphila, Parabacteroides johnsonii, Alistipes* sp., *Alistipes timonensis, Alistipes senegalesis, Parabacteroides gordonii, Parabacteroides* sp.HGS0025, *Eubacterum limosum, Parabacteroides* sp. CAG:2 and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising:
1) *Phascolarctobacterium faccium,* or *Phascolarctobacterium* sp. CAG:207,
2) *Fusobacterium ulcerans,* or *Fusobacterium varium,*
3) *Bacteroides dorei,* or *Bacteroides fluxus,*
4) *Bacteroides uniformis,* or *Bacteroides* sp. D20,
5) *Subdoligranulum* sp., *Ruthenibacterium lactatiformans, Ruminococcaceae bacterium* cv2, or *Gemminger formicilis,*
6) *Paraprevotella xylaniphila,*
7) *Parabacteroides johnsonii,*
8) *Alistipes* sp., *Alistipes timonensis,* or *Alistipes senegalesis,*
9) *Parabacteroides gordonii,* or *Parabacteroides* sp. HGS0025,
10) *Eubacterum limosum,* and
11) *Parabacteroides* sp. CAG:2 or *Parabacteroides distasonis.*

In one aspect, the disclosure provides compositions comprising a purified bacterial mixture consisting of:
1) *Phascolarctobacterium faecium,* or *Phascolarctobacterium* sp. CAG:207,
2) *Fusobacterium ulcerans,* or *Fusobacterium varium,*
3) *Bacteroides* dorei, or *Bacteroides fluxus,*
4) *Bacteroides uniformis,* or *Bacteroides* sp. D20,
5) *Subdoligranulum* sp., *Ruthenibacterium lactatiformans, Ruminococcaceae bacterium* cv2, or *Gemminger formicilis,*
6) *Paraprevotella xylaniphila,*
7) *Parabacteroides johnsonii,*

8) *Alistipes* sp., *Alistipes timonensis*, or *Alistipes senegalesis*.
9) *Parabacteroides gordonii*, or *Parabacteroides* sp. HGS0025,
10) *Eubacterum limosum*, and
11) *Parabacteroides* sp. CAG:2 or *Parabacteroides distasonis*.

In one aspect, the disclosure provides compositions comprising a purified bacterial mixture comprising one or more bacterial strains of species selected from the group consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides* distasonis.

In one aspect, the disclosure provides compositions comprising a purified bacterial mixture consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*.

In one aspect, the disclosure provides compositions comprising a purified bacterial mixture essentially consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides* distasonis.

In one aspect, the disclosure provides compositions comprising a purified bacterial mixture comprising one or more bacterial strains of species selected from the group consisting of *Phascolarctobacterium* sp. CAG:207, *Fusobacterium ulcerans*, *Bacteroides dorei*, *Bacteroides* sp. D20, *Ruminococcaceae* bacterium cv2, *Paraprevotella xylaniphila*, *Parabacteroides johnsonii*, *Alistipes senegalesis*, *Parabacteroides* sp. HGS0025, *Eubacterum limosum*, and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture consisting of *Phascolarctobacterium* sp. CAG:207, *Fusobacterium ulcerans*, *Bacteroides dorei*, *Bacteroides* sp. D20, *Ruminococcaceae* bacterium cv2, *Paraprevotella xylaniphila*, *Parabacteroides johnsonii*, *Alistipes senegalesis*, *Parabacteroides* sp. HGS0025, *Eubacterum limosum*, and *Parabacteroides* sp. CAG:2.

In one aspect, the disclosure provides compositions comprising a purified bacterial mixture essentially consisting of *Phascolarctobacterium* sp. CAG:207, *Fusobacterium ulcerans*, *Bacteroides dorei*, *Bacteroides* sp. D20, *Ruminococcaceae* bacterium cv2, *Paraprevotella xylaniphila*, *Parabacteroides johnsonii*, *Alistipes senegalesis*, *Parabacteroides* sp. HGS0025, *Eubacterum limosum*, and *Parabacteroides* sp. CAG:2.

In one aspect, the disclosure provides compositions comprising a purified bacterial mixture comprising two or more bacterial strains of species selected from the group consisting of *Phascolarctobacterium faecium*, *Fusobacterium ulcerans*, *Bacteroides dorei*, *Bacteroides uniformis*, *Subdoligranulum* sp., *Paraprevotella xylaniphila*, *Parabacteroides johnsonii*, *Alistipes* sp., *Parabacteroides gordonii*, *Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium*, *Phascolarctobacterium* sp. CAG:207, *Fusobacterium ulcerans*, *Fusobacterium varium*, *Bacteroides dorei*, *Bacteroides fluxus*, *Bacteroides uniformis*, *Bacteroides* sp. D20 *Subdoligranulum* sp., *Ruthenibacterium lactatiformans*, *Ruminococcaceae* bacterium cv2, *Gemminger formicilis*, *Paraprevotella xylaniphila*, *Parabacteroides johnsonii*, *Alistipes* sp., *Alistipes senegalesis*, *Parabacteroides gordonii*, *Parabacteroides* sp. HGS0025, *Eubacterum limosum*, *Parabacteroides* sp. CAG:2 and *Parabacteroides distasonis*. In some embodiments of the compositions provided herein, the purified bacterial mixture comprises, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 1 bacterial strains.

In one aspect, the disclosure provides compositions comprising a purified bacterial mixture comprising two or more bacterial strains of species selected from the group consisting of *Phascolarctobacterium* sp. CAG:207. *Fusobacterium ulcerans*, *Bacteroides dorei*, *Bacteroides* sp. D20, *Ruminococcaceae* bacterium cv2, *Paraprevotella xylaniphila*, *Parabacteroides johnsonii*, *Alistipes senegalesis*, *Parabacteroides* sp.HGS0025, *Eubacterum limosum*, and *Parabacteroides* sp. CAG:2. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140. *Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains of species selected from the group consisting of *Bacteroides dorei, Bacteroides uniformis, Paraprevotella xylaniphila, Parabacteroides johnsonii, Alistipes* sp., *Parabacteroides gordonii*, and *Parabacteroides distasonis*. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains of species selected from the group consisting of *Bacteroides dorei, Bacteroides uniformis, Paraprevotella xylaniphila, Parabacteroides johnsonii, Alistipes* sp., *Parabacteroides gordonii*, and *Parabacteroides distasonis*. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19. SEQ ID NO:20, or SEQ ID NO:21. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% sequence identity with SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19. SEQ ID NO:20, or SEQ ID NO:21. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO: 11. In some embodiments of the compositions provided herein, the one or more bacterial strain comprises 16S rDNA sequences of at least 96%, at least 97%, at least 98%, or at least 99% sequence identity with SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO: 11. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO: 11. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO:54, SEQ ID NO:55, SEQ ID NO:56. SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11.

In one aspect, the disclosure provides compositions comprising a purified bacterial mixture comprising:
a bacterial strain comprising a 16S rDNA sequence of at least 97% homology to SEQ ID NO:1.

a bacterial strain comprising a 16S rDNA sequence of at least 97% homology to SEQ ID NO:2, a bacterial strain comprising a 16S rDNA sequence of at least 97% homology to SEQ ID NO:3, a bacterial strain comprising a 16S rDNA sequence of at least 97% homology to SEQ ID NO:4, a bacterial strain comprising a 16S rDNA sequence of at least 97% homology to SEQ ID NO:5, a bacterial strain comprising a 16S rDNA sequence of at least 97% homology to SEQ ID NO:6, a bacterial strain comprising a 16S rDNA sequence of at least 97% homology to SEQ ID NO:7, a bacterial strain comprising a 16S rDNA sequence of at least 97% homology to SEQ ID NO:8, a bacterial strain comprising a 16S rDNA sequence of at least 97% homology to SEQ ID NO:9, a bacterial strain comprising a 16S rDNA sequence of at least 97% homology to SEQ ID NO:10, and a bacterial strain comprising a 16S rDNA sequence of at least 97% homology to SEQ ID NO: 11.

In one aspect, the disclosure provides compositions comprising a purified bacterial mixture consisting of bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of:

a bacterial strain comprising a 16S rDNA sequence of at least 97% homology to SEQ ID NO:1, a bacterial strain comprising a 16S rDNA sequence of at least 97% homology to SEQ ID NO:2, a bacterial strain comprising a 16S rDNA sequence of at least 97% homology to SEQ ID NO:3, a bacterial strain comprising a 16S rDNA sequence of at least 97% homology to SEQ ID NO:4, a bacterial strain comprising a 16S rDNA sequence of at least 97% homology to SEQ ID NO:5, a bacterial strain comprising a 16S rDNA sequence of at least 97% homology to SEQ ID NO:6, a bacterial strain comprising a 16S rDNA sequence of at least 97% homology to SEQ ID NO:7, a bacterial strain comprising a 16S rDNA sequence of at least 97% homology to SEQ ID NO:8, a bacterial strain comprising a 16S rDNA sequence of at least 97% homology to SEQ ID NO:9, a bacterial strain comprising a 16S rDNA sequence of at least 97% homology to SEQ ID NO:10, and a bacterial strain comprising a 16S rDNA sequence of at least 97% homology to SEQ ID NO:11.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9. SEQ ID NO: 10, or SEQ ID NO: 11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO: 11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11.

In one aspect, the disclosure provides compositions comprising a purified bacterial mixture comprising bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising:

a bacterial strain comprising a 16S rDNA sequence of at least 97% sequence identity with SEQ ID NO:1, a bacterial strain comprising a 16S rDNA sequence of at least 97% sequence identity with SEQ ID NO:2, a bacterial strain comprising a 16S rDNA sequence of at least 97% sequence identity with SEQ ID NO:3, a bacterial strain comprising a 16S rDNA sequence of at least 97% sequence identity with SEQ ID NO:4, a bacterial strain comprising a 16S rDNA sequence of at least 97% sequence identity with SEQ ID NO:5, a bacterial strain comprising a 16S rDNA sequence of at least 97% sequence identity with SEQ ID NO:6.

a bacterial strain comprising a 16S rDNA sequence of at least 97% sequence identity with SEQ ID NO:7, a bacterial strain comprising a 16S rDNA sequence of at least 97% sequence identity with SEQ ID NO:8, a bacterial strain comprising a 16S rDNA sequence of at least 97% sequence identity with SEQ ID NO:9, a bacterial strain comprising a 16S rDNA sequence of at least 97% sequence identity with SEQ ID NO:10, and a bacterial strain comprising a 16S rDNA sequence of at least 97% sequence identity with SEQ ID NO: 11.

In one aspect, the disclosure provides compositions comprising a purified bacterial mixture comprising:

a bacterial strain comprising a 16S rDNA sequence of at least 99% sequence identity with SEQ ID NO:1, a bacterial strain comprising a 16S rDNA sequence of at least 99% sequence identity with SEQ ID NO:2.

a bacterial strain comprising a 16S rDNA sequence of at least 99% sequence identity with SEQ ID NO:3, a bacterial strain comprising a 16S rDNA sequence of at least 99% sequence identity with SEQ ID NO:4, a bacterial strain comprising a 16S rDNA sequence of at least 99% sequence identity with SEQ ID NO:5, a bacterial strain comprising a 16S rDNA sequence of at least 99% sequence identity with SEQ ID NO:6, a bacterial strain comprising a 16S rDNA sequence of at least 99% sequence identity with SEQ ID NO:7, a bacterial strain comprising a 16S rDNA sequence of at least 99% sequence identity with SEQ ID NO:8, a bacterial strain comprising a 16S rDNA sequence of at least 99% sequence identity with SEQ ID NO:9, a bacterial strain comprising a 16S rDNA sequence of at least 99% sequence identity with SEQ ID NO:10, and a bacterial strain comprising a 16S rDNA sequence of at least 99% sequence identity with SEQ ID NO:11.

In one aspect, the disclosure provides compositions comprising a purified bacterial mixture comprising bacterial strains comprising 16S rDNA sequences with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, and SEQ ID NO: 11. In one aspect, the disclosure provides compositions comprising a purified bacterial mixture consisting of bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11.

In one aspect, the disclosure provides compositions comprising a purified bacterial mixture consisting of:
a bacterial strain comprising a 16S rDNA sequence of at least 97% sequence identity with SEQ ID NO:1,
a bacterial strain comprising a 16S rDNA sequence of at least 97% sequence identity with SEQ ID NO:2,
a bacterial strain comprising a 16S rDNA sequence of at least 97% sequence identity with SEQ ID NO:3,
a bacterial strain comprising a 16S rDNA sequence of at least 97% sequence identity with SEQ ID NO:4,
a bacterial strain comprising a 16S rDNA sequence of at least 97% sequence identity with SEQ ID NO:5,
a bacterial strain comprising a 16S rDNA sequence of at least 97% sequence identity with SEQ ID NO:6,
a bacterial strain comprising a 16S rDNA sequence of at least 97% sequence identity with SEQ ID NO:7,
a bacterial strain comprising a 16S rDNA sequence of at least 97% sequence identity with SEQ ID NO:8,
a bacterial strain comprising a 16S rDNA sequence of at least 97% sequence identity with SEQ ID NO:9,
a bacterial strain comprising a 16S rDNA sequence of at least 97% sequence identity with SEQ ID NO:10, and
a bacterial strain comprising a 16S rDNA sequence of at least 97% sequence identity with SEQ ID NO:11.

In one aspect, the disclosure provides compositions comprising a purified bacterial mixture consisting of:
a bacterial strain comprising a 16S rDNA sequence of at least 99% sequence identity with SEQ ID NO:1,
a bacterial strain comprising a 16S rDNA sequence of at least 99% sequence identity with SEQ ID NO:2,
a bacterial strain comprising a 16S rDNA sequence of at least 99% sequence identity with SEQ ID NO:3,
a bacterial strain comprising a 16S rDNA sequence of at least 99% sequence identity with SEQ ID NO:4,
a bacterial strain comprising a 16S rDNA sequence of at least 99% sequence identity with SEQ ID NO:5,
a bacterial strain comprising a 16S rDNA sequence of at least 99% sequence identity with SEQ ID NO:6,
a bacterial strain comprising a 16S rDNA sequence of at least 99% sequence identity with SEQ ID NO:7,
a bacterial strain comprising a 16S rDNA sequence of at least 99% sequence identity with SEQ ID NO:8,
a bacterial strain comprising a 16S rDNA sequence of at least 97% sequence identity with SEQ ID NO:9,
a bacterial strain comprising a 16S rDNA sequence of at least 99% sequence identity with SEQ ID NO:10, and
a bacterial strain comprising a 16S rDNA sequence of at least 99% sequence identity with SEQ ID NO:11.

In one aspect, the disclosure provides compositions comprising a purified bacterial mixture consisting of bacterial strains comprising 16S rDNA sequences with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising two or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising:
a bacterial strain comprising a 16S rDNA sequence of at least 97% sequence identity with SEQ ID NO:54,
a bacterial strain comprising a 16S rDNA sequence of at least 97% sequence identity with SEQ ID NO:55,
a bacterial strain comprising a 16S rDNA sequence of at least 97% sequence identity with SEQ ID NO:56,
a bacterial strain comprising a 16S rDNA sequence of at least 97% sequence identity with SEQ ID NO:57,
a bacterial strain comprising a 16S rDNA sequence of at least 97% sequence identity with SEQ ID NO:58,
a bacterial strain comprising a 16S rDNA sequence of at least 97% sequence identity with SEQ ID NO:59,
a bacterial strain comprising a 16S rDNA sequence of at least 97% sequence identity with SEQ ID NO:60,
a bacterial strain comprising a 16S rDNA sequence of at least 97% sequence identity with SEQ ID NO:61,
a bacterial strain comprising a 16S rDNA sequence of at least 97% sequence identity with SEQ ID NO:62,
a bacterial strain comprising a 16S rDNA sequence of at least 97% sequence identity with SEQ ID NO:63, and a bacterial strain comprising a 16S rDNA sequence of at least 97% sequence identity with SEQ ID NO:64.

In one aspect, the disclosure provides compositions comprising a purified bacterial mixture comprising:
a bacterial strain comprising a 16S rDNA sequence of at least 99% sequence identity with SEQ ID NO:54,
a bacterial strain comprising a 16S rDNA sequence of at least 99% sequence identity with SEQ ID NO:55,
a bacterial strain comprising a 16S rDNA sequence of at least 99% sequence identity with SEQ ID NO:56,
a bacterial strain comprising a 16S rDNA sequence of at least 99% sequence identity with SEQ ID NO:57,
a bacterial strain comprising a 16S rDNA sequence of at least 99% sequence identity with SEQ ID NO:58,
a bacterial strain comprising a 16S rDNA sequence of at least 99% sequence identity with SEQ ID NO:59,
a bacterial strain comprising a 16S rDNA sequence of at least 99% sequence identity with SEQ ID NO:60,
a bacterial strain comprising a 16S rDNA sequence of at least 99% sequence identity with SEQ ID NO:61,
a bacterial strain comprising a 16S rDNA sequence of at least 99% sequence identity with SEQ ID NO:62,
a bacterial strain comprising a 16S rDNA sequence of at least 99% sequence identity with SEQ ID NO:63, and
a bacterial strain comprising a 16S rDNA sequence of at least 99% sequence identity with SEQ ID NO:64.

In one aspect, the disclosure provides compositions comprising a purified bacterial mixture comprising bacterial strains comprising 16S rDNA sequences with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of:
a bacterial strain comprising a 16S rDNA sequence of at least 97% sequence identity with SEQ ID NO:54,
a bacterial strain comprising a 16S rDNA sequence of at least 97% sequence identity with SEQ ID NO:55,
a bacterial strain comprising a 16S rDNA sequence of at least 97% sequence identity with SEQ ID NO:56,
a bacterial strain comprising a 16S rDNA sequence of at least 97% sequence identity with SEQ ID NO:57,
a bacterial strain comprising a 16S rDNA sequence of at least 97% sequence identity with SEQ ID NO:58,
a bacterial strain comprising a 16S rDNA sequence of at least 97% sequence identity with SEQ ID NO:59,
a bacterial strain comprising a 16S rDNA sequence of at least 97% sequence identity with SEQ ID NO:60,
a bacterial strain comprising a 16S rDNA sequence of at least 97% sequence identity with SEQ ID NO:61,
a bacterial strain comprising a 16S rDNA sequence of at least 97% sequence identity with SEQ ID NO:62,
a bacterial strain comprising a 16S rDNA sequence of at least 97% sequence identity with SEQ ID NO:63, and
a bacterial strain comprising a 16S rDNA sequence of at least 97% sequence identity with SEQ ID NO:64.

In one aspect, the disclosure provides compositions comprising a purified bacterial mixture consisting of:
a bacterial strain comprising a 16S rDNA sequence of at least 99% sequence identity with SEQ ID NO:54,
a bacterial strain comprising a 16S rDNA sequence of at least 99% sequence identity with SEQ ID NO:55,
a bacterial strain comprising a 16S rDNA sequence of at least 99% sequence identity with SEQ ID NO:56,
a bacterial strain comprising a 16S rDNA sequence of at least 99% sequence identity with SEQ ID NO:57,
a bacterial strain comprising a 16S rDNA sequence of at least 99% sequence identity with SEQ ID NO:58,
a bacterial strain comprising a 16S rDNA sequence of at least 99% sequence identity with SEQ ID NO:59,
a bacterial strain comprising a 16S rDNA sequence of at least 99% sequence identity with SEQ ID NO:60,
a bacterial strain comprising a 16S rDNA sequence of at least 99% sequence identity with SEQ ID NO:61,
a bacterial strain comprising a 16S rDNA sequence of at least 99% sequence identity with SEQ ID NO:62,
a bacterial strain comprising a 16S rDNA sequence of at least 99% sequence identity with SEQ ID NO:63, and
a bacterial strain comprising a 16S rDNA sequence of at least 99% sequence identity with SEQ ID NO:64.

In one aspect, the disclosure provides compositions comprising a purified bacterial mixture consisting of bacterial strains comprising 16S rDNA sequences with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising one or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 95% sequence identity with SEQ ID NO:12, SEQ ID NO:13, SEQ ID NO:14. SEQ ID NO:15, SEQ ID NO:16, SEQ ID NO:17, SEQ ID NO:18, SEQ ID NO:19. SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24. SEQ ID NO:25, or SEQ ID NO:26. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19. SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising one or more bacterial strains comprising 16S rDNA sequences of at least 95% homology to SEQ ID NO: 12. SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising one or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 95% homology to SEQ ID NO: 12. SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% homology to SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:5, or SEQ ID NO:10. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:5, or SEQ ID NO: 10. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:5, or SEQ ID NO: 10. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:5, or SEQ ID NO: 10. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:5, or SEQ ID NO: 10. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with the SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% sequence identity with SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% sequence identity with SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39. SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39. SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39. SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the one or more bacterial strain comprises 16S rDNA sequences of at least 96%, at least 97%, at least 98%, or at least 99% sequence identify with the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, or at least 1 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29. SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50. SEQ ID NO:51, or SEQ ID NO:52. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45. SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45. SEQ ID NO:46, or SEQ ID NO:47. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:31 or SEQ ID NO:36. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:31 or SEQ ID NO:36. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:31 or SEQ ID NO:36. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:31 or SEQ ID NO:36. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 95% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In some embodiments of the compositions provided herein, at least 50% of the bacterial strains belong to the order of Bacteriodales. In some embodiments of the compositions provided herein, one or more of the bacterial strains belong to the order of Bacteriodales and one or more of the bacterial strains belong to the order of Clostridiales. In some embodiments of the compositions provided herein, at least 25% of the bacterial strains belong to the family of Bacteroidaceae. In some embodiments of the compositions provided herein, one or more of the bacterial strains belongs to the genus *Bacteroides*. In some embodiments of the compositions provided herein, the composition does not include bacterial strains that belong to the order of Bacteriodales. In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former. In some embodiments of the compositions provided herein, the composition comprises only obligate anaerobic bacterial strains. In some embodiments of the compositions provided herein, one or more of the bacterial strains does not have an antibiotic resistance gene. In some embodiments of the compositions provided herein, the antibiotic resistance gene renders the bacterial strain resistant to vancomycin. In some embodiments of the compositions provided herein, the bacterial strains are human-derived bacteria. In some embodiments of the compositions provided herein, the bacterial strains are derived from more than one human donor. In some embodiments of the compositions provided herein, the composition induces proliferation and/or accumulation of CD8+ T-cells.

In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

In one aspect, the disclosure provides a food product comprising any of the compositions provided herein and a nutrient.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor. In some embodiments of the compositions provided herein, the immune checkpoint inhibitor is a CTLA-4 inhibitor. In some embodiments of the compositions provided herein, the composition further comprises one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28, OX-40, 4-1BB, or CD40 antibody.

In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen.

In some embodiments of the compositions provided herein, the composition further comprises one or more anti-inflammatory agents. In some embodiments of the compositions provided herein, the anti-inflammatory agent is an NSAID.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFNγ-gamma production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the number of the bacterial strains of the administered composition engrafted in the intestine of the subject. In some embodiments of the compositions provided herein, administration of the composition to a subject results in an increase in the amount of bacteria of the bacterial strains of the administered composition in the intestine of the subject. In some embodiments of the compositions provided herein, administration of the composition to a subject results in an increase in the amount of bacteria of the bacterial strains of the administered composition engrafted in the intestine of the subject.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition. In some embodiments of the methods provided herein, the administration of the composition to the subject results in an increase of IFNγ-gamma production in the intestine of the subject when compared to the IFNγ-gamma production in the intestine of the subject before the administration of the composition. In some embodiments of the methods provided herein, the administration of the composition to the subject results in an increase of IFNγ-gamma production in the intestine of the subject by at least 10%, at least 20%, at least 30%, at least 40%, at least 50%, at least 100%, or at least 200% when compared to the IFNγ-gamma production in the intestine of the subject before the administration of the composition.

In some embodiments of the methods provided herein, the subject has cancer. In some embodiments of the methods provided herein, the cancer is carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent. In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28, OX-40, 4-1BB, or CD40 antibody.

In some embodiments of the methods provided herein, the method further includes administering one or more vaccines. In some embodiments of the methods provided herein, the vaccine is a dendritic cell vaccine.

In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus.

In some embodiments of the methods provided herein, the subject has an autoimmune disease or an allergic disease.

In some embodiments of the methods provided herein, the composition further includes one or more anti-inflammatory agents. In some embodiments of the methods provided herein, the anti-inflammatory is an NSAID. In some embodiments of the methods provided herein, the composition may be administered as one or more dose.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject.

In some embodiments of the methods provided herein, the subject is undergoing, or will be undergoing, cancer treatment.

In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment.

In some embodiments of the methods provided herein, the cancer treatment is cancer immunotherapy treatment.

In one aspect, the disclosure provides a method for reducing the risk of a viral infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject.

In some embodiments of the methods provided herein, determining the presence of one or more of the bacterial species is done by sequencing fecal matter of the subject. In some embodiments of the methods provided herein, determining the presence of one or more of the bacterial species is done by sequencing the 16S rDNA sequences of fecal matter of the subject.

In one aspect, the disclosure provides compositions and methods to induce activation of CD8+IFNγ-gamma producing T-cells in the intestinal tract.

In one aspect, the disclosure provides a composition comprising a purified bacterial mixture comprising one or more bacterial strains comprising 16S rDNA sequences of at least 95% homology to the sequences of the following NCBI accession numbers: LN998073, KR822463, CP011531, NR_112945, NZ-ACWW00000000, AB331897, AB261128, NZ-CAEG00000000, AB470343, AB595134, HE974920, NR_112933, AB490801. NZ-ACWB00000000, AY608696. CR626927, AB247141, NR_112935, AB249652, NR_113076 and AF139525. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In some embodiments of the compositions provided herein, the one or more bacterial strains comprises 16S rDNA sequences with at least 96%, at least 97%, at least 98%, or at least 99% homology with sequences provided herein.

In one aspect, the disclosure provides a composition that induces or activates CD8+IFNγ-producing T-cells, the composition comprising (i) one or more purified bacterial strains collected from human stool which possesses resistance to ampicillin, or (ii) a culture supernatant of (i). In some embodiments of the compositions provided herein, the composition comprises (a) a purified bacterial mixture comprising one or more bacterial strains of species selected from the group consisting of Phascolarctobacterium faecium: LN998073,
Fusobacterium ulcerans; KR822463,
Bacteroides dorei; CP011531,
Bacteroides uniformis; NR_112945,
Subdoligranulum sp. 4_3_54A2FAA; NZ-ACWW00000000,
Paraprevotella xylaniphila; AB331897,
Parabacteroides johnsonii; AB261128,
Alistipes sp. JC136; NZ-CAEG00000000.
Parabacteroides gordonii; AB470343,
Eubacterium limosum; AB595134,
Parabacteroides distasonis; HE974920,
Bacteroides cellulosilyticus: NR_112933,
Bacteroides clarus; AB490801,
Anaerostipes sp. 3_2_56FAA; NZ-ACWB00000000,
Bacteroides salyersiae; AY608696,
Bacteroides fragilis; CR626927,
Bacteroides uniformis; AB247141,
Bacteroides eggerthii; NR_112935,
Clostridium sp. TM-40; AB249652.
Parabacteroides goldsteinii; NR_113076, and
Bacteroides sp. AR29; AF139525, or (b) one or more bacterial strains comprising a 16S rRNA sequence having at least 97% homology to a 16S rRNA sequence of a species selected from the group consisting of
Phascolarctobacterium faecium: LN998073,
Fusobacterium ulcerans; KR822463,
Bacteroides dorei; CP011531,
Bacteroides uniformis: NR_112945,
Subdoligranulum sp. 4_3_54A2FAA; NZ-ACWW00000000,
Paraprevotella xylaniphila; AB331897,
Parabacteroides johnsonii; AB261128,
Alistipes sp. JC136; NZ-CAEG00000000,
Parabacteroides gordonii; AB470343,
Eubacterium limosum; AB595134,
Parabacteroides distasonis; HE974920,
Bacteroides cellulosilyticus; NR_112933.

*Bacteroides clarus*; AB490801,
*Anaerostipes* sp. 3_2_56FAA; NZ-ACWB00000000,
*Bacteroides salyersiae*; AY608696,
*Bacteroides fragilis*; CR626927.
*Bacteroides uniformis*; AB247141,
*Bacteroides eggerthii*; NR_112935,
*Clostridium* sp. TM-40; AB249652,
*Parabacteroides goldsteinii*: NR_113076, and
*Bacteroides* sp. AR29; AF139525

In some embodiments of the compositions provided herein, the composition comprises a purified bacterial mixture comprising (a) one or more bacterial strains of species selected from the group consisting of

*Phascolarctobacterium faecium*; LN998073,
*Fusobacterium ulcerans*; KR822463,
*Bacteroides dorei*: CP011531,
*Bacteroides uniformis*; NR_112945,
*Subdoligranulum* sp. 4_3_54A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*: AB595134, and
*Parabacteroides distasonis*; HE974920; or (b) one or more bacterial strains comprising a 16S rRNA sequence of a species belonging to the group consisting of

*Phascolarctobacterium faecium*; LN998073,
*Fusobacterium ulcerans*; KR822463,
*Bacteroides dorei*; CP011531.
*Bacteroides uniformis*; NR_112945,
*Subdoligranulum* sp. 4_3_54A2FAA; NZ-ACWW00000000,
*Paraprevotella xylaniphila*; AB331897.
*Parabacteroides johnsonii*; AB261128.
*Alistipes* sp. JC136; NZ-CAEG00000000,
*Parabacteroides gordonii*; AB470343,
*Eubacterium limosum*; AB595134, and
*Parabacteroides distasonis*; HE974920.

In some embodiments of the compositions provided herein, the CD8+IFNγ-producing T-cells express CD103 or Granzyme B.

In some embodiments of the compositions provided herein, the composition activates the immune system.

In one aspect, the disclosure provides a method for activating the immune system, the method comprising administration of one or more of the compositions provided herein.

In one aspect, the disclosure provides a method for activating CD8+IFNγ-producing T-cells, the method comprising administration of one or more of the compositions provided herein to a subject.

In one aspect, the disclosure provides a method for inducing the proliferation and/or accumulation of CD8+ T cells in the intestine, comprising administering to a subject any one or more of the compositions provided herein, wherein the administering results in the induction of proliferation and/or accumulation of CD8+ T cells in the intestine of the subject.

In one aspect, the disclosure provides a method for assisting in treatment, and/or preventing cancer or viral infection, comprising administering to a subject any one or more of the compositions provided herein, wherein the administering prevents, treats, assists in treatment, and/or prevents cancer or viral infection.

In one aspect, the disclosure provides vaccine compositions which induce immune response against bacterial strains of any one of the compositions disclosed herein.

In one aspect, the disclosure provides a vaccine composition containing antigen derived from constituents and/or metabolites of bacterial species of any one of the compositions provided herein.

In one aspect, the disclosure provides a method for inducing an immune response in a subject, comprising administering to the subject any of the vaccines provided herein, wherein the administering results in the induction of immune response of the subject.

In one aspect, the disclosure provides immune suppressive compositions.

In one aspect, the disclosure provides a composition comprising a chemical substance that possesses antibacterial activity towards bacterial species of any one of the compositions provided herein, or a chemical substance which binds a physiologically active substance secreted from bacterial species of any one of the compositions provided herein.

In some embodiments of the compositions provided herein, administration of the composition to a subject results in suppression of activity of CD8+ and IFNγ-producing T-cells in the subject.

In one aspect, the disclosure provides a method for suppressing CD8+ and IFNγ-producing T-cells in the subject, the method comprising administration of one or more of the compositions provided herein to the subject.

In one aspect, the disclosure provides a method for prevention, treatment or improvement in a disease originated by over-activation of CD8+ and IFNγ-producing T-cells of the subject the method comprising administering to the subject any one or more of the compositions provided herein to the subject.

In one aspect, the disclosure provides substances derived from the bacterial strains disclosed herein. In one aspect, the disclosure provides a physiologically active substance derived from a bacterial species of any one of the compositions provided herein. In one aspect, the disclosure provides a bacterial specific antigen of any one of the bacterial species of any one of the compositions provided herein.

In one aspect, the disclosure provides an antibody that specifically binds a bacterial species of any one of the compositions provided herein.

In one aspect, the disclosure provides a bacterial-specific nucleotide sequence contained in any one of the bacterial species of the compositions provided herein.

In one aspect, the disclosure provides animal models and test kits.

In one aspect, the disclosure provides an animal model comprising a non-human mammal, wherein the intestinal tract of the non-human mammal has been inoculated with the bacterial species of any one of the compositions provided herein. In some embodiments of the animal model provided herein, the non-human mammal has a disease originated by irregularity of CD8+IFNγ-producing T-cells.

In one aspect, the disclosure provides a kit for evaluating the activation of CD8+IFNγ-producing T cells, the kit comprising: intestinal epithelial cells, peripheral blood mononuclear cells, and a bacterial species of any one of the compositions provided herein.

In one aspect, the disclosure provides methods of detection of CD8+IFNγ-producing T cells in the human intestinal tract. In one aspect, the disclosure provides kits for evaluating activation of CD8+IFNγ-producing T cells. In some embodiments, the kits comprise intestinal epithelial cells, peripheral mononuclear cells, and the bacterial species of any of the compositions described herein.

In one aspect, the disclosure provides a method for screening bacteria or a physiologically active substance derived from human intestinal bacteria, wherein the substance induces activation of CD8+IFNγ producing T cells in the intestinal tract, comprising (i) allowing a non-human germ-free animal to ingest a physiologically active substance derived from human intestinal bacteria or bacteria. (ii) detecting the number, or activity of, CD8+IFNγ-producing T cells in the intestinal tract of the non-human aseptic animal, wherein if activation of CD8+IFNγ-producing T cells is detected, the physiologically active substance is identified as a substance that can activate CD8+IFNγ-producing T cells.

In one aspect, the disclosure provides a method for screening bacteria or a physiologically active substance derived from human intestinal bacteria a, wherein the substance induces proliferation or activation of CD8+IFNγ producing T cells in intestinal tract, comprising (i) adding a physiologically active substance derived from human intestinal bacteria or bacteria to the intestinal epithelial cells in a system comprising intestinal epithelial cells and peripheral blood mononuclear cells; (ii) detecting the number or activity of CD8+IFNγ-producing T cells in said system, wherein if the activation of CD8+IFNγ-producing T cells is detected, the physiologically active substance is identified as a substance that can activate CD8+IFNγ-producing T cells.

In one aspect, the disclosure provides a method for screening for a substance that induces activation of CD8+ IFNγ-producing T cells in intestinal tract, comprising (i) adding a physiologically active substance derived from bacteria or bacteria contained in a composition provided herein to a system containing intestinal epithelial cells and peripheral blood mononuclear cells, (ii) adding a test substance. (iii) detecting the number or activity of CD8+IFNγ-producing T cells in said system, wherein if the number or activity of CD8+IFNγ producing T cells detected in the is increased, the test substance is identified as a substance that induces activation of CD8+IFNγ-producing T cells.

In one aspect, the disclosure provides a method for screening a substance that induces activation of CD8+IFNγ-producing T cells in intestinal tract, comprising (i) the method for screening a non-human animal provided herein, (ii) detecting the number or activity of CD8+IFNγ-producing T cells in the intestinal tract of the non-human animal, wherein if the number or activity of CD8+IFNγ-producing T cells detected in the above step is increased, the test substance is identified as a substance that induces activation of CD8+IFNγ-producing T cells.

In one aspect, the disclosure provides a composition for stimulating immunity, the composition comprising, as an active ingredient, a human intestinal bacterium or a physiologically active substance derived from a bacterium obtained by the screening methods provided herein. In some embodiments of the compositions provided herein, the composition induces the activation of CD8+IFNγ-producing T cells.

In one aspect, the disclosure provides a vaccine composition comprising, as an active ingredient, human intestinal bacteria obtained by any of the screening methods provided herein, or an antigen specific to said bacterium.

In one aspect, the disclosure provides a method for screening a substance having an activity of inducing or exacerbating a disease caused by CD8+IFNγ-producing T cells, comprising (i) allowing a test substance to be ingested by a non-human animal provided herein, (ii) detecting the degree of a disease-associated damage caused by CD8+ IFNγ-producing T cells in said non-human animal, wherein the test substance is identified as a substance that induces a disease caused by CD8+IFNγ-producing T cells when the extent of the lesion detected in the above step is increased as compared to when no compound or placebo was added.

In one aspect, the disclosure provides a composition for inducing or exacerbating a disease caused by CD8+IFNγ-producing T cells, wherein the composition comprises, as an active ingredient, the substance obtained by any one of the screening methods provided herein.

In one aspect, the disclosure provides a composition comprising a processed human fecal sample, wherein the processed human fecal sample is obtained by contacting a human fecal sample with ampicillin, and wherein the processed human fecal sample induces the proliferation and/or accumulation of CD8+ T-cells. In some embodiments, the disclosure provides a method of treatment of a disease in a subject, the method comprising administering to the subject any one of the compositions provided herein in an effective amount to treat the disease in the subject. In some embodiments of the methods provided herein, the disease is cancer or an infection (e.g., a viral infection).

In one aspect, the disclosure provides a method comprising inoculating a human fecal sample in germ free mice, and determining if the human fecal sample induces the proliferation and/or accumulation of CD8+ T-cells.

In one aspect, the disclosure provides a method for determining if a human fecal sample induces proliferation and/or accumulation of CD8+ T cells, comprising inoculating germ-free mice with a human fecal sample, and determining if the human fecal sample induces the proliferation and/or accumulation of CD8+ T-cells. In one aspect, the disclosure provides a method for identifying a human fecal donor, comprising inoculating germ-free mice with a human fecal sample, and determining if the human fecal sample induces the proliferation and/or accumulation of CD8+ T-cells, wherein if the fecal sample induces the proliferation and/or accumulation of CD8+ T-cells, the human subject is identified as a human fecal donor.

In one aspect, the disclosure provides a method for analyzing expression levels of a marker in lymphocytes in a subject, comprising analyzing the expression levels of the marker, wherein the marker is induced by administering to the subject any of the compositions described herein, wherein the marker is CD44, gp70 MC38 peptide (KSPWFTTL: (SEQ ID NO: 53))-specific TCRβ, tumor antigen derived ligand-specific TCRβ, CD8, IFNγ, and/or GzmB.

In one aspect, the disclosure provides kits for analysis of expression levels of a marker in lymphocytes in a subject after induction, wherein the marker is induced by administering to the subject any of the compositions described herein, wherein the marker is CD44, gp70 MC38 peptide (KSPWFTTL; (SEQ ID NO: 53))-specific TCRβ, tumor antigen derived ligand-specific TCRβ, CD8, IFNγ, and/or GzmB.

In one aspect, the disclosure provides methods for screening a bacteria or a physiologically active substance derived from human intestinal bacteria, the method comprising, allowing a tumor-bearing non-human animal to ingest a physiologically active substance derived from human intestinal bacteria or bacteria, detecting the expression of a marker, in lymphocytes isolated from the tumor-bearing non-human animal, wherein if an increase in expression levels of the marker is detected, the physiologically active substance is identified as an immunostimulating agent for the tumor; and wherein the marker is CD44, gp70 MC38 peptide (KSPWFTTL; (SEQ ID NO: 53))-specific TCRβ, tumor antigen derived ligand-specific TCRβ, CD8, IFNγ, and/or GzmB.

In one aspect, the disclosure provides a companion diagnostic method for tumor therapy with an immune checkpoint inhibitor, the method comprising analyzing expression levels of a marker in lymphocytes before and after induction by administering to the subject any of the compositions described herein with or without co-administration of the immune checkpoint inhibitor, wherein if the expression levels of the marker in the lymphocytes of the subject are increased by at least 10%, at least 20%, at least 30%, at least 40%, at least 50%, at least 100%, or at least 200% as compared to the expression levels in the lymphocytes of the subject before the administration of the composition, co-administration of the inhibitor and any of the compositions described herein to the subject, the therapy is continued, wherein if the expression levels in the lymphocytes of the subject are not increased as compared to the expression levels in the lymphocytes of the subject, co-administration of the inhibitor and any of the compositions described herein is discontinued or reanalyzed after repeating the administration of any of the compositions described herein to the subject. In some embodiments, the methods further comprise analyzing expression levels of tumor antigen derived ligand-specific TCRβs in lymphocytes with specific antibodies that bind to the tumor antigen derived ligand-specific TCRβs or MHC multimers that bind to the tumor antigen derived ligand-specific TCRβs. In some embodiments, the methods are use in a tumor therapy with an immune checkpoint inhibitor, wherein the immune checkpoint inhibitor is a PD-1 inhibitor, PD-L1 inhibitor, or CTLA-4 inhibitor. In some embodiments, the methods further comprise assessing PD-1 expression in T-cells in the subject. In some embodiments, the methods further comprise assessing PD-L1 expression in cancer cells in the subject. In some embodiments, the methods further comprise assessing CTLA-4 expression in T-cells in the subject.

In one aspect, the disclosure provides kits for carrying out companion diagnostic methods, wherein the kit comprises one or more molecules for monitoring of the expression levels of a marker in lymphocytes, wherein the marker is CD44, gp70 MC38 peptide (KSPWFTTL; (SEQ ID NO: 53))-specific TCRβ, tumor antigen derived ligand-specific TCRβ, CD8, IFNγ, and/or GzmB.

In one aspect, the disclosure provides methods for evaluating the immune activation with the degree of IFNγ production in splenocytes, the method comprising administering to a subject any of the compositions described herein.

In one aspect, the disclosure provides kits for evaluating the immune activation with the degree of IFNγ production in splenocytes, comprising one or more IFNγ marker molecules and one or more bacterial species of any of the compositions described herein.

In one aspect, the disclosure provides methods for identifying an immunostimulating agent for a tumor the method comprising screening a human intestinal bacteria or a physiologically active substance derived from human intestinal bacteria, the method comprising, (i) allowing a tumor-bearing non-human animal to ingest the human intestinal bacteria or the physiologically active substance derived from the human intestinal bacteria, and (ii) detecting IFNγ in splenocytes isolated from the tumor-bearing non-human animal, wherein if induction of IFNγ is detected, the human intestinal bacteria or physiologically active substance is identified as an immunostimulating agent for the tumor.

In one aspect, the disclosure provides a companion diagnostic method for tumor therapy with an immune checkpoint inhibitor, the method comprising evaluating the immune activation with the degree of IFNγ production in splenocytes before and after induction by administering to the subject any of the compositions described herein with or without co-administration of the inhibitor, wherein if the degree of IFNγ production in the splenocytes in the subject is increased by at least 10%, at least 20%, at least 30%, at least 40%, at least 50%, at least 100%, or at least 200% as compared to the degree of IFNγ production in the splenocytes in the subject before the administration of the composition, co-administration of the inhibitor and any of the compositions described herein to the subject is continued, wherein if the degree of IFNγ production in the splenocytes of the subject is not increased, the co-administration of the inhibitor and any of the compositions described herein is discontinued or reanalyzed after repeat administration of any of the compositions described herein to the subject.

In some embodiments, the method further comprises analyzing expression levels of tumor antigens of the therapy target in splenocytes with the specific antibodies or the MHC multimers. In some embodiments, the method is for tumor therapy with an immune checkpoint inhibitor, wherein the tumor inhibitor is a PD-1 inhibitor, PD-L1 inhibitor, or CTLA-4 inhibitor. In some embodiments, the method further comprises assessing PD-1 expression in T-cells in the subject. In some embodiments, the method further comprises assessing PD-L1 expression in cancer cells in the subject. In some embodiments, the method further comprises assessing CTLA-4 expression in T-cells in the subject.

In one aspect, the disclosure provides kits for carrying out the companion diagnostic methods described herein, comprising one or more IFNγ marker molecules.

In one aspect, the disclosure provides compositions comprising a purified bacterial mixture comprising one or more bacterial strains of species selected from the group consisting of *Phascolarctobacterium faecium, Fusobacterium* sp., *Bacteroides* dorei, bacterium IARFR67, *Ruminococcaceae bacterium, Paraprevotella xylaniphila, Parabacteroides johnsonii, Bacteroides* sp., *Parabacteroides gordonii, Eubacterium limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains of species selected from the group consisting of *Phascolarctobacterium faecium, Fusobacterium* sp., *Bacteroides dorei*, bacterium IARFR67, *Ruminococcaceae bacterium, Paraprevotella xylaniphila, Parabacteroides johnsonii, Bacteroides* sp., *Parabacteroides gordonii, Eubacterium limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides* goldsteinii, and *Bacteroides* sp., In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains of species selected from the group consisting of *Phascolarctobacterium faecium, Fusobacterium* sp., *Bacteroides* dorei, bacterium IARFR67, *Ruminococcaceae bacterium, Paraprevotella xylaniphila, Parabacteroides johnsonii, Bacteroides* sp., *Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains of species selected from the group consisting of *Phascolarctobacterium faecium. Fusobacterium* sp., *Ruminococcaceae bacterium*, and *Eubacterum limosum*. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains of species selected from the group consisting of *Bacteroides dorei*, bacterium IARFR67, *Paraprevotella xylaniphila, Parabacteroides johnsonii, Bacteroides* sp., *Parabacteroides gordonii*, and *Parabacteroides distasonis*. In some embodiments of the compositions provided herein, the purified bacterial mixture comprises at least 2, at least 3, at least 4, at least 5, at least 6, or at least 7 bacterial strains.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. The figures are illustrative only and are not required for enablement of the disclosure. For purposes of clarity, not every component may be labeled in every drawing. In the drawings:

(FIG. 1A) The expression of CD8 and IFNγ by the gated CD3 and TCRP positive cells of representative mice. (FIG. 1B) Summarized data of the percentages of IFNγ positive cells within CD3, TCRβ and CD8+ cells. Each plot represents individual mice.** P<0.01 (Student's t-test).

FIGS. 2A and 2B show data of experiments with lymphocytes that were isolated from the small intestinal mucosal lamina propria of SPF and germ-free mice and stimulated with PMA/ionomycin for 3.5 hours. CD3, TCRβ, CD8, CD103, IFNγ and GzmB were stained with antibodies and analyzed by flow cytometry. (FIG. 2A) The expression of IFNγ and CD103 (upper row) or GzmB (lower row) by the gated CD8 T cells of representative mice. (FIG. 2B) Summarized data of the percentages of each IFNγ positive cell fraction in CD3, TCRβ and CD8+ cells. Each plot represents individual mice. * P<0.05 (Student's t-test).

(FIG. 3A) The expression of CD8 and IFNγ by the gated CD3 and TCRβ positive cells of representative mice. (FIG. 3B) Summarized data of the percentages of IFNγ positive cells in CD3, TCRβ and CD8+ cells. Each plot represents individual mice. * P<0.05,** P<0.01 (one-way ANOVA).

FIGS. 4A and 4B show data of experiments in which after co-housing of SPF mice from Charles River Laboratories with CLEA Japan for 2 or 6 weeks, lymphocytes were isolated from intestinal (SI) and colon mucosal lamina propria and stimulated with PMA/ionomycin for 3.5 h. CD3, TCRβ, CD8 and IFNγ were stained with antibodies and analyzed by flow cytometry. (FIG. 4A) The expression of CD8 and IFNγ by the gated CD3 and TCRP positive cells of representative mice. (FIG. 4B) Summarized data of the percentages of IFNγ positive cells in CD3, TCRβ and CD8+ cells. Each plot represents individual mice. * P<0.05,** P<0.01 (one-way ANOVA).

(FIG. 5A) The expression of CD8 and IFNγ by the gated CD3 and TCRβ positive cells of representative mice. (FIG. 5B) Summarized data of the percentages of IFNγ positive cells in CD3, TCRβ and CD8+ cells. Each plot represents individual mice.** P<0.01 (one-way ANOVA).

(FIG. 6A) The expression of CD8 and IFNγ by the gated CD3 and TCRβ positive cells of representative mice. (FIG. 6B) Summarized data of the percentages of IFNγ positive cells in CD3, TCRβ and CD8+ cells. Each plot represents individual mice. * P<0.05 (one-way ANOVA).

FIGS. 7A and 7B show 16S rRNA gene sequence data of the cecal microbiota of the mice prepared in FIGS. 6A and 6B, which were comprehensively analyzed using the next generation sequencer. (FIG. 7A) Figure of the proportion of operational taxonomic unit (OTU). On the right end, the OTU corresponding to the isolated strains of the B

5-AMP-2 mouse is shown in green. (FIG. 7B) Identification of isolated strains and the homologous bacterial name (Closest sequence) and similarity (S—ab score) are shown.

FIGS. 8A and 8B show data on the mixture of 21 isolated strains which was orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry. (FIG. 8A) The expression of CD8 and IFNγ by the gated CD3 and TCRβ positive cells of representative mice. (FIG. 8B) Summarized data of the percentages of IFNγ positive cells in CD3, TCRβ and CD8+ cells. Each plot represents individual mice.** P<0.01 (Student's t-test).

(FIG. 9A) The expression of IFNγ and CD103 (upper row) or GzmB (lower row) by the gated CD8 T cells of representative mice. (FIG. 9B) Summarized data of the percentages of each IFNγ positive cell fraction in CD3, TCRβ and CD8+ cells. Each plot represents individual mice. * P<0.05,** P<0.01 (Student's t-test).

FIGS. 10A and 10B show data on the mixture of the 21 strains or 11 strains (11 strain mixture corresponds to strains #1-11; See Table 1), which were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry. (FIG. 10A) The expression of CD8 and IFNγ by the gated CD3 and TCRβ positive cells of representative mice. (FIG. 10B) Summarized data of the percentages of IFNγ positive cells in CD3, TCRβ and CD8+ cells. Each plot represents individual mice.* P<0.001,**P<0.0001 (one-way ANOVA).

FIG. 11 shows the compositions of the 10-mix and 11-mix bacterial strains that were inoculated into GF mice (See FIGS. 12A and 12B).

(FIG. 12A) The expression of CD8 and IFNγ by the gated CD3 and TCRβ positive cells of representative mice. (FIG. 12B) Summarized data of the percentages of CD8+IFNγ+ cells in CD3+ TCRβ+ cells (left), IFNγ+ cells in CD8T cells (middle) and the numbers of CD8+IFNγ+ cells (right). Each plot represents individual mice. P<0.01,* P<0.001,****P<0.0001 (one-way ANOVA).

FIGS. 14A and 14B show data of the mixtures of the 11 strains, 7 or 4 strains mixtures listed in FIG. 13, which were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry. (FIG. 14A) The expression of CD8 and IFNγ by the gated CD3 and TCRβ positive cells of representative mice. (FIG. 14B) Summarized data of the percentages of CD8+IFNγ+ cells in CD3+ TCRβ+ cells (left). IFNγ+ cells in CD8T cells (middle) and the numbers of CD8+IFNγ+ cells (right). Each plot represents individual mice. * P<0.05, P<0.01,*P<0.001 (one-way ANOVA).

FIGS. 16A and 16B show data on lymphocytes isolated from tumor cells. At day 23 or 27, lymphocytes were isolated from tumors and stimulated with PMA/ionomycin for 4 hours. CD3. TCRβ, CD8 and IFNγ were stained with antibodies and analyzed by flow cytometry. (FIG. 16A) The expression of CD8 and IFNγ by the gated CD3 and TCRβ positive cells of representative mice. (FIG. 16B) Summarized data of the percentages of CD8+IFNγ+ cells in CD3+ TCRβ+ cells (left), IFNγ+ cells in CD8T cells (middle) and the numbers of CD8+IFNγ+ cells (right). Each plot represents individual mice. * P<0.05, P<0.01,* P<0.001 (one-way ANOVA).

(FIG. 17A-17B) The expression of gp70-specific TCRβ, CD44, GzmB and IFNγ by the gated CD3, TCRβ and CD8+ cells of representative mice. (FIG. 17C). Summarized data of the percentages of each IFNγ positive cell fraction in CD8T cells. Each plot represents individual mice. P<0.01,* P<0.001,**** P<0.0001 (one-way ANOVA).

FIG. 20 shows data on 26 isolated strains, including 11 selected strains.

FIGS. 27A-27B shows tumor volume plots of individual mice treated in the experiments described in Example 4 (control, 11-mix; αCTLA-4 Ab; 11-mix+αCTLA-4 Ab).

FIG. 37A shows the percentage of CD8+IFNγ+ cells in the CD3+ TCRβ+CD8α+ population of cells isolated from the tumors. FIG. 37B shows the number of CD8+IFNγ+ cells isolated from the tumors. FIG. 37C shows the number of CD8+IFNγ+ cells per gram of tumors.** $P<0.01$, * $P<0.05$ (one-way ANOVA).

FIG. 39A shows the percentage of IFNγ+ GzmB+ cells in the CD3+ TCRβ+CD8α+ population of cells isolated from the tumors. FIG. 39B shows the percentage of Th1 cells in the CD3+ TCRβ+CD4+ population of cells isolated from the tumors. FIG. 39C shows the percentage of Th17 cells in the CD3+ TCRβ+CD4+ population of cells isolated from the tumors. FIG. 39D shows the percentage of Treg cells in the CD3+ TCRβ+CD4+ population of cells isolated from the tumors.

FIG. 41A shows the percentage of CD8+IFNγ+ cells in the CD3+ TCRβ+CD8α+ population of cells isolated from the indicated mice. FIG. 41B shows the number of CD8+IFNγ+ cells isolated from the indicated mice. FIG. 41C shows the percentage of IFNγ+ cells in the population of CD8T cells isolated from the indicated mice.

FIG. 42A shows the percentage of IFNγ+CD103+ cells in the CD3+ TCRβ+CD8α+ population of cells isolated from the indicated mice. FIG. 42B shows the percentage of Th17 cells in the CD3+ TCRβ+CD4+ population of cells isolated from the indicated mice. FIG. 42C shows the percentage of Th1 cells in the CD3+ TCRβ+CD4+ population of cells isolated from the indicated mice.

FIGS. 43A-43C and 44 show the results from the experiments of Example 8. The experiments show that BATF3 is required for the 11-mix to induce CD8-T cells. BATF3 is not required to induce Th17. FIG. 43A shows the percentage of IFNγ+ in the CD3+ TCRβ+CD8α+(CD8 T cell) population of cells isolated from the indicated mice. FIG. 43B shows the number of CD8+IFNγ+ cells. FIG. 43C shows the percentage of Th17 cells in the CD3+ TCRβ+CD4+ population of cells isolated from the indicated mice.** $P<0.0001$,* $P<0.001$,** $P<0.01$, * $P<0.05$ (one-way ANOVA).

FIG. 45 shows that feces+11-mix is effective in clearing *Listeria* from infected mice, as evidenced in a decrease in the amount of *Listeria* CFUs in the feces.

FIG. 46 shows that the body weight of *Listeria* infected mice treated with feces and the 11-mix is higher than treatment with feces only.

FIGS. 47A and 47B shows data relating to Example 2. The mixtures of the 11 strains, 7 or 4 strains mixtures listed in FIG. 13, were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry (FIG. 47A). The expression of CD8 and IFNγ by the gated CD3 and TCRβ positive cells of representative mice is show in FIG. 47B, as indicated by the percentage of IFNγ cells in CD8T cells. Each plot represents individual mice. * $P<0.05$,  $P<0.01$, * $P<0.001$ (one-way ANOVA).

DESCRIPTION OF EMBODIMENTS

Detailed Description

Figure 1A:
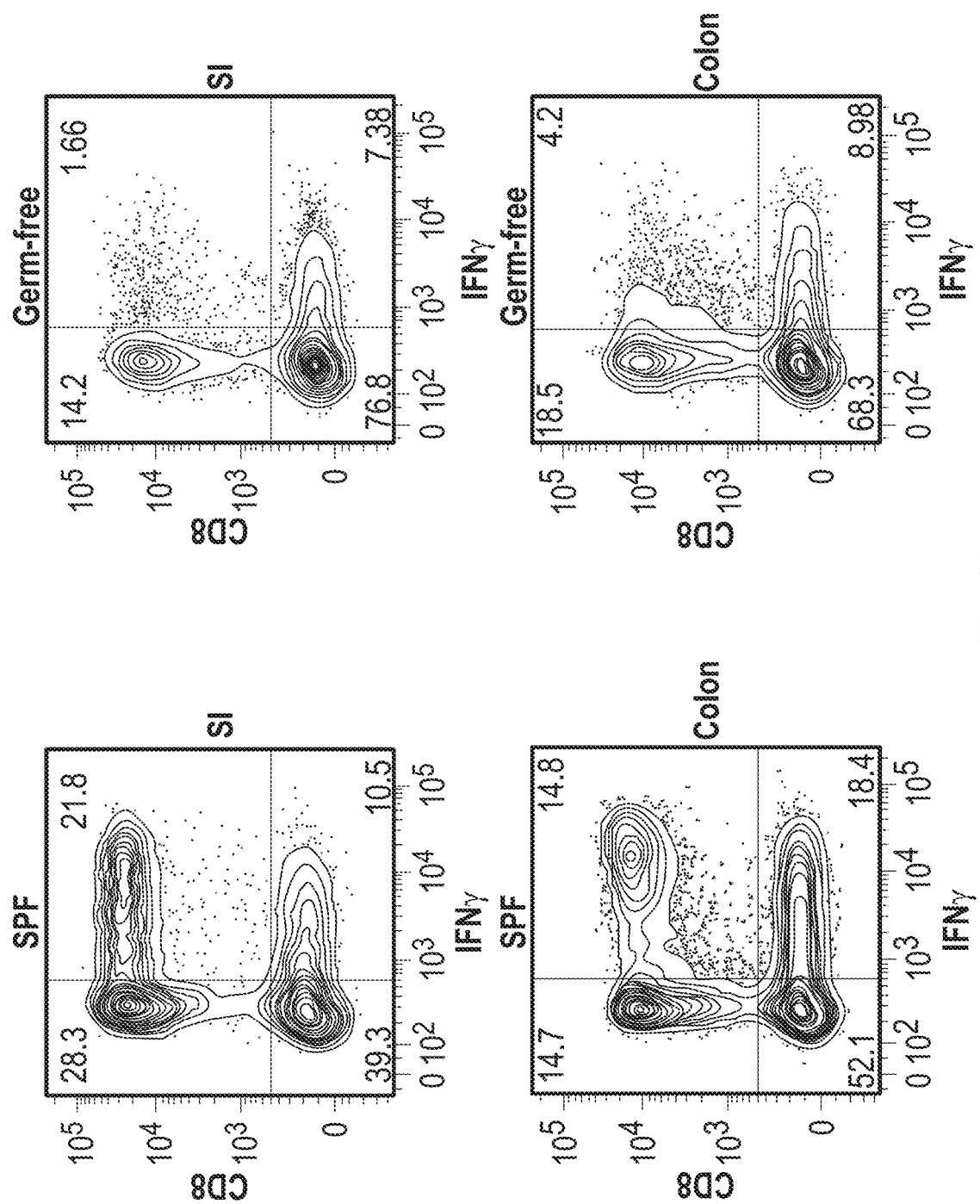
FIGS. 1A and 1B show data of experiments with lymphocytes that were isolated from small intestine (SI) and colon mucosal lamina propria of SPF and germ-free (GF) mice and stimulated with PMA/ionomycin for 3.5 hours. CD3, TCRβ, CD8 and IFNγ were stained with antibodies and analyzed by flow cytometry.

Provided herein are compositions and methods for the induction and/or proliferation of CD8+ T-cells, and methods for the treatment of diseases and conditions that can be treated through the induction and/or proliferation of CD8+ T-cells, including infectious diseases and cancers.

In one aspect, the disclosure provides compositions comprising one or more bacterial strains with unique biological properties. In one aspect, the compositions of the bacterial strains disclosed herein, also referred to as bacterial compositions, can induce the proliferation and/or accumulation of CD8+ T-cells. In one aspect, the compositions of the bacterial strains disclosed herein can induce the proliferation and/or accumulation of CD8+ T-cells.

In one aspect, the bacteria of the compositions disclosed herein can be identified by their 16S rRNA (or 16S rDNA) nucleic acid sequence. In general, bacteria are classified as belonging to a specific species and/or genus based on their 16S rRNA nucleic acid sequence. Bacteria, such as bacteria derived from the microbiome, may also be classified into phylogenetic clusters with other closely related strains and species. (See e.g., Rajilic-Stojanovic, M., and de Vos, W. M. (2014). The first 1000 cultured species of the human gastrointestinal microbiota. FEMS Microbiol Rev 38, 996-1047). Methods for determining the identity of specific bacterial species based on their 16S rRNA (or 16S rDNA) nucleic acid sequence are well known in the art (See e.g., Jumpstart Consortium Human Microbiome Project Data Generation Working. G. (2012). Evaluation of 16S rDNA-based community profiling for human microbiome research. PLoS One 7, e39315).

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3. SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19. SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14. SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9. SEQ ID NO: 10, or SEQ ID NO: 11. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO: 11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO: 11. In some embodiments of the compositions provided herein, the purified bacterial mixture comprises at least 3, at least 4, at least 5, at least 6, at least 7, at least 8, at least 9, at least 10, or at least 1 bacterial strains.

In one aspect, the disclosure provides compositions comprising a purified bacterial mixture comprising two or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% sequence identity with SEQ ID NO:12, SEQ ID NO:13, SEQ ID NO:14. SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising one or more bacterial strains comprising 16S rDNA sequences of at least 97% homology to SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising one or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% homology to SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:5, or SEQ ID NO: 10. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:5, or SEQ ID NO: 10. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:5, or SEQ ID NO: 10. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with SEQ ID NO: 1, SEQ ID NO:2, SEQ ID NO:5, or SEQ ID NO: 10. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO: 11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44. SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44. SEQ ID NO:45, SEQ ID NO:46, or SEQ ID NO:47. In some embodiments of the compositions provided herein, the purified bacterial mixture comprises at least 2, least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44. SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29. SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45. SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50. SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% sequence identity with SEQ ID NO:29, SEQ ID NO:30, SEQ ID NO:32. SEQ ID NO:33, SEQ ID NO:34, SEQ ID NO:35, or SEQ ID NO:37. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a bacterial strain comprising a 16S rDNA sequence with a nucleic acid sequence selected from the group consisting of SEQ ID NOs:1-26. In one aspect, the disclosure provides compositions comprising as an active ingredient a bacterial strain comprising a 16S rDNA sequence with a nucleic acid sequence selected from the group consisting of SEQ ID NOs:1-26. It should be appreciated that for all compositions provided herein, in some embodiments, the bacterial strain or the bacterial strains are the active ingredient of the composition.

In one aspect, the disclosure provides compositions comprising a bacterial strain comprising a 16S rDNA sequence with a nucleic acid sequence selected from the group consisting of SEQ ID NOs:1-21. In one aspect, the disclosure provides compositions comprising as an active ingredient a bacterial strain comprising a 16S rDNA sequence with a nucleic acid sequence selected from the group consisting of SEQ ID NOs:1-21.

In one aspect, the disclosure provides compositions comprising a bacterial strain comprising a 16S rDNA sequence with a nucleic acid sequence selected from the group consisting of SEQ ID NOs:1-11. In one aspect, the disclosure provides compositions comprising as an active ingredient a bacterial strain comprising a 16S rDNA sequence with a nucleic acid sequence selected from the group consisting of SEQ ID NOs:1-11.

In one aspect, the disclosure provides compositions comprising a bacterial strain comprising a 16S rDNA sequence with a nucleic acid sequence selected from the group consisting of SEQ ID NOs:54-64. In one aspect, the disclosure provides compositions comprising as an active ingredient a bacterial strain comprising a 16S rDNA sequence with a nucleic acid sequence selected from the group consisting of SEQ ID NOs:54-64.

It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs:1-26. In addition, for example, the disclosure provides compositions comprising purified bacterial strains comprising a 16S rDNA sequence with a nucleic acid sequence selected from the group consisting of SEQ ID NOs:1-26. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more bacterial strains, wherein the one or more bacterial strains comprise a 16S rDNA sequence with a nucleic acid sequence selected from the group consisting of SEQ ID NOs:1-26. In one aspect, the disclosure provides compositions comprising one or more bacterial strains wherein the one or more bacterial strains comprise 16S rDNA sequences having at least 97% homology with nucleic acid sequences selected from the group consisting of SEQ ID NOs:1-26. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% homology with nucleic acid sequences selected from the group consisting of SEQ ID NOs:1-26. In one aspect, the disclosure provides compositions comprising one or more bacterial strains wherein the one or more bacterial strains comprise 16S rDNA sequences having at least 97% sequence identity with nucleic acid sequences selected from the group consisting of SEQ ID NOs:1-26. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% sequence identity with nucleic acid sequences selected from the group consisting of SEQ ID NOs:1-26.

In one aspect, the disclosure provides compositions comprising two or more purified bacterial strains wherein the two or more purified bacterial strains comprise 16S rDNA sequences having at least 97% homology with nucleic acid sequences selected from the group consisting of SEQ ID NOs:1-26. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% homology with nucleic acid sequences selected from the group consisting of SEQ ID NOs:1-26.

In one aspect, the disclosure provides compositions comprising two or more purified bacterial strains wherein the two or more purified bacterial strains comprise 16S rDNA sequences having at least 97% sequence identity with nucleic acid sequences selected from the group consisting of SEQ ID NOs:1-26. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% sequence identity with nucleic acid sequences selected from the group consisting of SEQ ID NOs:1-26.

In one aspect, the disclosure provides bacterial strains and combinations of bacterial strains that are homologous or have a high percent of homology with bacterial strains comprising 16S rDNA sequences selected from the group consisting of SEQ ID NOs:1-26. As discussed previously, in some embodiments, the bacterial strains are purified. The bacterial strains disclosed herein that have a 16S rDNA sequence with a nucleic acid sequence selected from the group consisting of SEQ ID NOs:1-26 have a high percent of homology (e.g., greater than 90%) or sequence identity, with 16S rDNA sequences of bacterial strains that have been described in various databases (See e.g., the National Center for Biotechnology Information). Table 1 provides the closest known species by homology when the 16S rDNA sequences comprising SEQ ID NOs:1-26 are compared to 16S rDNA sequences of bacterial species available in public databases.

By way of example, the bacterial strain comprising a 16S rDNA sequence with SEQ ID NO:1 disclosed herein has the highest homology with a bacterial strain of the species *Phascolarctobacterium faecium* as defined by NCBI Accession #LN998073 (having 16S rDNA sequence SEQ ID NO:27). While the bacterial strain with SEQ ID NO:1 has homology with other published bacterial strains as well, the highest homology is with a bacterial strain of the species *Phascolarctobacterium faecium* as defined by NCBI Accession #LN998073. It should be appreciated that multiple bacterial strains disclosed herein may have the highest homology with the same species.

It should further be appreciated that the bacterial strains disclosed herein that have a 16S rDNA sequence with a nucleic acid sequence selected from the group consisting of SEQ ID NOs:1-26, are also homologous to other strains based on their whole genome sequence, or subset of their whole genome sequence.

Thus, it should be appreciated that, in one aspect, the disclosure also provides compositions and methods comprising bacterial species with close homology to the bacterial strains that have a 16S rDNA sequence with a nucleic acid sequence selected from the group consisting of SEQ ID NOs:1-26.

In one aspect, the disclosure provides compositions comprising one or more bacterial strains wherein the one or more bacterial strains are of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis,*

*Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*

In one aspect, the disclosure provides compositions comprising one or more bacterial strains wherein the one or more bacterial strains are of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anacrostipes caccae, Bacteroides salyersiae, Bacteroides fragilis; Bacteroides uniformis, Bacteroides eggerthii, Clostridium* sp., *Parabacteroides goldsteinii*, and *Bacteroides* sp.

In one aspect, the disclosure provides compositions comprising one or more bacterial strains wherein the one or more bacterial strains are of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*.

In one aspect, the disclosure provides compositions comprising one or more bacterial strains wherein the one or more bacterial strains are of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*.

In one aspect, the disclosure provides compositions comprising one or more bacterial strains wherein the one or more bacterial strains are of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*.

In one aspect, the disclosure provides compositions comprising a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*.

In one aspect, the disclosure provides compositions comprising a purified bacterial mixture comprising one or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes senegalesis, Parabacteroides gordonii, Parabacteroides* sp.HGS0025, *Eubacterum limosum, Parabacteroides* sp. CAG:2 and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising:

1) *Phascolarctobacterium faecium*, or *Phascolarctobacterium* sp. CAG:207;
2) *Fusobacterium ulcerans*, or *Fusobacterium varium;*
3) *Bacteroides dorei*, or *Bacteroides fluxus,*
4) *Bacteroides uniformis*, or *Bacteroides* sp. D20, 5) *Subdoligranulum* sp., *Ruthenibacterium lactatiformans*, *Ruminococcaceae bacterium* cv2, or *Gemminger formicilis*,
6) *Paraprevotella xylaniphila*,
7) *Parabacteroides johnsonii*.
8) *Alistipes* sp., *Alistipes timonensis*, or *Alistipes senegalesis*,
9) *Parabacteroides gordonii*, or *Parabacteroides* sp. HGS0025,
10) *Eubacterum limosum*, and
11) *Parabacteroides* sp. CAG:2 or *Parabacteroides distasonis*.

In one aspect, the disclosure provides compositions comprising a purified bacterial mixture consisting of:
1) *Phascolarctobacterium faecium*, or *Phascolarctobacterium* sp. CAG:207;
2) *Fusobacterium ulcerans*, or *Fusobacterium varium*;
3) *Bacteroides dorei*, or *Bacteroides fluxus*,
4) *Bacteroides uniformis*, or *Bacteroides* sp. D20,
5) *Subdoligranulum* sp., *Ruthenibacterium lactatiformans*, *Ruminococcaceae bacterium* cv2, or *Gemminger formicilis*,
6) *Paraprevotella xylaniphila*,
7) *Parabacteroides johnsonii*,
8) *Alistipes* sp., *Alistipes timonensis*, or *Alistipes senegalesis*,
9) *Parabacteroides gordonii*, or *Parabacteroides* sp. HGS0025,
10) *Eubacterum limosum*, and
11) *Parabacteroides* sp. CAG:2 or *Parabacteroides distasonis*.

In one aspect, the disclosure provides compositions comprising a purified bacterial mixture comprising one or more bacterial strains of species selected from the group consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*.

In one aspect, the disclosure provides compositions comprising a purified bacterial mixture consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*.

In one aspect, the disclosure provides compositions comprising a purified bacterial mixture comprising one or more bacterial strains of species consisting of *Phascolarctobacterium* sp. CAG:207, *Fusobacterium ulcerans*, *Bacteroides dorei*, *Bacteroides* sp. D20, *Ruminococcaceae bacterium* cv2, *Paraprevotella xylaniphila*, *Parabacteroides johnsonii*, *Alistipes senegalesis*, *Parabacteroides* sp. HGS0025, *Eubacterum limosum*, and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium* sp. CAG:207, *Fusobacterium ulcerans*, *Bacteroides dorei*, *Bacteroides* sp. D20, *Ruminococcaceae bacterium* cv2, *Paraprevotella xylaniphila*, *Parabacteroides johnsonii*, *Alistipes senegalesis*, *Parabacteroides* sp. HGS0025, *Eubacterum limosum*, and *Parabacteroides* sp. CAG:2.

In one aspect, the disclosure provides compositions comprising a purified bacterial mixture consisting of *Phascolarctobacterium* sp. CAG:207, *Fusobacterium ulcerans*, *Bacteroides dorei*, *Bacteroides* sp. D20, *Ruminococcaceae bacterium* cv2, *Paraprevotella xylaniphila*, *Parabacteroides johnsonii*, *Alistipes senegalesis*, *Parabacteroides* sp. HGS0025, *Eubacterum limosum*, and *Parabacteroides* sp. CAG:2.

In one aspect, the disclosure provides compositions comprising a purified bacterial mixture comprising two or more bacterial strains of species selected from the group consisting of *Phascolarctobacterium faecium*, *Phascolarctobacterium* sp. CAG:207, *Fusobacterium ulcerans*, *Fusobacterium varium*, *Bacteroides dorei*, *Bacteroides fluxus*, *Bacteroides uniformis*, *Bacteroides* sp. D20 *Subdoligranulum* sp., *Ruthenibacterium lactatiformans*, *Ruminococcaceac bacterium* cv2, *Gemminger formicilis*, *Paraprevotella xylaniphila*, *Parabacteroides johnsonii*, *Alistipes* sp., *Alistipes timonensis*, *Alistipes senegalesis*, *Parabacteroides gordonii*, *Parabacteroides* sp.HGS0025, *Eubacterum limosum*, *Parabacteroides* sp. CAG:2 and *Parabacteroides distasonis*. In some embodiments of the compositions provided herein, the purified bacterial mixture comprises, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium*, *Fusobacterium varium*, *Bacteroides dorei*, *Bacteroides uniformis*, *Ruthenibacterium lactatiformans*, *Paraprevotella xylaniphila*, *Parabacteroides johnsonii*, *Alistipes senegalesis*, *Parabacteroides gordonii*, *Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium* sp. CAG:207, *Fusobacterium ulcerans*, *Bacteroides dorei*, *Bacteroides* sp. D20, *Ruminococcaceae bacterium* cv2, *Paraprevotella xylaniphila*, *Parabacteroides johnsonii*, *Alistipes senegalesis*, *Parabacteroides* sp.HGS0025, *Eubacterum limosum*, and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Bacteroides cellulosilyticus*, *Bacteroides clarus*, *Anaerostipes caccae*, *Bacteroides salyersiae*, *Bacteroides*

*fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains of species selected from the group consisting of *Bacteroides dorei, Bacteroides uniformis, Paraprevotella xylaniphila, Parabacteroides johnsonii, Alistipes* sp., *Parabacteroides gordonii*, and *Parabacteroides distasonis*. In some embodiments of the compositions provided herein, the purified bacterial mixture comprises, at least 3, at least 4, at least 5, at least 6, or at least 7 bacterial strains.

It should be appreciated that the compositions may include multiple strains of a particular species. Thus, for illustration, a non-limiting example of the compositions disclosed herein, comprises one strain of *Bacteroides salyersiae* and two strains of *Bacteroides uniformis*.

The disclosure provides also encompasses compositions comprising bacterial strains that are close in homology to and/or fall within the species *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*.

Thus, in one embodiment, the compositions of the disclosure include one or more bacterial strains comprising 16S rDNA sequences having at least 97% homology with nucleic acid sequences selected from the group consisting of SEQ ID NOs:27-52. In some embodiments, the compositions of the disclosure include two or more bacterial strains comprising 16S rDNA sequences having at least 97% homology with nucleic acid sequences selected from the group consisting of SEQ ID NOs:27-52.

Thus, in one embodiment, the compositions of the disclosure include one or more bacterial strains comprising 16S rDNA sequences having at least 97% sequence identity with nucleic acid sequences selected from the group consisting of SEQ ID NOs:27-52. In some embodiments, the compositions of the disclosure include two or more bacterial strains comprising 16S rDNA sequences having at least 97% sequence identity with nucleic acid sequences selected from the group consisting of SEQ ID NOs:27-52.

In one aspect, the compositions of the disclosure include two or more purified bacterial strains comprising 16S rDNA sequences having at least 97% homology with nucleic acid sequences selected from the group consisting of SEQ ID NOs:1-26. In some embodiments, the compositions of the disclosure include two or more purified bacterial strains comprising 16S rDNA sequences having at least 97% sequence identity with nucleic acid sequences selected from the group consisting of SEQ ID NOs:1-26. In some embodiments, the compositions of the disclosure include two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments, the compositions of the disclosure include two or more purified bacterial strains comprising 16S rDNA sequences having at least 97% homology with nucleic acid sequences selected from the group consisting of SEQ ID NO:27-52. In some embodiments, the compositions of the disclosure include two or more purified bacterial strains comprising 16S rDNA sequences having at least 97% sequence identity with nucleic acid sequences selected from the group consisting of SEQ ID NO:27-52.

In some embodiments, the disclosure provides compositions with two or more purified bacterial strains that comprise 16S rDNA sequences with nucleic acid sequences selected from the group consisting of SEQ ID NOs:1-26. In some embodiments, the disclosure provides compositions with five or more purified bacterial strains that comprise 16S rDNA sequences with nucleic acid sequences selected from the group consisting of SEQ ID NOs:1-26. In some embodiments, the disclosure provides compositions with at least ten purified bacterial strains, wherein the bacterial strains comprise 16S rDNA sequences with nucleic acid sequences SEQ ID NOs:1-26, respectively. In some embodiments, the disclosure provides a composition consisting of ten purified bacterial strains, wherein the bacterial strains comprise 16S rDNA sequences with nucleic acid sequences SEQ ID NOs:1-26, respectively. In some embodiments, the disclosure provides a composition essentially consisting of eleven purified bacterial strains, wherein the bacterial strains comprise 16S rDNA sequences with nucleic acid sequences SEQ ID NOs:1-26, respectively. As used herein, essentially consisting of refers to a composition that includes no additional bacterial strains.

In some embodiments, the disclosure provides compositions with bacterial strains that comprise 16S rDNA sequences having at least 97% homology with nucleic acid sequences selected from the group consisting of: SEQ ID NOs:1-26. In some embodiments, the disclosure provides compositions with two or more purified bacterial strains that comprise 16S rDNA sequences having at least 97% homology with nucleic acid sequences selected from the group consisting of SEQ ID NOs:1-26. In some embodiments, the disclosure provides compositions with five or more purified bacterial strains that comprise 16S rDNA having at least 97% homology with nucleic acid sequences selected from the group consisting of SEQ ID NOs:1-26. In some embodiments, the disclosure provides compositions with at least ten purified bacterial strains, wherein the bacterial strains comprise 16S rDNA sequences having at least 97% homology with nucleic acid sequences SEQ ID NOs:1-26, respectively. In some embodiments, the disclosure provides a composition consisting of ten purified bacterial strains, wherein the bacterial strains comprise 16S rDNA sequences having at least 97% homology with nucleic acid sequences SEQ ID NOs:1-26, respectively. In some embodiments, the disclosure provides a composition essentially consisting of ten purified bacterial strains, wherein the bacterial strains comprise 16S rDNA sequences having at least 97% homology with nucleic acid sequences SEQ ID NOs:1-26, respectively.

In some embodiments, the disclosure provides compositions with bacterial strains that comprise 16S rDNA sequences having at least 97% sequence identity with nucleic acid sequences selected from the group consisting of: SEQ ID NOs:1-26. In some embodiments, the disclosure provides compositions with two or more purified bacterial strains that comprise 16S rDNA sequences having at least 97% sequence identity with nucleic acid sequences selected from the group consisting of SEQ ID NOs:1-26. In some embodiments, the disclosure provides compositions with five or more purified bacterial strains that comprise 16S rDNA having at least 97% sequence identity with nucleic acid sequences selected from the group consisting of SEQ ID NOs:1-26. In some embodiments, the disclosure provides compositions with at least ten purified bacterial strains, wherein the bacterial strains comprise 16S rDNA sequences having at least 97% sequence identity with nucleic acid sequences SEQ ID NOs:1-26, respectively. In some embodiments, the disclosure provides a composition consisting of ten purified bacterial strains, wherein the bacterial strains comprise 16S rDNA sequences having at least 97% sequence identity with nucleic acid sequences SEQ ID NOs:1-26, respectively. In some embodiments, the disclosure provides a composition essentially consisting of ten purified bacterial strains, wherein the bacterial strains comprise 16S rDNA sequences having at least 97% sequence identity with nucleic acid sequences SEQ ID NOs:1-26, respectively.

In one aspect, the disclosure provides a composition comprising bacterial strains that are related to the following bacterial species: *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum* (See e.g., Table 1). It should be appreciated that multiple bacterial strains of the compositions disclosed herein can have the same related bacterial species. In some embodiments, the disclosure provides compositions with two or more purified bacterial strains comprising 16S rDNA sequences having at least 97% homology with nucleic acid sequences selected from the group consisting of SEQ ID NO:27-52. In some embodiments, the disclosure provides compositions with two or more purified bacterial strains comprising 16S rDNA sequences having at least 97% sequence identity with nucleic acid sequences selected from the group consisting of SEQ ID NO:27-52.

In one aspect, the disclosure provides bacterial strains with 16S rDNA sequences that have homology to a nucleic acid sequence of any one of the sequences of the bacterial strains or species described herein. In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP. BESTFIT, FASTA, and TFASTA in the Wisconsin Genetics Software Package. Genetics Computer Group. Madison. Wis.), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

In one aspect, the disclosure provides compositions comprising multiple purified bacterial strains. In one aspect, the 16S rDNA sequences of purified bacterial strains of the compositions were compared to 16S rDNA sequences of known bacterial species/strains in a bacterial genome database to identify the closest known related bacterial species to the bacterial strains disclosed herein (See e.g., Table 1 and Table 3). It should be appreciated that multiple bacterial strains of the compositions disclosed herein may have the same closest related bacterial species. In one aspect, the disclosure provides compositions comprising one or more bacterial strains or species with 16S rDNA sequences that have homology to a nucleic acid sequence of any one of the sequences provided by SEQ ID NOs:1-26. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-52. In one aspect, the disclosure provides compositions comprising one or more bacterial strains or species with 16S rDNA sequences that have homology to a nucleic acid sequence of any one of the sequences provided by SEQ ID NOs:1-21. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-47. In one aspect, the disclosure provides compositions comprising one or more bacterial strains or species with 16S rDNA sequences that have homology to a nucleic acid sequence of any one of the sequences provided by SEQ ID NOs:1-11. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-37. In one aspect, the disclosure provides compositions comprising one or more bacterial strains or species with 16S rDNA sequences that have homology to a nucleic acid sequence of any one of the sequences provided by SEQ ID NOs:12-26. In some embodiments, the species with 16S rDNA sequences with homology to a nucleic acid sequence of any one of the closest related species to any of the strains described herein, correspond to bacterial strains with 16S rDNA sequences provided by SEQ ID NOs:38-52. In one aspect, the disclosure provides compositions comprising one or more bacterial strains or species with 16S rDNA sequences that have homology to a nucleic acid sequence of any one of the sequences provided by SEQ ID NOs:12-21. In some embodiments, the species with 16S rDNA sequences with homology to a nucleic acid sequence of any one of the closest related species to any of the strains described herein, correspond to bacterial strains with 16S rDNA sequences provided by SEQ ID NOs:38-47.

In some embodiments, the compositions disclosed herein provide at least one of the bacterial strains (e.g., purified bacterial strains) described herein. In some embodiments, the compositions that comprise at least one bacterial strain, comprise at least one bacterial strain with a 16S rDNA sequence selected from any one of SEQ ID NOs:1-26. In some embodiments, the compositions that comprise at least one bacterial strain, comprise at least one bacterial strain with a 97% homology to 16S rDNA sequence selected from any one of SEQ ID NOs:1-26. In some embodiments, the compositions that comprise at least one bacterial strain, comprise at least one bacterial strain with a 97% sequence identity with a 16S rDNA sequence selected from any one of SEQ ID NOs:1-26.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more bacterial strains (e.g., purified bacterial strains).

In some embodiments of the compositions provided herein, at least 50% of the bacterial strains belong to the order of Bacteriodales. In some embodiments of the compositions provided herein, at least 50% of the bacterial strains belong to the genus *Bacteroides* or *Parabacteroides*. In some embodiments of the compositions provided herein, one or more strains belongs to the genus *Bacteroides* and one or more strains belongs to the genus *Parabacteroides*. In some embodiments of the compositions provided herein, at least 25% of the bacterial strains belong to the family of Bacteroidaceae. In some embodiments of the compositions provided herein, one or more of the bacterial strains belongs to the genus *Bacteroides*. In some embodiments of the compositions provided herein, one or more of the bacterial strains belongs to the genus *Parabacteroides*.

In some embodiments of the compositions provided herein, the composition does not include bacterial strains that belong to the order of Bacteriodales.

In some embodiments of the compositions provided herein, one or more of the bacterial strains belong to the order of Bacteriodales and one or more of the bacterial strains belong to the order of Clostridiales. In some embodiments of the compositions provided herein, at least 50% of the bacterial strains belong to the order of Bacteriodales and one or more of the bacterial strains belong to the order of Clostridiales. In some embodiments of the compositions provided herein, at least 75% of the bacterial strains belong to the order of Bacteriodales and one or more of the bacterial strains belong to the order of Clostridiales. In some embodiments of the compositions provided herein, at least 90% of the bacterial strains belong to the order of Bacteriodales and one or more of the bacterial strains belong to the order of Clostridiales.

In some embodiments, the compositions provided herein do not include *E. coli*. In some embodiments, the compositions provided herein do not include *Bifidobacterium*. In some embodiments, the compositions provided herein do not include *Bacillus*. In some embodiments, the compositions provided herein do not include *Enterococcus*. In some embodiments, the compositions provided herein do not include *Barnesiella*. In some embodiments, the compositions provided herein do not include *B. fragilis*. In some embodiments, the compositions provided herein do not include *B. thetaiotaomicron*. In some embodiments, the compositions provided herein do not include *Akkermansia*. In some embodiments, the compositions provided herein do not include *Proteobacteria*. In some embodiments, the compositions provided herein do not include *Burkholderia*. In some embodiments, the compositions provided herein do not include *clostridium* species belonging to Cluster IV. In some embodiments, the compositions provided herein do not include *Faecalibacterium*. In some embodiments, the compositions provided herein do not include *clostridium* species belonging to Cluster XIVa. In some embodiments, the compositions do not comprise fungi, such as Monilla species.

In one aspect, the disclosure provides purified fractions of human stool sample that can induce CD8 T cells.

In some embodiments of the compositions provided herein, one or more of the bacterial strains are human-derived bacteria. In some embodiments of the compositions provided herein, all of the bacterial strains are human-derived bacteria. In some embodiments of the compositions provided herein, the bacterial strains are derived from more than one human donor.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments of the compositions provided herein, the composition includes one or more anaerobic bacteria. In some embodiments of the compositions provided herein, the composition includes only anaerobic bacteria. In some embodiments of the compositions provided herein, the composition includes one or more facultative anaerobic bacteria. In some embodiments of the compositions provided herein, the composition includes only facultative anaerobic bacteria. In some embodiments of the compositions provided herein, the composition includes one or more obligate anaerobic bacteria. In some embodiments of the compositions provided herein, the composition includes only obligate anaerobic bacteria.

In some embodiments of the compositions provided herein, one or more of the bacterial strains does not have an antibiotic resistance gene. In some embodiments of the compositions provided herein, the bacterial strains do not have an antibiotic resistance gene that renders the bacterial strain resistant to vancomycin.

In some embodiments of the compositions provided herein, the compositions do not include bacterial strains that are resistant to one or more antibiotics. It should be appreciated that it may be desirable to have a mechanism to remove the bacterial compositions provided herein from the body after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. (An "antibiotic that is efficacious in a human" as used herein is an antibiotic that has been used to successfully treat bacterial infections in a human).

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former.

In some embodiments, the compositions described herein comprise spore forming and non-spore forming bacterial strains. In some embodiments, the compositions described herein comprise spore-forming bacterial strains. In some embodiments, the compositions described herein comprise only spore-forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (as discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected. As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In one aspect, the disclosure provides bacterial strains and mixtures of bacterial strains with unique biological properties. In some embodiments of the compositions provided herein, the composition induces proliferation and/or accumulation of CD8+ T-cells. In some embodiments, the bacterial strains of the compositions provided herein can induce proliferation and/or accumulation of CD8+ T-cells, because of the synergy between the bacterial strains. Thus, without being limiting to a specific mechanism, in some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells. The bacterial compositions may do so, for instance through the use of nutrients in the intestinal tract (e.g., the colon or the cecum), and/or metabolic interactions that result in metabolites and/or cellular signals that stimulate the induction of proliferation and/or accumulation of CD8+ T-cells. In addition, without being limiting to a specific mechanism, in some embodiments, the combination of the bacterial strains of the compositions provided herein act synergistically in the induction of proliferation and/or accumulation of CD8+ T-cells because the combination of the strains is superior in engrafting specific niches in the intestinal tract (e.g., the colon or the cecum) that will result in the induction of proliferation and/or accumulation of CD8+ T-cells (e.g., by providing a favorable microenvironment). In some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells, and the combination is well suited to engraft in specific niches, that result in localization of the metabolites and/or cellular signals to a target for the induction of proliferation and/or accumulation of CD8+ T-cells Treatment of Diseases Cancer In one aspect, the disclosure includes compositions and methods for the treatment of diseases in a subject. In some embodiments of the methods provided herein, the subject has cancer. In one aspect, the cancers that can be treated according to the compositions and methods provided herein, include without limitation, carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent.

In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the cancer immunotherapy agent is a cancer vaccine that acts to increase the response of a subject's immune system to cancer cells. For example, cancer vaccines include cancer antigen(s) that act to induce or stimulate an immune response against cells bearing the cancer antigen(s). The immune response induced or stimulated can include an antibody (humoral) immune response and/or a T-cell (cell-mediated) immune response. CD8+ T-cells can differentiate into cytotoxic T-cells that kill target cells bearing the antigen recognized by CD4+ T-cells. Induction of CD8+ T-cells can, therefore, enhance the immune response to cancer antigens provided in a cancer vaccine.

In some embodiments of the methods provided herein, the cancer immunotherapy agent is a CAR-T therapeutic. CAR-T cells include T-cells taken from a patient that are genetically engineered to produce chimeric antigen receptors (CARs) on their surface. The CARs are engineered to recognize a specific antigen on cancer cells. After the CAR-T cells are infused into the patient, they recognize and kill cancer cells that express the specific antigen on their surfaces. Induction of CD8+ T-cells is useful to provide cells for conversion into CAR-T cells.

In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28, OX-40, 4-1BB, or CD40 antibody.

In some embodiments of the methods provided herein, the method further includes administering one or more vaccines. In some embodiments of the methods provided herein, the vaccine is a dendritic cell vaccine.

In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor, PD-L-1 inhibitor, CTLA-4 inhibitor, IDO1 inhibitor, LAG3 inhibitor or TIM3 inhibitor. In some embodiments of the compositions provided herein, the immune checkpoint inhibitor is a PD-1 inhibitor. In some embodiments, the PD-1 inhibitor is nivolumab. In some embodiments, the PD-1 inhibitor is pembrolizumab. In some embodiments, the PD-1 inhibitor is pidiluzimab. In some embodiments of the compositions provided herein, the immune checkpoint inhibitor is a PD-L-1 inhibitor. In some embodiments, the PD-L-1 inhibitor is atezolizumab. In some embodiments, the PD-L-1 inhibitor is avelumab. In some embodiments, the PD-L-1 inhibitor is durvalumab. In some embodiments of the methods provided herein, the immune checkpoint inhibitor is a CTLA-4 inhibitor. In some embodiments, the CTLA-4 inhibitor is an anti-CTLA-4 antibody. Examples of anti-CTLA-4 antibodies include, without limitation, ipilimumab, tremelimumab (CP-675,206), 9H10, 4F10, and 9D9. In some embodiments, the CTLA-4 inhibitor is ipilimumab. In some embodiments, the CTLA-4 inhibitor is tremelimumab. It should further be appreciated that multiple anticancer agents (e.g., immune checkpoint inhibitors) may be included in the compositions and methods disclosed herein. For instance, in a non-limiting example, the compositions and methods disclosed include both a PD-1 inhibitor and a CTLA-4 inhibitor.

In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis*, and a PD-1 inhibitor.

In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis*, and a PD-L-1 inhibitor.

In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis*, and a CTLA-4 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11, and a PD-1 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11, and a PD-L-1 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11, and a CTLA-4 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11, and a PD-1 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11, and a PD-L-1 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11, and a CTLA-4 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a PD-1 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a PD-L-1 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a CTLA-4 inhibitor.

In some embodiments of the compositions provided herein, the composition further includes one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28, OX-40, 4-1BB, or CD40 antibody.

In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

Infectious Disease

In one aspect, the disclosure includes compositions and methods for the treatment of diseases in a subject. In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus.

In some embodiments, the compositions provided herein can be used as a pharmaceutical composition for preventing or treating (reducing, partially or completely the adverse effects of) an infectious disease, such as a bacterial infection, a viral infection, a parasitic infection, and a fungal infection.

Bacterial infections that can be treated according to the methods provided herein include, but are not limited to *P. aeruginosa, E. coli, C. tetani, N. gonorrhoeae, C. botulinum, Klebsiella* sp., *Serratia* sp., *Pseudomanas* sp., *P. cepacia, Acinetobacter* sp., *S. epidermis, E. faecalis, S. pneumonias, S. aureus; S. mutans. Haemophilus* sp., *Neisseria* Sp., *N. meningitides, Bacteroides* sp., *Citrobacter* sp., *Branhamella* sp., *Salmonella* sp., *Shigella* sp., *S. pyogenes, Proteus* sp., *Clostridium* sp., *Erysipelothrix* sp., *Listeria* sp., *Pasteurella multocida, Streptobacillus* sp., *Spirillum* sp., *Fusospirocheta* sp., *Treponema pallidum, Borrelia* sp., *Actinomycetes, Mycoplasma* sp., *Chlamydia* sp., *Rickettsia* sp., *Spirochaeta, Borellia burgdorferi, Legionella* sp., *Mycobacteria* sp, *Ureaplasma* sp, *Streptomyces* sp., *Trichomoras* sp., *P. mirabilis; Vibrio cholera*, enterotoxigenic *Escherichia coli, Clostridium difficile, Salmonella typhi, C. diphtheria, Mycobacterium leprae, Mycobacterium lepromatosi*. Bacterial infections caused by drug resistant bacteria that can be treated according to the methods provided herein include, but are not limited to *Clostridium perfringens; Clostridium botulinum; Clostridium tributrycum; Clostridium sporogenes; Escherichia coli; Pseudomonas aeruginosa*, such as Multidrug Resistant *Pseudomonas aeruginosa*; Vancomycin Resistant Enterococci (VRE); Carbapenem Resistant Enterobacteriaceae (CRE); *Neisseria gonorrheae*: Acinetobacter, Multidrug Resistant Acinetobacter; Campylobacter, Multidrug-resistant Campylobacter, Candida, Fluconazole-Resistant Candida, Extended spectrum beta-lactamase (ESBL) producing Enterobacteriaceae; *Salmonella, Salmonella Typhimurium*, Drug resistant non-typhoid *Salmonella* spp.; Drug resistant *Salmonella Typhi*: Drug resistant *Shigella; Staphylococcus aureus*, such as Methicillin Resistant *S. aureus* or vancomycin resistant *S. aureus*: Drug resistant *Streptococcus pneumoniae*; Drug resistant Tuberculosis; Erythromycin Resistant Group A *Streptococcus*; Clindamycin resistant Group B *Streptococcus*, and any combinations thereof.

Viral infections that can be treated according to the methods provided herein include, but are not limited to, picornaviridae, caliciviridae, togaviridae, flaviviridae, coronaviridae, rhabdoviridae, filoviridae, paramyxoviridae, orthomyxoviridae, bunyaviridae, arenaviridae, reoviridae, retroviridae, hepadnaviridae, parvoviridae, papovaviridae, adenoviridae, herpesviridae, poxviridae, rotavirus, parainfluenza virus, influenza virus A and B, hepatitis virus, syphilis, HIV, rabies virus, Epstein-Barr virus, and herpes simplex virus.

Viral infections that can be treated according to the methods provided herein include, but are not limited to *Plasmodium falciparum, P. vivax, P. ovale, P. malaria, Toxoplasma gondii, Leishmania mexicana, L. tropica, L. major, L. aethiopica, L. donovani, Trypanosoma cruzi, T. brucei, Schistosoma mansoni, S. haematobium, S. japonium, Trichinella spiralis, Wuchereria bancrofti, Brugia malayli, Entamoeba histolytica, Enterobius vermicuolarus, Taenia solium, T. saginata, Trichomonas vaginatis, T. hominis, T. tenax; Giardia lamblia, Cryptosporidium parvum, Pneumocytis carinii, Babesia bovis, B. divergens, B. microti, Isospore belli, L hominis, Dientamoeba jragiles, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latum, Echinococcus granulosus, E. multilocularis, Paragonimus westermani, P. caliensis, Chlonorchis sinensis, Opisthorchis felineas, G. Viverini, Fasciola hepatica, Sarcoptes scabiei, Pediculus humanus, Phthirius pubis*, and *Dermatobia hominis*.

Fungal infections that can be treated according to the methods provided herein include, but are not limited to *Cryptococcus neoformans, Blastomyces dermatitidis, Aiellomyces dermatitidis, Histoplasfria capsulatum, Coccidioides immitis, Candida* species, including *C. albicans, C. tropicalis, C. parapsilosis, C. guilliermondii* and *C. krusei, Aspergillus* species, including *A. fumigatus, Aflavus, A. niger, Rhizopus* species, *Rhizomucor* species, *Cunninghammella* species, *Apophysomyces* species, including *A. saksenaea, A. mucor* and *A. absidia, Sporothrix schenckii, Paracoccidioides brasiliensis, Pseudallescheria boydii, Torulopsis glabrata;* and *Dermatophyres* species.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen. In some embodiments, the bacterial compositions are administered as an adjuvant in combination with antigenic material. The antigenic material can include one or more portions of the protein coat, protein core, or functional proteins and peptides of a pathogen, or a full pathogen (live, killed, inactivated, or attenuated), or may comprise one or a plurality of cancer epitopes or cancer antigens. The antigenic material can be co-administered, administered before, or after the bacterial composition. The bacterial composition may also be administered with existing mucosal vaccines such as influenza vaccines. (e.g. FluMist from MedImmune or NASOVAC from Serum Institute of India), rotavirus vaccines (e.g. RotaTeq from Merck or Rotarix from GlaxoSmithKline), typhoid vaccines (e.g. Vivotif from Crucell, Ty21A), cholera vaccines (e.g. Orochol from Crucell, Shanchol from Shantha Biotechnics), traveller's diarrhea vaccines (e.g. Dukoral from Crucell), and with antigens of live attenuated Influenza A virus HI strain, live attenuated Influenza A virus H3 strain, Influenza B virus, live attenuated H1N1 influenza virus (swine flu), live attenuated rotavirus, mono- and multi-valent poliovirus, live attenuated *Salmonella Typhi*, live recombinant *Vibrio cholerae* lacking cholera toxin subunit A, whole killed *Vibrio cholerae* 01 classical and El Tor biotypes with or without cholera toxin subunit B, cancer antigens, cancer epitopes, and combinations thereof.

Autoimmune Disease or Allergic Disease

In one aspect, the disclosure includes compositions and methods for the treatment of diseases in a subject. In some embodiments of the methods provided herein, the subject has an autoimmune disease or an allergic disease.

The compositions and methods of the current disclosure can be used for preventing or treating autoimmune disease and allergic disease. Autoimmune disease that can be treated include, but are not limited to, inflammatory bowel disease, systemic lupus erythematosus, rheumatoid arthritis, multiple sclerosis, or Hashimoto's disease. Allergic diseases that can be treated include, but are not limited to, food allergy, pollenosis, or asthma.

Additional examples of autoimmune and allergic disease that can be treated according to the methods and compositions provided herein include, without limitation, rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, *chlamydia, yersinia* and *salmonella* associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus *foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with *acanthosis nigricans*, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulin dependent diabetes mellitus, sympathetic ophthalmia, pulmonary hypertension secondary to connective tissue disease, Goodpasture's syndrome, pulmonary manifestation of polyarteritis nodosa, acute rheumatoid fever, rheumatoid spondylitis. Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, eosinophilic gastroenteritis, and diarrhea.

In some embodiments of the methods and compositions provided herein, the composition further comprises one or more anti-inflammatory agents. In some embodiments of the methods and compositions provided herein, the anti-inflammatory agent is a non-steroidal anti-inflammatory drug (NSAID). Exemplary NSAIDs include, but are not limited to, aspirin, ibuprofen, naproxen, celecoxib, rofecoxib, diclofenac, diflunisal, etodolac, fenoprofen, flurbiprofen, ketoprofen, ketorolac, mefenamic acid, meloxicam, nabumetone, oxaprozin, piroxicam, sulindac, tolmetin and combinations thereof. In some embodiments, the NSAID is an immune selective anti-inflammatory derivative (ImSAID).

Treatment of Disease

In one aspect, the disclosure provides compositions and methods of treatment for disease in a subject. In one aspect, and without being limiting, the compositions disclosed herein can treat disease because their administration results in the induction of proliferation and/or accumulation of CD8+ T-cells. In some embodiments, the disclosure provides compositions and methods of treatment for disease in a subject for diseases that can be treated by the induction of proliferation and/or accumulation of CD8+ T-cells. In some embodiments, the diseases that can be treated by the induction of proliferation and/or accumulation of CD8+ T-cell is cancer, an infectious disease, an autoimmune disease or allergic disease.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition In some embodiments of the methods provided herein, the administration of the composition to the subject results in an increase of IFNγ-gamma production in the intestine of the subject when compared to the IFNγ-gamma production in the intestine of the subject before the administration of the composition. In some embodiments of the methods provided herein, the administration of the composition to the subject results in an increase of IFNγ-gamma production in the intestine of the subject by at least 10%, at least 20%, at least 30%, at least 40%, at least 50%, at least 100%, or at least 200% when compared to the IFNγ-gamma production in the intestine of the subject before the administration of the composition.

Any of the compositions described herein may be administered to a subject in a therapeutically effective amount or a dose of a therapeutically effective amount to treat or prevent a disease (e.g., cancer or infectious disease). The terms "treat" or "treatment" refer to reducing or alleviating one or more of the symptoms associated with a disease (e.g., cancer or infectious disease). The terms "prevent" or "prevention" encompass prophylactic administration and may reduce the incidence or likelihood of the occurrence of the disease (e.g., cancer or infectious disease). For instance, in some embodiments, administration of the compositions provided herein result in a healthy microbiome that induces proliferation and/or accumulation of CD8+ T-cells thereby protecting a subject against cancer and/or infectious disease.

As used herein, a "therapeutically effective amount" of composition, such as a pharmaceutical composition, is any amount that results in a desired response or outcome in a subject, such as those described herein, including but not limited to prevention of infection, an immune response or an enhanced immune response and/or augmentation of cancer treatment. It should be appreciated that the term effective amount may be expressed in number of bacteria or CFUs to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to treat the disease, e.g., enhance survival of the subject, suppress an infection and/or treat the cancer.

Any of the methods described herein may be for the treatment of cancer in a subject. As used herein, methods of treating cancer involve relieving or alleviating at least one symptom associated with the cancer, or slowing or reversing the cancer progression. A method of treating cancer may, for example, eliminate or reduce a subject's tumor burden, reduce the number or replication of cancer cells, and/or prevent, delay or inhibit metastasis.

Also provided herein are methods for the treatment or prevention of an infectious disease in a subject. As used herein, methods of treating an infectious disease may involve relieving or alleviating at least one symptom associated with infection, or slowing or reversing the progression of the infection. A method of treating an infectious disease may, for example, eliminate or reduce the load of an infectious organism (e.g., bacteria, virus, fungus, or parasite), or inhibit or reduce one or more symptoms of the infection. As also used herein, the terms "prevent." "prevention," and "preventing," include the administration of a composition to a subject to reduce, or delay the onset of the manifestation of clinical or subclinical symptoms, complications, pathologies or biochemical indicia of the infection, or to reduce or inhibit the spread/transmission of the infectious organism (e.g., bacteria, virus, fungus, or parasite).

Aspects of the present disclosure are related to methods for treating a disease or condition in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject.

The compositions and methods described herein may be utilized in conjunction with other types of therapy (i.e., combination treatment), such as additional therapeutic agents. Examples of additional combination therapies include, without limitation, surgery, radiation, gene therapy, and administration of additional therapeutic agents, such as chemotherapeutics, antibiotics, antivirals, anti-fungals, anti-parasitics, immunomodulatory agents, anti-inflammatory agents. In general, combination therapies can be administered simultaneously or sequentially (in any order) with the compositions and methods described herein. In some embodiments, any of the compositions described herein is administered simultaneously with one or more additional therapeutic agents, for example in a single dose or in multiple doses that are administered at substantially the same time.

In some embodiments, the compositions described herein are administered to a subject concomitantly with one or more additional therapeutic agents. In some embodiments, the compositions described herein are administered to a subject followed by administration of one or more additional therapeutic agent. In some embodiments, any of the compositions described herein is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the one or more additional therapeutic agent. Alternatively, in some embodiments, one or more therapeutic agent administered to a subject followed by administration of any of the compositions described herein. In some embodiments, one or more therapeutic agent is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of any the compositions described herein.

Additional Methods

Also within the scope of the present disclosure are methods of assessing whether one or more bacterial strains of any of the compositions described herein are present in the intestine of a subject. In some embodiments, if fewer than a threshold number of bacterial strains are detected in the intestine of the subject, any of the compositions described herein are administered to the subject to increase the number of the bacterial strains in the intestine of the subject. In some embodiments, the method further comprises identifying the subject as a candidate for a treatment of the disease based on the number of bacterial strains detected in the intestine.

Measuring the levels of the biomarker sets may also be useful in the evaluation and treatment of a disease.

In general, the bacterial population of the intestine (e.g., presence or absence of one or more bacterial strains) may be determined by assessing a sample obtained from the subject, such as a fecal sample.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFNγ-gamma production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the engrafted number of the bacterial strains of the administered composition in the intestine of the subject. In some embodiments of the compositions provided herein, administration of the composition to a subject results in an increase in the abundance of total bacteria of the bacterial strains of the administered composition in the intestine of the subject. In some embodiments of the compositions provided herein, administration of the composition to a subject results in an increase in the engrafted total bacterial strains of the administered composition in the intestine of the subject.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject.

In some embodiments of the methods provided herein, the subject is undergoing, or will be undergoing, cancer treatment.

In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment.

In some embodiments of the methods provided herein, the cancer treatment is cancer immunotherapy treatment.

In one aspect, the disclosure provides a method for reducing the risk of a viral infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject.

In some embodiments of the methods provided herein, determining the presence of one or more of the bacterial species is done by sequencing fecal matter of the subject.

Pharmaceutical Compositions

In one aspect, the disclosure provides pharmaceutical compositions comprising the bacterial strains and combinations of bacterial strains provided herein. In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132, PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, AAPS PharmSciTech, 2016, 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., Int J Pharm 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease. Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions disclosed herein, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^7$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{11}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$ between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$ between $10^{-6}$ and $10^{-5}$, or between $10^{-7}$ and $10^{-6}$ grams of all of the bacteria combined per dosage amount.

In one aspect, the disclosure provides a food product comprising any of the compositions provided herein and a nutrient. Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein.

In some embodiments, the subject may be administered one or more doses of an antibiotic prior to or concurrently with a bacterial composition. Antibiotics may be administered for a variety of reasons. For instance, antibiotics may be administered to remove bacterial species from the colon and/or intestine prior to administration of the bacterial compositions provided herein. Antibiotics may also be administered to suppress unwanted infections in the case of cancer treatment. In some instances, antibiotics may be administered as a treatment method for an infectious disease.

In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

Diagnostics and Prognostic Methods

Also described herein are diagnostic methods (e.g., companion diagnostics) for use in determining whether a subject should receive a treatment, such as a composition as described herein and/or any of the immune checkpoint inhibitors described herein. Such methods can be used for diagnosing a disease, monitoring the progress of a disease, assessing the efficacy of a treatment for the disease, and/or identifying patients suitable for a particular treatment.

Accordingly, the methods described herein are based on the level of a marker in a sample (e.g., a biological sample containing lymphocytes) obtained from a subject. In some embodiments, the methods involve analyzing the presence and/or level of a marker in one or more samples from a subject.

In some embodiments, the level of the marker in a sample obtained from a subject can then be compared with a reference sample or a control sample to determine a value indicating the amount of the marker in the sample. In some embodiments, a value for a marker is obtained by comparing the level of a marker in a sample to the level of another marker (e.g., an internal control or internal standard) in the sample. The value of the marker can be compared to a reference value to determine whether the subject has or is at risk for the disease. In some embodiments, the level of the marker is compared to a predetermined threshold for the marker, a deviation from which may indicate the subject has a disease. In some embodiments, if the level or value of the marker is higher than a reference level or value, the subject can be identified as having or at risk for a disease, as described herein. In some embodiments, if the level or value of the marker is lower than a reference level or value, the subject can be identified as having or at risk for a disease, as described herein.

In some embodiments, the level of the marker in a sample from a subject is compared to the level of the marker in another sample obtained from the same subject, for example, a sample obtained from the subject at a different time. In some embodiments, the level of the marker in a sample from a subject is compared to the level of the marker in a sample obtained from the subject at an earlier time, such as prior to administration of any of the compositions described herein. In some embodiments, the level of the marker in a sample from a subject is compared to the level of the marker in a sample obtained from the subject at a later time, such as after administration of any of the compositions described herein.

In some embodiments, if the level or value of the marker is higher in a sample as compared to the level or value of the marker in a sample from the subject obtained prior to administration of a composition described herein, the subject is administered an immune checkpoint inhibitor and a composition described herein. In some embodiments, if the level or value of the marker is higher in a sample as compared to the level or value of the marker in a sample from the subject obtained prior to administration of a composition described herein, the subject continues a therapy involving administration of an immune checkpoint inhibitor and a composition described herein. In some embodiments, the level or value of the marker in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, if the level or value of the marker is not increased (e.g., equal to or lower) in a sample as compared to the level or value of the marker in a sample from the subject obtained prior to administration of a composition described herein, administration of an immune checkpoint inhibitor and a composition described herein is discontinued. In some embodiments, if the level or value of the marker is not increased (e.g., equal to or lower) in a sample as compared to the level or value of the marker in a sample from the subject obtained prior to administration of a composition described herein, the administration of an immune checkpoint inhibitor and a composition described herein is reanalyzed after administration of a composition as described herein. In some embodiments, the level or value of the marker in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, the level of the marker is determined by analyzing the expression of the marker (e.g., protein or nucleic acid level) and/or the cell type in which the marker is expressed. Any method known the art may be used to analyze the expression of the marker and/or cell type in which the marker is expressed.

Also provided herein are methods based on the level or degree of IFNγ production in a sample (e.g., a biological sample containing splenocytes) obtained from a subject. In some embodiments, the methods involve analyzing the presence and/or level of IFNγ production in one or more samples from a subject.

In some embodiments, the level of IFNγ production in a sample obtained from a subject can then be compared with a reference sample or a control sample to determine a value indicating the amount of the IFNγ production in the sample. In some embodiments, a value for IFNγ production is obtained by comparing the level of IFNγ production in a sample to the level of another molecule (e.g., an internal control or internal standard) in the sample. The value of IFNγ production can be compared to a reference value to determine whether the subject has or is at risk for the disease. In some embodiments, the level of IFNγ production is compared to a predetermined threshold for IFNγ production, a deviation from which may indicate the subject has a disease. In some embodiments, if the level or value of IFNγ production is higher than a reference level or value, the subject can be identified as having or at risk for a disease, as described herein. In some embodiments, if the level or value of IFNγ production is lower than a reference level or value, the subject can be identified as having or at risk for a disease, as described herein.

In some embodiments, the level of IFNγ production in a sample from a subject is compared to the level of IFNγ production in another sample obtained from the same subject, for example, a sample obtained from the subject at a different time. In some embodiments, the level of IFNγ production in a sample from a subject is compared to the level of IFNγ production in a sample obtained from the subject at an earlier time, such as prior to administration of any of the compositions described herein. In some embodiments, the level of IFNγ production in a sample from a subject is compared to the level of IFNγ production in a sample obtained from the subject at a later time, such as after administration of any of the compositions described herein.

In some embodiments, if the level or value of IFNγ production is higher in a sample as compared to the level or value of IFNγ production in a sample from the subject obtained prior to administration of a composition described herein, the subject is administered an immune checkpoint inhibitor and a composition described herein. In some embodiments, if the level or value of IFNγ production is higher in a sample as compared to the level or value of IFNγ production in a sample from the subject obtained prior to administration of a composition described herein, the subject continues a therapy involving administration of an immune checkpoint inhibitor and a composition described herein. In some embodiments, the level or value of IFNγ production in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFNγ production in a sample prior to administration of a composition as described herein.

In some embodiments, if the level or value of IFNγ production is not increased (e.g., equal to or lower) in a sample as compared to the level or value of IFNγ production in a sample from the subject obtained prior to administration of a composition described herein, administration of an immune checkpoint inhibitor and a composition described herein is discontinued. In some embodiments, if the level or value of IFNγ production is not increased (e.g., equal to or lower) in a sample as compared to the level or value of IFNγ production in a sample from the subject obtained prior to administration of a composition described herein, the administration of an immune checkpoint inhibitor and a composition described herein is reanalyzed after administration of a composition as described herein. In some embodiments, the level or value of IFNγ production in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFNγ production in a sample prior to administration of a composition as described herein.

In some embodiments, the level of IFNγ production is determined by analyzing the expression of IFNγ (e.g., protein or nucleic acid level) and/or the cell type by which IFNγ is produced. Any method known the art may be used to analyze the expression of IFNγ and/or identify the cell type that produces IFNγ.

The control level can also be a predetermined level or threshold. Such a predetermined level can represent the level of the marker or IFNγ production in a population of subjects that do not have or are not at risk for the target disease. It can also represent the level of the marker or IFNγ production in a population of subjects that have the target disease.

The predetermined level can take a variety of forms. For example, it can be single cutoff value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the metabolite in a control population.

As used herein, "an elevated level" or "an increased level" means that the level of the marker or IFNγ production is higher than a reference value or the level in another sample, such as a sample obtained from the subject prior to administration of any of the compositions described herein. An elevated level of a marker or IFNγ production includes a level of the marker or IFNγ production that is, for example, 1%, 5%, 10%, 20%, 30%, 40%, 50%, 60%, 70%, 50%, 60%, 70%, 80%, 90%, 100%, 150%, 200%, 300%, 400%, 500% or more above a reference value or above the level in another sample from the subject. In some embodiments, the level of the marker or IFNγ production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more, higher than the level in a reference sample or the level in another sample from the subject.

As used herein, "a decreased level" means that the level of the marker or IFNγ production is lower than a reference value or the level in another sample, such as a sample obtained from the subject prior to administration of any of the compositions described herein. A decreased level of the marker or IFNγ production includes a level of the marker or IFNγ production that is, for example, 1%, 5%, 10%, 20%, 30%, 40%, 50%, 60%, 70%, 80%, 90%, 100%, 150%, 200%, 300%, 400%, 500% or more lower than a reference value or the level in another sample from the subject. In some embodiments, the level of the marker or IFNγ production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more lower than the level of the marker or IFNγ production in a reference sample or the level in another sample from the subject.

A subject identified in the methods described herein may be subject to a suitable treatment, such as treatment with a combination of an immune checkpoint inhibitor and any of the composition, as described herein.

The assay methods and kits described herein also can be applied for evaluation of the efficacy of a treatment for a disease, such as those described herein, given the correlation between the level of the marker or IFNγ production and such diseases. For examples, multiple biological samples can be collected from a subject to whom a treatment is performed either before and after the treatment or during the course of the treatment. The levels of a marker or IFNγ production may be indicative as to whether the treatment is effective.

If the subject is identified as not responsive to the treatment, a higher dose and/or frequency of dosage of the composition and/or immune checkpoint inhibitors are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a marker or IFNγ production can also be relied on to identify a disease may be treatable, for example by administering the compositions described herein.

Screening Methods

Provided herein are methods for screening bacteria or physiologically active substances derived from bacteria to identify bacteria or physiologically active substances thereof that produce a desired response. For example, in some embodiments, the screening methods are used to identify bacteria or physiologically active substances derived from bacteria that induce activation of CD8+IFNγ-producing T cells. In some embodiments, the screening methods are used to identify bacteria or physiologically active substances derived from bacteria that induce activation of CD8+IFNγ-producing T cells. In some embodiments, the screening methods are used to identify bacteria or physiologically active substances derived from bacteria as an immunostimulatory agent.

Also provided herein are methods for screening test substances to identify substances that induce activation induce or exacerbate a disease caused by CD8+IFNγ-producing T cells.

In general, the screening methods may be performed in vitro (e.g., using cells) or in vivo (e.g., using non-human animal models). In some embodiments, the methods involve contacting a population of cells (e.g., intestinal epithelial cells, peripheral blood mononuclear cells) with a test substance (e.g., bacteria or physiologically active substances thereof) and assessing a response. In some embodiments, the response is the number and/or activity of a desired cell population (e.g., CD8+IFNγ T cells).

In some embodiments, the methods involve inoculating a non-human animal model with a test substance (e.g., bacteria or physiologically active substances thereof) and assessing a response. In some embodiments, the non-human animal model ingests the test substance. In some embodiments, the response is the number and/or activity of a desired cell population (e.g., CD8+IFNγ T cells). In some embodiments, the response is an improvement of a disease or symptom thereof, or induction/exacerbation of a disease or symptom thereof.

In some embodiments, the bacteria and/or the physiologically active substances derived from bacteria identified in any of the screening methods described herein may be administered to a subject, for example for the treatment of a disease.

Kits

The present disclosure also provides kits for use in evaluating the immune system activation, for example based on the degree or level of IFNγ production in splenocytes, involving administering to a subject any of the compositions as described herein. In some embodiments, a sample may be obtained from the subject prior to, during, and/or after administration of any of the compositions described herein.

In some embodiments, the kit contains one or more molecules for detecting and/or measuring the amount of IFNγ production in a sample. In some embodiments, the molecule that detects or measures the amount of IFNγ production can comprise one or more binding agents that specifically bind to IFNγ. In some embodiments, the binding agent is an antibody that specifically binds to IFNγ. In some embodiments, the binding agent is part of a reporter system, such as a receptor on a cell that binds to the IFNγ and induces expression of a gene encoding a reporter molecule. In some embodiments, the kit also contains a standard or control sample to which the amount of IFNγ in the sample(s) obtained from the subject may be compared.

In some embodiments, the kit may be for carrying out any of the companion diagnostic methods described herein.

In some embodiments, the kit contains one or more molecules for detecting and/or measuring the amount or presence of any one of the bacterial species described herein, or component thereof. In some embodiments, the molecule that detects or measures the amount of a bacterial strain can comprise one or more binding agents that specifically bind to the bacterial strain. In some embodiments, the binding agent specifically binds to a feature of one or more bacterial species that identifies the bacterial species. In some embodiments, the binding agent is a nucleic acid that specifically binds to a nucleic acid sequence of one or more of the bacterial species described herein, such as a specific 16S rRNA sequence. In some embodiments, the kit also contains a standard or control sample to which the sample(s) obtained from the subject may be compared.

The present disclosure also provides kits for use in determining a treatment method, for example, a tumor therapy, involving analyzing the expression of a marker (e.g., CD44, CD8, IFNγ, GzmB, gp70 MC38 peptide (KSPWFTTL; (SEQ ID NO: 53))-specific TCRβ, or an antigen-derived ligand-specific TCRβ), prior to, during, and/or after administration of any of the compositions described herein. Also provided herein are kits comprising companion diagnostics for tumor therapy with an immune checkpoint inhibitor (e.g., a PD-1 inhibitor).

In some embodiments, the kit includes one or more components for analyzing or monitoring expression levels of a marker, such as CD44, CD8, IFNγ, GzmB, or a tumor antigen-derived ligand-specific TCRβ. In some embodiments, the marker is analyzed by detecting the presence of the marker, by measuring the level (amount) of the marker, and/or a specific cell type on which the marker is presented. In some embodiments, the molecule that detects or measures the amount of the marker can comprise one or more binding agents that specifically bind to the marker. In some embodiments, the binding agent is an antibody that specifically binds to the marker. In some embodiments, the binding agent is an MHC multimer that specifically binds to the marker.

In some embodiments, the marker is analyzed by detecting the presence of a nucleic acid encoding the marker, by measuring the level (amount) of a nucleic acid encoding the marker, and/or a specific cell type in which the nucleic acid encoding the marker is expressed. In some embodiments, the kit includes one or more reagents for the isolation of nucleic acids (e.g., RNA) from a sample obtained from subject.

In some embodiments, the kits further comprise a detection agent (e.g., an antibody binding to the binding agent) for detecting binding of the agent to the target (e.g., IFNγ, bacterial species) in the sample. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In some embodiments, the kit may further include one or more therapeutics and/or compositions for administering to the subject. For example, in some embodiments, the kit may include one or more immune checkpoint inhibitor (e.g., PD-1 inhibitor, PD-L1 inhibitor, CTLA-4 inhibitor). In some embodiments, the kit may include a composition comprising one or more of the bacterial strains described herein.

In some embodiments, the kits may be for screening bacteria or substances derived from bacteria, for example of activation of CD8+IFNγ-producing T cells. In some embodiments, the kits include cells, such as cells of a cell line. In some embodiments, the cells are intestinal epithelial cells, peripheral blood mononuclear cells.

In some embodiments, the kit or device further includes a support member. In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput detection assays.

In the kit or detecting device, one or more of the binding agents may be immobilized on a support member, which can be a membrane, a bead, a slide, or a multi-well plate. Selection of an appropriate support member for the immunoassay will depend on various factor such as the number of samples and method of detecting the signal released from label conjugated to the second agent.

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of immune system activation, selecting a treatment, and/or diagnostic purposes. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like.

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Table 1 below provides sequence identifier numbers (SEQ ID NOs) used in the compositions of the experiments disclosed herein. The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

Strains and species with highest homology

| Strain # | SEQ ID NO | Strain ID | Species with highest homology | NCBI accession # of 16S locus | SEQ ID of NCBI 16S locus |
| --- | --- | --- | --- | --- | --- |
| 1 | 1 | 2G5 | Phascolarctobacterium faecium | LN998073 | 27 |
| 2 | 2 | 1A6 | Fusobacterium ulcerans | KR822463 | 28 |
| 3 | 3 | 1B11 | Bacteroides dorei | CP011531 | 29 |
| 4 | 4 | 2G1 | Bacteroides uniformis | NR112945 | 30 |
| 5 | 5 | 2B1 | Subdoligranulum sp. | KM098109 | 31 |
| 6 | 6 | 2A6 | Paraprevotella xylaniphila | NR113078 | 32 |
| 7 | 7 | 2F11 | Parabacteroides johnsonii | NR041464 | 33 |
| 8 | 8 | 1E7 | Alistipes sp. | LT223566 | 34 |
| 9 | 9 | 1H9 | Parabacteroides gordonii | NR112835 | 35 |
| 10 | 10 | 1C1 | Eubacterum limosum | NR113248 | 36 |
| 11 | 11 | 2G9 | Parabacteroides distasonis | NR041342 | 37 |
| 12 | 12 | 2B7 | Bacteroides cellulosilyticus | NR112933 | 38 |
| 13 | 13 | 2C1 | Bacteroides clarus | NR112893 | 39 |
| 14 | 14 | 1B4 | Anaerostipes caccae | HE974918 | 40 |
| 15 | 15 | 2A3 | Bacteroides salyersiae | NR043016 | 41 |
| 16 | 16 | 2A12 | Bacteroides fragilis | AB618791 | 42 |
| 17 | 17 | 1A2 | Bacteroides uniformis | AB215083 | 43 |
| 18 | 18 | 2B11 | Bacteroides eggerthii | NR112935 | 44 |
| 19 | 19 | 2D2 | Clostridium sp. | AB249652 | 45 |
| 20 | 20 | 2E8 | Parabacteroides goldsteinii | NR113076 | 46 |
| 21 | 21 | 1H8 | Bacteroides sp. | NR112944 | 47 |
| 22 | 22 | 3F2 | Lachnospiraceae bacterium HGA0140 | JX519760 | 48 |
| 23 | 23 | 1G1 | Hungatella hathewayi | AJ311620 | 49 |
| 24 | 24 | 1E6 | Clostridium lavalense | EF564278 | 50 |
| 25 | 25 | 1F3 | Ruminococcus sp. | KT156811 | 51 |
| 26 | 26 | 1A1 | Clostridium innocuum | HM008265 | 52 |

The nucleic acid sequences of the 16S rDNA, or portion thereof, for the bacterial strains described herein are provided below:

```
strain 1 2G5_Phascolarctobacterium faecium_LN998073
                                                    SEQ ID NO: 1
GAC-
GAACGCTGGCGGCGTGCCTAACACATGCAAGTCGAACGGAGAATTTTATTT
CGGTAGAATTCTTAGTGGCGAACGGGTGAGTAACGCGTAGGCAACCTACC
CTTTAGACGGGACAACATTCCGAAAGGAGTGCTAATACCGGATGTGATC
ATCTTGCCGCATGGCAGGATGAAGAAAGATGGCCTCTACAAGTAAGCTATC
GCTAAAGGATGGGCCTGCGTCTGATTAGCTAGTTGGTAGTGTAACGGACTA
CCAAGGCGATGATCAGTAGCCGGTCTGAGAGGATGAACGGCCACATTGGG
ACTGAGACACGGCCCAAACTCCTACGGGAGGCAGCAGTGGGGAATCTTCC
GCAATGGACGAAAGTCTGACGGAGCAACGCCGCGTGAGTGATGAAGGATT
TCGGTCTGTAAAGCTCTGTTGTTTATGACGAACGTGCAGTGTGTGAACAAT
GCATTGCAATGACGGTAGTAAACGAGGAAGCCACGGCTAACTACGTGCCA
GCAGCCGCGGTAATACGTAGGTGGCGAGCGTTGTCCGGAATTATTGGGCGT
AAAGAGCATGTAGGCGGCTTAATAAGTCGAGCGTGAAAATGCGGGGCTCA
ACCCCGTATGGCGCTGGAAACTGTTAGGCTTGAGTGCAGGAGAGGAAAGG
GGAATTCGCAGTGTAGCGGTGAAATGCGTAGATATTGGGAGGAACACCAG
TGGCGAAGGCGCCTTTCTGGACTGTGTCTGACGCTGAGATGCGAAAGCCAG
GGTAGCGAACGGGATTAGATACCCCGGTAGTCCTGGCCGTAAACGATGGG
TACTAGGTGTAGGAGGTATCGACCCCTTCTGTGCCGGAGTTAACGCAATAA
GTACCCCGCCTGGGGAGTACGGCCGCAAGGTTGAAACTCAAAGGAATTGA
CGGGGGCCCGCACAAGCGGTGGAGTATGTGGTTTAATTCGACGCAACGCG
AAGAACCTTACCAAGGCTTGACATTGATTGAACGCTCTAGAGATAGAGATT
TCCCTTCGGGGACAAGAAAACAGGTGGTGCATGGCTGTCGTCAGCTCGTGT
CGTGAGATGTTGGGTTAAGTCCCGCAACGAGCGCAACCCCTATCCTATGTT
ACCAGCAAGTAAAGTTGGGGACTCATGGGAGACTGCCAGGGACAACCTGG
AGGAAGGCGGGGATGACGTCAAGTCATCATGCCCCTTATGTCTTGGGCTAC
ACACGTACTACAATGGTCGGAAACAGAGGGAAGCGAAGCCGCGAGGCAG
AGCAAACCCCAGAAACCCGATCTCAGTTCGGATCGCAGGCTGCAACCCGC
CTGCGTGAAGTCGGAATCGCTAGTAATCGCAGGTCAGCATACTGCGGTGAA
TACGTTCCCGGGCCTTGTACACACCGCCCGTCACACCACGAAAGTTGGTAA
CACCCGAAGCCGGTGAGGTAACCTA
strain 2 1A6_Fusobacterium ulcerans_KR822463
                                                    SEQ ID NO: 2
GATGAACGCT-
GACAGAATGCTTAACACATGCAAGTCTACTTGATCCTTCGGGTGAAGGTGG
CGGACGGGTGAGTAACGCGTAAAGAACTTGCCTTACAGACTGGGACAACA
TTTGGAAACGAATGCTAATACCGGATATTATGATTGGGTCGCATGATCTGA
TTATGAAAGCTATATGCGCTGTGAGAGAGCTTTGCGTCCCATTAGTTAGTT
GGTGAGGTAACGGCTCACCAAGACGATGATGGGTAGCCGGCCTGAGAGGG
```

```
TGAACGGCCACAAGGGGACTGAGACACGGCCCTTACTCCTACGGGAGGCA

GCAGTGGGAATATTGGACAATGGACCAAAAGTCTGATCCAGCAATTCTGT

GTGCACGAAGAAGTTTTTCGGAATGTAAAGTGCTTTCAGTTGGGAAGAAGT

CAGTGACGGTACCAACAGAAGAAGCGACGGCTAAATACGTGCCAGCAGCC

GCGGTAATACGTATGTCGCAAGCGTTATCCGGATTTATTGGGCGTAAAGCG

CGTCTAGGCGGCTTAGTAAGTCTGATGTGAAAATGCGGGGCTCAACCCCGT

ATTGCGTTGGAAACTGCTAAACTAGAGTACTGGAGAGGTAGGCGGAACTA

CAAGTGTAGAGGTGAAATTCGTAGATATTTGTAGGAATGCCGATGGGGAA

GCCAGCCTACTGGACAGATACTGACGCTAAAGCGCGAAAGCGTGGGTAGC

AAACAGGATTAGATACCCTGGTAGTCCACGCCGTAAACGATGATTACTAGG

TGTTGGGGGTCGAACCTCAGCGCCCAAGCTAACGCGATAAGTAATCCGCCT

GGGGAGTACGTACGCAAGTATGAAACTCAAAGGAATTGACGGGGACCCGC

ACAAGCGGTGGAGCATGTGGTTTAATTCGACGCAACGCGAGGAACCTTAC

CAGCGTTTGACATCCCAAGAAGTTAACAGAGATGTTTTCGTGCCTCTTCGG

AGGAACTTGGTGACAGGTGGTGCATGGCTGTCGTCAGCTCGTGTCGTGAGA

TGTTGGGTTAAGTCCCGCAACGAGCGCAACCCCTTTCGTATGTTACCATCA

TTAAGTTGGGGACTCATGCGAGACTGCCTGCGATGAGCAGGAGGAAGGTG

GGGATGACGTCAAGTCATCATGCCCCTTATACGCTGGGCTACACACGTGCT

ACAATGGGTAGTACAGAGAGCTGCAAACCTGCGAGGGTAAGCTAATCTCA

TAAAACTATTCTTAGTTCGGATTGTACTCTGCAACTCGAGTACATGAAGTT

GGAATCGCTAGTAATCGCAAATCAGCTATGTTGCGGTGAATACGTTCTCGG

GTCTTGTACACACCGCCCGTCACACCACGAGAGTTGGTTGCACCTGAAGTA

ACAGGCCTAACCGTAA strain 3 1B11_Bacteroides dorei_CP011531
                                                  SEQ ID NO: 3
AGTTTGNNNTATGGCTCAGGATGAACGCTAGCTACAGGCTTAACACATGC

AAGTCGAGGGGCAGCATGGTCTTAGCTTGCTAAGGCTGATGGCGACCGGC

GCACGGGTGAGTAACACGTATCCAACCTGCCGTCTACTCTTGGCCAGCCTT

CTGAAAGGAAGATTAATCCAGGATGGGATCATGAGTTCACATGTCCGCATG

ATTAAAGGTATTTTCCGGTAGACGATGGGGATGCGTTCCATTAGATAGTAG

GCGGGGTAACGCCCCACCTAGTCAACGATGGATAGGGGTTCTGAGAGGAA

GGTCCCCCACATTGGAACTGAGACACGGTCCAAACTCCTACGGGAGGCAG

CAGTGAGGAATATTGGTCAATGGGCGATGGCCTGAACCAGCCAAGTAGCG

TGAACGATGACTGCCCTATGGGTTGTAAACTTCTTTTATAAAGGAATAAAG

TCGGGTATGCATACCCGTTTGCATGTACTTTATGAATAAGGATCGGCTAAC

TCCGTGCCAGCAGCCGCGGTAATACGGAGGATCCGAGCGTTATCCGGATTT

ATTGGGTTTAAAGGGAGCGTAGATGGATGTTTAAGTCAGTTGTGAAAGTTT

GCGGCTCAACCGTAAAATTGCAGTTGATACTGGATGTCTTGAGTGCAGTTG

AGGCAGGCGGAATTCGTGGTGTAGCGGTGAAATGCTTAGATATCACGAAG

AACTCCGATTGCGAAGGCAGCCTGCTAAGCTGCAACTGACATTGAGGCTCG

AAAGTGTGGGTATCAAACAGGATTAGATACCCTGGTAGTCCACACGGTAA

ACGATGAATACTCGCTGTTTGCGATATACGGCAAGCGGCCAAGCGAAAGC
```

```
GTTAAGTATTCCACCTGGGGAGTACGCCGGCAACGGTGAAACTCAAAGGA

ATTGACGGGGGCCCGCACAAGCGGAGGAACATGTGGTTTAATTCGATGAT

ACGCGAGGAACCTTACCCGGGCTTAAATTGCACTCGAATGATCCGGAAAC

GGTTCAGCTAGCAATAGCGAGTGTGAAGGTGCTGCATGGTTGTCGTCAGCT

CGTGCCGTGAGGTGTCGGCTTAAGTGCCATAACGAGCGCAACCCTTGTTGT

CAGTTACTAACAGGTGATGCTGAGGACTCTGACAAGACTGCCATCGTAAGA

TGTGAGGAAGGTGGGGATGACGTCAAATCAGCACGGCCCTTACGTCCGGG

GCTACACACGTGTTACAATGGGGGGTACAGAGGGCCGCTACCACGCGAGT

GGATGCCAA7CCCTAAAACCCCTCTCAGTTGGGACTGGAGTCTGCAACCCG

ACTCCACGAAGCTGGATTCGCTAGTAATCGCGCATCAGCCACGGCGCGGTG

AATACGTTCCCGGGCCTTGTACACACCGCCCGTCAAGCCATGGGAGCCGGG

GGTACCTGAAGTGCGTAACCGCGAGGAT
``` strain 4 2G1_Bacteroides uniformis_NR_112945

SEQ ID NO: 4

```
GATGAACGC-

TAGCTACAGGCTTAACACATGCAAGTCGAGGGGCAGCATGAACTTAGCTTG

CTAAGTTTGATGGCGACCGGCGCACGGGTGAGTAACACGTATCCAACCTGC

CGATGACTCGGGGATAGCCTTTCGAAAGAAAGATTAATACCCGATGGCAT

AGTTCTTCCGCATGGTAGAACTATTAAAGAATTTCGGTCATCGATGGGGAT

GCGTTCCATTAGGTTGTTGGCGGGGTAACGGCCCACCAAGCCTTCGATGGA

TAGGGGTTCTGAGAGGAAGGTCCCCCACATTGGAACTGAGACACGGTCCA

AACTCCTACGGGAGGCAGCAGTGAGGAATATTGGTCAATGGACGAGAGTC

TGAACCAGCCAAGTAGCGTGAAGGATGACTGCCCTATGGGTTGTAAACTTC

TTTTATACGGGAATAAAGTGAGGCACGTGTGCCTTTTTGTATGTACCGTAT

GAATAAGGATCGGCTAACTCCGTGCCAGCAGCCGCGGTAATACGGAGGAT

CCGAGCGTTATCCGGATTTATTGGGTTTAAAGGGAGCGTAGGCGGACGCTT

AAGTCAGTTGTGAAAGTTTGCGGCTCAACCGTAAAATTGCAGTTGATACTG

GGTGTCTTGAGTACAGTAGAGGCAGGCGGAATTCGTGGTGTAGCGGTGAA

ATGCTTAGATATCACGAAGAACTCCGATTGCGAAGGCAGCCTGCTTGGACTG

TAACTGACGCTGATGCTCGAAAGTGTGGGTATCAAACAGGATTAGATACCC

TGGTAGTCCACACCAGTAAACGATGAATACTCGCTGTTTGCGATATACAGT

AAGCGGCCAAGCGAAAGCGTTAAGTATTCCACCTGGGGAGTACGCCGGCA

ACGGTGAAACTCAAAGGAATTGACGGGGGCCCGCACAAGCGGAGGAACAT

GTGGTTTAATTCGATGATACGCGAGGAACCTTACCCGGGCTTGAATTGCAA

CTGAATGATGTGGAGACATGTCAGCCGCAAGGCAGTTGTGAAGGTGCTGC

ATGGTTGTCGTCAGCTCGTGCCGTGAGGTGTCGGCTTAAGTGCCATAACGA

GCGCAACCCTTATCGATAGTTACCATCAGGTGATGCTGGGGACTCTGTCGA

GACTGCCGTCGTAAGATGTGAGGAAGGTGGGGATGACGTCAAATCAGCAC

GGCCCTTACGTCCGGGGCTACACACGTGTTACAATGGGGGGTACAGAAGG

CAGCTACACGGCGACGTGATGCTAATCCCGAAAGCCTCTCTCAGTTCGGAT

TGGAGTCTGCAACCCGACTCCATGAAGCTGGATTCGCTAGTAATCGCGCAT
```

```
CAGCCACGGCGCGGTGAATACGTTCCCGGGCCTTGTACACACCGCCCGTCA

AGCCATGAAAGCCGGGGGTACCTGAAGTGCGTAACCGCAAGGAG
``` strain 5
2B1_Subdoligranulum sp. 4_3_54A2FAA_NZ-ACWW00000000
SEQ ID NO: 5

```
GAC-

GAACGCTGGCGGCGCGCCTAACACATGCAAGTCGAACGGAGCTGTTTTCTC

TGAAGTTTTCGGATGGAAGAGAGTTCAGCTTAGTGGCGAACGGGTGAGTA

ACACGTGAGCAACCTGCCTTTCAGTGGGGGACAACATTTGGAAACGAATG

CTAATACCGCATAAGACCACAGTGTCGCATGGCACAGGGGTCAAAGGATT

TATCCGCTGAAAGATGGGCTCGCGTCCGATTAGCTAGATGGTGAGGTAACG

GCCCACCATGGCGACGATCGGTAGCCGGACTGAGAGGTTGAACGGCCACA

TTGGGACTGAGACACGGCCCAGACTCCTACGGGAGGCAGCAGTGGGGAAT

ATTGCACAATGGGGGAAACCCTGATGCAGCGACGCCGCGTGGAGGAAGAA

GGTCTTCGGATTGTAAACTCCTGTCCCAGGGGACGATAATGACGGTACCCT

GGGAGGAAGCACCGGCTAACTACGTGCCAGCAGCCGCGGTAAAACGTAGG

GTGCAAGCGTTGTCCGGAATTACTGGGTGTAAAGGGAGCGCAGGCGGATT

GGCAAGTTGGGAGTGAAATCTATGGGCTCAACCCATAAATTGCTTTCAAAA

CTGTCAGTCTTGAGTGGTGTAGAGGTAGGCGGAATTCCCGGTGTAGCGGTG

GAATGCGTAGATATCGGGAGGAACACCAGTGGCGAAGGCGGCCTACTGGG

CACTAACTGACGCTGAGGCTCGAAAGCATGGGTAGCAAACAGGATTAGAT

ACCCTCCTAGTCCATCCCGTAAACGATGATTACTAGGTGTCCGAGGATTGA

CCCCTTCCGTGCCGCAGTTAACACAATAAGTAATCCACCTGGGGAGTACGA

CCGCAAGGTTGAAACTCAAAGGAATTGACGGGGGCCCGCACAAGCAGTGG

AGTATGTGGTTTAATTCGAAGCAACGCGAAGAACCTTACCAGGTCTTGACA

TCGGATGCATACCTAAGAGATTAGGGAAGTCCTTCGGGACATCCAGACAG

GTGGTGCATGGTTGTCGTCAGCTCGTGTCGTGAGATGTTGGGTTAAGTCCC

GCAACGAGCGCAACCCTTATCGTTAGTTACTACGCAAGAGGACTCTAGCGA

GACTGCCGTTGACAAAACGGAGGAAGGTGGGGATGACGTCAAATCATCAT

GCCCTTTATGACCTGGGCTACACACGTACTACAATGGCTATTAACAGAGAG

AAGCGATACCGCGAGGTGGAGCAAACCTCACAAAAATAGTCTCAGTTCGG

ATCGCAGGCTGCAACCCGCCTGCGTGAAGCCGGAATTGCTAGTAATCGCGG

ATCAGCATGCCGCGGTGAATACGTTCCCGGGCCTTGTACACACCGCCCGTC

ACACCATGAGAGCCGGGGGACCCGAAGTCGGTAGTCTAACCGC
``` strain 6 2A6_Paraprevotella xylaniphila_AB331897
SEQ ID NO: 6

```
GATGAACGC-

TAGCTACAGGCTTAACACATGCAAGTCGAGGGGCAGCATGAACTTAGCTTG

CTAAGTTTGATGGCGACCGGCGCACGGGTGAGTAACGCGTATCCAACCTGC

CCTTTACCCGGGGATAGCCTTCTGAAAAGGAAGTTTAATACCCGATGAATT

CGTTTAGTCGCATGGCTNGATGAATAAAGATTAATTGGTAAAGGATGGGG

ATGCGTCCCATTAGCTTGTTGGCGGGGTAACGGCCCACCAAGGCGACGATG

GGTAGGGGTTCTGAGAGGAAGGTCCCCCACATTGGAACTGAGACACGGTC
```

-continued

```
CAAACTCCTACGGGAGGCAGCAGTGAGGAATATTGGTCAATGGGCGCGAG

CCTGAACCAGCCAAGTAGCGTGGAGGACGACGGCCCTACGGGTTGTAAAC

TCCTTTTATAAGGGGATAAAGTTGGCCATGTATGGCCATTTGCAGGTACCT

TATGAATAAGCATCGGCTAATTCCGTGCCAGCAGCCGCGGTAATACGGAA

GATGCGAGCGTTATCCGGATTTATTGGGTTTAAAGGGAGCGTAGGCGGGCT

GTCAAGTCAGCGGTCAAATGGCGCGGCTCAACCGCGTTCCGCCGTTGAAAC

TGGCAGCCTTGAGTATGCACAGGGTACATGGAATTCGTGGTGTAGCGGTGA

AATGCTTAGATATCACGAGGAACTCCGATCGCGCAGGCATTGTACCGGGGC

ATTACTGACGCTGAGGCTCGAAGGTGCGGGTATCAAACAGGATTAGATAC

CCTGGTAGTCCGCACAGTAAACGATGAATGCCCGCTGTCGGCGACATAGTG

TCGGCGGCCAAGCGAAAGCGTTAAGCATTCCACCTGGGGAGTACGCCGGC

AACGGTGAAACTCAAAGGAATTGACGGGGGCCCGCACAAGCGGAGGAAC

ATGTGGTTTAATTCGATGATACGCGAGGAACCTTACCCGGGCTTGAATCGC

AGGTGCATGGGCCGGAGACGGCCCTTTCCTTCGGGACTCCTGCGAAGGTGC

TGCATGGTTGTCGTCAGCTCGTGCCGTGAGGTGTCGGCTTAAGTGCCATAA

CGAGCGCAACCCCCTCCCCAGTTGCCACCGGGTAATGCCGGGCACTTTGG

GGACACTGCCACCGCAAGGTGCGAGGAAGGTGGGGATGACGTCAAATCAG

CACGGCCCTTACGTCCGGGGCGACACACGTGTTACAATGGGGGGTACAGA

GGGCCGCTGCCCGGTGACGGTTGGCCAATCCCTAAAAGCCCTCTCAGTTCG

GACTGGAGTCTGCAACCCGACTCCACGAAGCTGGATTCGCTAGTAATCGCG

CATCAGCCATGGCGCGGTGAATACGTTCCCGGGCCTTGTACACACCGCCCG

TCAAGCCATGAAAGCCGGGGGTGCCTGAAGTCCGTNNCCGCGA
``` strain 7 2F11_*Parabacteroides johnsonii*_AB261128                  SEQ ID NO: 7

```
GATGAACGC-

TAGCGACAGGCTTAACACATGCAAGTCGAGGGGCAGCATGGTAAGTAGCA

ATACTTATTGATGGCGACCGGCGCACGGGTGAGTAACGCGTATGCAACTTA

CCTATCAGAGGGGGATAGCCCGGCGAAAGTCGGATTAATACTCCATAAAA

CAGGGGTTCCGCATGGGACTATTTGTTAAAGATTCATCGCTGATAGATAGG

CATGCGTTCCATTAGGCAGTTGGCGGGGTAACGGCCCACCAAACCGACGAT

GGATAGGGGTTCTGAGAGGAAGGTCCCCCACATTGGTACTGAGACACGGA

CCAAACTCCTACGGGAGGCAGCAGTGAGGAATATTGGTCAATGGCCGAGA

GGCTGAACCAGCCAAGTCGCGTGAAGGATGAAGGATCTATGGTTTGTAAA

CTTCTTTTATAGGGGAATAAAGTGTGGGACGTGTTCCATTTTGTATGTACCC

TATGAATAAGCATCGGCTAACTCCGTGCCAGCAGCCGCGGTAATACGGAG

GATGCGAGCGTTATCCGGATTTATTGGGTTTAAAGGGTGCGTAGGTGGTAA

TTTAAGTCAGCGGTGAAAGTTTGTGGCTCAACCATAAAATTGCCGTTGAAA

CTGGGTTACTTGAGTGTGTTTGAGGTAGCGGAATGCGTGGTGTAGCGGTG

AAATGCATAGATATCACGCAGAACTCCAATTGCGAAGGCAGCTTACTAAA

CCATAACTGACACTGAAGCACGAAAGCGTGGGTATCAAACAGGATTAGAT

ACCCTGGTAGTCCACGCAGTAAACGATGATTACTAGGAGTTTGCGATACAC

AGTAAGCTCTACAGCGAAAGCGTTAAGTAATCCACCTGGGGAGTACGCCG
```

```
GCAACGGTGAAACTCAAAGGAATTGACGGGGGCCCGCACAAGCGGAGGA
ACATGTGGTTTAATTCGATGATACGCGAGGAACCTTACCCGGGTTTGAACG
TAGTCAGACCGACCTTGAAAGAGGTTTTCTAGCAATAGCTGATTACGAGGT
GCTGCATGGTTGTCGTCAGCTCGTGCCGTGAGGTGTCGGCTTAAGTGCCAT
AACGAGCGCAACCCTTATCACTAGTTACTAACAGGTTAAGCTGAGGACTCT
GGTGAGACTGCCAGCGTAAGCTGTGAGGAAGGTGGGGATGACGTCAAATC
AGCACGGCCCTTACATCCGGGGCGACACACGTGTTACAATGGCATGGACA
AAGGGCAGCTACCTGGCGACAGGATGCTAATCTCTAAACCATGTCTCAGTT
CGGATCGGAGTCTGCAACTCGACTCCGTGAAGCTGGATTCGCTAGTAATCG
CGCATCAGCCATGGCGCGGTGAATACGTTCCCGGGCCTTGTACACACCGCC
CGTCAAGCCATGGGAGCCGGGGGTACCTGAAGTCCGTAACCGCAA
``` strain 8 1E7_Alistipes sp. JC136_NZ-CAEG00000000     SEQ ID NO: 8

```
GAT-
GAACGCTAGCGGCAGGCCTAACACATGCAAGTCGAGGGGCAGCGGGATTG
AAGCTTGCTTCAGTTGCCGGCGACCGGCGCACGGGTGCGTAACGCGTATGC
AACCTACCCATAACAGGGGGATAACACTGAGAAATCGGTACTAATATCCC
ATAACATCAAGAGGGGCATCCCTTTTGGTTGAAAACTCCGGTGGTTATGGA
TGGGCATGCGTTGTATTAGCTAGTTGGTGAGGTAACGGCTCACCAAGGCGA
CGATACATAGGGGGACTGAGAGGTTAACCCCCCACATTGGTACTGAGACA
CGGACCAAACTCCTACGGGAGGCAGCAGTGAGGAATATTGGTCAATGGAC
GCAAGTCTGAACCAGCCATGCCGCGTGCAGGATGACGGCTCTATGAGTTGT
AAACTGCTTTTGTACGAGGGTAAACCCGGATACGTGTATCCGGCTGAAAGT
ATCGTACGAATAAGGATCGGCTAACTCCGTGCCAGCAGCCGCGGTAATAC
GGAGGATTCAAGCGTTATCCGGATTTATTGGGTTTAAAGGGTGCGTAGGCG
GTTTGATAAGTTAGAGGTGAAATACCGGTGCTTAACACCGGAACTGCCTCT
AATACTGTTGAGCTAGAGAGTAGTTGCGGTAGGCGGAATGTATGGTGTAGC
GGTGAAATGCTTAGAGATCATACAGAACACCGATTGCNGAAGGCAGCTTA
CCAAACTATATCTGACGTTNGAGGCACGAAAGCGTGGGGGAGCAAACAGG
ATTAGATACCCTGGTAGTCCACGCAGTAAACGATGATAACTCGCTGTCGGC
GATACACAGTCGGTGGCTAAGCGAAAGCGATAAGTTATCCACCTGGGGAG
TACGTTCGCAAGAATGAAACTCAAAGGAATTGACGGGGGCCCGCACAAGC
GGAGGAACATGTGGTTTAATTCGATGATACGCGAGGAACCTTACCCGGGCT
TGAAAGTTACTGACGATTCTGGAAACAGGATTTCCCTTCGGGGCAGGAAAC
TAGGTGCTGCATGGTTGTCGTCAGCTCGTGCCGTGAGGTGTCGGGTTAAGT
CCCATAACGAGCGCAACCCCTACCGTTAGTTGCCATCAGGTCAAGCTGGGC
ACTCTGGCGGGACTGCCGGTGTAAGCCGAGAGGAAGGTGGGGATGACGTC
AAATCAGCACGGCCCTTACGTCCGGGGCTACACACGTGTTACAATGGTAGG
TACAGAGGGCAGCTACCCAGTGATGGGATGCGAATCTCGAAAGCCTATCTC
AGTTCGGATTGGAGGCTGAAACCCGCCTCCATGAAGTTGGATTCGCTAGTA
ATCGCGCATCAGCCATGGCGCGGTGAATACGTTCCCGGGCCTTGTACACAC
```

```
                                          -continued
CGCCCGTCAAGCCATGGAAGCTGGGGGTGCCTGAAGTTCGTGAC strain 9 1H9_Parabacteroides gordonii_AB470343
                                                          SEQ ID NO: 9
GATGAACGC-

TAGCGACAGGCTTAACACATGCAAGTCGAGGGGCAGCAGGAAGTAGCAAT

ACTTTGCTGGCGACCGGCGCACGGGTGAGTAACGCGTATGCAACCTACCTA

TCAGAGGGGATAACCCGGCGAAAGTCGGACTAATACCGCATAAAACAGG

GGTCCCGCATGGGAATATTTGTTAAAGATTTATTGCTGATAGATGGGCATG

CGTTCCATTAGATAGTTGGTGAGGTAACGGCTCACCAAGTCTTCGATGGAT

AGGGGTTCTGAGAGGAAGGTCCCCCACACTGGTACTGAGACACGGACCAG

ACTCCTACGGGAGGCAGCAGTGAGGAATATTGGTCAATGGGCGAGAGCCT

GAACCAGCCAAGTCGCGTGAAGGATGAAGGATCTATGGTTCGTAAACTTCT

TTTATAGGGGAATAAAGTGCAGGACGTGTCCTGTTTTGTATGTACCCTATG

AATAAGGATCGGCTAACTCCGTGCCAGCAGCCGCGGTAATACGGAGGATC

CGAGCGTTATCCGGATTTATTGGGTTTAAAGGGTGCGTAGGTGGCTTTTTA

AGTCAGCGGTGAAAGTTTGTGGCTCAACCATAAAATTGCCGTTGAAACTGG

AGGGCTTGAGTATATTTGAGGTAGGCGGAATGCGTGGTGTAGCGGTGAAA

TGCATAGATATCACGCAGAACTCCAATTGCGAAGGCAGCTTACTAAACTAT

AACTGACACTGAAGCACGAAAGCGTGGGGATCAAACAGGATTAGATACCC

TGGTAGTCCACGCAGTAAACGATGATTACTAGGAGTTTGCGATACACAGTA

AGCTCTACAGCGAAAGCGTTAAGTAATCCACCTGGGGAGTACGCCGGCAA

CGGTGAAACTCAAAGGAATTGACGGGGGCCCGCACAAGCGGAGGAACATG

TGGTTTAATTCGATGATACGCGAGGAACCTTACCCGGGTTTGAACGTAAGT

TGACCGGAGTGGAAACACTCTTTCTAGCAATAGCAATTTACGAGGTGCTGC

ATGGTTGTCGTCAGCTCGTGCCGTGAGGTGTCGGCTTAAGTGCCATAACGA

GCGCAACCCTTATCTTTAGTTACTAACAGGTCGAGCTGAGGACTCTAAAGA

GACTGCCAGCGTAAGCTGTGAGGAAGGTGGGGATGACGTCAAATCAGCAC

GGCCCTTACATCCGGGGCGACACACGTGTTACAATGGTGGGGACAAAGGG

CAGCTACCTGGCGACAGGATGCTAATCTCCAAACCCCATCTCAGTTCGGAT

CGAAGTCTGCAACCCGACTTCGTGAAGCTGGATTCGCTAGTAATCGCGCAT

CAGCCATGGCGCGGTGAATACGTTCCCGGGCCTTGTACACACCGCCCGTCA

AGCCATGGGAGTTGGGGGTACCTAAAGTCCGTNACCGCAAG strain 10 1C1_Eubacterium limosum_AB595134
                                                          SEQ ID NO: 10
GAC-

GAACGCTGGCGGTATGCTTAACACATGCAAGTCGAACGAGAAGGTTTTGAT

GGATCCTTCGGGTGACATTAGAACTGGAAAGTGGCGAACGGGTGAGTAAC

GCGTGGGTAACCTGCCCTATGGAAAGGAATAGCCTCGGGAAACTGGGAGT

AAAGCCTTATATTATGGTTTTGTCGCATGGCAAGATCATGAAAACTCCGGT

GCCATAGGATGGACCCGCGTCCCATTAGCTAGTTGGTGAGATAACAGCCCA

CCAAGGCGACGATGGGTAACCGGTCTGAGAGGGCGAACGGTCACACTGGA

ACTGAGACACGGTCCAGACTCCTACGGGAGGCAGCAGTGGGGAATATTGC

GCAATGGGGGCAACCCTGACGCAGCAATACCGCGTGAGTGAAGAAGGTTT
```

TCGGATCGTAAAGCTCTGTTATTGGGGAAGAAGAATGACGGTACCCAATG

AGGAAGTCCCGGCTAACTACGTGCCAGCAGCCGCGGTAATACGTAGGGGA

CAAGCGTTGTCCGGAATGACTGGGCGTAAAGGGCGCGTAGGCGGTCTATT

AAGTCTGATGTGAAAGGTACCGGCTCAACCGGTGAAGTGCATTGGAAACT

GGTAGACTTGAGTATTGGAGAGGCAAGTGGAATTCCTAGTGTAGCGGTGA

AATGCGTAGATATTAGGAGGAACACCAGTGGCGAAGGCGGCTTGCTGGAC

AAATACTGACGCTGAGGTGCGAAAGCGTGGGGAGCGAACAGGATTAGATA

CCCTGGTAGTCCACGCCGTAAACGATGAATGCTAGGTGTTGGGGAAACTCA

GTGCCGCAGTTAACACAATAAGCATTCCGCCTGGGGAGTACGACCGCAAG

GTTGAAACTCAAAGGAATTGACGGGGACCCGCACAAGCAGCGGAGCATGT

GGTTTAATTCGAAGCAACGCGAAGAACCTTACCAGGTCTTGACATCGTCTG

ACGAGCCTAGAGATAGGAAGTTTCCTTCGGGAACAGAGAGACAGGTGGTG

CATGGTTGTCGTCAGCTCGTGTCGTGAGATGTTGGGTTAAGTCCCGCAACG

AGCGCAACCCCTGCCTTTAGTTGCCAGCATTAAGTTGGGCACTCTAGAGGG

ACTGCCGTAGACAATACGGAGGAAGGTGGGGACGACGTCAAATCATCATG

CCCCTTATGACCTGGGCTACACACGTGCTACAATGGTCTGAACAGAGGGCC

GCGAAGCCGCGAGGTGAAGCAAATCCCTTAAAACAGATCCCAGTTCGGAT

TGCAGGCTGCAACTCGCCTGCATGAAGTTGGAGTTGCTAGTAATCGCGGAT

CAGAATGCCGCGGTGAATGCGTTCCCGGGTCTTGTACACACCGCCCGICAC

ACCACGAGAGTTGGCAACACCCGAAGCCTGTGAGAGAACCGTAAGGACTC

AGCAGT strain 11 2G9_Parabacteroides distasonis_HE974920

SEQ ID NO: 11

GAT-

GAACGCTAGCGACAGGCTTAACACATGCAAGTCGAGGGGCAGCACAGGTA

GCAATACCGGGTGGCGACCGGCGCACGGGTGAGTAACGCGTATGCAACTT

GCCTATCAGAGGGGGATAACCCGGCGAAAGTCGGACTAATACCGCATGAA

GCAGGOGCCCCGCATGGGGATATTTGCTAAAGATTCATCGCTGATAGATAG

GCATGCGTTCCATTAGGCAGTTGGCGGGGTAACGGCCCACCAAACCGACG

ATGGATAGGGGTTCTGAGAGGAAGGTCCCCCACATTGGTACTGAGACACG

GACCAAACTCCTACGGGAGGCAGCAGTGAGGAATATTGGTCAATGGCCGA

GAGGCTGAACCAGCCAAGTCGCGTGAGGGATGAAGGTTCTATGGATCGTA

AACCTCTTTTATAAGGGAATAAAGTGCGGGACGTGTCCCGTTTTGTATGTA

CCTTATGAATAAGGATCGGCTAACTCCGTGCCAGCAGCCGCGGTAATACGG

AGGATCCGAGCGTTATCCGGATTTATTGGGTTTAAAGGGTGCGTAGGCGGC

CTTTTAAGTCAGCGGTGAAAGTCTGTGGCTCAACCATAGAATTGCCGTTGA

AACTGGGGGCTTGAGTATGTTTGAGGCAGGCGGAATGCGTGGTGTAGCG

GTGAAATGCATAGATATCACGCAGAACCCCGATTGCGAAGGCAGCCTGCC

AAGCCATTACTGACGCTGATGCACGAAAGCGTGGGGATCAAACAGGATTA

GATACCCTGGTAGTCCACGCAGTAAACGATGATCACTAGCTGTTTGCGATA

CACTGTAAGCGGCACAGCGAAAGCGTTAAGTGATCCACCTGGGGACTACG

-continued

CCGGCAACGGTGAAACTCAAAGGAATTGACGGGGGCCCGCACAAGCGGAG

GAACATGTGGTTTAATTCGATGATACGCGAGGAACCTTACCCGGGTTTGAA

CGCATTCGGACCGAGGTGGAAACACCTTTTCTAGCAATAGCCGTTTGCGAG

GTGCTGCATGGTTGTCGTCAGCTCGTGCCGTGAGGTGTCGGCTTAAGTGCC

ATAACGAGCGCAACCCTTGCCACTAGTTACTAACAGGTAAAGCTGAGGACT

CTGGTGGGACTGCCAGCGTAAGCTGCGAGGAAGGCGGGGATGACGTCAAA

TCAGCACGGCCCTTACATCCGGGGCGACACACGTGTTACAATGGCGTGGAC

AAAGGGAAGCCACCTGGCGACAGGGAGCGAATCCCCAAACCACGTCTCAG

TTCGGATCGGAGTCTGCAACCCGACTCCGTGAAGCTGGATTCGCTAGTAAT

CGCGCATCAGCCATGGCGCGGTGAATACGTTCCCGGGCCTTGTACACACCG

CCCGTCAAGCCATGGGAGCCNGGGGTACCTGAAGTCCGTAACCGCGA strain 12 2B7_*Bacteroides cellulosilyticus*_NR_112933

SEQ ID NO: 12

GAT-

GAACGCTAGCTACAGGCTTAACACATGCAAGTCGAGGGGCAGCATGACCT

AGCAATAGGTTGATGGCGACCGGCGCACGGGTGAGTAACACGTATCCAAC

CTACCGGTTATTCCGGGATAGCCTTTCGAAAGAAAGATTAATACCGGATAG

TATAACGAGAAGGCATCTTTTTGTTATTAAAGAATTTCGATAACCGATGGG

GATGCGTTCCATTAGTTTGTTGGCGGGGTAACGGCCCACCAAGACATCGAT

GGATAGGGGTTCTGAGAGGAAGGTCCCCCACATTGGAACTGAGACACGGT

CCAAACTCCTACGGGAGGCAGCAGTGAGGAATATTGGTCAATGGACGAGA

GTCTGAACCAGCCAAGTAGCGTGAAGGATGACTGCCCTATGGGTTGTAAAC

TTCTTTTATATGGGAATAAAGTGAGCCACGTGTGGCTTTTTGTATGTACCAT

ACGAATAAGGATCGGCTAACTCCGTGCCAGCAGCCGCGGTAATACGGAGG

ATCCGAGCGTTATCCGGATTTATTGGGTTTAAAGGGAGCGTAGGCGGACTA

TTAAGTCAGCTGTGAAAGTTTGCGGCTCAACCGTAAAATTGCAGTTGATAC

TGGTCGTCTTGAGTGCAGTAGAGGTAGGCGGAATTCGTGGTGTAGCGGTGA

AATGCTTAGATATCACGAAGAACTCCGATTGCGAAGGCAGCTTACTGGACT

GTAACTGACGCTGATGCTCGAAAGTGTGGGTATCAAACAGGATTAGATACC

CTGGTAGTCCACACAGTAAACGATGAATACTCGCTGTTTGCGATATACAGC

AAGCGGCCAAGCGAAAGCATTAAGTATTCCACCTGGGGAGTACGCCGGCA

ACGGTGAAACTCAAAGGAATTGACGGGGGCCCGCACAAGCGGAGGAACAT

GTGGTTTAATTCGATGATACGCGAGGAACCTTACCCGGGCTTAAATTGCAT

CTGAATAATTTGGAAACAGATTAGCCGTAAGGCAGATGTGAAGGTGCTGC

ATGGTTGTCGTCAGCTCGTGCCGTGAGGTGTCGGCTTAAGTGCCATAACGA

GCGCAACCCTTATCTTTAGTTACTAACAGGTCATGCTGAGGACTCTAGAGA

GACTGCCGTCGTAAGATGTGAGGAAGGTGGGGATGACGTCAAATCAGCAC

GGCCCTTACGTCCGGGGCTACACACGTGTTACAATGGGGGGTACAGAAGG

CAGCTACACAGCGATGTGATGCTAATCCCAAAAGCCTCTCTCAGTTCGGAT

TGGAGTCTGCAACCCGACTCCATGAAGCTGGATTCGCTAGTAATCGCGCAT

CAGCCACGGCGCGGTGAATACGTTCCCGGGCCTTGTACACACCGCCCGTCA

AGCCATGAAAGCCGGGGGTACCTGAAGTCCGTAAC

-continued strain 13 2C1_Bacteroides clarus_AB490801
SEQ ID NO: 13
GATGAACGCTAGC-
TACAGGCTTAACACATGCAAGTCGAGGGGCAGCGGGGTTGAAGCTTGCTTC
AACCGCCGGCGACCGGCGCACGGGTGAGTAACACGTATCCAACCTGCCGA
TAACTCCGGGATAGCCTTTCGAAAGAAAGATTAATACCGGATGGCATAGTT
TTCCCGCATGGAATAACTATTAAAGAATTTCGGTTATCGATGGGGATGCGT
TCCATTAGGCAGTTGGCGGGGTAACGGCCCACCAAACCGACGATGGATAG
GGGTTCTGAGAGGAAGGTCCCCCACATTGGAACTGAGACACGGTCCAAAC
TCCTACGGGAGGCAGCAGTGAGGAATATTGGTCAATGGACGAGAGTCTGA
ACCAGCCAAGTAGCGTGAAGGATGACTGCCCTATGGGTTGTAAACTTCTTT
TATACGGGAATAAAGTTGGCCACGTGTGGTTTTTTGCATGTACCGTATGAA
TAAGGATCGGCTAACTCCGTGCCAGCAGCCGCGGTAATACGGAGGATCCG
AGCGTTATCCGGATTTATTGGGTTTAAAGGGAGCGTAGGCGGGGTATTAAG
TCAGTTGTGAAAGTTTGCGGCTCAACCGTAAAATTGCAGTTGATACTGGTA
TCCTTGAGTGCAGCAGAGGTGGGCGGAATTCGTGGTGTAGCGGTGAAATG
CTTAGATATCACGAAGAACTCCGATTGCGAAGGCAGCTCACTGGAGTGTAA
CTGACGCTGATGCTCGAAAGTGTGGGTATCAAACAGGATTAGATACCCTGG
TAGTCCACACAGTAAACGATGAATACTCGCTGTTGGCGATACAATGTCAGC
GGCCAAGCGAAAGCATTAAGTATTCCACCTGGGGAGTACGCCGGCAACGG
TGAAACTCAAAGGAATTGACGGGGCCCGCACAAGCGGAGGAACATGTGG
TTTAATTCGATGATACGCGAGGAACCTTACCCGGGCTTGAATTGCAACTGA
CTGAGCTGGAAACAGTTCTTTCTTCGGACAGTTGTGAAGGTGCTGCATGGT
TGTCGTCAGCTCGTGCCGTGAGGTGTCGGCTTAAGTGCCATAACGAGCGCA
ACCCTTTATCTATAGTTACCATCAGGTCATGCTGGGGACTCTATGGAGACTG
CCGTCGTAAGATGTGAGGAAGGTGGGGATGACGTCAAATCAGCACGGCCC
TTACGTCCGGGGCTACACACGTGTTACAATGGGGGGTACAGAAGGCAGCT
ACACGGCGACGTGATGCTAATCCCAAAAACCTCTCTCAGTTCGGATTGGAG
TCTGCAACCCGACTCCATGAAGCTGGATTCGCTAGTAATCGCGCATCAGCC
ACGGCGCGGTGAATACGTTCCCGGGCCTTGTACACACCGCCCGTCAAGCCA
TGAAAGCCGGGGGTACCTGAAGTACGTAACCGCAA strain 14 1B4_Anaerostipes sp. 3_2_56FAA_NZ-ACWB00000000
SEQ ID NO: 14
GATGAACGCTGGCGGCGTGCTTAACACATGCAAGTCGAACGAAGCATTTA
GGATTGAAGTTTTCGGATGGATTTCCTATATGACTGAGTGGCGGACGGGTG
AGTAACGCGTGGGGAACCTGCCCTATACAGGGGGATAACAGCTGGAAACG
GCTGCTAATACCGCATAAGCGCACAGAATCGCATGATTCAGTGTGAAAAG
CCCTGGCAGTATAGGATGGTCCCGCGTCTGATTAGCTGGTTGGTGAGGTAA
CGGCTCACCAAGGCGACGATCAGTAGCCGGCTTGAGAGAGTGAACGGCCA
CATTGGGACTGAGACACGGCCCAAACTCCTACGGGAGGCAGCAGTGGGGA
ATATTGCACAATGGGGGAAACCCTGATGCAGCGACGCCGCGTGAGTGAAG
AAGTATTTCGGTATGTAAAGCTCTATCAGCAGGGAAGAAAACAGACGGTA -continued CCTGACTAAGAAGCCCCGGCTAACTACGTGCCAGCAGCCGCGGTAATACGT
AGGGGGCAAGCGTTATCCGGAATTACTGGGTGTAAAGGGTGCGTAGGTGG
CATGGTAACTCAGAAGTGAAACCCCGGCGCTTAACCCCGGGACTGCTTTTG
AAACTGTCATGCTGGAGTGCAGGAGAGGTAAGCGGAATTCCTAGTGTAGC
GGTGAAATGCGTAGATATTAGGAGGAACACCAGTGGCGAAGGCGGCTTAC
TGGACTGTCACTGACACTGATGCACGAAAGCGTGGCTGAGCAAACAGGATT
AGATACCCTGGTAGTCCACGCCGTAAACGATGAATACTAGGTGTCGGGGCC
GTAGAGGCTTCGGTGCCGCAGCAAACGCAGTAAGTATTCCACCTGGGGAG
TACGTTCGCAAGAATGAAACTCAAAGGANTTGACGGGGACCGCNNNAGCG
GTGGAGCATGTGOTTAATTCGAAGCACGCGAAG strain 15 2A3_*Bacteroides salyersiae*_AY608696

SEQ ID NO: 15

GATGAACGC-
TAGCTACAGGCTTAACACATGCAAGTCGAGGGGCATCAGGGTGTAGCAAT
ACACCGCTGGCGACCGGCGCACGGGTGAGTAACACGTATCCAACCTGCCCT
TTACTCGGGGATAGCCTTTCGAAAGAAAGATTAATACCCGATGGTATAACA
TGACCTCCTGGTTTTGTTATTAAAGAATTTCGGTAGAGGATGGGGATGCGT
TCCATTAGGCAGTTGGCGGGGTAACGGCCCACCAAACCTTCGATGGATAGG
GGTTCTGAGAGGAAGGTCCCCCACATTGGAACTGAGACACGGTCCAAACT
CCTACGGGAGGCAGCAGTGAGGAATATTGGTCAATGGGCGAGAGCCTGAA
CCAGCCAAGTAGCGTGAAGGATGACCGCCCTATGGGTTGTAAACTTCTTTT
ATATGGGAATAAAGTCTGCCACGTGTGGCATTTTGTATGTACCATATGAAT
AAGGATCGGCTAACTCCGTGCCAGCAGCCGCGGTAATACGGAGGATCCGA
GCGTTATCCGGATTTATTGGGTTTAAAGGGAGCGTAGGTGGACATGTAAGT
CAGTTGTGAAAGTTTGCGGCTCAACCGTAAAATTGCAGTTGAAACTGCGTG
TCTTGAGTACAGTAGAGGTGGGCGGAATTCGTGGTGTAGCGGTGAAATGCT
TAGATATCACGAAGAACTCCGATTGCGAAGGCAGCTCACTGGACTGCAACT
GACACTGATGCTCGAAAGTGTGGGTATCAAACAGGATTAGATACCCTGGTA
GTCCACACAGTAAACGATGAATACTCGCTGTTTGCGATATACAGTAAGCGG
CCAAGCGAAAGCATTAAGTATTCCACCTGGGGAGTACGCCGGCAACGGTG
AAACTCAAAGGAATTGACGGGGCCCGCACAAGCGGAGGAACATGTGGTT
TAATTCGATGATACGCGAGGAACCTTACCCGGGCTTAAATTGCAAATGAAT
ATGCCGGAAACGGCATAGCCGCAAGGCATTTGTGAAGGTGCTGCATGGTT
GTCGTCAGCTCGTGCCGTGAGGTGTCGGCTTAAGTGCCATAACGAGCGCAA
CCCTTATCTTCAGTTACTAACAGGTCATGCTGAGGACTCTGGAGAGACTGC
CGTCGTAAGATGTGAGGAAGGTGGGGATGACGTCAAATCAGCACGGCCCT
TACGTCCGGGGCTACACACGTGTTACAATGGGGGGTACAGAAGGCCGCTA
CACAGCGATGTGATGCCAATCCCTAAAGCCCCTCTCAGTTCGGATCGAAGT
CTGCAACCCGACTTCGTGAAGCTGGATTCGCTAGTAATCGCGCATCAGCCA
CGGCGCGGTGAATACGTTCCCGGGCCTTGTACACACCGCCCGTCAAGCCAT
GGGAGCCGGGGGTACCTGAAGTACGTAAC strain 16 2A12_Bacteroides fragilis_CR626927
SEQ ID NO: 16

GATGAACGC-
TAGCTACAGGCTTAACACATGCAAGTCGAGGGGCATCAGGAAGAAAGCTT
GCTTTCTTTGCTGGCGACCGGCGCACGGGTGAGTAACACGTATCCAACCTG
CCCTTTACTCGGGGATAGCCTTTCGAAAGAAAGATTAATACCCGATAGCAT
AATGATTCCGCATGGTTTCATTATTAAAGGATTCCGGTAAAGGATGGGGAT
GCGTTCCATTAGGTTGTTGGTGAGGTAACGGCTCACCAAGCCTTCGATGGA
TAGGGGTTCTGAGAGGAAGGTCCCCCACATTGGAACTGAGACACGGTCCA
AACTCCTACGGGAGGCAGCAGTGAGGAATATTGGTCAATGGGCGCTAGCC
TGAACCAGCCAAGTAGCGTGAAGGATGAAGGCTCTATGGGTCGTAAACTT
CTTTTATATAAGAATAAAGTGCAGTATGTATACTGTTTTGTATGTATTATAT
GAATAAGGATCGGCTAACTCCGTGCCAGCAGCCGCGGTAATACGGAGGAT
CCGAGCGTTATCCGGATTTATTGGGTTTAAAGGGAGCGTAGGTGGACTGGT
AAGTCAGTTGTGAAAGTTTGCGGCTCAACCGTAAAATTGCAGTTGATACTG
TCAGTCTTGAGTACAGTAGAGGTGGGCGGAATTCGTGGTGTAGCGGTGAA
ATGCTTAGATATCACGAAGAACTCCGATTGCGAAGGCAGCTCACTGGACTG
CAACTGACACTGATGCTCGAAAGTGTGGGTATCAAACAGGATTAGATACCC
TGGTAGTCCACACAGTAAACGATGAATACTCGCTGTTTGCGATATACAGTA
AGCGGCCAAGCGAAAGCATTAAGTATTCCACCTGGGGAGTACGCCGGCAA
CGGTGAAACTCAAAGGAATTGACGGGGGCCCGCACAAGCGGAGGAACATG
TGGTTTAATTCGATGATACGCGAGGAACCTTACCCGGGCTTAAATTGCAGT
GGAATGATGTGGAAACATGTCAGTGAGCAATCACCGCTGTGAAGGTGCTG
CATGGTTGTCGTCAGCTCGTGCCGTGAGGTGTCGGCTTAAGTGCCATAACG
AGCGCAACCCTTATCTTTAGTTACTAACAGGTTATGCTGAGGACTCTAGAG
AGACTGCCGTCGTAAGATGTGAGGAAGGTGGGGATGACGTCAAATCAGCA
CGGCCCTTACGTCCGGGGCTACACACGTGTTACAATGGGGGGTACAGAAG
GCAGCTAACGGGTGACCGTATGCTAATCCCAAAAGCCTCTCTCAGTTCGGA
TCGAAGTCTGCAACCCGACTTCGTGAAGCTGGATTCGCTAGTAATCGCGCA
TCAGCCACGGCGCGGTGAATACGTTCCCGGGCCTTGTACACACCGCCCGTC
AAGCCATGGGAGCCGGGGGTACCTGAAGTACGTAACCGCAA strain 17 1A2_Bacteroides uniformis_AB247141
SEQ ID NO: 17

GATGAACGC-
TAGCTACAGGCTTAACACATGCAAGTCGAGGGGCATCAGGAAGAAAGCTT
GCTTTCTTTGCTGGCGACCGGCGCACGGGTGAGTAACACGTATCCAACCTG
CCGATGACTCGGGGATAGCCTTTCGAAAGAAAGATTAATACCCGATGGTAT
ATCTGAAAGGCATCTTTCAGCTATTAAAGAATTTCGGTCATTGATGGGGAT
GCGTTCCATTAGGTTGTTGGCGGGTAACGGCCCACCAAGCCATCGATGGA
TAGGGGTTCTGAGAGGAAGGTCCCCCACATTGGAACTGAGACACGGTCCA
AACTCCTACGGGAGGCAGCAGTGAGGAATATTGGTCAATGGACGAGAGTC
TGAACCAGCCAAGTAGCGTGAAGGATGACTGCCCTATGGGTTGTAAACTTC
TTTTATACGGGAATAAAGTTAGGCACGTGTGCCTTTTTGTATGTACCGTATG

```
AATAAGGATCGGCTAACTCCGTGCCAGCAGCCGCGGTAATACGGAGGATC
CGAGCGTTATCCGGATTTATTGGGTTTAAAGGGAGCGTAGGCGGATGCTTA
AGTCAGTTGTGAAAGTTTGCGGCTCAACCGTAAAATTGCAGTTGATACTGG
GTGTCTTGAGTACAGTAGAGGCAGGCGGAATTCGTGGTGTAGCGGTGAAA
TGCTTAGATATCACGAAGAACTCCGATTGCGAAGGCAGCTTGCTGGACTGT
AACTGACGCTGATGCTCGAAAGTGTGGGTATCAAACAGGATTAGATACCCT
GGTAGTCCACACAGTAAACGATGAATACTCGCTGTTTGCGATATACAGTAA
GCGGCCAAGCGAAAGCGTTAAGTATTCCACCTGGGGAGTACGCCGGCAAC
GGTGAAACTCAAAGGAATTGACGGGGGCCCGCACAAGCGGAGGAACATGT
GGTTTAATTCGATGATACGCGAGGAACCTTACCCGGGCTTAAATTGCAAAT
GAATGTTCTGGAAACAGATCAGCCGCAAGGCATTTGTGAAGGTGCTGCATG
GTTGTCGTCAGCTCGTGCCGTGAGGTGTCGGCTTAAGTGCCATAACGAGCG
CAACCCTTATCGATAGTTACCATCAGGTTATGCTGGGGACTCTGTCGAGAC
TGCCGTCGTAAGATGTGAGGAAGGTGGGGATGACGTCAAATCAGCACGGC
CCTTACGTCCGGGGCTACACACGTGTTACAATGGGGGGTACAGAAGGCAG
CTACACGGCGACGTGATGCTAATCCCTAAAACCTCTCTCAGTTCGGATTGG
AGTCTGCAACCCGACTCCATGAAGCTGGATTCGCTAGTAATCGCGCATCAG
CCACGGCGCGGTGAATACGTTCCCGGGCCTTGTACACACCGCCCGTCAAGC
CATGAAAGCCGGGGGTACCTGAAGTGCGT
```
strain 18 2B11_*Bacteroides eggerthii*_NR_112935

SEQ ID NO: 18
```
GATGAACGC-
TAGCTACAGGCTTAACACATGCAAGTCGAGGGGCAGCATGATTGAAGCTT
GCTTCAATCGATGGCGACCGGCGCACGGGTGAGTAACACGTATCCAACCTG
CCGATAACTCGGGGATAGCCTTTCGAAAGAAAGATTAATACCCGATAGCAT
AGTATTTCCGCATGGTTTCACTATTAAAGAATTTCGGTTATCGATGGGGAT
GCGTTCCNTTAGATAGTTGGCGGGGTAACGGCCCACCAAGTCAACGATGG
ATAGGGGTTCTGAGAGGAAGGTCCCCCACATTGGAACTGAGACACGGTCC
AAACTCCTACGGGAGGCAGCAGTGAGGAATATTGGTCAATGGACGAGAGT
CTGAACCAGCCAAGTAGCGTGAAGGATGACTGCCCTATGGGTTGTAAACTT
CTTTTATACGGGAATAAAGTGGAGTATGCATACTCCTTTGTATGTACCGTAT
GAATAAGGATCGGCTAACTCCGTGCCAGCAGCCGCGGTAATACGGAGGAT
CCGAGCGTTATCCGGATTTATTGGGTTTAAAGGGAGCGTAGGCGGGTGCTT
AAGTCAGTTGTGAAAGTTTGCGGCTCAACCGTAAAATTGCAGTTGATACTG
GGCGCCTTGAGTGCAGCATAGGTAGGCGGAATTCGTGGTGTAGCGGTGAA
ATGCTTAGATATCACGAAGAACTCCGATTGCGAAGGCAGCTTACTGGACTG
TAACTGACGCTGATGCTCGAAAGTGTGGGTATCAAACAGGATTAGATACCC
TGGTAGTCCACACAGTAAACGATGAATACTCGCTGTTGGCGATACACAGTC
AGCGGCCAAGCGAAAGCATTAAGTATTCCACCTGGGGAGTACGCCGGCAA
CGGTGAAACTCAAAGGAATTGACGGGGGCCCGCACAAGCGGAGGAACATG
TGGTTTAATTCGATGATACGCGAGGAACCTTACCCGGGCTTAAATTGCAGC
```

```
GGAATGTAGTGGAAACATTACAGCCTTCGGGCCGCTGTGAAGGTGCTGCAT

GGTTGTCGTCAGCTCGTGCCGTGAGGTGTCGGCTTAAGTGCCATAACGAGC

GCAACCCTTATCTATAGTTACTATCAGGTCATGCTGAGGACTCTATGGAGA

CTGCCGTCGTAAGATGTGAGGAAGGTGGGGATGACGTCAAATCAGCACGG

CCCTTACGTCCGGGGCTACACACGTGTTACAATGGGGGGTACAGAAGGCA

GCTACCTGGCGACAGGATGCTAATCCCTAAAACCTCTCTCAGTTCGGATTG

GAGTCTGCAACCCGACTCCATGAAGCTGGATTCGCTAGTAATCGCGCATCA

GCCACGGCGCGGTGAATACGTTCCCGGGCCTTGTACACACCGCCCGTCAAG

CCATGAAAGCCGGGGGTACCTGAAGTACGTAACCGCAAGGAGC
``` strain 19 2D2_Clostridium sp. TM-40_AB249652
SEQ ID NO: 19
```
GAT-
GAACGCTGGCGGCGTGCCTAATACATGCAAGTCGGACGCAATGCTTCGGC

ATTGAGTGGCGAACGGGTGAGTAATACATAAGCAACCTGCCCCTGTGAGG

GGGATAACTGCTGGAAACGGCAGCTAAGACCGCATATGCATACATGACGC

ATGTCGAGTATGTTAAATATCCCACGGGATAGCACAGGGATGGGCTTATGA

CGCATTAGCTAGCTGGTGAGGTAGAGGCTCACCAGGGCGACGATGCGTAG

CCGGCCTGAGAGGGTGGACGGCCACACTGGGACTGAGACACGGCCCAGAC

TCCTACGGGAGGCAGCAGTAGGGAATTTTCGGCAATGGGCGAAAGCCTGA

CCGAGCAACGCCGCGTGAAGGAAGAAGTCATTCGTGATGTAAACTTCTGTT

ATAAAGGAAGAACGGCGCCTGTAGGGAATGACAGGCGAGTGACGGTACTT

TATGAGGAAGCCACGGCTAACTACGTGCCAGCAGCCGCGGTAATACGTAG

GTGGCGAGCGTTATCCGGAATCATTGGGCGTAAAGAGGGAGCAGGCGGCA

GTGCAGGTCTGCGGTGAAAGCCCGAAGCTAAACTTCGGTAAGCCGTGGAA

ACCGCACAGCTAGAGAGCATCAGAGGATCGCGGAATTCCATGTGTAGCGG

TGAAATGCGTAGATATATGGAGGAACACCAGTGGCGAAGGCGGCGGTCTG

GGGTGCAGCTGACGCTCAGTCCCGAAAGCGTGGGGAGCAAATAGGATTAG

ATACCCTAGTAGTCCACGCCGTAAACGATGAGTGCTAAGTGTTGGGGGTCA

GACCTCAGTGCTGCAGTTAACGCAATAAGCACTCCGCCTGAGTAGTACGTT

CGCAAGAATGAAACTCAAAGGAATTGACGGGGCCCGCACAAGCGGTGGA

GCATGTGGTTTAATTCGAAGCAACGCGAAGAACCTTACCAGGTCTTGACAT

GGAGATAAAGGCTCTGGAGACAGAGAGATAGGTATATCTCACACAGGTGG

TGCATGGTTGTCGTCAGCTCGTGTCGTGAGATGTTGGGTTAAGTCCCGCAA

CGAGCGCAACCCCTGTTGCCAGTTGCCAGCATTAGGTTGGGGACTCTGGCG

AGACTGCCTCTGCAAGGAGGAGGAAGGCGGGGATGACGTCAAATCATCAT

GCCCCTTATGACCTGGGCTACACACGTGCTACAATGGACGGATCAGAGGG

AGGCGAAGCCGCGAGGTGGAGCGAAACCCAGAAACCCGTTCACAGTTCGG

ACTGCAGTCTGCAACTCGACTGCACGAAGCTGGAATCGCTAGTAATCGCGA

ATCAGCATGTCGCGGTGAATACGTTCTCGGGCCTTGTACACACCGCCCGTC

ACACCATGAGAGTTGGTAACACCCGAAGCCGGTGGCCCAACCGCAA
```

-continued strain 20 2E8_Parabacteroides goldsteinii_NR_113076

SEQ ID NO: 20

GAT-
GAACGCTAGCGACAGGCTTAACACATGCAAGTCGAGGGGCAGCACGATGT
AGCAATACATTGGTGGCGACCGGCGCACGGGTGAGTAACGCGTATGCAAC
CTACCTATCAGAGGGGAATAACCCGGCGAAAGTCGGACTAATACCGCATA
AAACAGGGGTTCCACATGGAAATATTTGTTAAAGAATTATCGCTGATAGAT
GGGCATGCGTTCCATTAGATAGTTGGTGAGGTAACGGCTCACCAAGTCCAC
GATGGATAGGGGTTCTGAGAGGAAGGTCCCCCACACTGGTACTGAGACAC
GGACCAGACTCCTACGGGAGGCAGCAGTGAGGAATATTGGTCAATGGGCG
AGAGCCTGAACCAGCCAAGTCGCGTGAAGGATGAAGGATCTATGGTTTGT
AAACTTCTTTTATATGGGAATAAAGTGAGGAACGTGTTCCTTTTTGTATGTA
CCATATGAATAAGCATCGGCTAACTCCGTGCCAGCAGCCGCGGTAATACGG
AGGATGCGAGCGTTATCCGGATTTATTGGGTTTAAAGGGTGCGTAGGTGGT
TAATTAAGTCAGCGGTGAAAGTTTGTGGCTCAACCATAAAATTGCCGTTGA
AACTGGTTGACTTGAGTATATTTGAGGTAGGCGGAATGCGTGGTGTAGCGG
TGAAATGCATAGATATCACGCAGAACTCCGATTGCGAAGGCAGCTTACTAA
ACTATAACTGACACTGAAGCACGAAAGCGTGGGGATCAAACAGGATTAGA
TACCCTGGTAGTCCACGCAGTAAACGATGATTACTAGCTGTTTGCGATACA
CAGTAAGCGGCACAGCGAAAGCGTTAAGTAATCCACCTGGGGAGTACGCC
GGCAACGGTGAAACTCAAAGGAATTGACGGGGCCCGCACAAGCGGAGG
AACATGTGGTTTAATTCGATGATACGCGAGGAACCTTACCCGGGTTTGAAC
GCATATTGACAGCTCTGGAAACAGAGTCTCTAGTAATAGCAATTTGCGAGG
TGCTGCATGGTTGTCGTCAGCTCGTGCCGTGAGGTGTCGGCTTAAGTGCCA
TAACGAGCGCAACCCTTATCACTAGTTACTAACAGGTCATGCTGAGGACTC
TAGTGAGACTGCCAGCGTAAGCTGTGAGGAAGGTGGGGATGACGTCAAAT
CAGCACGGCCCTTACATCCGGGGCGACACACGTGTTACAATGGTGGGGAC
AAAGGGCAGCTACCGTGTGAGCGGATGCAAATCTCCAAACCCCATCTCAGT
TCGGATCGAAGTCTGCAACCCGACTTCGTGAAGCTGGATTCGCTAGTAATC
GCGCATCAGCCATGGCGCGGTGAATACGTTCCCGGGCCTTGTACACACCGC
CCGTCAAGCCATGGGAGTTGGGGGTACCTAAAGTCCGTAACCGC strain 21 1H8_Bacteroides Sp. AR29_AF139525

SEQ ID NO: 21

GATGAACGC-
TAGCTACAGGCTTAACACATGCAAGTCGAGGGGCAGCATTTCAGTTTGCTT
GCAAACTGGAGATGGCGACCGGCGCACGGGTGAGTAACACGTATCCAACC
TGCCGATAACTCGGGGATAGCCTTTCGAAAGAAAGATTAATACCCGATGGT
ATAATNAGACCGCATGGTCTTGTTATTAAAGAATTTCGGTTATCGATGGGG
ATGCGTTCCATTAGGCAGTTGGTGAGGTAACGGCTCACCAAACCTTCGATG
GATAGGGGTTCTGAGAGGAAGGTCCCCCACATTGGAACTGAGACACGGTC
CAAACTCCTACGGGAGGCAGCAGTGAGGAATATTGGTCAATGGGCGCAGG
CCTGAACCAGCCAAGTAGCGTGAAGGATGACTGCCCTATGGGTTGTAAACT
TCTTTTATATGGGAATAAAGTTTTCCACGTGTGGAATTTTGTATGTACCATA

-continued

```
TGAATAAGGATCGGCTAACTCCGTGCCAGCAGCCGCGGTAATACGGAGGA
TCCGAGCGTTATCCGGATTTATTGGGTTTAAAGGGAGCGTAGGTGGACAGT
TAAGTCAGTTGTGAAAGTTTGCGGCTCAACCGTAAAATTGCAGTTGATACT
GGCTGTCTTGAGTACAGTAGAGGTGGGCGGAATTCGTGGTGTAGCGGTGA
AATGCTTAGATATCACGAAGAACTCCGATTGCGAAGGCAGCTCACTGGACT
GCAACTGACACTGATGCTCGAAAGTGTGGGTATCAAACAGGATTAGATAC
CCTGGTAGTCCACACAGTAAACGATGAATACTCGCTGTTTGCGATATACAG
TAAGCGGCCAAGCGAAAGCATTAAGTATTCCACCTGGGGAGTACGCCGGC
AACGGTGAAACTCAAAGGAATTGACGGGGGCCCGCACAAGCGGAGGAAC
ATGTGGTTTAATTCGATGATACGCGAGGAACCTTACCCGGGCTTAAATTGC
ATTTGAATATATTGGAAACAGTATAGCCGTAAGGCAAATGTGAAGGTGCTG
CATGGTTGTCGTCAGCTCGTGCCGTGAGGTGTCGGCTTAAGTGCCATAACG
AGCGCAACCCTTATCTTTAGTTACTAACAGGTCATGCTGAGGACTCTAGAG
AGACTGCCGTCGTAAGATGTGA strain 22 >3F2-PREMIX.fasta
                                          SEQ ID NO: 22
NNNNNNNNNNTGCAGTCGAACGAAGCGATTTGAATGAAGTTTTCGGATGG
ATTTCAANTTGACTGAGTGGCGGACGGGTGAGTAACGCGTGGGTAACCTGC
CCCATACAGGGGGATAACAGTTAGAAATGACTGCTAATACCGCATAAGAC
CACAGNNCCGCATGGTGCAGGGGTAAAAACTCCGGTGGTATGGGATGGAC
CCGCGTCTGATTAGCTTGTTGGCGGGGTAACGGCCCACCAAGGCGACGATC
AGTAGCCGACCTGAGAGGGTGACCGGCCACATTGGGACTGAGACACGGCC
CAAACTCCTACGGGAGGCAGCAGTGGGGAATATTGCACAATGGGGGAAAC
CCTGATGCAGCGACGCCGCGTGAGTGATGAAGTATTTCGGTATGTAAAGCT
CTATCAGCAGGGAAGAAAATGACGGTACCTGACTAAGAAGCCCCGGCTAA
CTACGTGCCAGCAGCCGCGGTAATACGTAGGGGGCAAGCGTTATCCGGATT
TACTGGGTGTAAAGGGAGCGTAGACGGCTGTGCAAGTCTGGAGTGAAAGC
CCGGGGCTCAACCCCGGGACTGCTTTGGAAACTGTACGGCTGGAGTGCTGG
AGAGGCAAGCGGAATTCCTAGTGTAGCGGTGAAATGCGTAGATATTAGGA
GGAACACCAGTGGCGAAGGCGGCTTGCTGGACAGTAACTGACGTTGAGGC
TCGAAAGCGTGGGGAGCAAACAGGATTAGATACCCTGGTAGTCCACGCCG
TAAACGATGAATGCTAGGTGTCGGGGAGCAAAGCTCTTCGGTGCCGCCGC
AAACGCAATAAGCATTCCACCTGGGGAGTACGTTCGCAAGAATGAAACTC
AAAGGANTTGACGGGGACCGCACANNGGTGGAGCATGTGGTTATTCGAGC
ACGCGAAANCTTACCAGTCTTGNNNCCCCTGANGNNNNGTATGTCGCTNCT
NNGNNNNGGN strain 23 >1G1_3-PREMIX.fasta
                                          SEQ ID NO: 23
AGTTTGATTATGGCTCAGGATGAACGCTGGCGGCGTGCTTAACACATGCA
AGTCGAGCGAAGCGGTTTCAATGAAGTTTTCGGATGGATTTGAAATTGACT
TAGCGGCGGACGGGTGAGTAACGCGTGGGTAACCTGCCTTACACTGGGGG
ATAACAGTTAGAAATGACTGCTAATACCGCATAAGCGCACAGGGCCGCAT
```

```
GGTCCGGTGTGAAAAACTCCGGTGGTGTAAGATGGACCCGCGTCTGATTAG

GTAGTTGGCGGGGTAACGGCCCACCAAGCCGACGATCAGTAGCCGACCTG

AGAGGGTGACCGGCCACATTGGGACTGAGACACGGCCCAAACTCCTACGG

GAGGCAGCAGTGGGGAATATTGGACAATGGGCGAAAGCCTGATCCAGCGA

CGCCGCGTGAGTGAAGAAGTATTTCGGTATGTAAAGCTCTATCAGCAGGGA

AGAAAATGACGGTACCTGACTAAGAAGCCCCGGCTAACTACGTGCCAGCA

GCCGCGGTAATACGTAGGGGGCAAGCGTTATCCGGATTTACTGGGTGTAAA

GGGAGCGTAGACGGTTTAGCAAGTCTGAAGTGAAAGCCCGGGGCTCAACC

CCGGTACTGCTTTGGAAACTGTTAGACTTGAGTGCAGGAGAGGTAAGTGGA

ATTCCTAGTGTAGCGGTGAAATGCGTAGATATTAGGAGGAACACCAGTGG

CGAAGGCGGCTTACTGGACTGTAACTGACGTTGAGGCTCGAAAGCGTGGG

GAGCAAACAGGATTAGATACCCTGGTAGTCCACGCCGTAAACGATGAATA

CTAGGTGTCGGGGGGCAAAGCCCTTCGGTGCGGCCGCAAACGCAATAAGT

ATTCCACCTGGGGAGTACGTTCGCAAGAATGAAACTCAAAGGAATTGACG

GGGACCCGCACAAGCGGTGGAGCATGTGGTTTAATTCGAAGCAACGCGAA

GAACCTTACCAAGTCTTGACATCCCACTGAAAACACTTTAACCGGTGTCCC

TCTTCGGAGCAGTGGAGACAGGTGGTGCATGGTTGTCGTCAGCTCGTGTCG

TGAGATGTTGGGTTAAGTCCCGCAACGAGCGCAACCCTTATCCTTAGTAGC

CAGCGAGTAGAGTCGGGCACTCTGGGAGACTGCCAGGGATAACCTGGAG

GAAGGTGGGGATGACGTCAAATCATCATGCCCCTTATGATTTGGGCTACAC

ACGTGCTACAATGGCGTAAACAAAGGGAGGCAAAGGAGCGATCTGGAGCA

AACCCCAAAAATAACGTCTCAGTTCGGATTGCAGGCTGCAACTCGCCTGCA

TGAAGCTGGAATCGCTAGTAATCGCGAATCAGAATGTCGCGGTGAATACGT

TCCCGGGTCTTGTACACACCGCCCGTCACACCATGGGAGTTGGTAACGCCC

GAAGTCAGTGACCCAACCGCAAGGAGGNAGCTGCCGAANNNNNNNN strain 24 >1E6_27Fmod-PREMIX_Length_957
                                                SEQ ID NO: 24
AGTTTGNNNNNGCTCAGGATGAACGCTGGCGGCGTGCCTAACACATGCA

AGTCGAACGAAGCATTTCAGATGAAGTTTTCGGATGGATTCTGAGATGACT

GAGTGGCGGACGGGTGAGTAACACGTGGATAACCTGCCTCACACTGGGGG

ACAACAGTTAGAAATGACTGCTAATACCGCATAAGCGCACAGTACCGCAT

GGTACAGTGTGAAAAACTCCGGTGGTGTGAGATGGATCCGCGTCTGATTAG

CCAGTTGGCGGGGTAACGGCCCACCAAAGCGACGATCAGTAGCCGACCTG

AGAGGGTGACCGGCCACATTGGGACTGAGACACGGCCCAAACTCCTACGG

GAGGCAGCAGTGGGGAATATTGCACAATGGGCGAAAGCCTGATGCAGCGA

CGCCGCGTGAGTGAAGAAGTATTTCGGTATGTAAAGCTCTATCAGCAGGGA

AGATAATGACGGTACCTGACTAAGAAGCCCCGGCTAACTACGTGCCAGCA

GCCGCGGTAATACGTAGGGGGCAAGCGTTATCCGGATTTACTGGGTGTAAA

GGGAGCGTAGACGGCATGGCAAGTCTGAAGTGAAAACCCAGGGCTCAACC

CTGGGACTGCTTTGGAAACTGTCAAGCTAGAGTGCAGGAGAGGTAAGTGG

AATTCCTAGTGTAGCGGTGAAATGCGTAGATATTAGGAGGAACACCAGTG

GCGAAGGCGGCTTACTGGACTGTAACTGACGTTGAGGCTCGAAAGCGTGG
```

```
GGAGCAAACAGGATTAGATACCCTGGTAGTCCACGCCGTAAACGATGAGT
GCTAGGTGTTGGGGGGCAAAGCCCTTCGGTGCCGTCGCAAACGCAATAAG
CACTCCACCTGGGGAGTACGTTCGCAAGAATGAAACTCAAAGGAATTGAC
GGGGACCCGCACAAGCGGTGGAGCATGTGGTTTAATTCGAAGCAACGCGA
AGAACCTTACCAAGTCTTGACATCCTCTTGACCGGCGTGTAACGGCGCCn
TCCTTCGGGACAAGAGAGACAGGTGGTGCATGGTTGTCGTCAGCTCGTGTC
GTGAGATGTTGGGTTAAGTCCCGCAACGAGCGCAACCCTTATCCTTAGTAG
CCAGCATTAAGATGGGCACTCTAGGGAGACTGCCAGGGACAACCTGGAGG
AAGGTGGGGATGACGTCAAATCATCATGCCCCTTATGATTTGGGCTACACA
CGTGCTACAATGGCGTAAACAAAGGGAAGCGACCCTGCGAAGGTGAGCAA
ATCTCAAAAATAACGTCCCAGTTCGGACTGTAGTCTGCAACCCGACTACAC
GAAGCNNGAATCGCTAGTAATCGCGAATGAGAATGTCGCGGTGAATACGN
TCCCGGGTCTTGTACACACCGCCCGTCACACCATGGGAGTCAGCAACGNCC
GAAGTCAGTGACCCAACCGAAAGGAGGGAGNTGCNGAAGNNGNNNNN
``` strain 25 >1F3_27Fmod-PREMIX.fasta  SEQ ID NO: 25

```
AGTTTGANNTTGGCTCAGGATGAACGCTGGCGGCGTGCCTAACACATGCA
AGTCGAGCGAAGCGCTGTTTTCAGAATCTTCGGAGGAAGAGGACAGTGAC
TGAGCGGCGGACGGGTGAGTAACGCGTGGGCAACCTGCCTCATACAGGGG
GATAACAGTTAGAAATGACTGCTAATACCGCATAAGCGCACAGGACCGCA
TGGTGTAGTGTGAAAAACTCCGGTGGTATGAGATGGACCCGCGTCTGATTA
GGTAGTTGGTGGGGTAAAGGCCTACCAAGCCGACGATCAGTAGCCGACCT
GAGAGGGTGACCGGCCACATTGGGACTGAGACACGGCCCAAACTCCTACG
GGAGGCAGCAGTGGGGAATATTGCACAATGGGGGAAACCCTGATGCAGCG
ACGCCGCGTGAAGGAAGAAGTATTTCGGTATGTAAACTTCTATCAGCAGGG
AAGAAGATGACGGTACCTGAGTAAGAAGCACCGGCTAAATACGTGCCAGC
AGCCGCGGTAATACGTATGGTGCAAGCGTTATCCGGATTTACTGGGTGTAA
AGGGAGCGTAGACGGATAGGCAAGTCTGGAGTGAAAACCCAGGGCTCAAC
TCTGGGACTGCTTTGGAAACTGCAGATCTGGAGTGCCGGAGAGGTAAGCG
GAATTCCTAGTGTAGCGGTGAAATGCGTAGATATTAGGAGGAACACCAGT
GGCGAAGGCGGCTTACTGGACGGTGACTGACGTTGAGGCTCGAAAGCGTG
GGGAGCAAACAGGATTAGATACCCTGGTAGTCCACGCCGTAAACGATGAC
TACTAGGTGTCGGTGTGCAAAGCACATCGGTGCCGCAGCAAACGCAATAA
GTAGTCCACCTGGGGAGTACGTTCGCAAGAATGAAACTCAAAGGAATTGA
CGGGGACCCGCACAAGCGGTGGAGCATGTGGTTTAATTCGAAGCAACGCG
AAGAACCTTACCTGGTCTTGACATCCGGATGACGGGCGAGTAATGTCGCCG
TCCCTTCGGGGCATCCGAGACAGGTGGTGCATGGTTGTCGTCAGCTCGTGT
CGTGAGATGTTGGGTTAAGTCCCGCAACGAGCGCAACCCTTATCTTCAGTA
GCCAGCATATAAGGTGGGCACTCTGGAGAGACTGCCAGGGAGAACCTGGA
GGAAGGTGGGGATGACGTCAAATCATCATGCCCCTTATGGCCAGGGCTAC
ACACGTGCTACAATGGCGTAAACAAAGGGAAGCGAGAGGGTGACCTGAAG
```

-continued
```
CGAATCCCAAAAATAACGTCTCAGTTCGGATTGTAGTCTGCAACTCGACTA
CATGAAGCTGGAATCGCTAGTAATCGCGGATCAGCATGCCGCGGTGAATA
CGTTCCCGGGTCTTGTACACACCGCCCGTCACACCATGGGAGTCAGTAACG
CCCGAAGCCANTGACCCAACCTTAGAGGAGGGAGNNNNNNNNNNNNN
``` strain 26 1A1_27Fmod-PREMIX_Length_998

SEQ ID NO: 26
```
AGTTTGATTATGGCTCAGGATGAACGCTGGCGGCATGCCTAATACATGCA
AGTCGAACGAAGTTTCGAGGAAGCTTGCTTCCAAAGAGACTTAGTGGCGA
ACGGGTGAGTAACACGTAGGTAACCTGCCCATGTGTCCGGGATAACTGCTG
GAAACGGTAGCTAAAACCGGATAGGTATACAGAGCGCATGCTCAGTATAT
TAAAGCGCCCATCAAGGCGTGAACATGGATGGACCTGCGGCGCATTAGCT
AGTTGGTGAGGTAACGGCCCACCAAC3GCGATGATGCGTAGCCGGCCTGAG
AGGGTAAACGGCCACAITGGGACTGAGACACGGCCCAAACTCCTACGGGA
GGCAGCAGTAGGGAATTTTCGTCAATGGGGGAAACCCTGAACGAGCAATG
CCGCGTGAGTGAAGAAGGTCTTCGGATCGTAAAGCTCTGTTGTAAGTGAAG
AACGGCTCATAGAGGAAATGCTATGGGAGTGACGGTAGCTTACCAGAAAG
CCACGGCTAACTACGTGCCAGCAGCCGCGGTAATACGTAGGTGGCAAGCG
TTATCCGGAATCATTGGGCGTAAAGGGTGCGTAGGTGGCGTACTAAGTCTG
TAGTAAAAGGCAATGGCTCAACCATTGTAAGCTATGGAAACTGGTATGCTG
GAGTGCAGAAGAGGGCGATGGAATTCCATGTGTAGCGGTAAAATGCGTAG
ATATATGGAGGAACACCAGTGGCGAAGGCGGTCGCCTGGTCTGTAACTGA
CACTGAGGCACGAAAGCGTGGGGAGCAAATAGGATTAGATACCCTAGTAG
TCCACGCCGTAAACGATGAGAACTAAGTGTTGGAGGAATTCAGTGCTGCA
GTTAACGCAATAAGTTCTCCGCCTGGGGAGTATGCACGCAAGTGTGAAACT
CAAAGGAATTGACGGGGCCCGCACAAGCGGTGGAGTATGTGGTTTAATT
CGAAGCAACGCGAAGAACCTTACCAGGCCTTGACATGGAAACAAATACCC
TAGAGATAGGGGGATAATTATGGATCACACAGGTGGTGCATGGTTGTCGTC
AGCTCGTGTCGTGAGATGTTGGGTTAAGTCCCGCAACGAGCGCAACCCTTG
TCGCATGTTACCAGCATCAAGTTGGGGACTCATGCGAGACTGCCGGTGACA
AACCGGAGGAAGGTGGGGATGACGTCAAATCATCATGCCCCTTATGGCCT
GGGCTACACACGTACTACAATGGCGACCACAAAGAGCAGCGACACAGTGA
TGTGAAGCAATCTCATAAAGGTCGTCTCAGTTCGGATTGAAGTCTGCAAC
TCGACTTCATGAAGTCGGAATCGCTAGTAATCGCAGATCAGCATGCTGCGG
TGAATACGTTCTCGGGCCTTGTACACACCGCCCGTCAAACCATGGGAGTCA
GTAATACCCGAAGCCGGTGGCATAACCNTAAGGNNNNNCCNNNNNNA
```

SEQ ID NO:27 16S RNA sequence corresponding to LN998073

SEQ ID NO:28 16S RNA sequence corresponding to KR822463

SEQ ID NO:29 16S RNA sequence corresponding to CP011531

SEQ ID NO:30 16S RNA sequence corresponding to NR112945

SEQ ID NO:31 16S RNA sequence corresponding to KM098109

SEQ ID NO:32 16S RNA sequence corresponding to NR113078

SEQ ID NO:33 16S RNA sequence corresponding to NR041464

SEQ ID NO:34 16S RNA sequence corresponding to LT223566

SEQ ID NO:35 16S RNA sequence corresponding to NR112835

SEQ ID NO:36 16S RNA sequence corresponding to NR113248

SEQ ID NO:37 16S RNA sequence corresponding to NR041342

SEQ ID NO:38 16S RNA sequence corresponding to NR112933

SEQ ID NO:39 16S RNA sequence corresponding to NR112893

SEQ ID NO:40 16S RNA sequence corresponding to HE974918

SEQ ID NO:41 16S RNA sequence corresponding to NR043016

SEQ ID NO:42 16S RNA sequence corresponding to AB618791

SEQ ID NO:43 16S RNA sequence corresponding to AB215083

SEQ ID NO:44 16S RNA sequence corresponding to NR112935

SEQ ID NO:45 16S RNA sequence corresponding to AB249652

SEQ ID NO:46 16S RNA sequence corresponding to NR113076

SEQ ID NO:47 16S RNA sequence corresponding to NR112944

SEQ ID NO:48 16S RNA sequence corresponding to JX519760

SEQ ID NO:49 16S RNA sequence corresponding to AJ311620

SEQ ID NO:50 16S RNA sequence corresponding to EF564278

SEQ ID NO:51 16S RNA sequence corresponding to KT156811

SEQ ID NO:52 16S RNA sequence corresponding to HM008265

Additional sequences of interest are provided below:

H81A6_16S_ribosomal_RNA

SEQ ID NO: 54

CGAAGAGTTTGATCCTGGCTCAGGATGAACGCTGACAGAATGCTTAACAC

ATGCAAGTCTACTTGATCCTTCGGGTGAAGGTGGCGGACGGGTGAGTAACG

CGTAAAGAACTTGCCTTACAGACTGGGACAACATTTGGAAACGAATGCTA

ATACCGGATATTATGATTGGGTCGCATGATCTGATTATGAAAGCTATATGC

GCTGTGAGAGAGCTTTGCGTCCCATTAGTTAGTTGGTGAGGTAACGGCTCA

CCAAGACGATGATGGGTAGCCGGCCTGAGAGGGTGAACGGCCACAAGGGG

ACTGAGACACGGCCCTTACTCCTACGGGAGGCAGCAGTGGGGAATATTGG

ACAATGGACCAAAAGTCTGATCCAGCAATTCTGTGTGCACGAAGAAGTTTT

TCGGAATGTAAAGTGCTTTCAGTTGGGAAGAAGTCAGTGACGGTACCAAC

AGAAGAAGCGACGGCTAAATACGTGCCAGCAGCCGCGGTAATACGTATGT

CGCAAGCGTTATCCGGATTTATTGGGCGTAAAGCGCGTCTAGGCGGCTTAG

TAAGTCTGATGTGAAAATGCGGGGCTCAACCCCGTATTGCGTTGGAAACTG

CTAAACTAGAGTACTGGAGAGGTAGGCGGAACTACAAGTGTAGAGGTGAA

ATTCGTAGATATTTGTAGGAATGCCGATGGGGAAGCCAGCCTACTGGACAG

ATACTGACGCTAAAGCGCGAAAGCGTGGGTAGCAAACAGGATTAGATACC

CTGGTAGTCCACGCCGTAAACGATGATTACTAGGTGTTGGGGGTCGAACCT

CAGCGCCCAAGCTAACGCGATAAGTAATCCGCCTGGGGAGTACGTACGCA

AGTATGAAACTCAAAGGAATTGACGGGGACCCGCACAAGCGGTGGAGCAT

GTGGTTTAATTCGACGCAACGCGAGGAACCTTACCAGCGTTTGACATCCCA

AGAAGTTAACAGAGATGTTTTCGTGCCTCTTCGGAGGAACTTGGTGACAGG

TGGTGCATGGCTGTCGTCAGCTCGTGTCGTGAGATGTTGGGTTAAGTCCCG

CAACGAGCGCAACCCCTTTCGTATGTTACCATCATTAAGTTGGGGACTCAT

GCGAGACTGCCTGCGATGAGCAGGAGGAAGGTGGGGATGACGTCAAGTCA

TCATGCCCCTTATACGCTGGGCTACACACGTGCTACAATGGGTAGTACAGA

GAGCTGCAAACCTGCGAGGGTAAGCTAATCTCATAAAACTATTCTTAGTTC

GGATTGTACTCTGCAACTCGAGTACATGAAGTTGGAATCGCTAGTAATCGC

AAATCAGCTATGTTGCGGTGAATACGTTCTCGGGTCTTGTACACACCGCCC

GTCACACCACGAGAGTTGGTTGCACCTGAAGTAACAGGCCTAACCGTAAG

GAGGGATGTTCCGAGGGTGTGATTAGCGATTGGGGTGAAGTCGTAACAAG

GTATCCGTACGGGAACGTGCGGATGGATCACCTCCTT

H82F11_16S_ribosomal_RNA
SEQ ID NO: 55
CGAAGAGTTTGATCCTGGCTCAGGATGAACGCTAGCGACAGGCTTAACA

CATGCAAGTCGAGGGGCATCATGGTAAGTAGCAATACTTATTGATGGCGAC

CGGCGCACGGGTGAGTAACGCGTATGCAACTTACCTATCAGAGGGGGATA

GCCCGGCGAAAGTCGGATTAATACTCCATAAAACAGGGGTTCCGCATGGG

ACTATTTGTTAAAGATTCATCGCTGATAGATAGGCATGCGTTCCATTAGGC

AGTTGGCGGGGTAACGGCCCACCAAACCGACGATGGATAGGGGTTCTGAG

AGGAAGGTCCCCCACATTGGTACTGAGACACGGACCAAACTCCTACGGGA

GGCAGCAGTGAGGAATATTGGTCAATGGCCGAGAGGCTGAACCAGCCAAG

TCGCGTGAAGGATGAAGGATCTATGGTTTGTAAACTTCTTTTATAGGGAA

TAAAGTGTGGGACGTGTTCCATTTTGTATGTACCCTATGAATAAGCATCGG

CTAACTCCGTGCCAGCAGCCGCGGTAATACGGAGGATGCGAGCGTTATCCG

GATTTATTGGGTTTAAAGGGTGCGTAGGTGGTAATTTAAGTCAGCGGTGAA

AGTTTGTGGCTCAACCATAAAATTGCCGTTGAAACTGGGTTACTTGAGTGT

GTTTGAGGTAGGCGGAATGCGTGGTGTAGCGGTGAAATGCATAGATATCA

CGCAGAACTCCAATTGCGAAGGCAGCTTACTAAACCATAACTGACACTGA

AGCACGAAAGCGTGGGTATCAAACAGGATTAGATACCCTGGTAGTCCACG

CAGTAAACGATGATTACTAGGAGTTTGCGATACACAGTAAGCTCTACAGCG

AAAGCGTTAAGTAATCCACCTGGGGAGTACGCCGGCAACGGTGAAACTCA

AAGGAATTGACGGGGGCCCGCACAAGCGGAGGAACATGTGGTTTAATTCG

ATGATACGCGAGGAACCTTACCCGGGTTTGAACGTAGTCAGACCGACCTTG

AAAGAGGTTTTCTAGCAATAGCTGATTACGAGGTGCTGCATGGTTGTCGTC

AGCTCGTGCCGTGAGGTGTCGGCTTAAGTGCCATAACGAGCGCAACCCTTA

TCACTAGTTACTAACAGGTTAAGCTGAGGACTCTGGTGAGACTGCCAGCGT

AAGCTGTGAGGAAGGTGGGGATGACGTGAAATCAGCACGGCCCTTACATC

CGGGGCGACACACGTGTTACAATGGCATGGACAAAGGGCAGCTACCTGGC

GACAGGATGCTAATCTCTAAACCATGTCTCAGTTCGGATCGGAGTCTGCAA

CTCGACTCCGTGAAGCTGGATTCGCTAGTAATCGCGCATCAGCCATGGCGC

GGTGAATACGTTCCCGGGCCTTGTACACACCGCCCGTCAAGCCATGGGAGC

CGGGGGTACCTGAAGTCCGTAACCGCAAGGATCGGCCTAGGGTAAAACTG

GTGACTGGGGCTAAGTCGTAACAAGGTAGCCGTACCGGAAGGTGCGGCTG

GAACACCTCCTT

H82A6_16S_ribosomal_RNA
SEQ ID NO: 56
AATAAAGATTAATTGGTAAAGGATGGGGATGCGTCCCATTAGCTTGTTGG

CGGGGTAACGGCCCACCAAGGCGACGATGGGTAGGGGTTCTGAGAGGAAG

GTCCCCCACATTGGAACTGAGACACGGTCCAAACTCCTACGGGAGGCAGC

AGTGAGGAATATTGGTCAATGGGCGCGAGCCTGAACCAGCCAAGTAGCGT

GGAGGACGACGGCCCTACGGGTTGTAAACTCCTTTTATAAGGGGATAAAGT

TGGCCATGTATGGCCATTTGCAGGTACCTTATGAATAAGCATCGGCTAATT

-continued

```
CCGTGCCAGCAGCCGCGGTAATACGGAAGATGCGAGCGTTATCCGGATTTA

TTGGGTTTAAAGGGAGCGTAGGCGGGCAGTCAAGTCAGCGGTCAAATGGC

GCGGCTCAACCGCGTTCCGCCGTTGAAACTGGCAGCCTTGAGTATGCACAG

GGTACATGGAATTCGTGGTGTAGCGGTGAAATGCTTAGATATCACGAGGA

ACTCCGATCGCGCAGGCATTGTACCGGGGCATTACTGACGCTGAGGCTCGA

AGGTGCGGGTATCAAACAGGATTAGATACCCTGGTAGTCCGCACAGTAAA

CGATGAATGCCCGCTGTCGGCGACATAGTGTCGGCGGCCAAGCGAAAGCG

TTAAGCATTCCACCTGGGGAGTACGCCGGCAACGGTGAAACTCAAAGGAA

TTGACGGGGGCCCGCACAAGCGGAGGAACATGTGGTTTAATTCGATGATA

CGCGAGGAACCTTACCCGGGCTTGAATCGCAGGTGCATGGGCCGGAGACG

GCCCTTTCCTTCGGGACTCCTGCGAAGGTGCTGCATGGTTGTCGTCAGCTCG

TGCCGTGAGGTGTCGGCTTAAGTGCCATAACGAGCGCAACCCCCCTCCCCA

GTTGCCACCGGGTAATGCCGGGCACTTTGGGGACACTGCCACCGCAAGGTG

CGAGGAAGGTGGGGATGACGTCAAATCAGCACGGCCCTTACGTCCGGGGC

GACACACGTGTTACAATGGGGGGTACAGAGGGCCGCTGCCCGGTGACGGT

TGGCCAATCCCTAAAACCCCTCTCAGTTCGGACTGGAGTCTGCAACCCGAC

TCCACGAAGCTGGATTCGCTAGTAATCGCGCATCAGCCATGGCGCGGTGAA

TACGTTCCCGGGCCTTGTACACACCGCCCGTCAAGCCATGAAAGCCGGGGG

TGCCTGAAGTCCGTGACCGCGAGGGTCGGCCTAGGGTAAAACCGGTGATT

GGGGCTAAGTCGTAACAAGGTAGCCGTACCGGAAGGTGCGGCTGGAACAC

CTCCTTT
```

H82G9_16S_ribosomal_RNA SEQ ID NO: 57

```
CGAAGAGTTTGATCCTGGCTCAGGATGAACGCTAGCGACAGGCTTAACA

CATGCAAGTCGAGGGGCAGCACAGGTAGCAATACCGGGTGGCGACCGGCG

CACGGGTGAGTAACGCGTATGCAACTTGCCTATCAGAGGGGGATAACCCG

GCGAAAGTCGGACTAATACCGCATGAAGCAGGGGCCCCGCATGGGGATAT

TTGCTAAAGATTCATCGCTGATAGATAGGCATGCGTTCCATTAGGCAGTTG

GCGGGGTAACGGCCCACCAAACCGACGATGGATAGGGGTTCTGAGAGGAA

GGTCCCCCACATTGGTACTGAGACACGGACCAAACTCCTACGGGAGGCAG

CAGTGAGGAATATTGGTCAATGGCCGAGAGGCTGAACCAGCCAAGTCGCG

TGAGGGATGAAGGTTCTATGGATCGTAAACCTCTTTTATAAGGGAATAAAG

TGCGGGACGTGTCCCGTTTTGTATGTACCTTATGAATAAGGATCGGCTAAC

TCCGTGCCAGCAGCCGCGGTAATACGGAGGATCCGAGCGTTATCCGGATTT

ATTGGGTTTAAAGGGTGCGTAGGCGGCCTTTTAAGTCAGCGGTGAAAGTCT

GTGGCTCAACCATAGAATTGCCGTTGAAACTGGGGGCTTGAGTATGTTTG

AGGCAGGCGGAATGCGTGGTGTAGCGGTGAAATGCATAGATATCACGCAG

AACCCCGATTGCGAAGGCAGCCTGCCAAGCCATTACTGACGCTGATGCACG

AAAGCGTGGGGATCAAACAGGATTAGATACCCTGGTAGTCCACGCAGTAA

ACGATGATGACTAGCTGTTTGCGATACACTGTAAGCGGCACAGCGAAAGC

GTTAAGTGATCCACCTGGGGAGTACGCCGGCAACGGTGAAACTCAAAGGA

ATTGACGGGGGCCCGCACAAGCGGAGGAACATGTGGTTTAATTCGATGAT
```

ACGCGAGGAACCTTACCCGGGTTTGAACGCATTCGGACCGAGGTGGAAAC

ACCTTTTCTAGCAATAGCCGTTTGCGAGGTGCTGCATGGTTGTCGTCAGCTC

GTGCCGTGAGGTGTCGGCTTAAGTGCCATAACGAGCGCAACCCTTGCCACT

AGTTACTAACAGGTAAAGCTGAGGACTCTGGTGGGACTGCCAGCGTAAGC

TGCGAGGAAGGCGGGGATGACGTCAAATCAGCACGGCCCTTACATCCGGG

GCGACACACGTGTTACAATGGCGTGGACAAAGGGAAGCCACCTGGCGACA

GGGAGCGAATCCCCAAACCACGTCTCAGTTCGGATCGGAGTCTGCAACCCG

ACTCCGTGAAGCTGGATTCGCTAGTAATCGCGCATCAGCCATGGCGCGGTG

AATACGTTCCCGGGCCTTGTACACACCGCCCGTCAAGCCATGGGAGCCGGG

GGTACCTGAAGTCCGTAACCGCGAGGATCGGCCTAGGGTAAAACTGGTGA

CTGGGGCTAAGTCGTAACAAGGTAGCCGTACCGGAAGGTGCGGCTGGAAC

ACCTCCTTT

H81E7_16S_ribosomal_RNA                                SEQ ID NO: 58
ATGGAGAGTTTGATCCTGGCTCAGGATGAACGCTAGCGGCAGGCCTAAC

ACATGCAAGTCGAGGGGCAGCGGGATTGAAGCTTGCTTCAGTTGCCGGCG

ACCGGCGCACGGGTGCGTAACGCGTATGCAACCTACCCATAACAGGGGGA

TAACACTGAGAAATCGGTACTAATATCCCATAACATCAAGAGGGGCATCCC

TTTTGGTTGAAAACTCCGGTGGTTATGGATGGGCATGCGTTGTATTAGCTA

GTTGGTGAGGTAACGGCTCACCAAGGCGACGATACATAGGGGACTGAGA

GGTTAACCCCCCACATTGGTACTGAGACACGGACCAAACTCCTACGGGAG

GCAGCAGTGAGGAATATTGGTCAATGGACGCAAGTCTGAACCAGCCATGC

CGCGTGCAGGATGACGGCTCTATGAGTTGTAAACTGCTTTTGTACGAGGGT

AAACCCGGATACGTGTATCCGGCTGAAAGTATCGTACGAATAAGGATCGG

CTAACTCCGTGCCAGCAGCCGCGGTAATACGGAGGATTCAAGCGTTATCCG

GATTTATTGGGTTTAAAGGGTGCGTAGGCGGTTTGATAAGTTAGAGGTGAA

ATACCGGTGCTTAACACCGGAACTGCCTCTAATACTGTTGAGCTAGAGAGT

AGTTGCGGTAGGCGAATGTATGGTGTAGCGGTGAAATGCTTAGAGATCAT

ACAGAACACCGATTGCGAAGGCAGCTTACCAAACTATATCTGACGTTGAG

GCACGAAAGCGTGGGGAGCAAACAGGATTAGATACCCTGGTAGTCCACGC

AGTAAACGATGATAACTCGCTGTCGGCGATACACAGTCGGTGGCTAAGCG

AAAGCGATAAGTTATCCACCTGGGGAGTACGTTCGCAAGAATGAAACTCA

AAGGAATTGACGGGGCCCGCACAAGCGGAGGAACATGTGGTTTAATTCG

ATGATACGCGAGGAACCTTACCCGGGCTTGAAAGTTACTGACGATTCTGGA

AACAGGATTTCCCTTCGGGGCAGGAAACTAGGTGCTGCATGGTTGTCGTCA

GCTCGTGCCGTGAGGTGTCGGGTTAAGTCCCATAACGAGCGCAACCCCTAC

CGTTAGTTGCCATCAGGTCAAGCTGGGCACTCTGGCGGGACTGCCGGTGTA

AGCCGAGAGGAAGGTGGGGATGACGTCAAATCAGCACGGCCCTTACGTCC

GGGGCTACACACGTGTTACAATGGTAGGTACAGAGGGCAGCTACCCAGTG

ATGGGATGCGAATCTCGAAAGCCTATCTCAGTTCGGATTGGAGGCTGAAAC

CCGCCTCCATGAAGTTGGATTCGCTAGTAATCGCGCATCAGCCATGGCGCG

-continued

GTGAATACGTTCCCGGGCCTTGTACACACCGCCCGTCAAGCCATGGAAGCT

GGGGGTGCCTGAAGTTCGTGACCGCAAGGAGCGACCTAGGGCAAAACCGG

TGACTGGGGCTAAGTCGTAACAAGGTAGCCGTACCGGAAGGTGCGGCTGG

AACACCTCCTTT

H81C1_16S_ribosomal_RNA
SEQ ID NO: 59

TATTGAGAGTTTGATCCTGGCTCAGGACGAACGCTGGCGGTATGCTTAAC

ACATGCAAGTCGAACGAGAAGGTTTTGATGGATCCTTCGGGTGATATCAGA

ACTGGAAAGTGGCGAACGGGTGAGTAACGCGTGGGTAACCTGCCCTATGG

AAAGGAATAGCCTCGGGAAACTGGGAGTAAAGCCTTATATTATGGTTTTGT

CGCATGGCAAGATCATGAAAACTCCGGTGCCATAGGATGGACCCGCGTCC

CATTAGCTAGTTGGTGAGATAACAGCCCACCAAGGCGACGATGGGTAACC

GGTCTGAGAGGGCGAACGGTCACACTGGAACTGAGACACGGTCCAGACTC

CTACGGGAGGCAGCAGTGGGGAATATTGCGCAATGGGGGCAACCCTGACG

CAGCAATACCGCGTGAGTGAAGAAGGTTTTCGGATCGTAAAGCTCTGTTAT

TGGGGAAGAAGAATGACGGTACCCAATGAGGAAGTCCCGGCTAACTACGT

GCCAGCAGCCGCGGTAATACGTAGGGGACAAGCGTTGTCCGGAATGACTG

GGCGTAAAGGGCGCGTAGGCGGTCTATTAAGTCTGATGTGAAAGGTACCG

GCTCAACCGGTGAAGTGCATTGGAAACTGGTAGACTTGAGTATTGGAGAG

GCAAGTGGAATTCCTAGTGTAGCGGTGAAATGCGTAGATATTAGGAGGAA

CACCAGTGGCGAAGGCGGCTTGCTGGACAAATACTGACGCTGAGGTGCGA

AAGCGTGGGGAGCGAACAGGATTAGATACCCTGGTAGTCCACGCCGTAAA

CGATGAATGCTAGGTGTTGGGGAAACTCAGTGCCGCAGTTAACACAATAA

GCATTCCGCCTGGGGAGTACGACCGCAAGGTTGAAACTCAAAGGAATTGA

CGGGGACCCGCACAAGCAGCGGAGCATGTGGTTTAATTCGAAGCAACGCG

AAGAACCTTACCAGGTCTTGACATCCTCTGACGAGCCTAGAGATAGGAAGT

TTCCTTCGGGAACAGAGAGACAGGTGGTGCATGGTTGTCGTCAGCTCGTGT

CGTGAGATGTTGGGTTAAGTCCCGCAACGAGCGCAACCCCTGCCTTTAGTT

GCCAGCATTAAGTTGGGCACTCTAGAGGGACTGCCGTAGACAATACGGAG

GAAGGTGGGGACGACGTCAAATCATCATGCCCCTTATGACCTGGGCTACAC

ACGTGCTACAATGGTCTGAACAGAGGGCCGGGAAGCCGCGAGGTGAAGCA

AATCCCTTAAAACAGATCCCAGTTCGGATTGCAGGCTGCAACTCGCCTGCA

TGAAGTTGGAGTTGCTAGTAATCGCGGATCAGAATGCCGCGGTGAATGCGT

TCCCGGGTCTTGTACACACCGCCCGTCACACCACGAGAGTTGGCAACACCC

GAAGCCTGTGAGAGAACCGTAAGGACTCAGCAGTCGAAGGTGGGGCTAGT

AATTGGGGTGAAGTCGTAACAAGGTAGCCGTATCGGAAGGTGCGGCTGGA

TCACCTCCTTT

H81B11_16S_ribosomal_RNA
SEQ ID NO: 60

ATGAAGAGTTTGATCCTGGCTCAGGATGAACGCTAGCTACAGGCTTAACA

CATGCAAGTCGAGGGGCAGCATGGTCTTAGCTTGCTAAGGCTGATGGCGAC

CGGCGCACGGGTGAGTAACACGTATCCAACCTGCCGTCTACTCTTGGCCAG

CCTTCTGAAAGGAAGATTAATCCAGGATGGGATCATGAGTTCACATGTCCG

-continued

```
CATGATTAAAGGTATTTTCCGGTAGACGATGGGGATGCGTTCCATTAGATA

GTAGGCGGGGTAACGGCCCACCTAGTCAACGATGGATAGGGGTTCTGAGA

GGAAGGTCCCCCACATTGGAACTGAGACACGGTCCAAACTCCTACGGGAG

GCAGCAGTGAGGAATATTGGTCAATGGGCGATGGCCTGAACCAGCCAAGT

AGCGTGAAGGATGACTGCCCTATGGGTTGTAAAGTTCTTTTATAAAGGAAT

AAAGTCGGGTATGCATACCCGTTTGCATGTACTTTATGAATAAGGATCGGC

TAACTCCGTGCCAGCAGCCGCGGTAATACGGAGGATCCGAGCGTTATCCGG

ATTTATTGGGTTTAAAGGGAGCGTAGATGGATGTTTAAGTCAGTTGTGAAA

GTTTGCGGCTCAACCGTAAAATTGCAGTTGATACTGGATGTCTTGAGTGCA

GTTGAGGCAGGCGGAATTCGTGGTGTAGCGGTGAAATGCTTAGATATCACG

AAGAACTCCGATTGCGAAGGCAGCCTGCTAAGCTGCAACTGACATTGAGG

CTCGAAAGTGTGGGTATCAAACAGGATTAGATACCCTGGTAGTCCACACGG

TAAACGATGAATACTCGCTGTTTGCGATATACGGCAAGCGGCCAAGCGAA

AGCGTTAAGTATTCCACCTGGGGAGTACGCCGGCAACGGTGAAACTCAAA

GGAATTGACGGGGGCCCGCACAAGCGGAGGAACATGTGGTTTAATTCGAT

GATACGCGAGGAACCTTACCCGGGCTTAAATTGCACTCGAATGATCCGGAA

ACGGTTCAGCTAGCAATAGCGAGTGTGAAGGTGCTGCATGGTTGTCGTCAG

CTCGTGCCGTGAGGTGTCGGCTTAAGTGCCATAACGAGCGCAACCCTTGTT

GTCAGTTACTAACAGGTGATGCTGAGGACTCTGACAAGACTGCCATCGTAA

GATGTGAGGAAGGTGGGGATGACGTCAAATCAGCACGGCCCTTACGTCCG

GGGCTACACACGTGTTACAATGGGGGGTACAGAGGGCCGCTACCACGCGA

GTGGATGCCAATCCCTAAAACCCCTCTCAGTTCGGACTGGAGTCTGCAACC

CGACTCCACGAAGCTGGATTCGCTAGTAATCGCGCATCAGCCACGGCGCGG

TGAATACGTTCCCGGGCCTTGTACACACCGCCCGTCAAGCCATGGGAGCCG

GGGGTACCTGAAGTGCGTAACCGCGAGGATCGCCCTAGGGTAAAACTGGT

GACTGGGGCTAAGTCGTAACAAGGTAGCCGTACCGGAAGGTGCGGCTGGA

ACACCTCCTT
```

H81H9_16S_ribosomal_RNA

SEQ ID NO: 61

```
CGAAGAGTTTGATCCTGGCTCAGGATGAACGCTAGCGACAGGCTTAACA

CATGCAAGTCGAGGGGCAGCAGGAAGTAGCAATACTTTGCTGGCGACCGG

CGCACGGGTGAGTAACGCGTATGCAACCTACCTATCAGAGGGGGATAACC

CGGCGAAAGTCGGACTAATACCGCATAAAACAGGGGTCCCGCATGGGAAT

ATTTGTTAAAGATTTATTGCTGATAGATGGGCATGCGTTCCATTAGATAGTT

GGTGAGGTAACGGCTCACCAAGTCTTCGATGGATAGGGGTTCTGAGAGGA

AGGTCCCCCACACTGGTACTGAGACACGGACCAGACTCCTACGGGAGGCA

GCAGTGAGGAATATTGGTCAATGGGCGAGAGCCTGAACCAGCCAAGTCGC

GTGAAGGATGAAGGATCTATGGTTCGTAAACTTCTTTTATAGGGGAATAAA

GTGCAGGACGTGTCCTGTTTTGTATGTACCCTATGAATAAGGATCGGCTAA

CTCCGTGCCAGCAGCGGCGGTAATACGGAGGATCCGAGCGTTATCCGGATT

TATTGGGTTTAAAGGGTGCGTAGGTGGCTTTTTAAGTCAGCGGTGAAAGTT
```

-continued

TGTGGCTCAACCATAAAATTGCCGTTGAAACTGGAGGGCTTGAGTATATTT
GAGGTAGGCGGAATGCGTGGTGTAGCGGTGAAATGCATAGATATCACGCA
GAACTCCAATTGCGAAGGCAGCTTACTAAACTATAACTGACACTGAAGCAC
GAAAGCGTGGGGATCAAACAGGATTAGATACCCTGGTAGTCCACGCAGTA
AACGATGATTACTAGGAGTTTGCGATACACAGTAAGCTCTACAGCGAAAG
CGTTAAGTAATCCACCTGGGGAGTACGCCGGCAACGGTGAAACTCAAAGG
AATTGACGGGGGCCCGCACAAGCGGAGGAACATGTGGTTTAATTCGATGA
TACGCGAGGAACCTTACCCGGGTTTGAACGTAAGTTGACCGGAGTGGAAA
CACTCTTTCTAGCAATAGCAATTTACGAGGTGCTGCATGGTTGTCGTCAGCT
CGTGCCGTGAGGTGTCGGCTTAAGTGCCATAACGAGCGCAACCCTTATCTT
TAGTTACTAACAGGTCGAGCTGAGGACTCTAAAGAGACTGCCAGCGTAAG
CTGTGAGGAAGGTGGGGATGACGTCAAATCAGCACGGCCCTTACATCCGG
GGCGACACACGTGTTACAATGGTGGGGACAAAGGGCAGCTACCTGGCGAC
AGGATGCTAATCTCCAAACCCCATCTCAGTTCGGATCGAAGTCTGCAACCC
GACTTCGTGAAGCTGGATTCGCTAGTAATCGCGCATCAGCCATGGCGCGGT
GAATACGTTCCCGGGCCTTGTACACACCGCCCGTCAAGCCATGGGAGTTGG
GGGTACCTAAAGTCCGTAACCGCAAGGATCGGCCTAGGGTAAAACCGATG
ACTGGGGCTAAGTCGTAACAAGGTAGCCGTACCGGAAGGTGCGGCTGGAA
CACCTCCTTT

H82B1_16S_ribosomal_RNA
SEQ ID NO: 62
AATGAAGAGTTTGATCCTGGCTCAGGACGAACGCTGGCGGCGCGCCTAA
CACATGCAAGTCGAACGGAGCTGTTTTCTCTGAAGTTTTCGGATGGAAGAG
AGTTCAGCTTAGTGGCGAACGGGTGAGTAACACGTGAGCAACCTGCCTTTC
AGTGGGGGACAACATTTGGAAACGAATGCTAATACCGCATAAGACCACAG
TGTCGCATGGCACAGGGGTCAAAGGATTTATCCGCTGAAAGATGGGCTCGC
GTCCGATTAGCTAGATGGTGAGGTAACGGCCCACCATGGCGACGATCGGT
AGCCGGACTGAGAGGTTGAACGGCCACATTGGGACTGAGACACGGCCCAG
ACTCCTACGGGAGGCAGCAGTGGGGAATATTGCACAATGGGGGAAACCCT
GATGCAGCGACGCCGCGTGGAGGAAGAAGGTCTTCGGATTGTAAACTCCT
GTCCCAGGGGACGATAATGACGGTACCCTGGGAGGAAGCACCGGCTAACT
ACGTGCCAGCAGCCGCGGTAAAACGTAGGGTGCAAGCGTTGTCCGGAATT
ACTGGGTGTAAAGGGAGCGCAGGCGGATTGGCAAGTTGGGAGTGAAATCT
ATGGGCTCAACCCATAAATTGCTTTCAAAACTGTCAGTCTTGAGTGGTGTA
GAGGTAGGCGGAATTCCCGGTGTAGCGGTGGAATGCGTAGATATCGGGAG
GAACACCAGTGGCGAAGGCGGCCTACTGGGCACTAACTGACGCTGAGGCT
CGAAAGCATGGGTAGCAAACAGGATTAGATACCCTGGTAGTCCATGCCGT
AAACGATGATTACTAGGTGTGGGAGGATTGACCCCTTCCGTGCCGCAGTTA
ACACAATAAGTAATCCACCTGGGGAGTACGACCGCAAGGTTGAAACTCAA
AGGAATTGACGGGGGCCCGCACAAGCAGTGGAGTATGTGGTTTAATTCGA
AGCAACGCGAAGAACCTTACCAGGTCTTGACATCGGATGCATACCTAAGA
GATTAGGGAAGTCCTTCGGGACATCCAGACAGGTGGTGCATGGTTGTCGTC -continued

AGCTCGTGTCGTGAGATGTTGGGTTAAGTCCCGCAACGAGCGCAACCCTTA

TCGTTAGTTACTACGCAAGAGGACTCTAGCGAGACTGCCGTTGACAAAACG

GAGGAAGGTGGGGATGACGTCAAATCATCATGCCCTTTATGACCTGGGCTA

CACACGTACTACAATGGCTATTAACAGAGAGAAGCGATACCGCGAGGTGG

AGCAAACCTCACAAAAATAGTCTCAGTTCGGATCGCAGGCTGCAACCCGCC

TGCGTGAAGCCGGAATTGCTAGTAATCGCGGATCAGCATGCCGCGGTGAAT

ACGTTCCCGGGCCTTGTACACACCGCCCGTCACACCATGAGAGCCGGGGGG

ACCCGAAGTCGGTAGTCTAACCGCAAGGAGGACGCCGCCGAAGGTAAAAC

TGGTGATTGGGGTGAAGTCGTAACAAGGTAGCCGTATCGGAAGGTGCGGC

TGGATCACCTCCTTT

H82G1_16S_ribosomal_RNA
SEQ ID NO: 63
ATGAAGAGTTTGATCCTGGCTCAGGATGAACGCTAGCTACAGGCTTAACA

CATGCAAGTCGAGGGGCAGCATGAACTTAGCTTGCTAAGTTTGATGGCGAC

CGGCGCACGGGTGAGTAACACGTATCCAACCTGCCGATGACTCGGGGATA

GCCTTTCGAAAGAAAGATTAATACCCGATGGCATAGTTCTTTCCGCATGGTG

GAACTATTAAAGAATTTCGGTCATCGATGGGGATGCGTTCCATTAGGTTGT

TGGCGGGGTAACGGCCCACCAAGCCTTCGATGGATAGGGGTTCTGAGAGG

AAGGTCCCCCACATTGGAACTGAGACACGGTCCAAACTCCTACGGGAGGC

AGCAGTGAGGAATATTGGTCAATGGACGAGAGTCTGAACCAGCCAAGTAG

CGTGAAGGATGACTGCCCTATGGGTTGTAAACTTCTTTTATACGGGAATAA

AGTGAGGCACGTGTGCCTTTTTGTATGTACCGTATGAATAAGGATCGGCTA

ACTCCGTGCCAGCAGCCGCGGTAATACGGAGGATCCGAGCGTTATCCGGAT

TTATTGGGTTTAAAGGGAGCGTAGGCGGACGCTTAAGTCAGTTGTGAAAGT

TTGCGGCTCAACCGTAAAATTGCAGTTGATACTGGGTGTCTTGAGTACAGT

AGAGGCAGGCGGAATTCGTGGTGTAGCGGTGAAATGCTTAGATATCACGA

AGAACTCCGATTGCGAAGGCAGCCTGCTGGACTGTAACTGACGCTGATGCT

CGAAAGTGTGGGTATCAAACAGGATTAGATACCCTGGTAGTCCACACAGT

AAACGATGAATACTCGCTGTTTGCGATATACAGTAAGCGGCCAAGCGAAA

GCGTTAAGTATTCCACCTGGGGAGTACGCCGGCAACGGTGAAACTCAAAG

GAATTGACGGGGCCCGCACAAGCGGAGGAACATGTGGTTTAATTCGATG

ATACGCGAGGAACCTTACCCGGGCTTGAATTGCAACTGAATGATGTGGAG

ACATGTCAGCCGCAAGGCAGTTGTGAAGGTGCTGCATGGTTGTCGTCAGCT

CGTGCCGTGAGGTGTCGGCTTAAGTGCCATAACGAGCGCAACCCTTATCGA

TAGTTACCATCAGGTGATGCTGGGACTCTGTCGAGACTGCCGTCGTAAGA

TGTGAGGAAGGTGGGGATGACGTCAAATCAGCACGGCCCTTACGTCCGGG

GCTACACACGTGTTACAATGGGGGGTACAGAAGGCAGCTACACGGCGACG

TGATGCTAATCCCGAAAGCCTCTCTCAGTTCGGATTGGAGTCTGCAACCCG

ACTCCATGAAGCTGGATTCGCTAGTAATCGCGCATCAGCCACGGCGCGGTG

AATACGTTCCCGGGCCTTGTACACACCGCCCGTCAAGCCATGAAAGCCGGG

GGTACCTGAAGTGCGTAACCGCAAGGAGCGCCCTAGGGTAAAACTGGTGA

-continued
TTGGGGCTAAGTCGTAACAAGGTAGCCGTACCGGAAGGTGCGGCTGGAAC

ACCTCCTT

H82G5_16S_ribosomal_RNA
SEQ ID NO: 64
ATTGGAGAGTTTGATCCTGGCTCAGGACGAACGCTGGCGGCGTGCCTAAC

ACATGCAAGTCGAACGGAGAATTTTATTTCGGTAGAATTCTTAGTGGCGAA

CGGGTGAGTAACGCGTAGGCAACCTACCCTTTAGACGGGGACAACATTCC

GAAAGGAGTGCTAATACCGGATGTGATCATCTTGCCGCATGGCAGGATGA

AGAAAGATGGCCTCTACAAGTAAGCTATCGCTAAAGGATGGGCCTGCGTCT

GATTAGCTAGTTGGTAGTGTAACGGACTACCAAGGCGATGATCAGTAGCCG

GTCTGAGAGGATGAACGGCCACATTGGGACTGAGACACGGCCCAAACTCC

TACGGGAGGCAGCAGTGGGGAATCTTCCGCAATGGACGAAAGTCTGACGG

AGCAACGCCGCGTGAGTGATGAAGGATTTCGGTCTGTAAAGCTCTGTTGTT

TATGACGAACGTGCAGTGTGTGAACAATGCATTGCAATGACGGTAGTAAA

CGAGGAAGCCACGGCTAACTACGTGCCAGCAGCCGCGGTAATACGTAGGT

GGCGAGCGTTGTCCGGAATTATTGGGCGTAAAGAGCATGTAGGCGGCTTA

ATAAGTCGAGCGTGAAAATGCGGGGCTCAACCCCGTATGGCGCTGGAAAC

TGTTAGGCTTGAGTGCAGGAGAGGAAAGGGGAATTCCCAGTGTAGCGGTG

AAATGCGTAGATATTGGGAGGAACACCAGTGGCGAAGGCGCCTTTCTGGA

CTGTGTCTGACGCTGAGATGCGAAAGCCAGGGTAGCGAACGGGATTAGAT

ACCCCGGTAGTCCTGGCCGTAAACGATGGGTACTAGGTGTAGGAGGTATCG

ACCCCTTCTGTGCCGGAGTTAACGCAATAAGTACCCCGCCTGGGGAGTACG

GCCGCAAGGTTGAAACTCAAAGGAATTGACGGGGGCCCGCACAAGCGGTG

GAGTATGTGGTTTAATTCGACGCAACGCGAAGAACCTTACCAAGGCTTGAC

ATTGATTGAACGCTCTAGAGATAGAGATTTCCCTTCGGGGACAAGAAAACA

GGTGGTGCATGGCTGTCGTCAGCTCGTGTCGTGAGATGTTGGGTTAAGTCC

CGCAACGAGCGCAACCCCTATCCTATGTTACCAGCAAGTAAAGTTGGGGAC

TCATGGGAGACTGCCAGGGACAACCTGGAGGAAGGCGGGGATGACGTCAA

GTCATCATGCCCCTTATGTCTTGGGCTACACACGTACTACAATGGTCGGAA

ACAGAGGGAAGCGAAGCCGCGAGGCAGAGCAAACCCCAGAAACCCGATC

TCAGTTCGGATCGCAGGCTGCAACCCGCCTGCGTGAAGTCGGAATCGCTAG

TAATCGCAGGTCAGCATACTGCGGTGAATACGTTCCCGGGCCTTGTACACA

CCGCCCGTCACACCACGAAAGTTGGTAACACCCGAAGCCGGTGAGGTAAC

CTATTAGGAGCCAGCCGTCTAAGGTGGGGCCGATGATTGGGGTGAAGTCGT

AACAAGGTAGCCGTATCGGAAGGTGCGGCTGGATCACCTCCTTT

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Identification of a CD8+ T-Cell Inducing Bacterial Cocktail

Figure 1B:
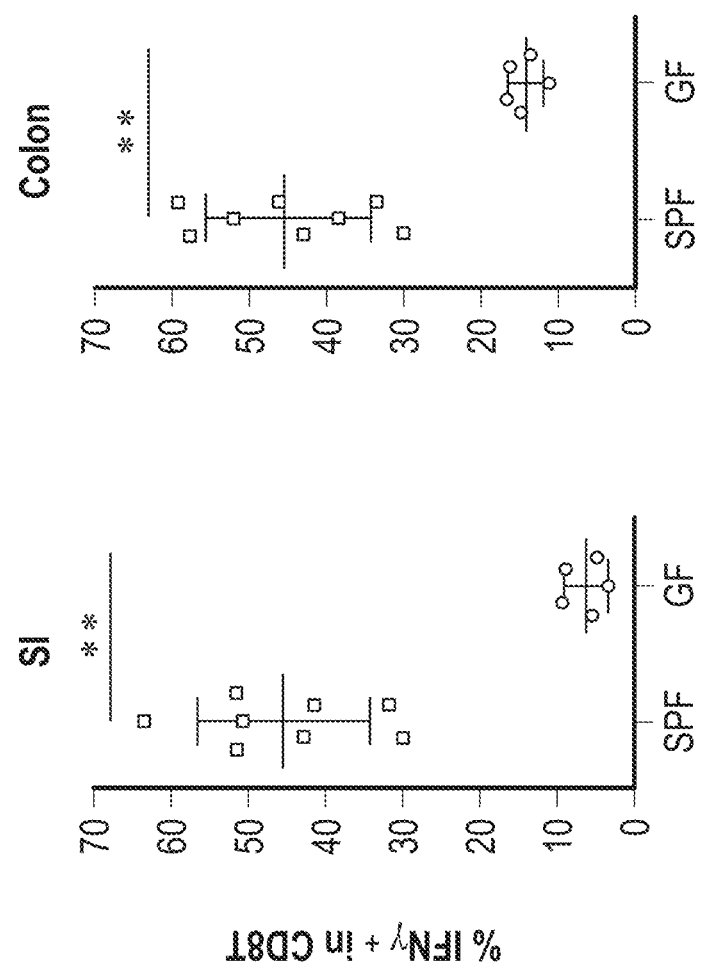
Figure 3B:
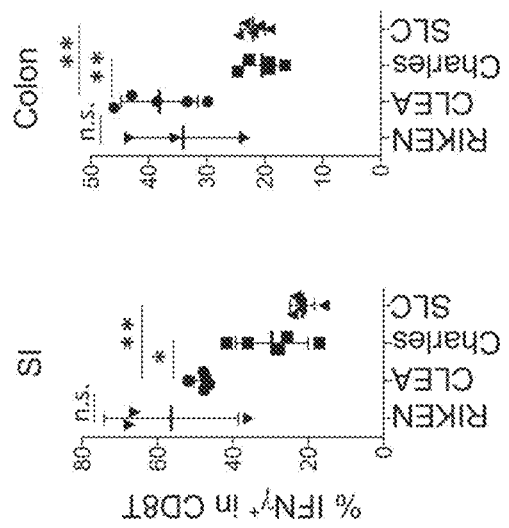
FIGS. 3A and 3B show data of experiments with lymphocytes that were isolated from small intestine (SI) and large intestine (Colon) mucosal lamina propria of SPF mice delivered from different laboratory animal facilities and stimulated with PMA/ionomycin for 3.5 hours. CD3, TCRβ, CD8 and IFNγ were stained with antibodies and analyzed by flow cytometry.
Figure 3A:
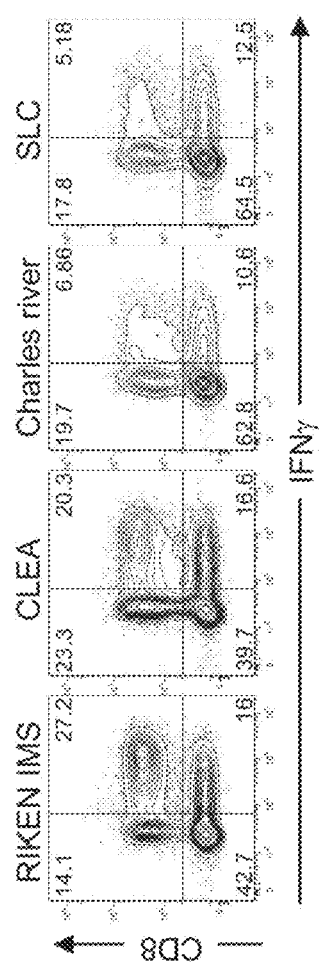

C57BL/6 mice kept under specific-pathogen free (SPF) conditions which possess resident microbiota have abundant IFNγ+CD8+ T-cells, whereas markedly few IFNγ+CD8+ T-cells were found in intestinal lamina propria of germ free mice (See FIG. 1). This indicates that gut microbiota induces the accumulation of IFNγ+CD8+ T-cells. A subset of IFNγ+CD8+ T cells also expressed CD103 as well as GranzymeB (see FIG. 2A), suggesting that the subset was tissue-resident memory T cells. FIG. 3A shows that remarkably small numbers of IFNγ+CD8+ T-cells were found in SPF C57BL/6 mice purchased from Charles River Laboratories Inc. and Japan SLC Inc. as compared to SPF C57BL/6 mice purchased from CLEA Japan Inc. and mice bred in RIKEN. When SPF C57BL/6 mice from Charles River Laboratories Inc. were cohoused together with CLEA mice in the same cage, an increase of IFNγ+CD8+ T-cells was observed in mice delivered from Charles River Laboratories Inc. (FIGS. 4A and 4B). This finding strongly supports a hypothesis that there are specific microbial species in the mouse microbiota which induce and accumulate IFNγ+CD8+ T cells in the intestine.

Next, it was investigated whether the human gut microbiota contained microbes which were able to induce IFNγ+CD8+ T cells. Stool samples were collected from six healthy human volunteers (A-F). The samples were individually administered orally into germ free C57BL/6 mice kept in sterile isolators (five or six mice per group). Four weeks after oral inoculation of stool samples, mice were sacrificed, and small intestine and colons were harvested and investigated for IFNγ+CD8+ T-cells by FACS.

Figure 5B:
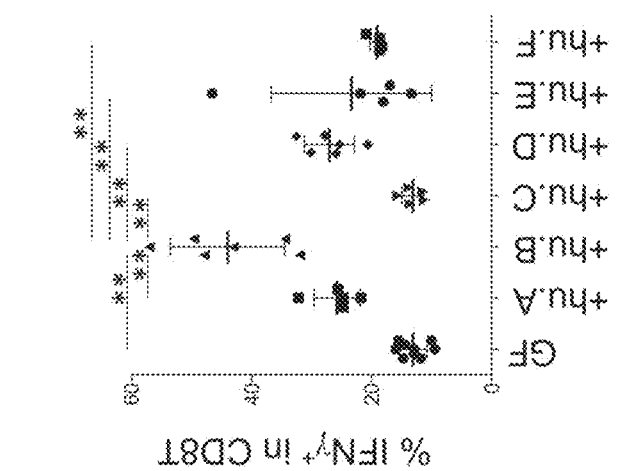
FIGS. 5A and 5B show data of experiments with stools from healthy volunteers (A-F) which were orally administered into germ free mice individually in sterile vinyl isolators. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry.
Figure 5A:
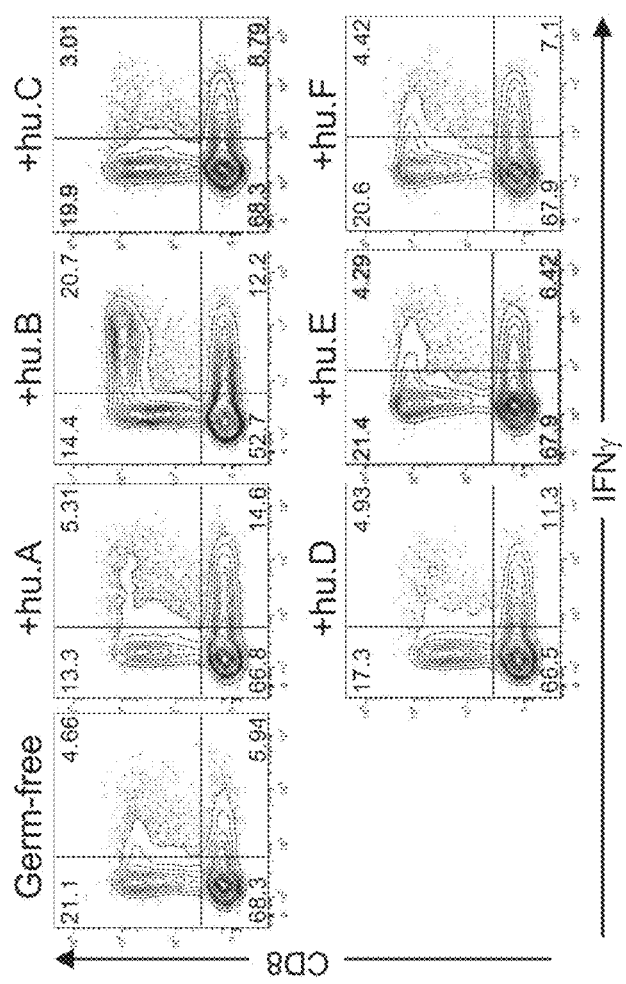
Figure 6A:
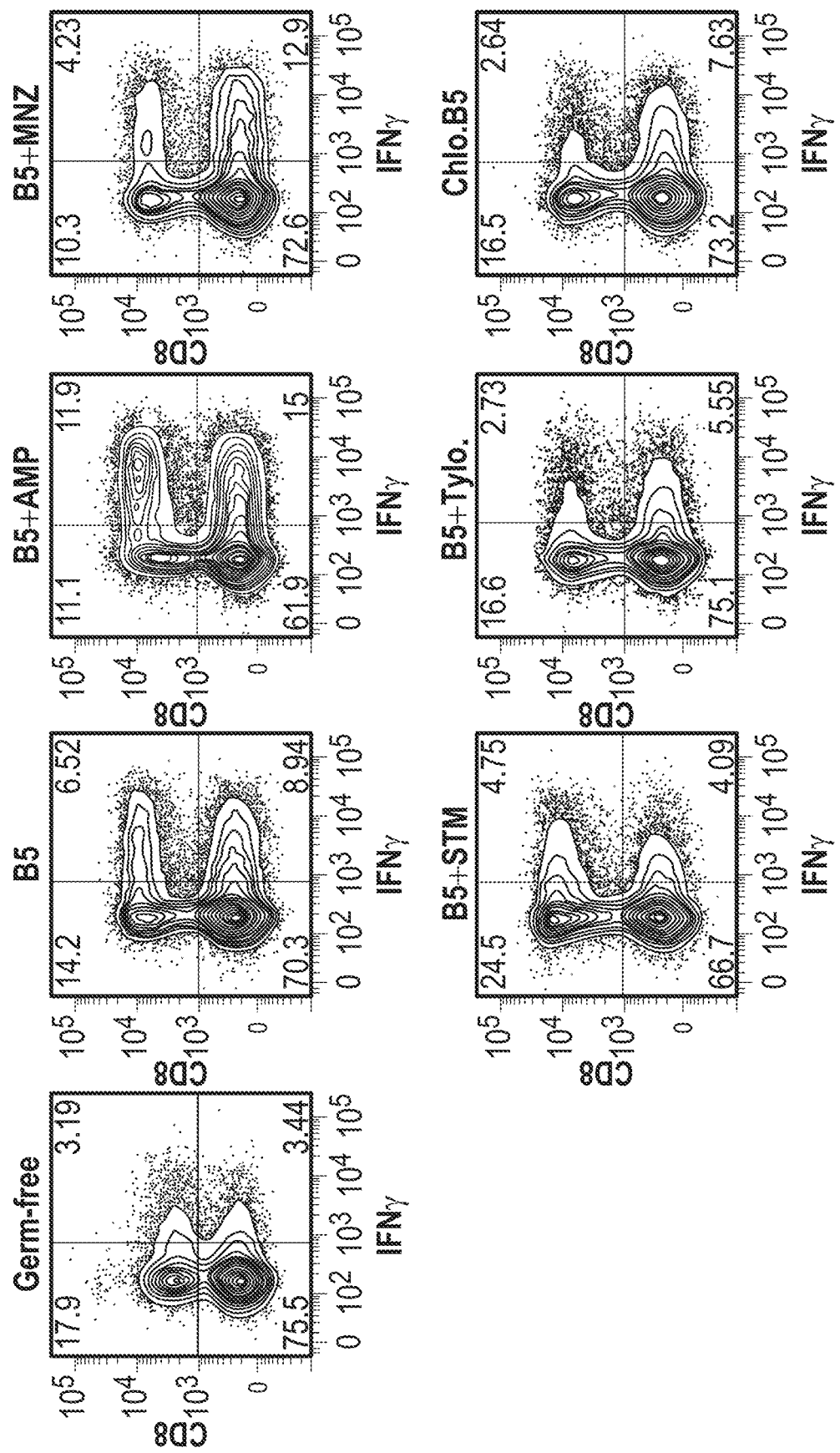
FIGS. 6A and 6B show data of experiments with the cecal contents of B #5 mouse, which was orally administered to germ free mice. One day later, their drinking waters were switched to ampicillin (AMP), metronidazole (MNZ), streptomycin (STM) or tylosin (Tylo.) until the end of experiment. The contents of the cecum of B #5 treated with 3% of chloroform were administered to germ free mice. Four weeks later, lymphocytes were isolated from the lamina propria of the large intestine and stimulated with PMA/ionomycin for 3.5 hours. CD3, TCRβ, CD8. IFNγ were stained with antibodies and analyzed by flow cytometry.
Figure 6B:
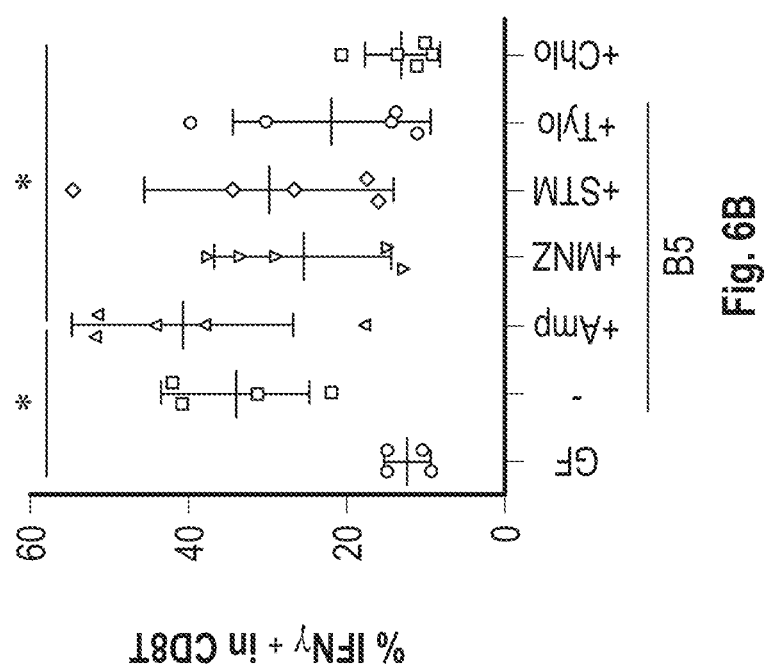

As shown in FIGS. 5A and 5B, colonic IFNγ+CD8+ T-cells were most remarkably induced in mice inoculated with a stool sample collected from donor B. Among mice inoculated with the donor B stool sample, we selected a mouse that exhibited the highest frequency of IFNγ+CD8+ T cells (called 'mouse B #5' hereafter). In order to concentrate microbes responsible for IFNγ+CD8+ T cell induction, cecal contents were collected from the mouse B #5 and inoculated into another germ-free mouse. The mice were then orally administrated drinking water with or without Ampicillin, Metronidazole, Streptomycin or Tylosin (five mice per group). Alternatively, cecal contents of mouse B #5 were treated with 3% chloroform and orally inoculated into another five germ-free mice ('B #5+Chrolo'). FIGS. 6A and 6B show that Ampicillin treatment enhanced induction of colonic lamina propria IFNγ+CD8+ T-cells by the mouse B #5 microbiota, whereas other antibiotics treatment or chloroform treatment reduced the induction capability of IFNγ+CD8+ T-Cells by the mouse B #5 microbiota.

Figure 7A:
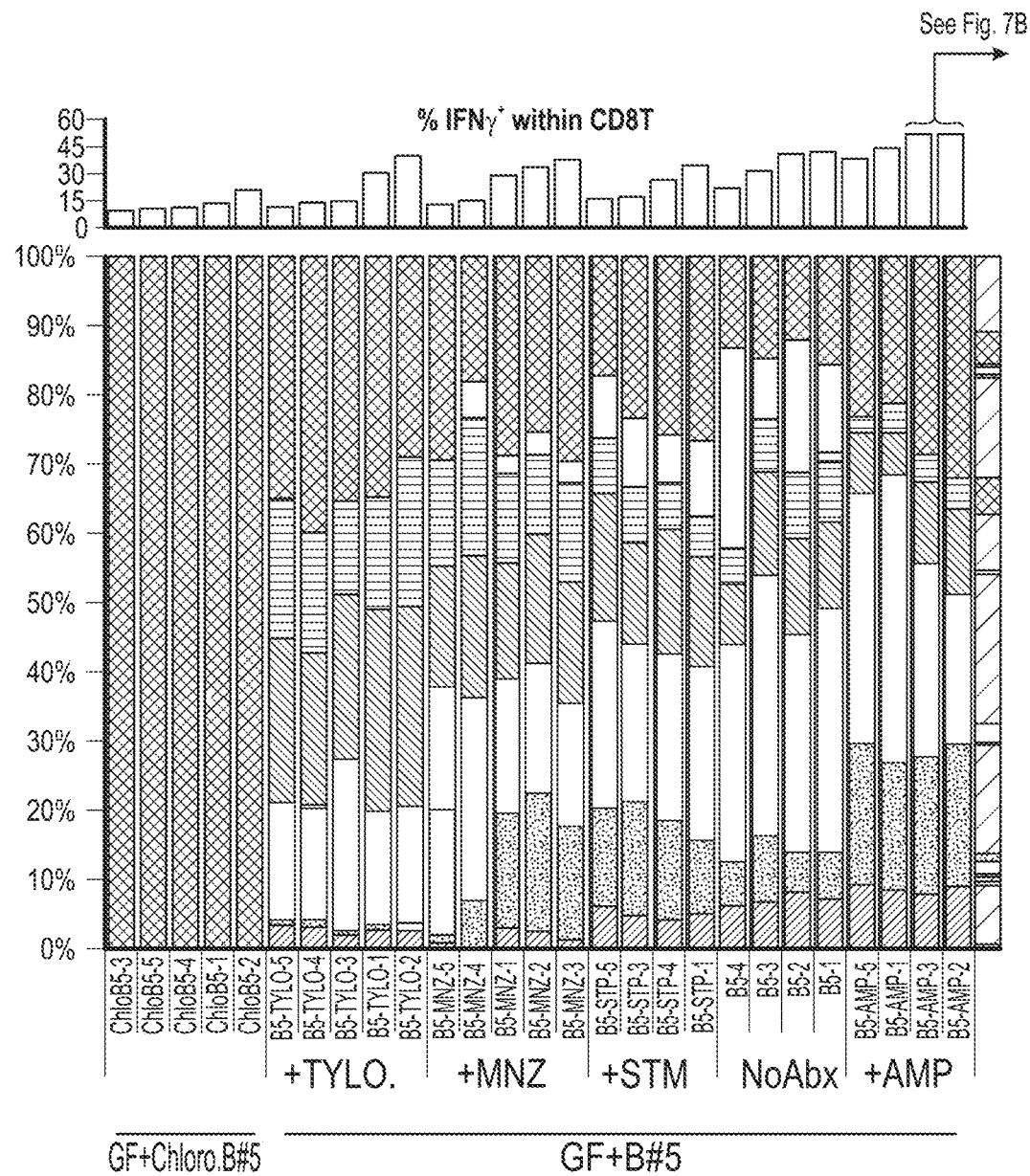
Figures 9A, 9B:
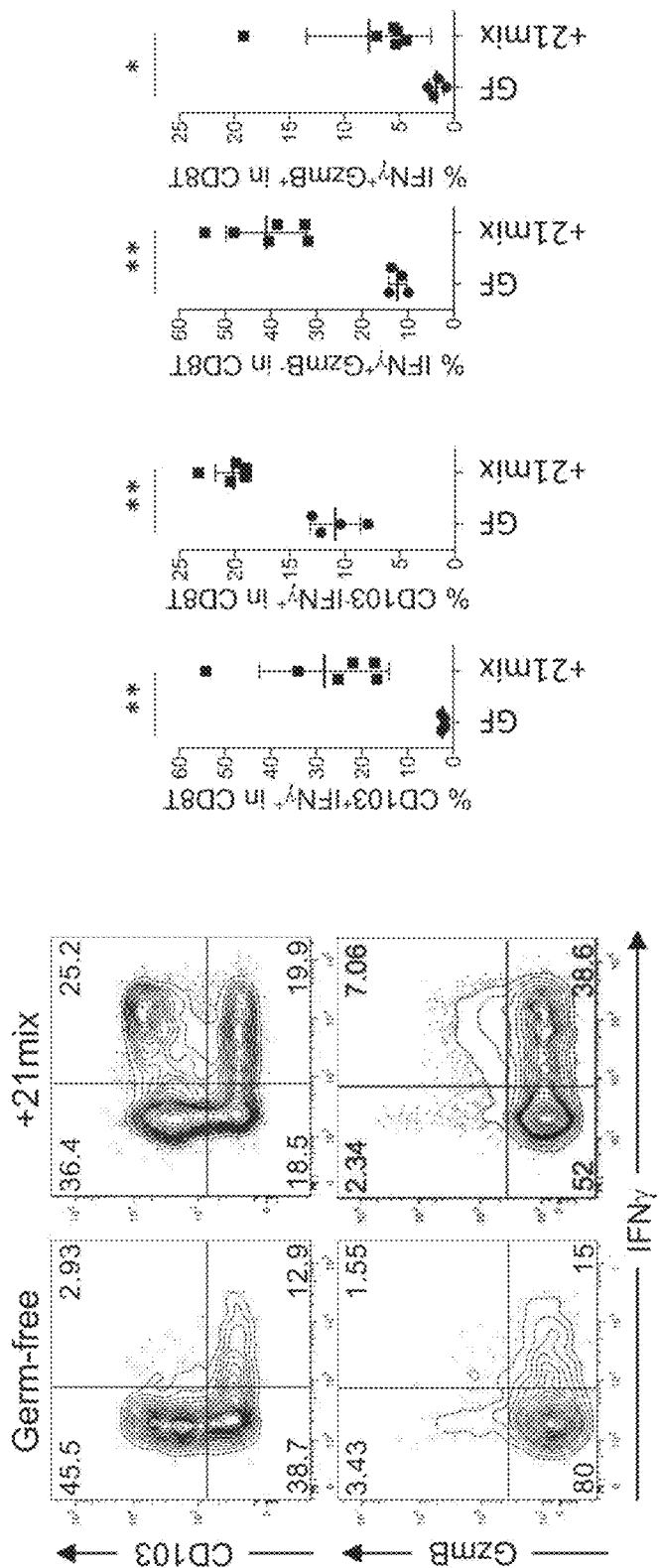
FIGS. 9A and 9B show data on the mixture of 21 isolated strains which was orally administered to germ free mice. Four weeks later, lymphocytes were isolated from the lamina propria of the large intestine and stimulated with PMA/ionomycin for 3.5 hours. CD3, TCRβ, CD8, CD103, IFNγ and GzmB were stained with antibodies and analyzed by flow cytometry.

FIGS. 7A and 7B show the operational taxonomic unit (OTU) analysis of intestinal contents of mice inoculated with mouse B #5 microbiota and treated with/without antibiotics or chloroform. Cecal contents were collected from two B #5+AMP mice that exhibited the highest frequency of IFNγ+CD8+ T cells (mouse B #5+AMP-2 and mouse B #5+AMP-3) and cultured in an anaerobic chamber. 304 colonies were picked and sequencing of the 16S rRNA gene revealed that 26 strains were isolated. Twenty-one strains were selected from the 26 strains, excluding 5 strains which were included in the microbiota of B #5+Chloro mice (therefore predicted to be unnecessary for induction of IFNγ+CD8+ T-cells). The mixture of 21 strains was orally inoculated into germ free mice and strong induction of IFNγ+CD8+ T-cells was observed (FIGS. 8A and 8B). IFNγ+CD8+ T cells induced by the 21 strains also expressed CD103 and a part of the IFNγ+CD8+ T-cells expressed Granzyme B as well (FIGS. 9A and 9B). A mixture of 11 strains with the highest correlation with IFNγ+CD8+ T-cells was inoculated into GF mice as well. The mixture of 11 strains (11 mix) was orally a strong induction of IFNγ+CD8+ T-cells, even when compared to the 21 strains mixture (21 mix) (FIGS. 10A and 10B). Identification of the bacterial species with the highest homology to each of the strains in the 11 mix is provided in Table 2, below.

TABLE 2

| Mixture of 11 strains | | | | | |
|---|---|---|---|---|---|
| Strain # | SEQ ID NO | Strain ID | Species with highest homology | NCBI accession # of 16S locus | SEQ ID of NCBI 16S locus |
| 1 | 1 | 2G5 | Phascolarctobacterium faecium | LN998073 | 27 |
| 2 | 2 | 1A6 | Fusobacterium ulcerans | KR822463 | 28 |
| 3 | 3 | 1B11 | Bacteroides dorei | CP011531 | 29 |
| 4 | 4 | 2G1 | Bacteroides uniformis | NR112945 | 30 |
| 5 | 5 | 2B1 | Subdoligranulum sp. | KM098109 | 31 |
| 6 | 6 | 2A6 | Paraprevotella xylaniphila | NR113078 | 32 |
| 7 | 7 | 2F11 | Parabacteroides johnsonii | NR041464 | 33 |
| 8 | 8 | 1E7 | Alistipes sp. | LT223566 | 34 |
| 9 | 9 | 1H9 | Parabacteroides gordonii | NR112835 | 35 |
| 10 | 10 | 1C1 | Eubacterum limosum | NR113248 | 36 |
| 11 | 11 | 2G9 | Parabacteroides distasonis | NR041342 | 37 |

Example 1A: Further Characterization of the Mixture of 11 Strains (Composition A)

The strains of Table 2 where characterized further by resequencing of the 16S sequences and by whole genome sequencing. The results of the further characterization are found in Table 3.

TABLE 3

Further characterization of the 11-mix (the mixture of 11 strains)

| Strain # | SEQ ID NO | Strain ID | species with highest homology based on original 16S analysis | NCBI accession ID | species with highest homology based on 16S resequencing | 16S Identity (%) of resequencing | species with highest homology based on whole genome sequencing (WGS) | WGS Identity (%) | WGS Coverage (%) | Alternative species with high(est) homology |
|---|---|---|---|---|---|---|---|---|---|---|
| 2 | 2 | 1A6 | Fusobacterium ulcerans | K0052822463 | Fusobacterium varium | 99 | Fusobacterium ulcerans | 93.2 | 78.6 | |
| 7 | 7 | 2F11 | Parabacteroides johnsonii | NR041464 | Parabacteroides johnsonii | 99 | Parabacteroides johnsonii | 99.9 | 90.5 | |
| 6 | 6 | 2A6 | Paraprevotella xylaniphila | NR113078 | Paraprevotella xylaniphila | 99 | Paraprevotella xylaniphila | 98.9 | 92.1 | |
| 11 | 11 | 2G9 | Parabacteroides distasonis | NR041342 | Parabacteroides distasonis | 99 | Parabacteroides sp. CAG: 2 | 99.4 | 95.4 | |
| 8 | 8 | 1E7 | Alistipes sp. | LT223566 | Alistipes senegalensis | 99 | Alistipes senegalensis | 98.7 | 72.2 | Alistipes timonensis |
| 10 | 10 | 1C1 | Eubacterium limosum | NR113248 | Eubacterium limosum | 99 | Eubacterium limosum | 95 | 81 | |
| 3 | 3 | 1B11 | Bacteroides dorei | CP011531 | Bacteroides dorei | 99 | Bacteroides dorei | 99.3 | 79.5 | Bacteroides fluxus |
| 9 | 9 | 1H9 | Parabacteroides gordonii | NR112835 | Parabacteroides gordonii | 97 | Parabacteroides sp. HGS0025 | 90 | 50 | |
| 5 | 5 | 2B1 | Subdolinogranulum sp. | KM098109 | Gemminger formicilis | 99 | Ruminococcaceae bacterium cv2 | 99.2 | 73.9 | Ruthenibacterium lactatiformans |
| 4 | 4 | 2G1 | Bacteroides uniformis | NR112945 | Bacteroides uniformis | 99 | Bacteroides sp. D20 | 98.5 | 81 | |
| 1 | 1 | 2G5 | Phascolarctobacterium faecium | LN998073 | Phascolarctobacterium faecium | 99 | Phascolarctobacterium sp. CAG: 207 | 99.2 | 87 | |

Figure 12A:
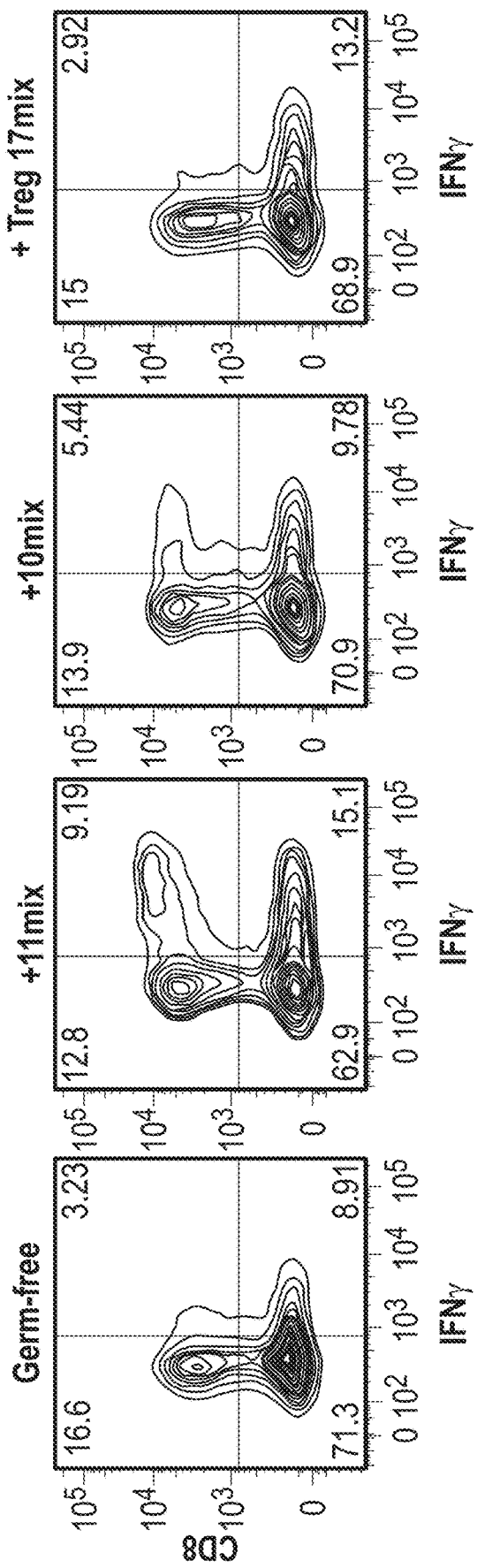
FIGS. 12A and 12B show data obtained from mixtures of 11 or 10 strains (see FIG. 11), or a mixture of 17 strains that are known Treg-inducers, which were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry.
Figure 12B:
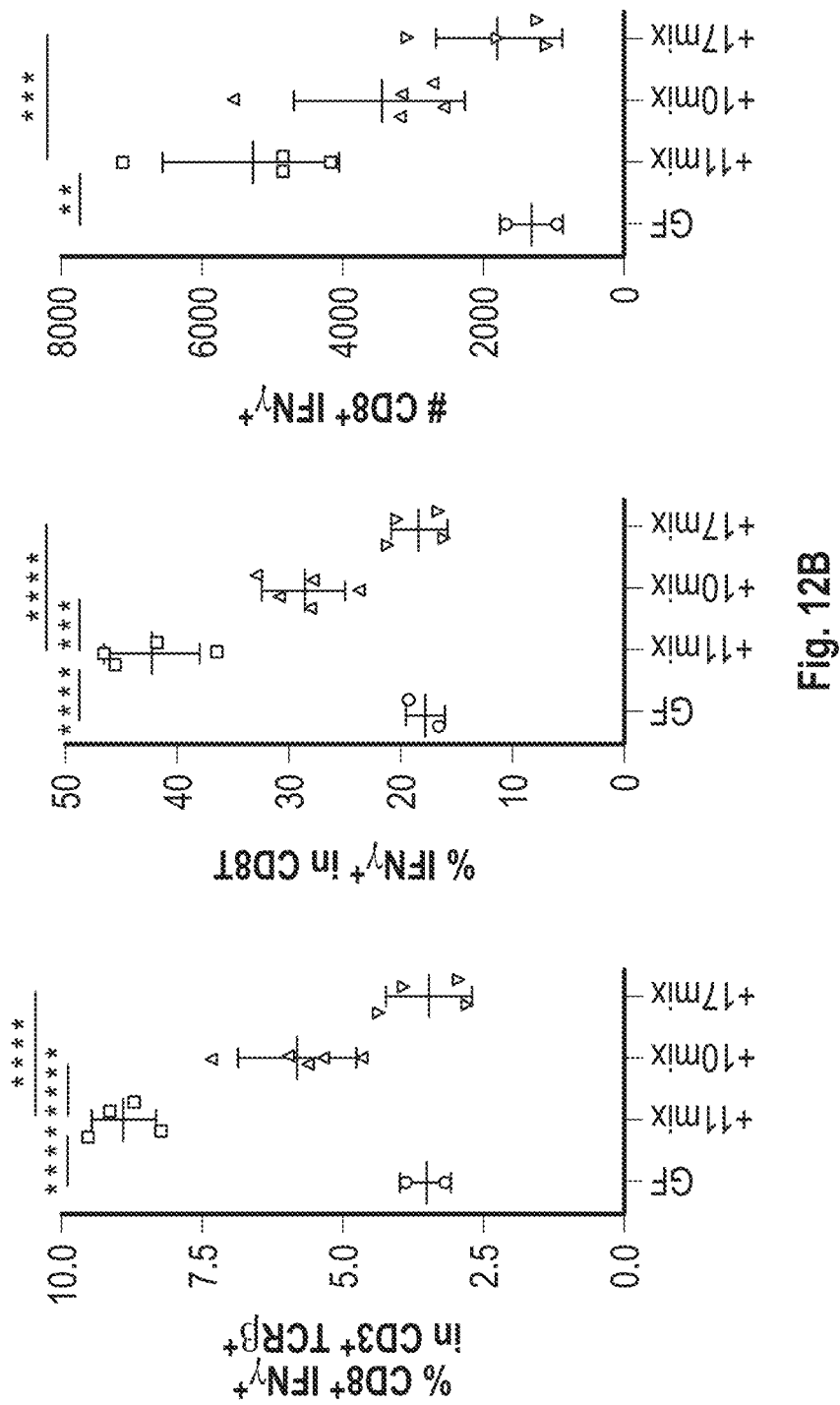

Example 2: Further Characterization of a CD8+ T-Cell Inducing Bacterial Cocktail Twenty six strains isolated from cecal contents of B #5+AMP mice that exhibited high frequencies of IFNγ+ CD8+ T cells are shown in FIG. 11. Among the 26 strains, 11 strains ("11 mix") were positively correlated with the frequency of IFNγ+CD8+ T cells. Therefore, these 11 strains were selected for further experiments, and the mixture of 11 strains ("11-mix") was inoculated into germ-free mice (see also Table 2). Colonization with the 11-mix resulted in a strong induction of colonic IFNγ+CD8+ T cells (FIGS. 10A, 10B, 12A, and 12B), whereas the other 10 strains ("10-mix") weakly induced IFNγ+CD8+ T cells compared to the levels induced by the 11-mix (FIGS. 12A and 12B). Mice inoculated with a mixture of 17 Treg-inducing bacterial strains (See e.g., WO2013/080561; Atarashi et al., Nature (2013) 500 (7461): 232-236; Narushima et al. Gut Microbes (2014) 5(3): 333-339) did not accumulate IFNγ+CD8+ T cells (FIGS. 12A and 12B).

Figure 13:
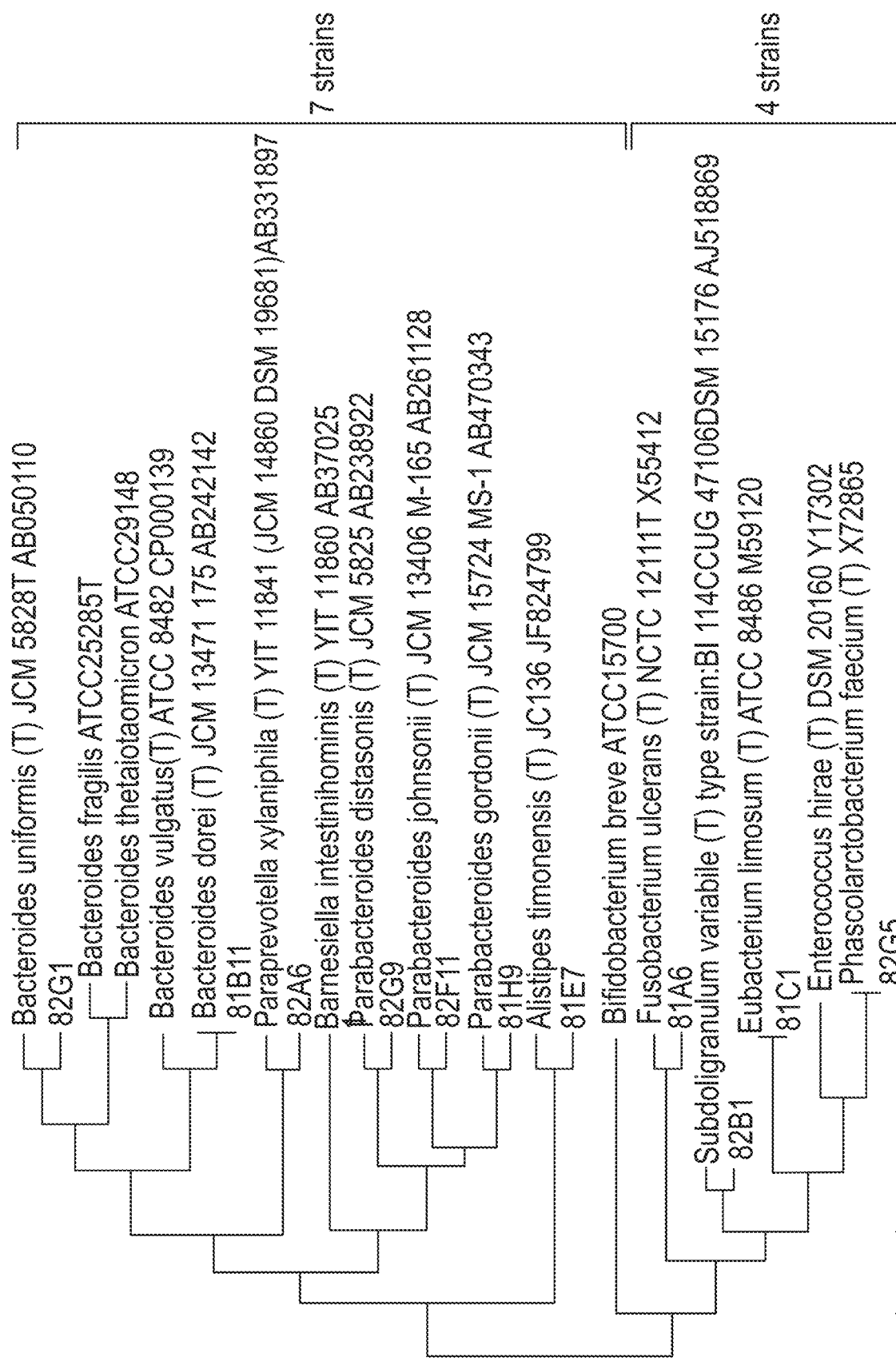
FIG. 13 shows a phylogenetic tree which was constructed from the 16S rRNA gene sequences of the 11 strains (See FIG. 11), their closest sequences and some type strains using the MEGA v5.0 package and the neighbor-joining method. The strains which were inoculated into GF mice as a 7 mix or 4 mix are shown as well (The results of the inoculation experiments are shown in FIGS. 14A and 14B).

A phylogenetic comparison using 16S rRNA gene sequences showed that the 11 strain mixture (also referred to as "the 11 mix") consists of 7 strains falling within Bacteroidales ("7 strains") and 4 strains of non-Bacteroidales: 2 Clostridiales, 1 Fusobacteriales and 1 Selenomonadales ("4 strains") (See FIG. 13 and Table 4).

Figure 14A:
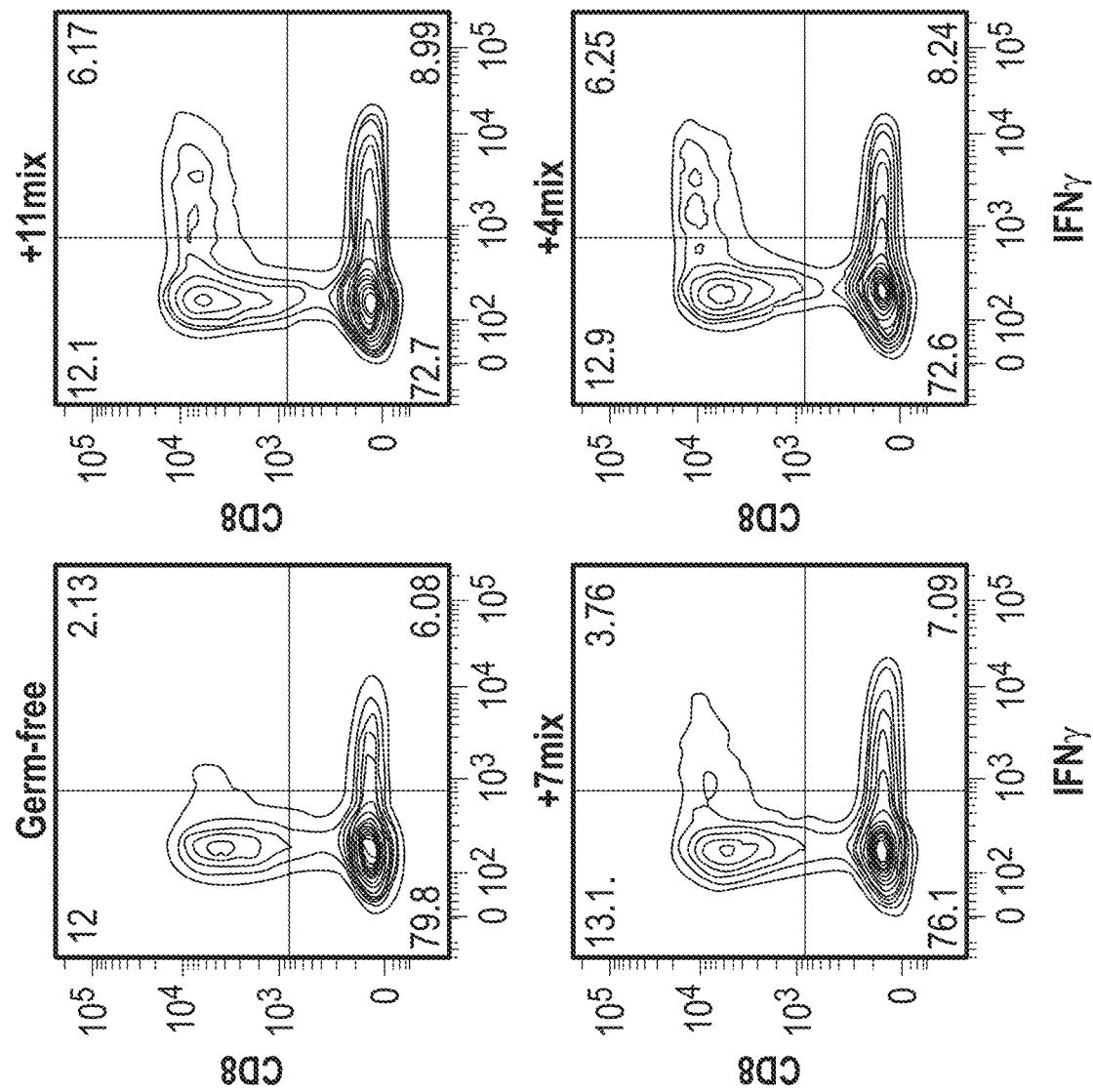

Inoculation with the mixture of 4 non-Bacteroidales strains ("4-mix") resulted in a strong accumulation of colonic IFNγ+CD8+ T cells, comparable to the level of colonic IFNγ+CD8+ T cells observed in mice colonized with the 11 mix. In contrast, colonization with 7 Bacteroidales strains ("7-mix") weakly induced IFNγ+CD8+ T cells (FIGS. 14A and 14B).

A repeat of the experiment is shown in FIG. 47, which shows that the 11-mix is more effective than either the 7-mix or the 4-mix. The data of the experiment shown in FIG. 47 have strong statistical support.

Identification of the bacterial species with the highest homology to each of the strains in the 4 mix is provided in Table 4, below.

TABLE 4

Mixture of 4 strains

| Strain # | SEQ ID NO | Strain ID | Species with highest homology | NCBI accession # of 16S locus | SEQ ID of NCBI 16S locus |
|---|---|---|---|---|---|
| 1 | 1 | 2G5 | Phascolarctobacterium faecium | LN998073 | 27 |
| 2 | 2 | 1A6 | Fusobacterium ulcerans | KR822463 | 28 |

TABLE 4-continued

Mixture of 4 strains

| Strain # | SEQ ID NO | Strain ID | Species with highest homology | NCBI accession # of 16S locus | SEQ ID of NCBI 16S locus |
|---|---|---|---|---|---|
| 5 | 5 | 2B1 | *Subdoligranulum* sp. | KM098109 | 31 |
| 10 | 10 | 1C1 | *Eubacterum limosum* | NR113248 | 36 |

Example 3: Anti-Cancer Characteristics of CD8+ T-Cell Inducing Bacterial Cocktail To investigate whether colonization with the 11 mix could enhance anticancer immune responses, a subcutaneous tumor model was used. SPF mice were treated with mixture of antibiotics (1 g/L ampicillin, 0.5 g/L vancomycin, 1 g/L metronidazole, and 1 g/L neomycin) via the drinking water from day −7 to day 2. A MC38 colon cancer cell line ($3 \times 10^5$ cells per mouse) was subcutaneously injected into the right flank of mice at day 0. Antibiotics treatment was stopped at day 2, and mice were gavaged with fecal microbiota from SPF mice mixed with or without 11-mix on day 3. For the 11-mix treatment groups, mice were gavaged with the 11 mix two or three times per week until the end of the experiment. For the anti-PD-1 antibody (Ab) treatment groups, mice were intraperitoneally injected with 200 μg of anti-PD1 monoclonal Ab (clone J43) at days 3, 5 and 9. Tumor size was measured using a caliper and tumor volume was determined as length×width 2×0.5.

Figure 15:
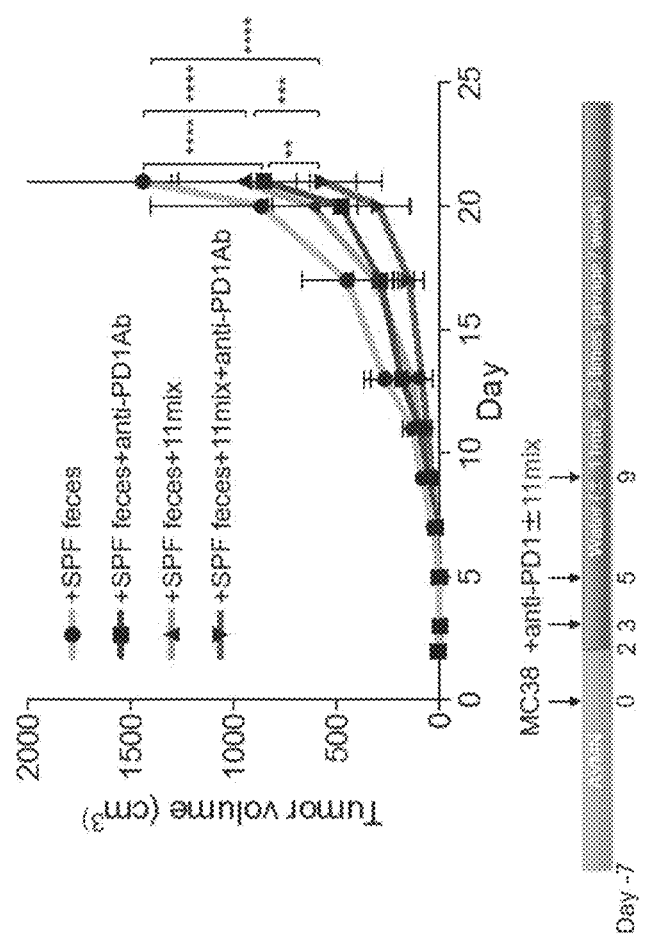
FIG. 15 shows data on experiments with six weeks-old SPF C57BL/6 mice, which were purchased from Japan SLC and treated with antibiotics (1 g/L Ampicillin, 0.5 g/L Vancomycin, 1 g/L Metronidazole and 1 g/L Neomycin; "AVMN") in their drinking water. Then, mice were subcutaneously injected into the right flank with $3\times10^5$ MC38 tumor cells line at day 0. When tumors appeared and were palpable, antibiotics treatment was stopped (day 2). Mice were injected intraperitoneally with 200 μg of anti-PD1 antibody (clone J43) at day 3, 5 and 9 ("+anti-PD1Ab"). Mice were gavaged with the 11 mix 2 or 3 times a week including day 3, 5 and 9 ("+11 mix"). Tumor size was measured using a caliper and tumor volume was determined as length×width$^2$×0.5. P<0.01,* P<0.001,**** P<0.0001 (two-way ANOVA).
Figure 16A:
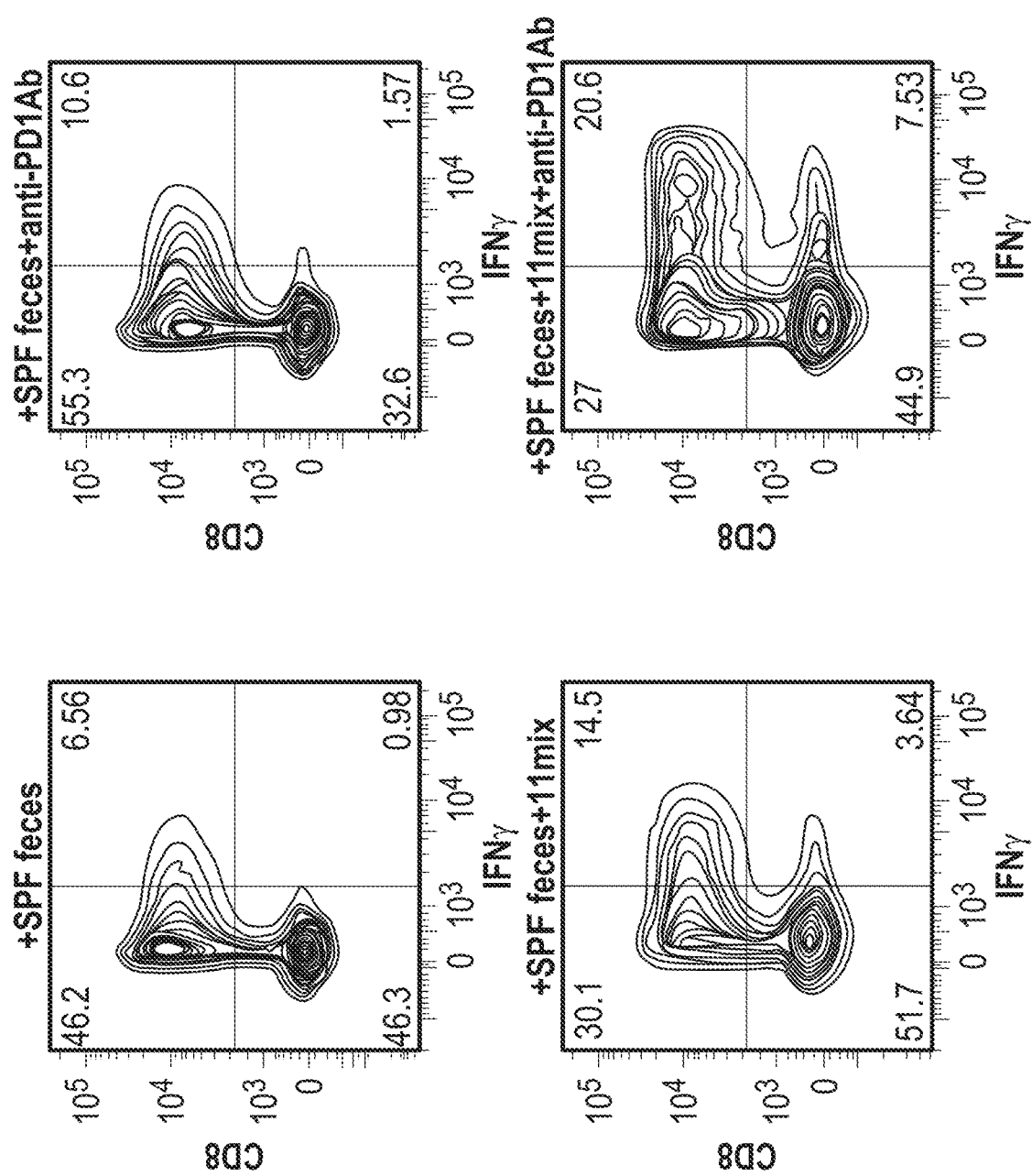
Figure 17A:
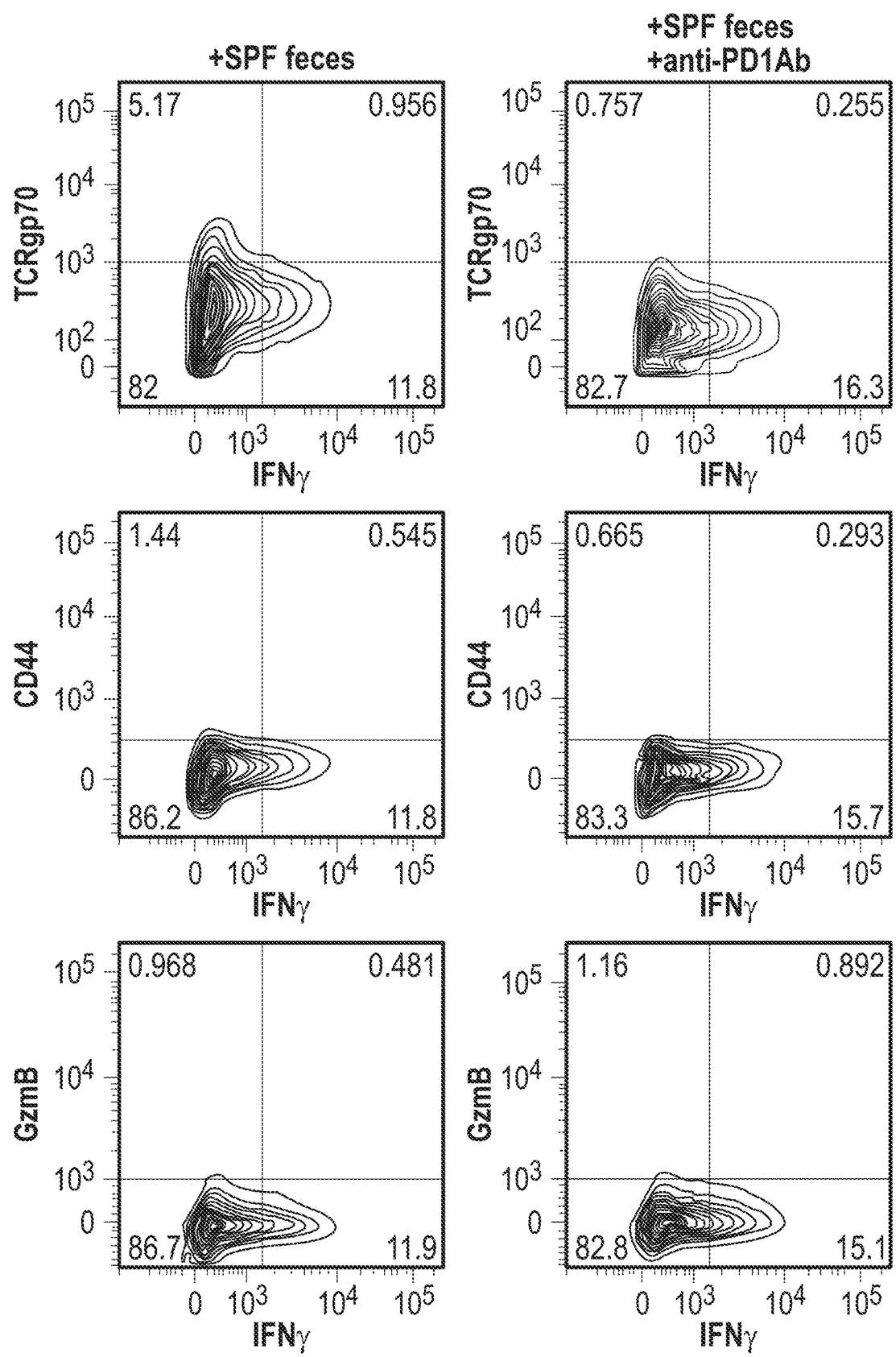
FIGS. 17A, 17A-17C show data on lymphocytes isolated from tumor cells. At day 23 or 27, lymphocytes were isolated from tumors and stimulated with PMA/ionomycin for 4 hours. CD3, TCRβ, CD8, gp70 MC38 peptide (KSPWFTTL (SEQ ID NO: 53))-specific TCRβ, CD44, GzmB and IFNγ were stained with antibodies and peptide-H2K$^b$ tetramer, and analyzed by flow cytometry.
Figure 17B:
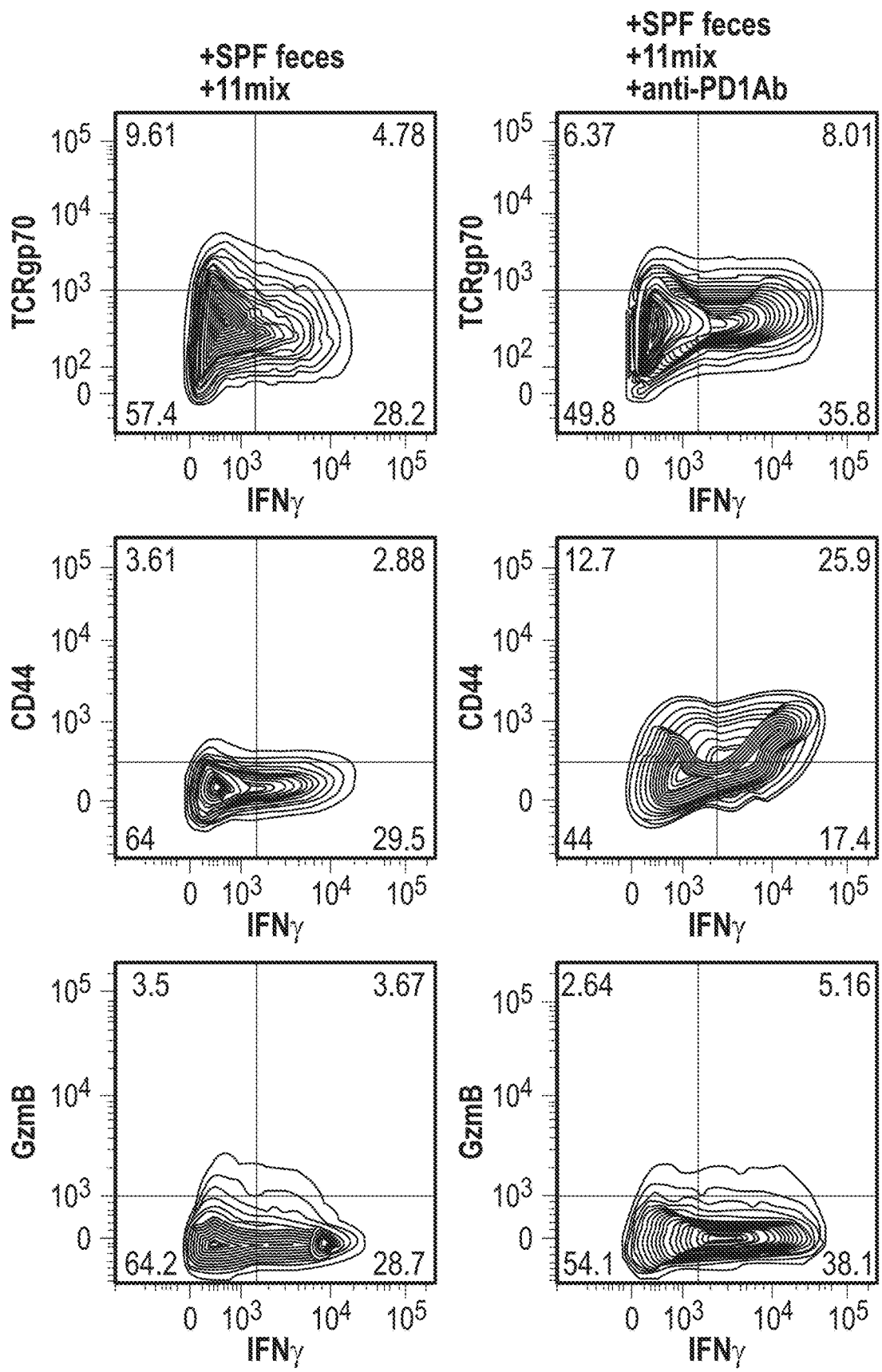
Figure 17C:
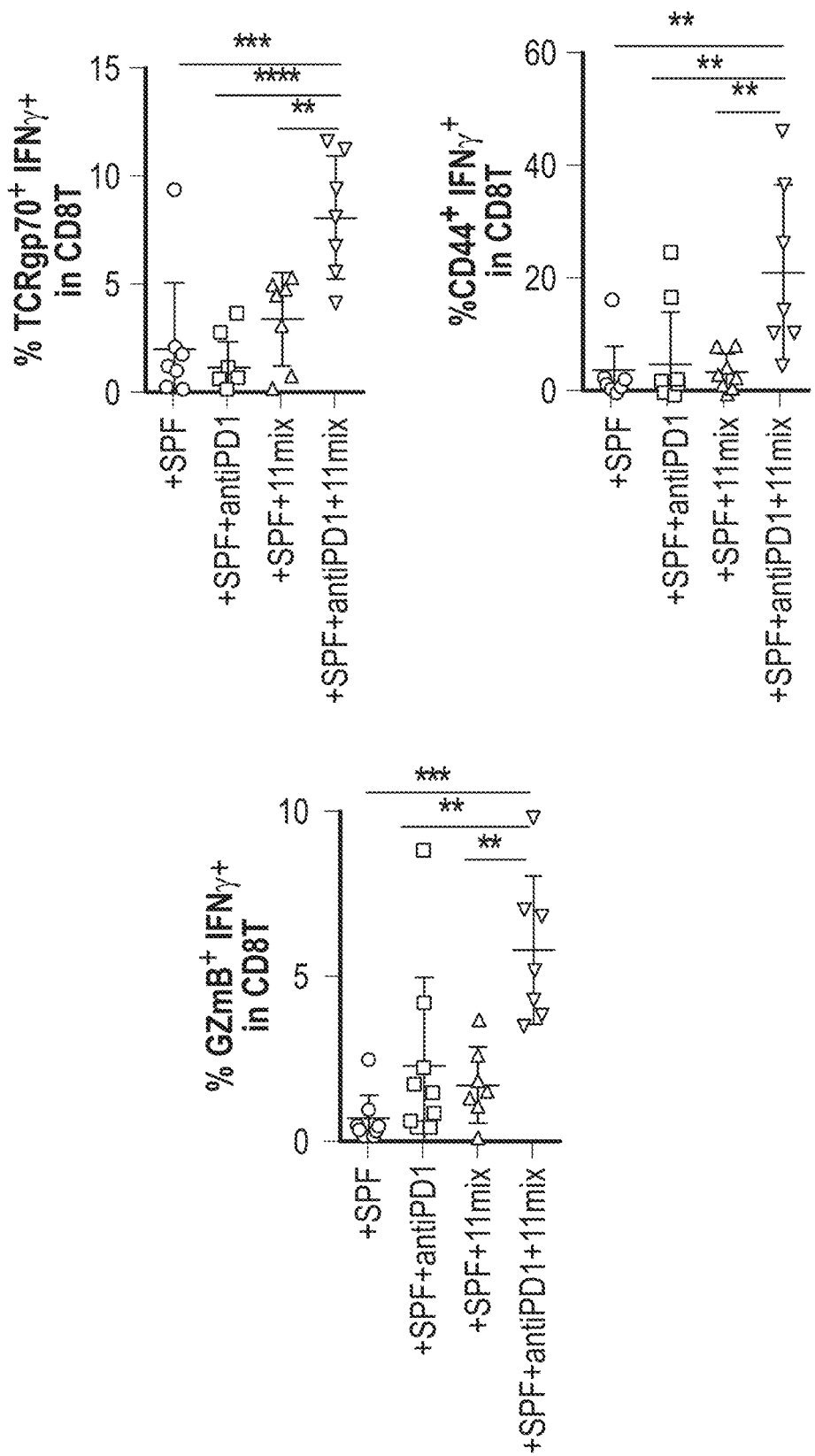
Figure 18:
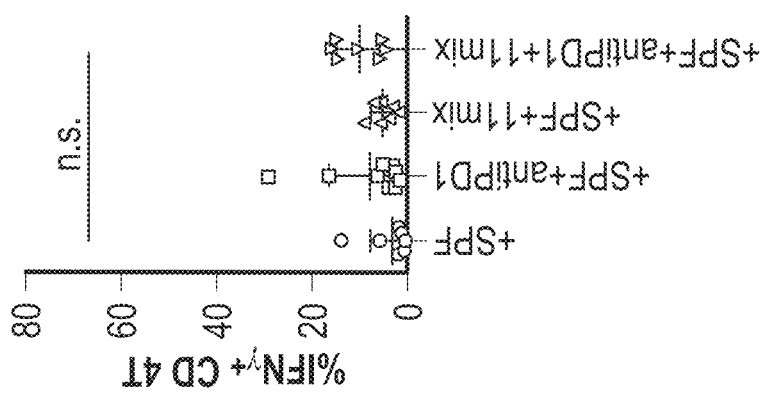
FIG. 18 shows data on lymphocytes isolated from tumor cells. The effect on IFNγ+CD4 T cells is shown in FIG. 18.
Figure 21:
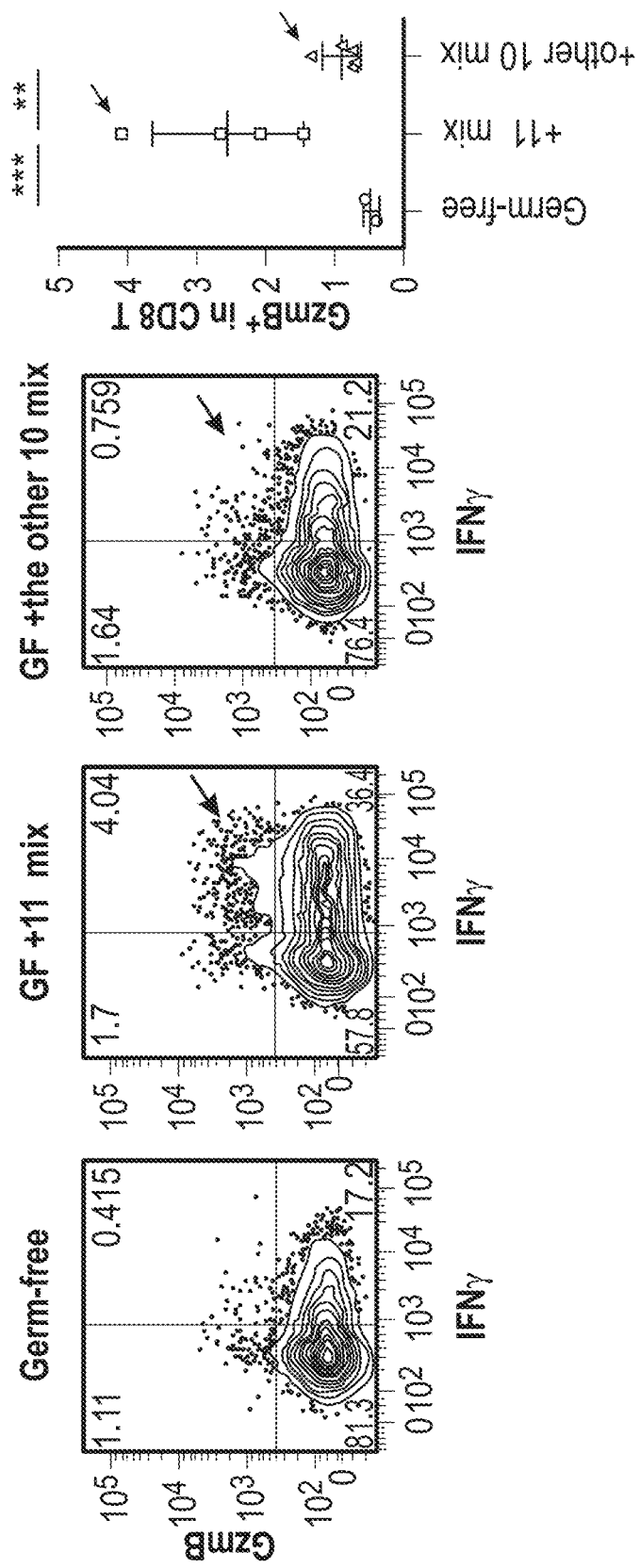
FIG. 21 shows data on induction of GzmB+IFNγ+CD8 T cells by 11-mix bacterial strains.
Figure 22:
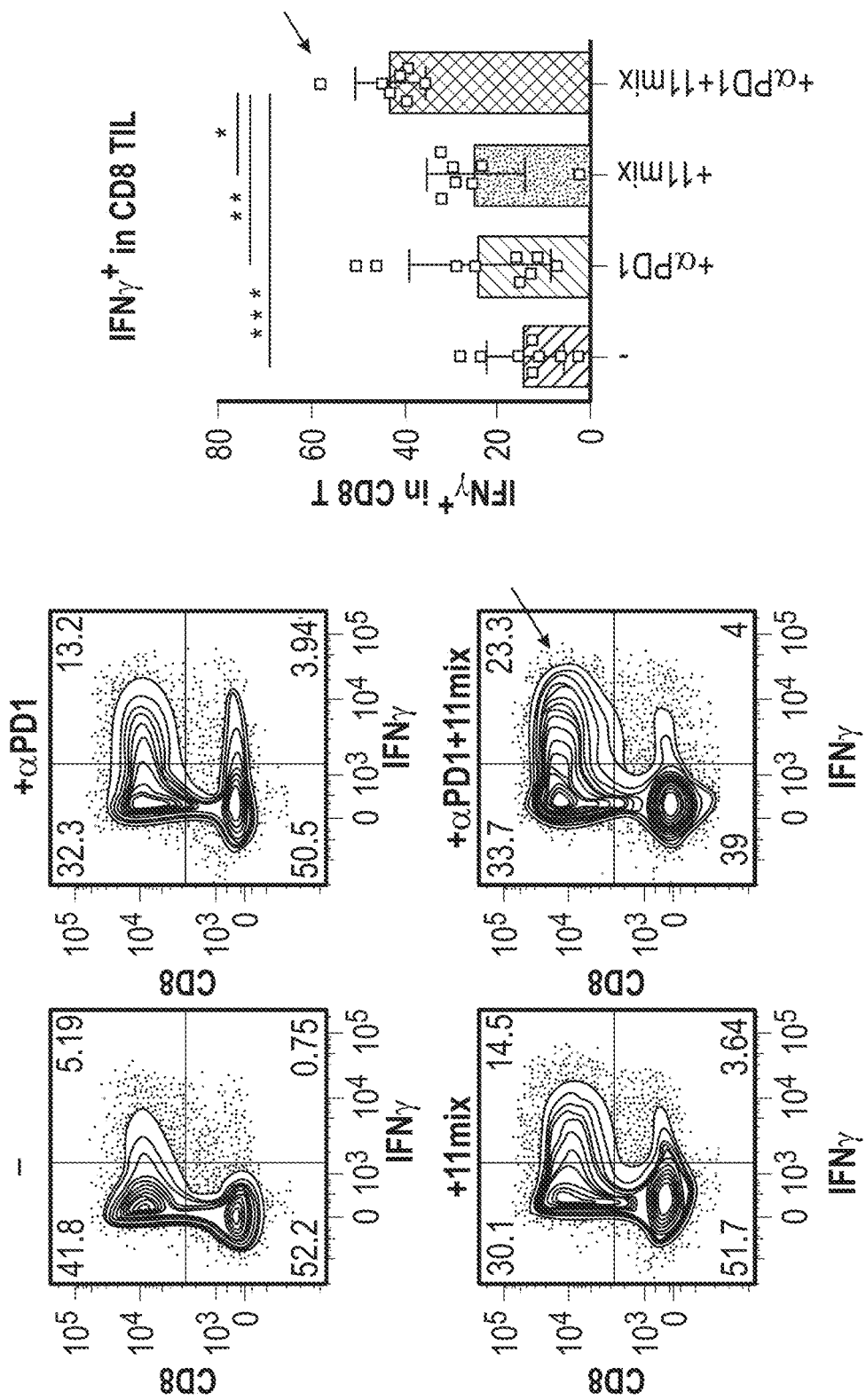
FIG. 22 shows that slower tumor growth was accompanied by increased infiltration of IFNγ CD8 T cells into the tumor.
Figure 23:
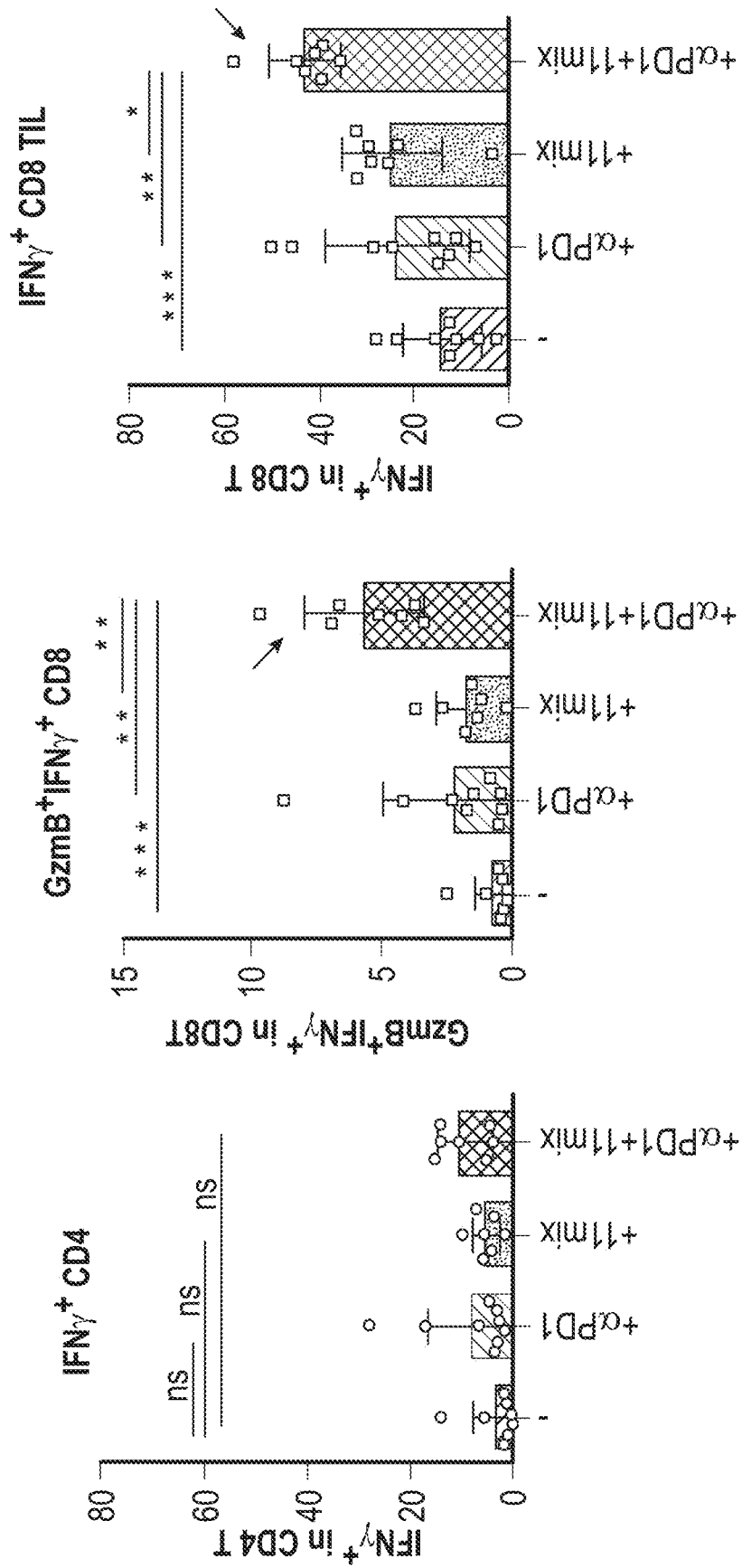
FIG. 23 shows that the combination of αPD1 Ab and 11-mix bacterial strains boosted infiltration of GzmB+IFNγ+ CD8 cytotoxic T cells into the tumor.

Treatment with the 11 mix alone (i.e., without anti-PD1 Ab) significantly suppressed MC38 tumor growth (see FIG. 15). The combination of the 11 mix and anti-PD1 Ab exhibited the strongest suppressive effect on the growth of tumor cells (see FIG. 15). Treatment with the 11 mix and anti-PD1 Ab resulted in elevated accumulation of IFN r+CD8+ T cells in the MC38 tumor mass (see FIGS. 16A and 16B). A subset of the IFN r+CD8+ T cells in tumors expressed T-cell receptors specific for gp70p15E604-611 (KSPWFTTL; SEQ ID NO: 53), which is an immunodominant epitope of MC38 (FIG. 17A). Furthermore, a subset of IFN γ+CD8+ T cells expressed CD44 and Granzyme B, suggesting that the IFN r+CD8+ T cells accumulated in the tumor included tumor-specific and memory-type cytotoxic CD8+ T cells (see FIGS. 17A and 17B). The effect on IFN r+CD4 T cells is shown in FIG. 18.

Figure 19:
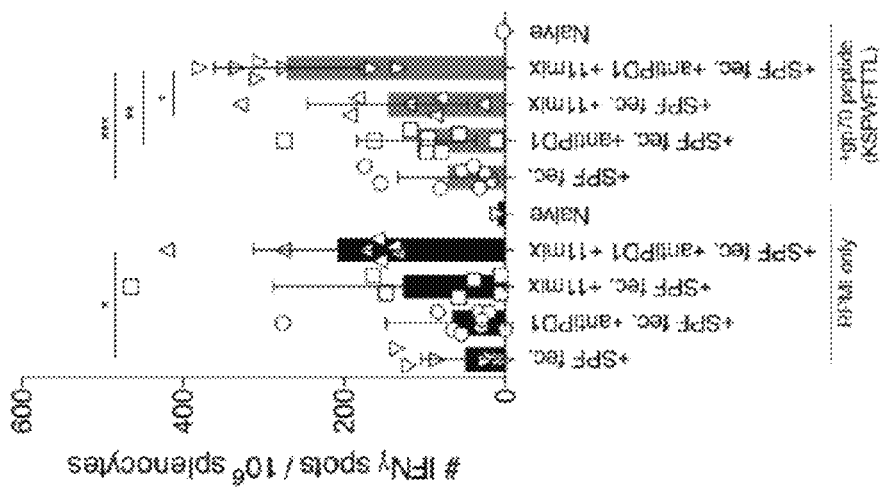
FIG. 19 shows data on lymphocytes isolated from tumor cells. At day 23 or 27, whole splenocytes were isolated and plated at $10^6$ cells per well and stimulated with 0.5 μg/mL gp70 MC38 peptide (KSPWFTTL (SEQ ID NO: 53)) for 36 hours at 37° C. Spots were developed using the Mouse IFNγ ELISPOT Ready-SET Go!® kit (eBioscience), and the number of spots was measured using an Immunospot Series 4 Analyzer and analyzed using ImmunoSpot software (Cellular Technology). Each plot represents individual mice. "Naive" is a mouse which was not treated with antibiotics, not injected with MC38 cells and not treated with 11 mix and anti-PD1 antibody.*P<0.05, P<0.01,* P<0.001 (one-way ANOVA).

Oral inoculation with the 11 mix resulted in the increased numbers of IFNγ-producing splenocytes, even in the absence of tumor antigen stimulation (see FIG. 19).

These results show that treatment with 11 mix in combination with, or without, anti-PD1 Ab systemically activate CD8 T cells that respond to tumor cells.

Figure 24:
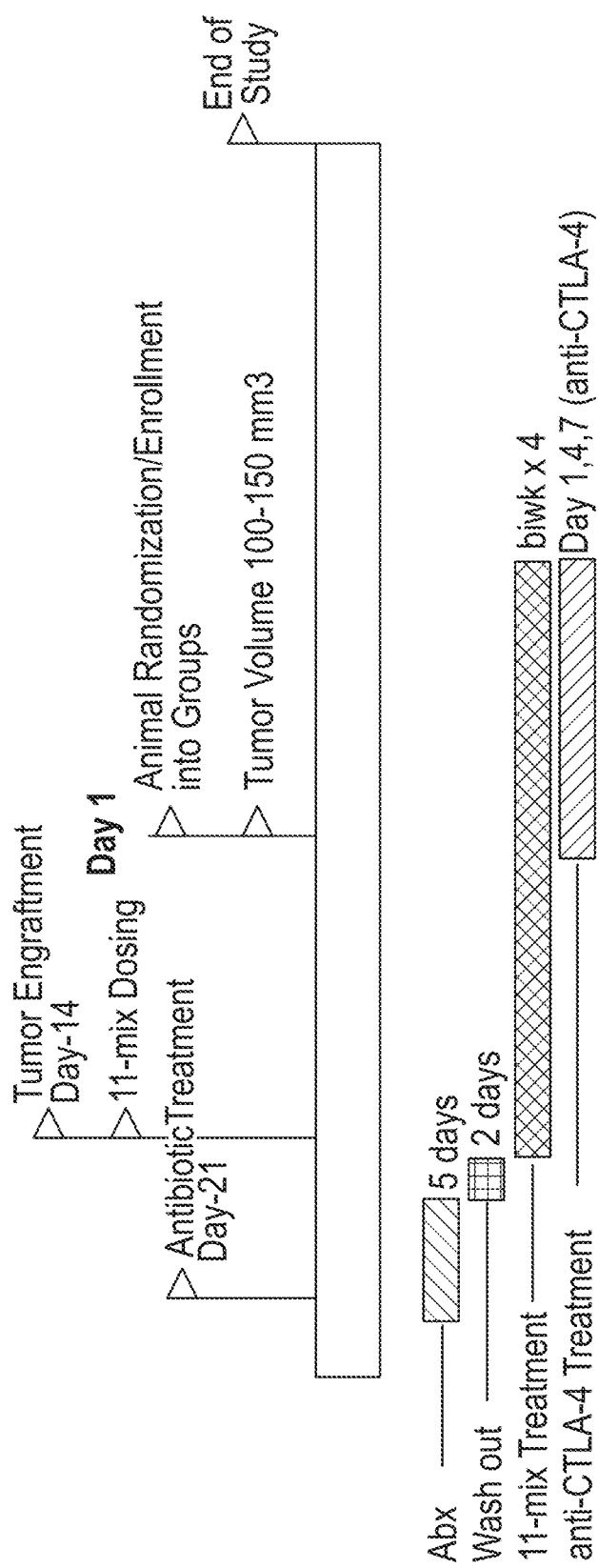
FIG. 24 shows a schematic of the experimental plan described in Example 4 relating to treatment with the 11-mix and/or an anti-CTLA-4 antibody.
Figure 25:
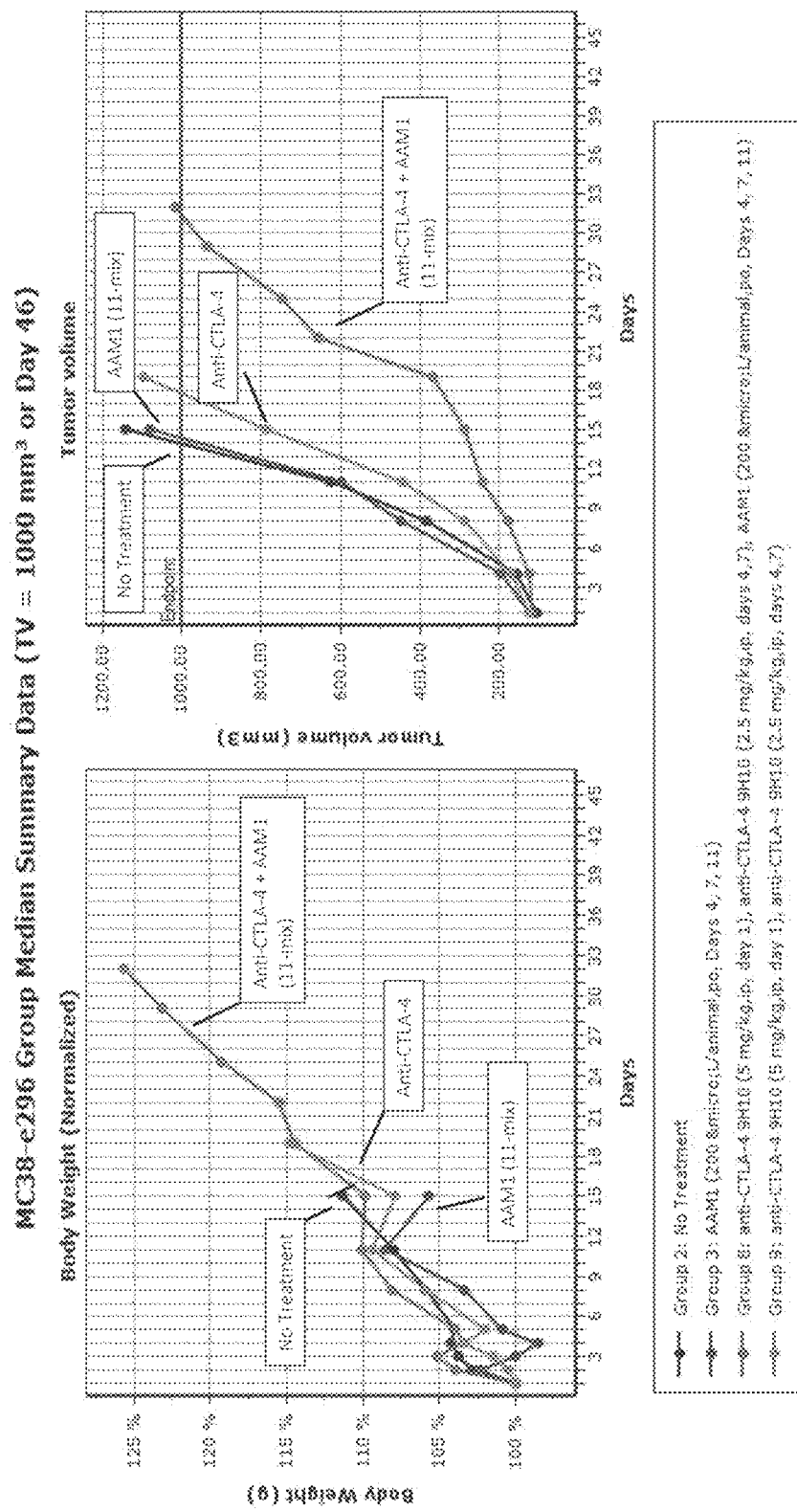
FIG. 25 shows body weight of mice that received the combination of αCTLA-4 Ab and the 11-mix of bacterial strains (left panel). Mice that received the combination of αCTLA-4 Ab and the 11-mix of bacterial strains had a significant reduction in tumor growth (right panel) in the experiment presented in FIG. 24 (Example 4).
Figure 26:
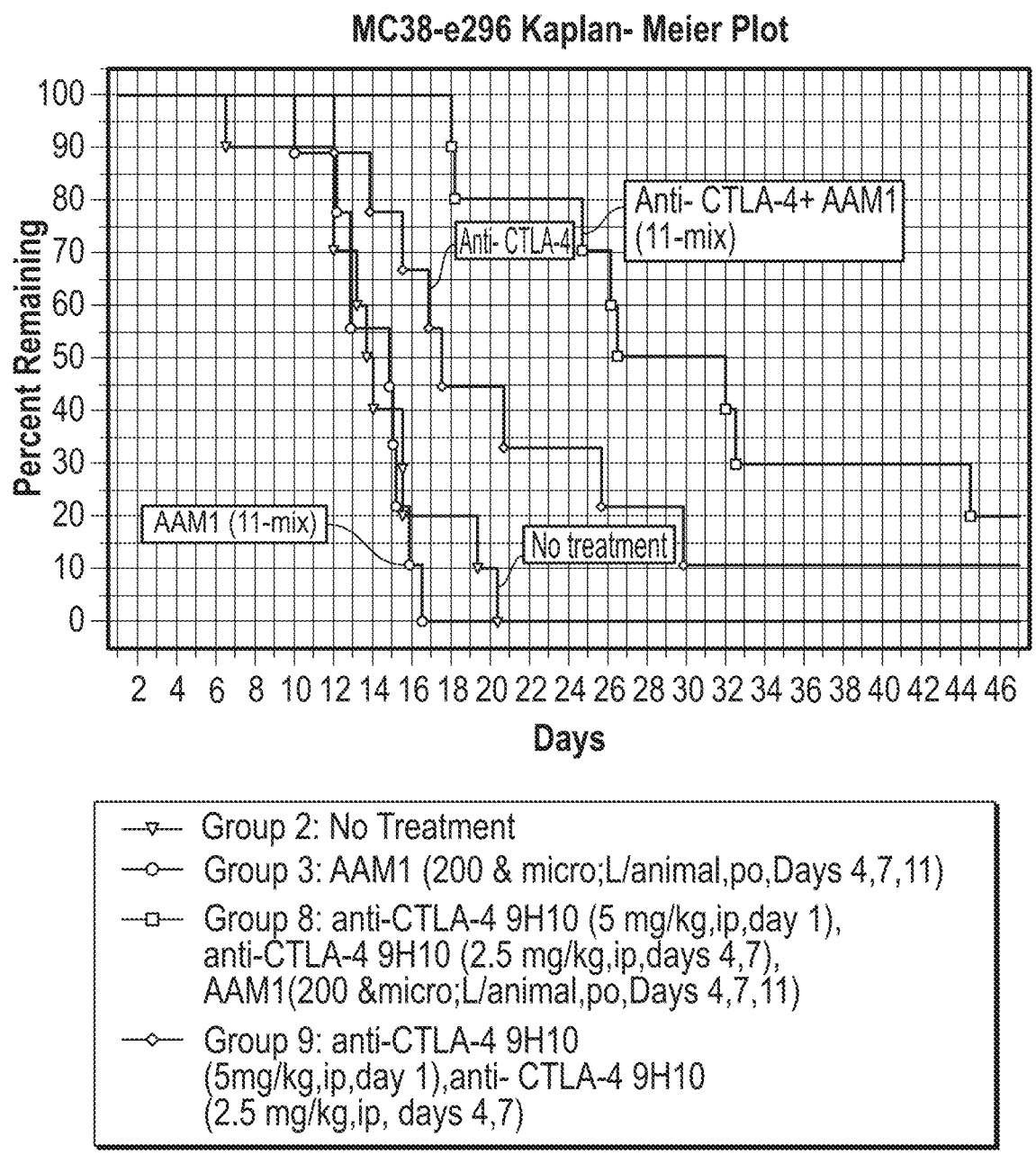
FIG. 26 shows that the combination of αCTLA-4 Ab and the 11-mix of bacterial strains had a significant effect on the survival of the mice in the experiment presented in FIG. 24 (Example 4).

Example 4: Anti-Cancer Characteristics of CD8+ T-Cell Inducing Bacterial Cocktail in Combination with CTLA-4 Immune Checkpoint Inhibitor To investigate whether colonization with the 11-mix in combination with immune checkpoint inhibitor CTLA4 could enhance anticancer immune response, a subcutaneous tumor model was used (FIG. 24). Mice were treated with mixture of antibiotics for 5 days (from day −21 to day −16), followed by a two-day period to wash out the antibiotics. A MC38 colon cancer cell line ($3 \times 10^5$ cells per mouse) was subcutaneously injected into the right flank of mice at day −14. The animals were randomized into the following treatment groups:

Group 1: No antibiotics, no treatments (provides a reference for standard progression of MC38 tumor model);

Group 2: Antibiotic pre-treatment, no treatment (provides a reference for the progression of the MC38 tumor model with antibiotic pre-treatment):

Group 3: 11-mix monotherapy (referred to as AAM1 in FIGS. 25 and 26); Group 8: anti-CTLA-4 antibody (9H10) and 11-mix (referred to as AAM1 in FIGS. 25 and 26) combination;

Group 9: anti-CTLA-4 antibody (9H10) monotherapy.

Bacterial cocktail treatments were also begun on day −14 and administered biweekly 4 times. For groups receiving the CTLA-4 immune checkpoint inhibitor, the treatment was begun once the tumor volume reached approximately 100 mm$^3$ (100-150 mm$^3$). The anti-CTLA-4 antibody was administered on days 1, 4, and 7. The mice were assessed for weight and survival through the course of the experiment. Tumor size and volume were measured.

Tumor Measurements

Figure 27B:
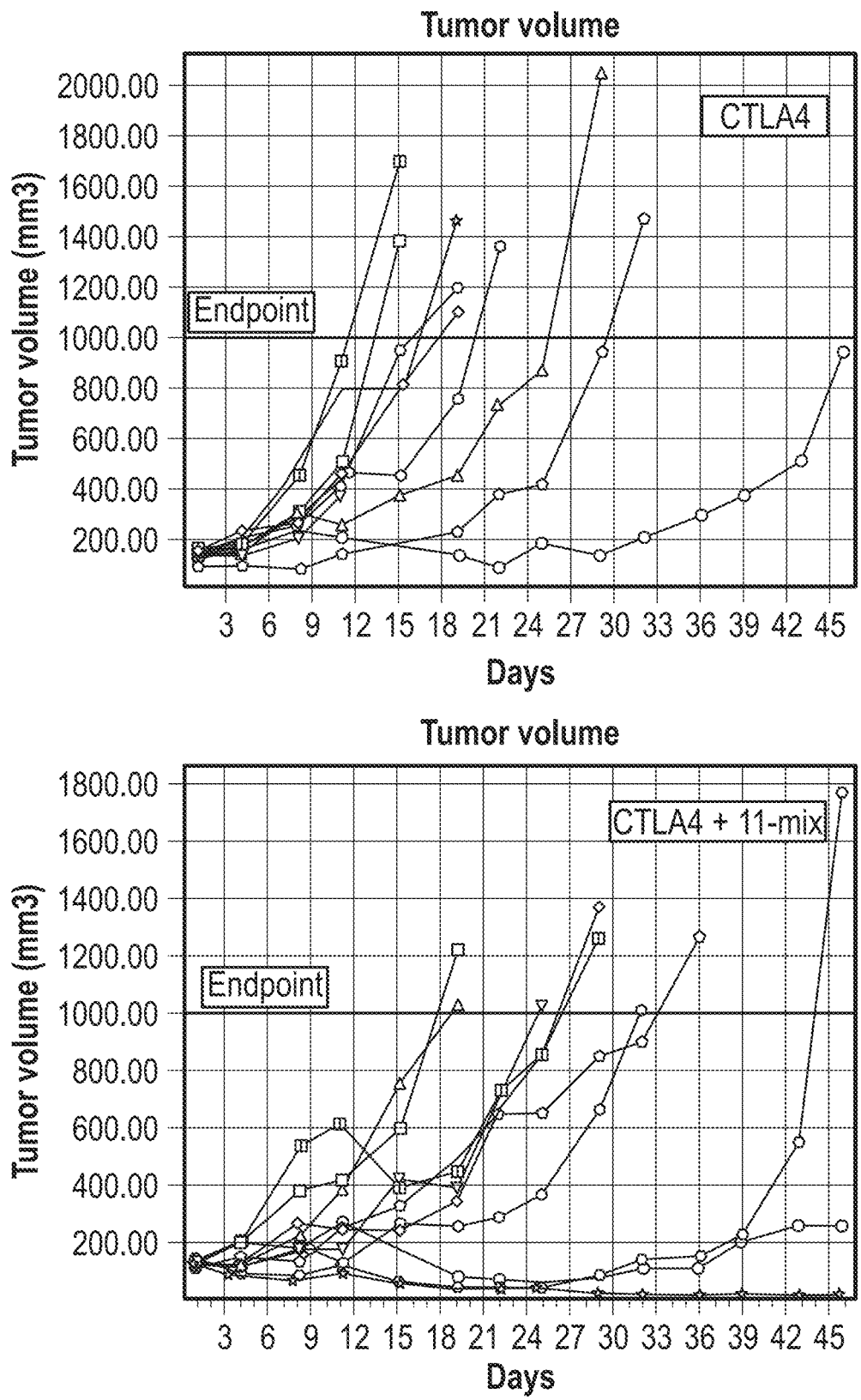

The group of mice that received the anti-CTLA-4 antibody alone (Group 9) had slightly reduced tumor growth compared to control mice. The combination of the 11-mix (referred to as "AAM1" in FIG. 25) and the anti-CTLA-4 antibody (Group 8) significantly reduced the tumor growth as compared to the 11-mix on its own and as compared to the anti-CTLA-4 antibody on its own. See FIG. 25. Tumor volume plots of individual mice are shown in FIG. 27.

Survival

The group of mice that received the anti-CTLA-4 antibody alone had slightly increased survival compared to control mice. The 11-mix by itself had no impact on survival. The combination of the 11-mix (referred to as "AAM1" in FIG. 26) and the anti-CTLA-4 antibody significantly enhanced survival of the treated mice (Group 8). See FIG. 26.

Figure 28:
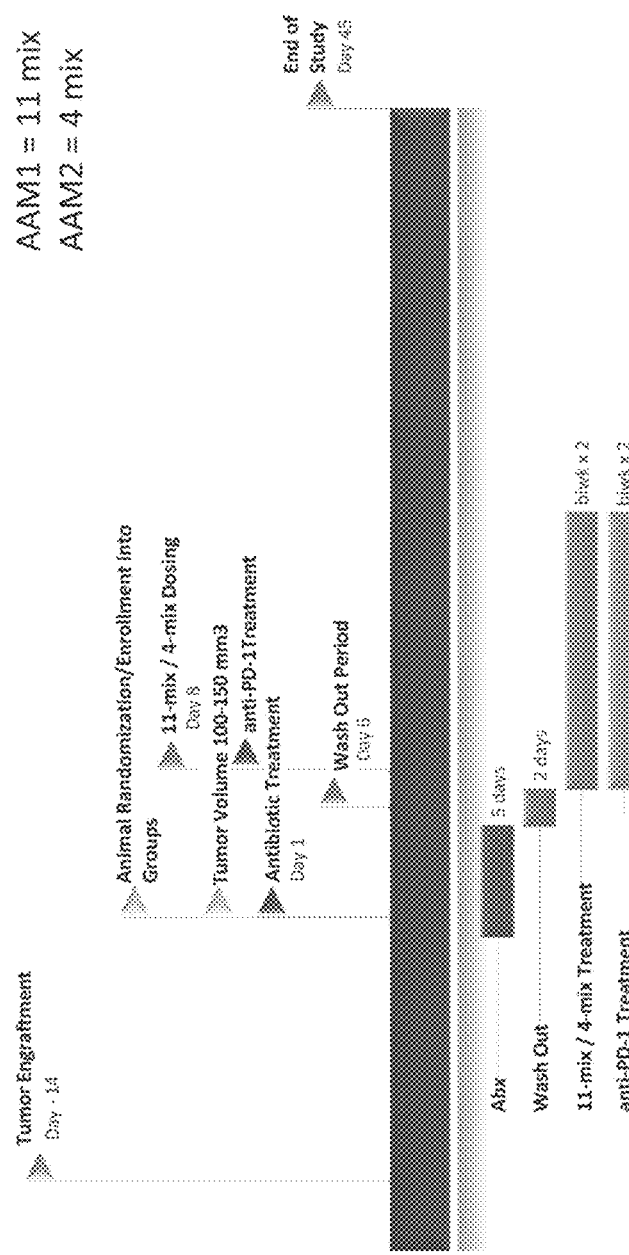
FIG. 28 shows a schematic of the experimental plan described in Example 5 relating to treatment with the 11-mix or 4-mix and/or an anti-PD-1 antibody.
Figure 29A:
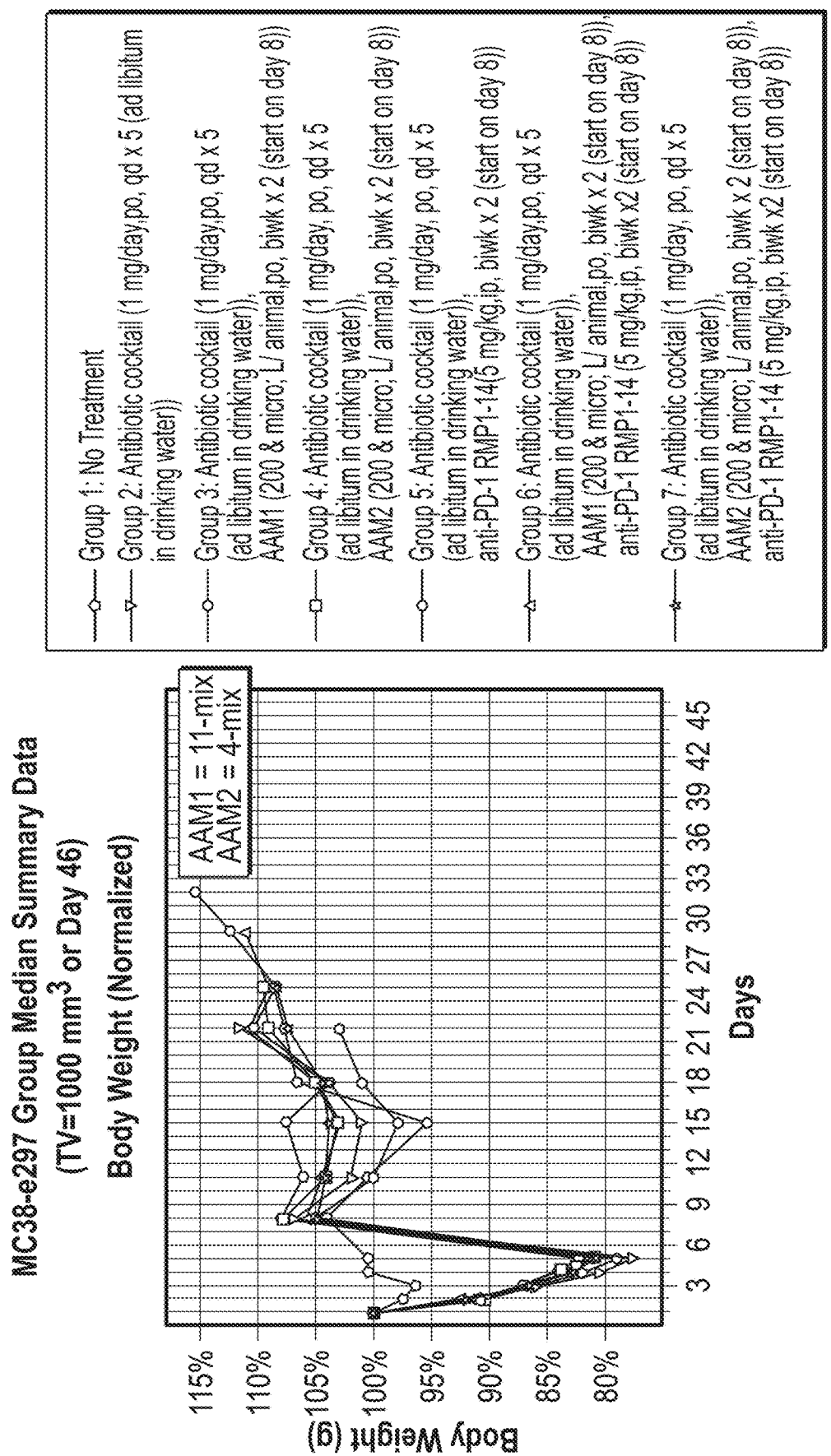
FIGS. 29A-29B shows body weight (left panel) and tumor volume (right panel) of mice that received the combination of αPD1 Ab and the 4-mix of bacterial strains or αPD1 Ab and the 11-mix of bacterial strains, and the various control groups.
Figure 29B:
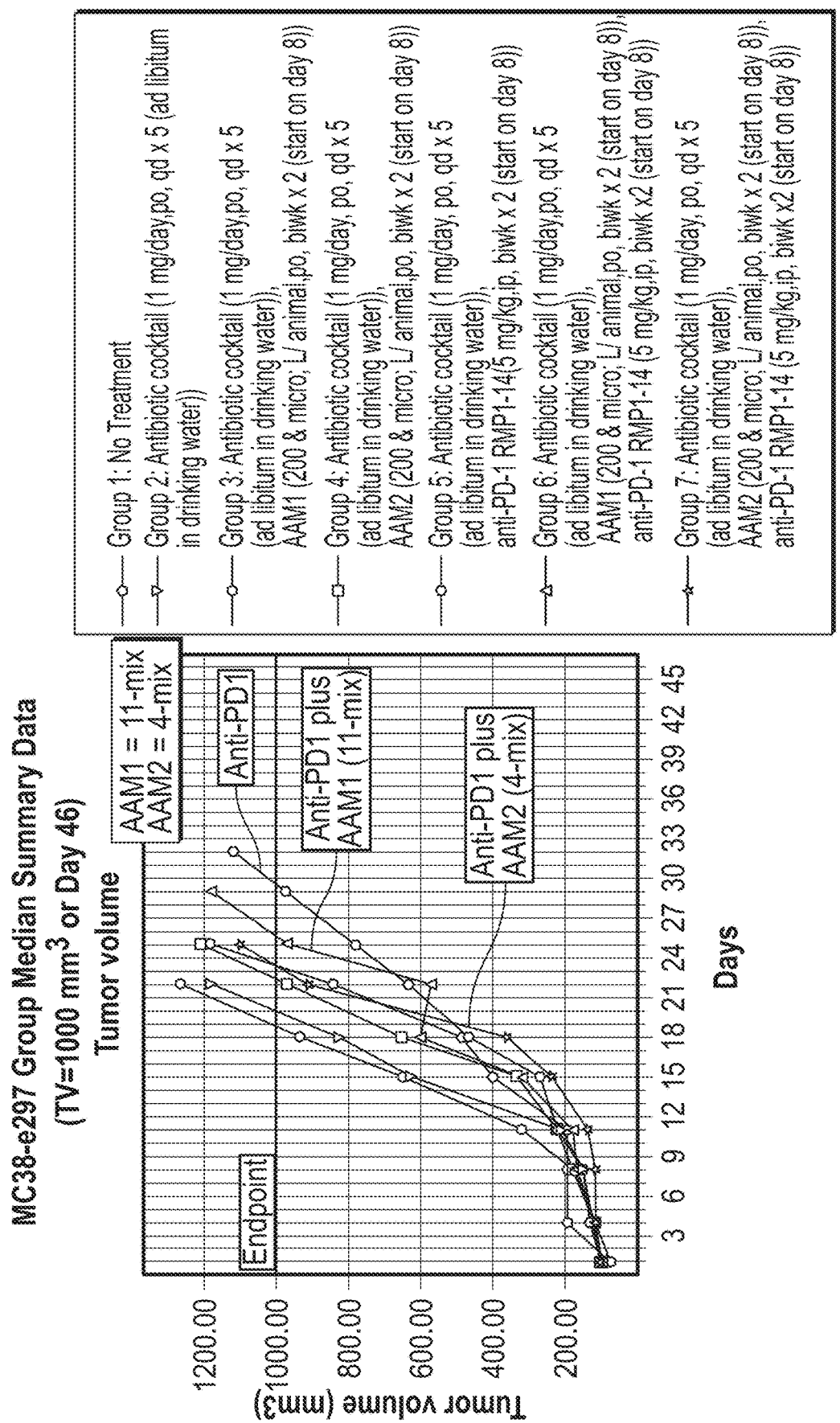

Example 5: Anti-Cancer Characteristics of CD8+ T-Cell Inducing Bacterial Cocktails in Combination with an Anti-PD1 Antibody To investigate whether colonization with the 4-mix or 11-mix in combination with immune checkpoint inhibitor anti-PD1 could enhance anticancer immune responses in the absence of antibiotic pretreatment and prior engraftment, a MC38 colon cancer cell line ($3 \times 10^5$ cells per mouse) was subcutaneously injected into the right flank of mice at day −14 (See FIG. 28). The animals were randomized into the following treatment groups:

Group 1: No treatment;

Group 3: 11-mix monotherapy (referred to as "AAM1" in FIGS. 28 and 29):

Group 4: 4-mix monotherapy (referred to as "AAM2" in FIGS. 28 and 29);

Group 5: anti-PD1 antibody (RMP1-14) monotherapy;
Group 6: anti-PD1 antibody (RMP1-14) and 11-mix (referred to as "AAM1" in FIGS. 28 and 29) combination; and
Group 7: anti-PD1 antibody (RMP1-14) and 4-mix (referred to as "AAM2" in FIGS. 28 and 29) combination.

The treatments were begun at day 1 (tumor volume approximately 100-150 mm$^3$). Bacterial cocktail treatment and the anti-PD1 antibody were administered biweekly twice. The mice were assessed for weight and survival through the course of the experiment. Tumor size and volume were measured.

Tumor Measurement

Figure 30A:
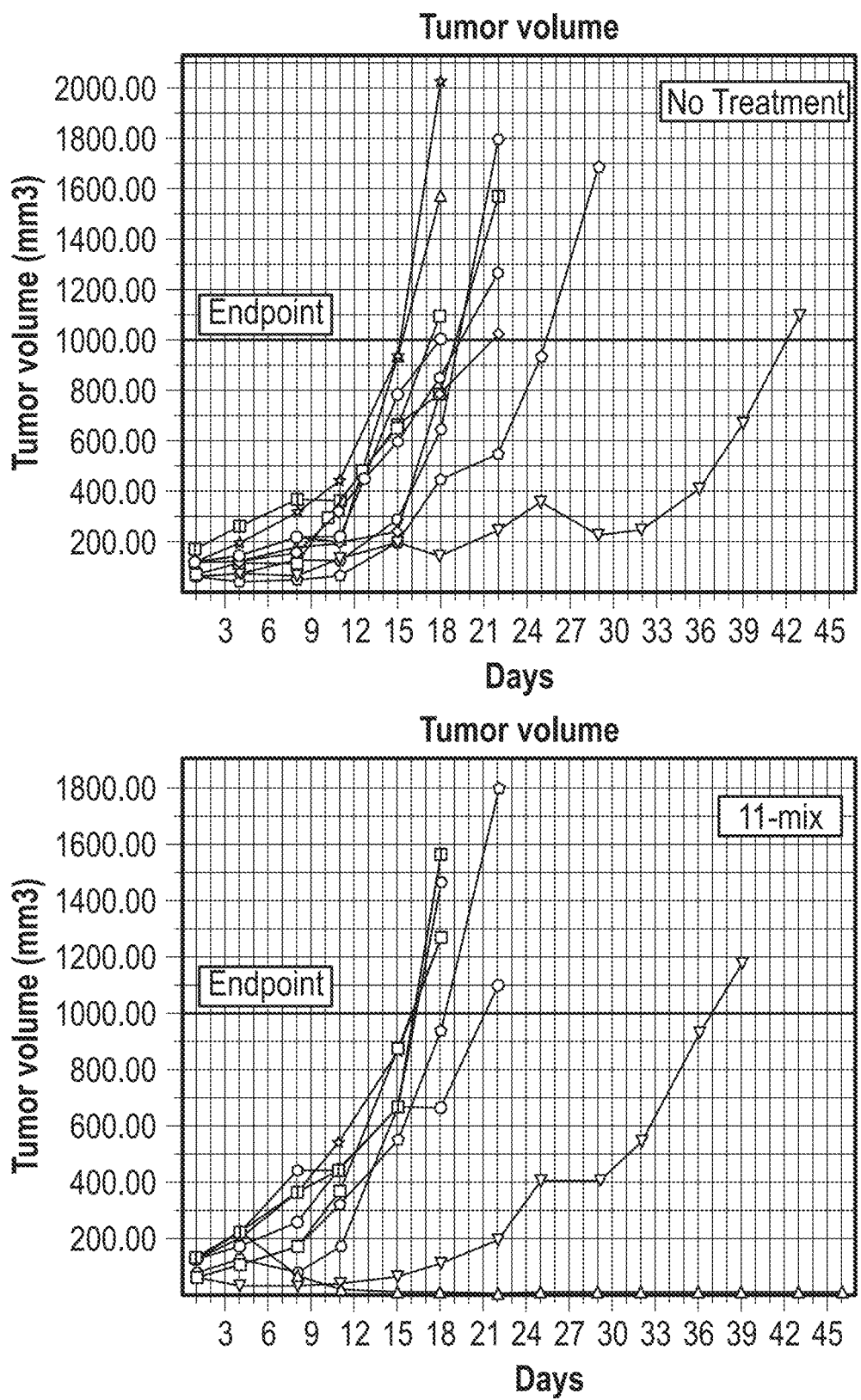
FIGS. 30A-30B shows tumor volume plots of individual mice treated in experiments of Example 5 (11-mix; αPD-1 Ab; 11-mix+αPD-1 Ab). The tumor volume did not increase in multiple animals in the 11-mix+αPD-1 Ab treatment group (bottom right panel).
Figure 30B:
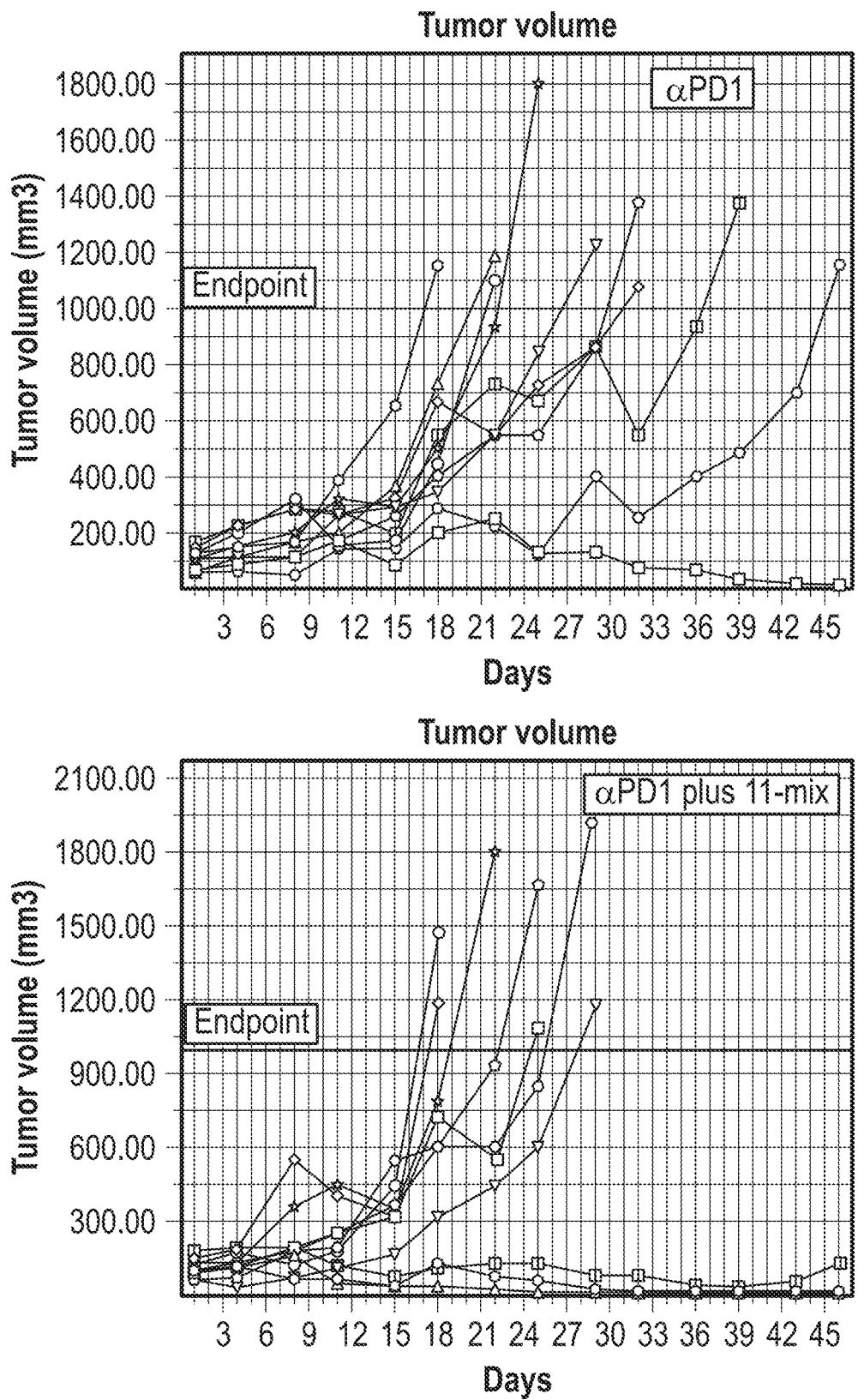
Figure 32A:
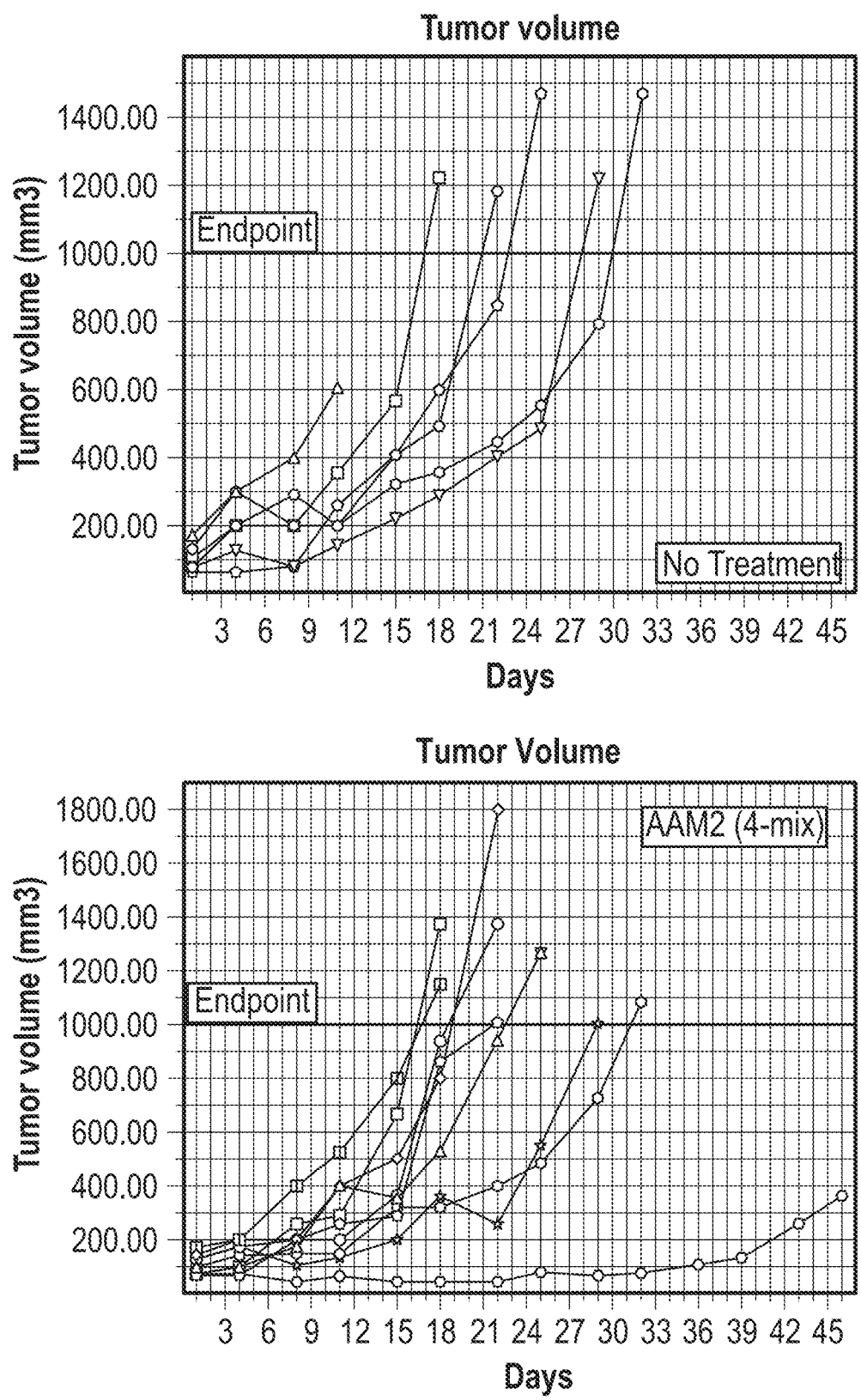
FIG. 32 shows tumor volume plots of individual mice treated in experiments of Example 5 (4-mix: αPD-1 Ab; 4-mix+αPD-1 Ab). The tumor volume did not increase in multiple animals in the 4-mix+αPD-1 Ab treatment (bottom right panel).
Figure 32B:
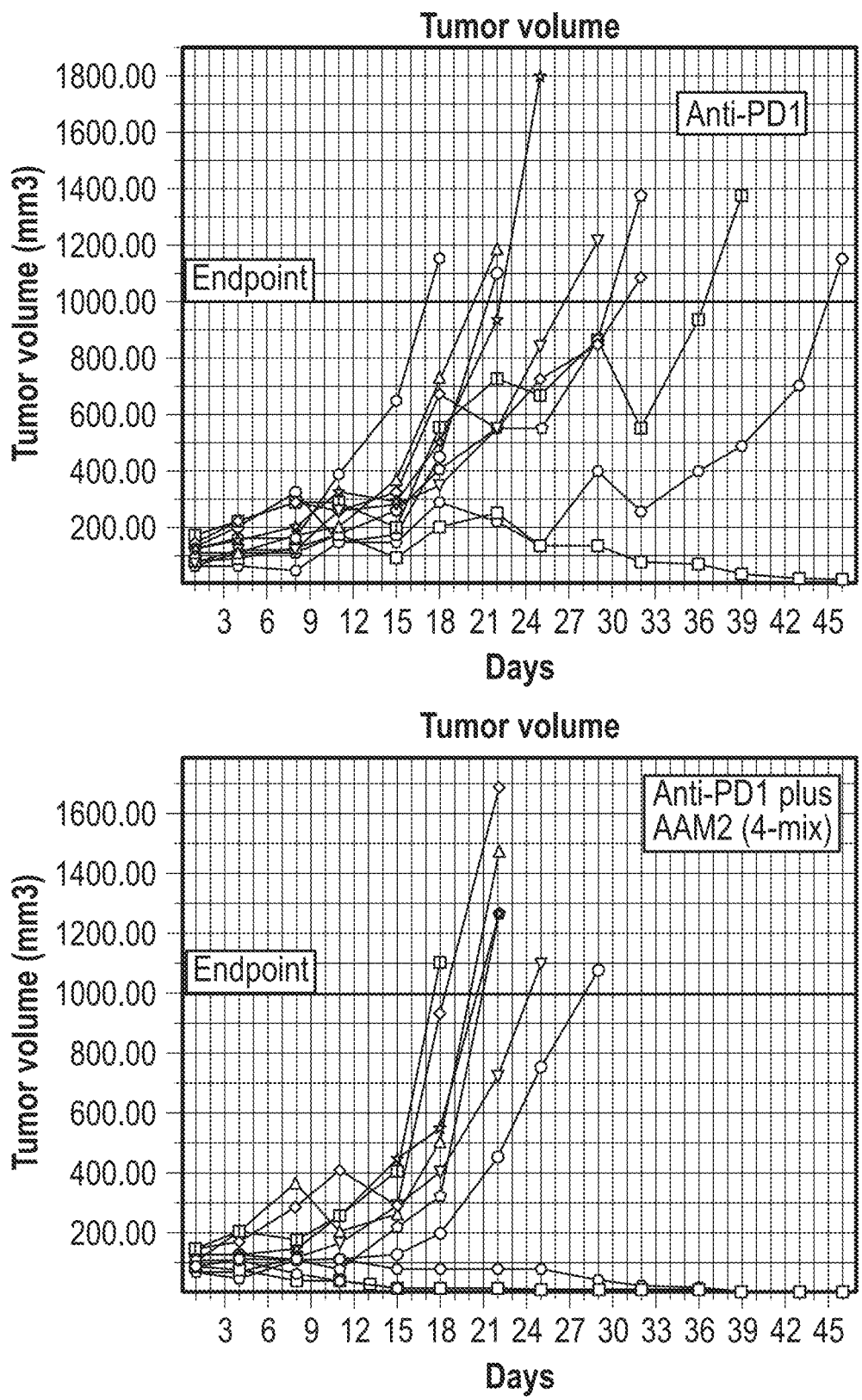

Treatment with the anti-PD1 antibody alone or in combination with either the 4-mix or the 11-mix resulted in a reduction in tumor growth as compared to no treatment. FIG. 30 shows tumor volume plots of the individual mice treated in experiments of Example 5 (control, 11-mix: αPD-1 Ab; 11-mix+αPD-1 Ab). The tumor volume did not increase in multiple animals in the 11-mix+αPD-1 Ab treatment group (bottom right panel). FIG. 32 shows tumor volume plots of individual mice treated in experiments of Example 5 (control, 4-mix; αPD-1 Ab; 4-mix+αPD-1 Ab). The tumor volume did not increase in multiple animals in the 4-mix+αPD-1 Ab treatment group (bottom right panel).

Survival

Figure 31:
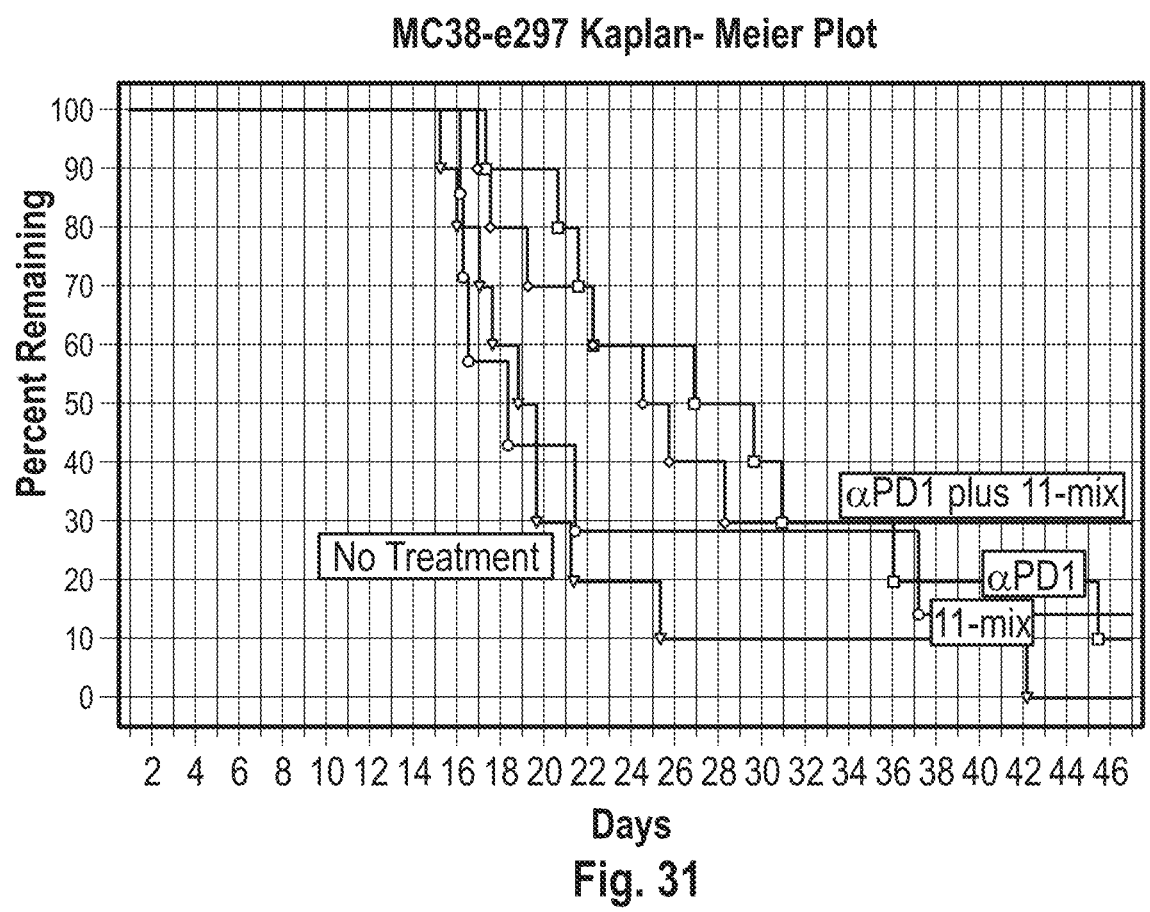
FIG. 31 shows survival plots of mice treated in experiments of Example 5 (11-mix; αPD-1 Ab; 11-mix+αPD-1 Ab).

Survival data are shown in FIG. 31 for the control, 11-mix; PD-1 Ab; and 11-mix+PD-1 Ab groups. The combination of the 11-mix and the αPD-1 Ab showed increased survival when compared to either the 11-mix or the αPD-1 Ab on its own.

Figure 33:
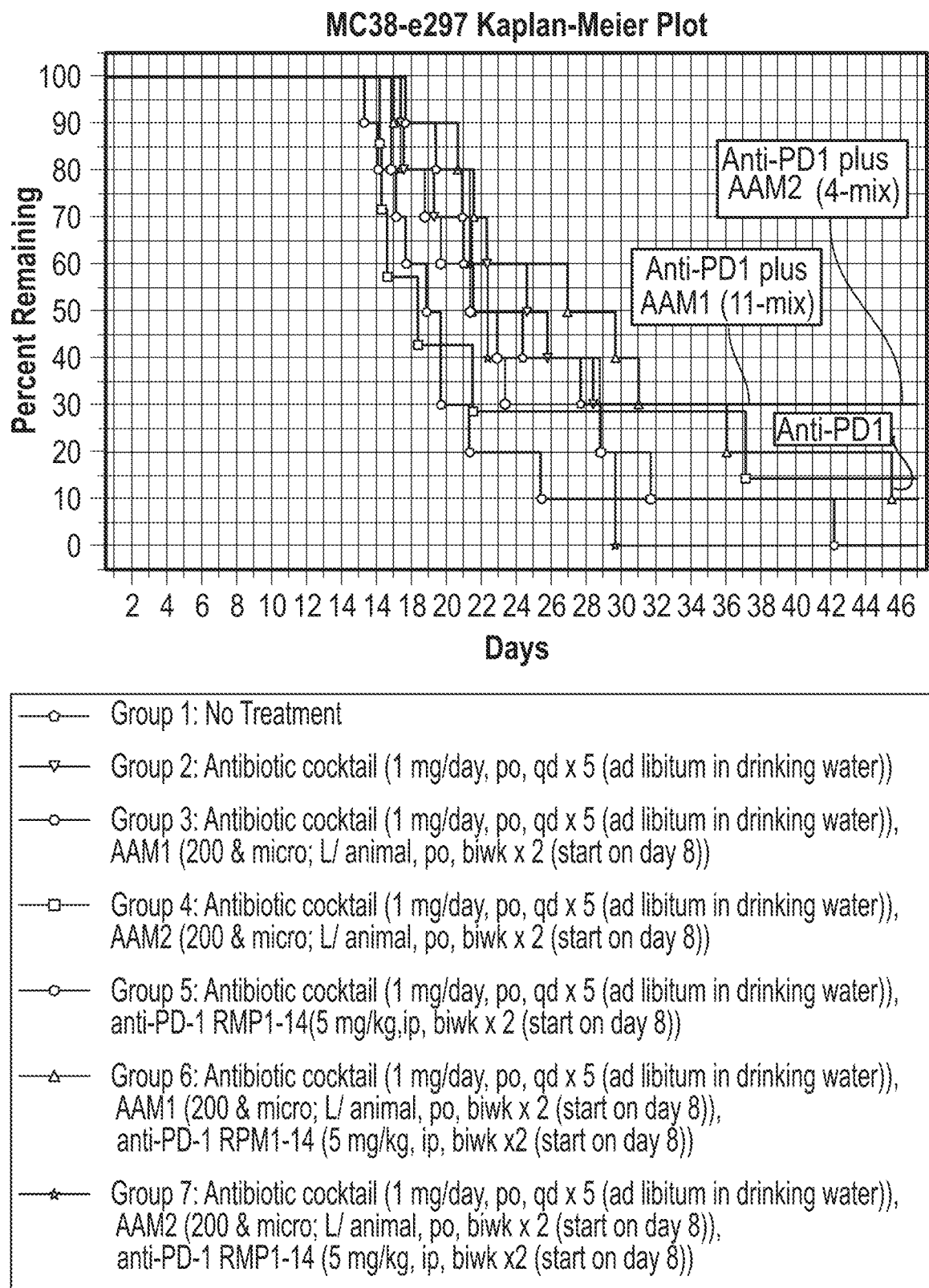
FIG. 33 shows plots of mice treated in experiments of Example 5. Highlighted are treatment with αPD-1 Ab, 11-mix+αPD-1 Ab, and 4-mix+αPD-1 Ab.

The combined survival data of mice in the control, 4-mix; αPD-1 Ab; 4-mix+αPD-1 Ab, 11-mix, and 11-mix+αPD-1 Ab groups are shown in FIG. 33. Both the combination of the 4-mix and the αPD-1 Ab and the combination of the 11-mix and the αPD-1 antibody showed increased survival when compared to the αPD-1 Ab on its own.

Example 6: Anti-Cancer Characteristics of CD8+ T-Cell Inducing Bacterial Cocktail Combination with an Anti-PD1 Antibody in a Melanoma Model A melanoma engraftment mouse model was used to evaluate the efficacy of the 11-mix in combination with a PD-1 antibody in the treatment of melanoma. As shown in the timelines in FIGS. 34 and 35, mice received antibiotics (Ampicillin, Vancomycin, Metronidazole, and Neomycin: "AVMN") from day −3 to day 2. On day 0, the mice were engrafted with 7×10$^5$ Braf Pten melanoma cells. The mice were grouped in the following treatment groups:
Specific Pathogen Free (SPF) feces;
SPF feces+anti-PD1 antibody;
SPF feces+11-mix; and
SPF feces+11-mix+anti-PD1 antibody.

Figure 34:
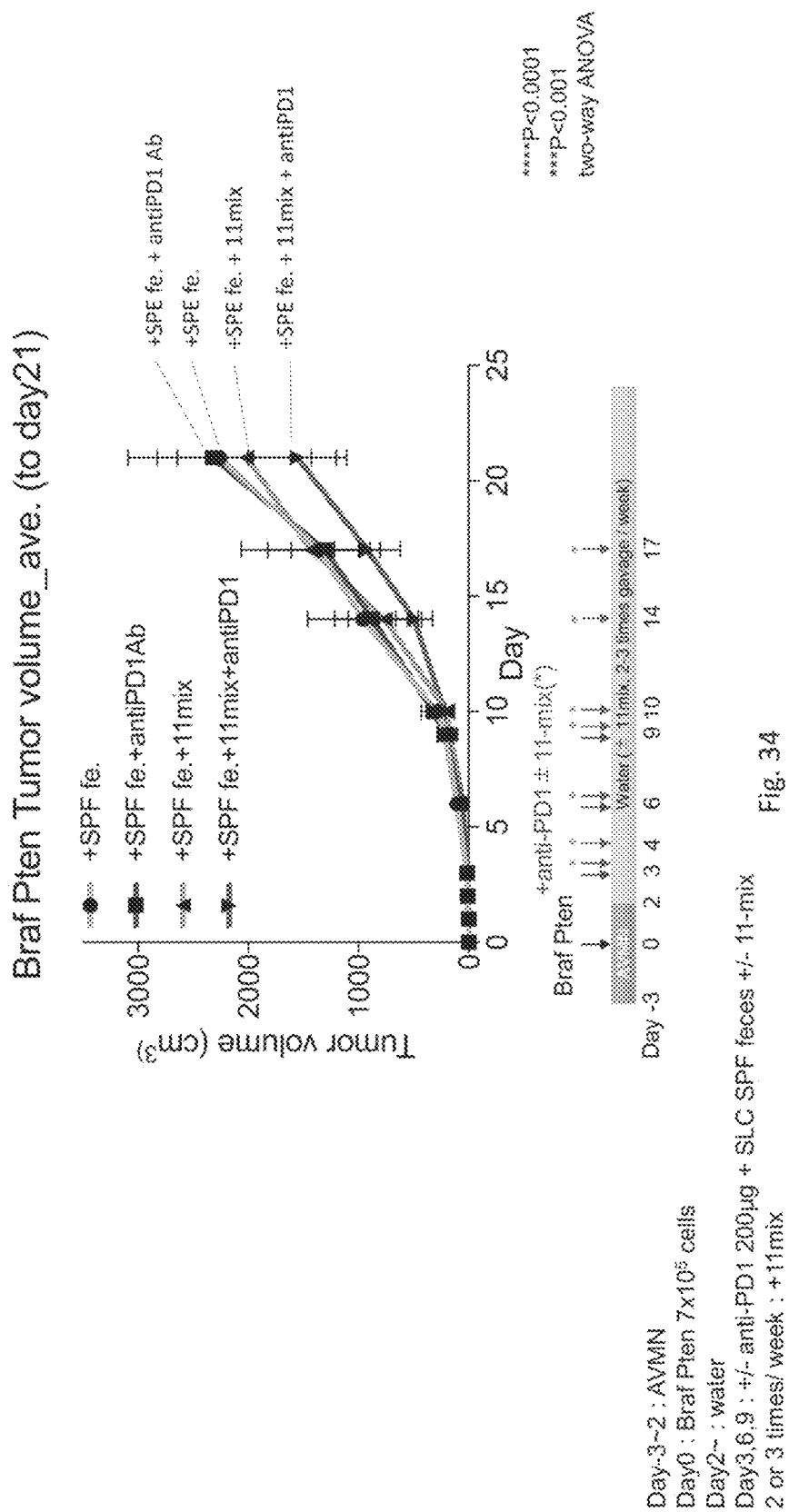
FIG. 34 shows data of experiments with the Braf Pten melanoma model (Example 6). Briefly, mice were administered antibiotics ("AVMN") from day −3 to day 2 and engrafted with 7×10$^5$ Braf Pten cells on day 0. On days 3, 6, and 9 the indicated groups of mice were administered an anti-PD1 antibody (arrows on the timeline) and SLC SPF feces from specific-pathogen free (SPF) mice obtained from Japan SLC (SLC SPF feces), with or without the 11-mix (arrows with asterisk on the timeline). The groups of mice indicated as having received the 11-mix were administered the 11-mix 2 or 3 times per week. The plot shows the average tumor volume at each of the timepoints for the groups of mice** $P<0.0001$.* $P<0.001$ (two-way ANOVA).
Figure 35:
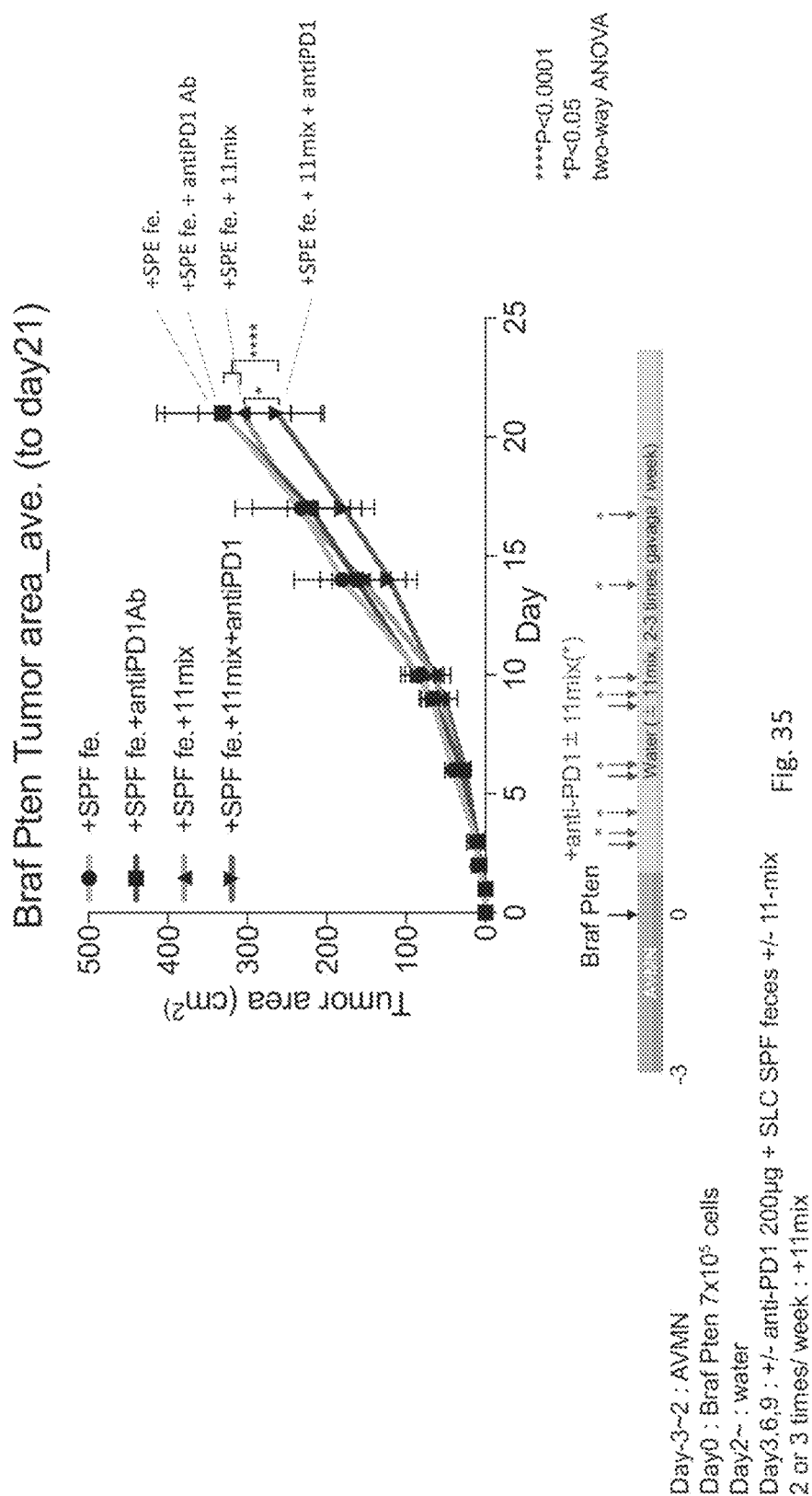
FIG. 35 shows data of experiments with the Braf Pten melanoma model (Example 6). Briefly, mice were administered antibiotics ("AVMN") from day −3 to day 2 and engrafted with 7×10$^5$ Braf Pten cells on day 0. On days 3, 6, and 9 the indicated groups of mice were administered an anti-PD1 antibody (arrows on the timeline) and SLC SPF feces from specific-pathogen free (SPF) mice obtained from Japan SLC (SLC SPF feces), with or without the 11-mix (arrows with asterisk on the timeline). The groups of mice indicated as having received the 11-mix were administered the 11-mix 2 or 3 times per week. The plot shows the average tumor area at each of the timepoints for the groups of mice.** $P<0.0001$,* $P<0.001$ (two-way ANOVA).
Figure 36:
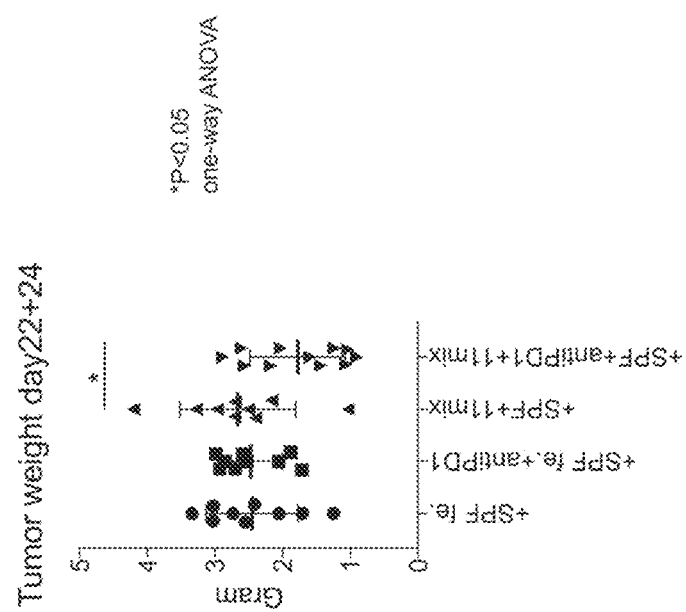
FIG. 36 shows data on the weight of tumors obtained on days 22 and 24 from the indicated groups of mice. * $P<0.05$ (one-way ANOVA).
Figures 37A, 37B, 37C:
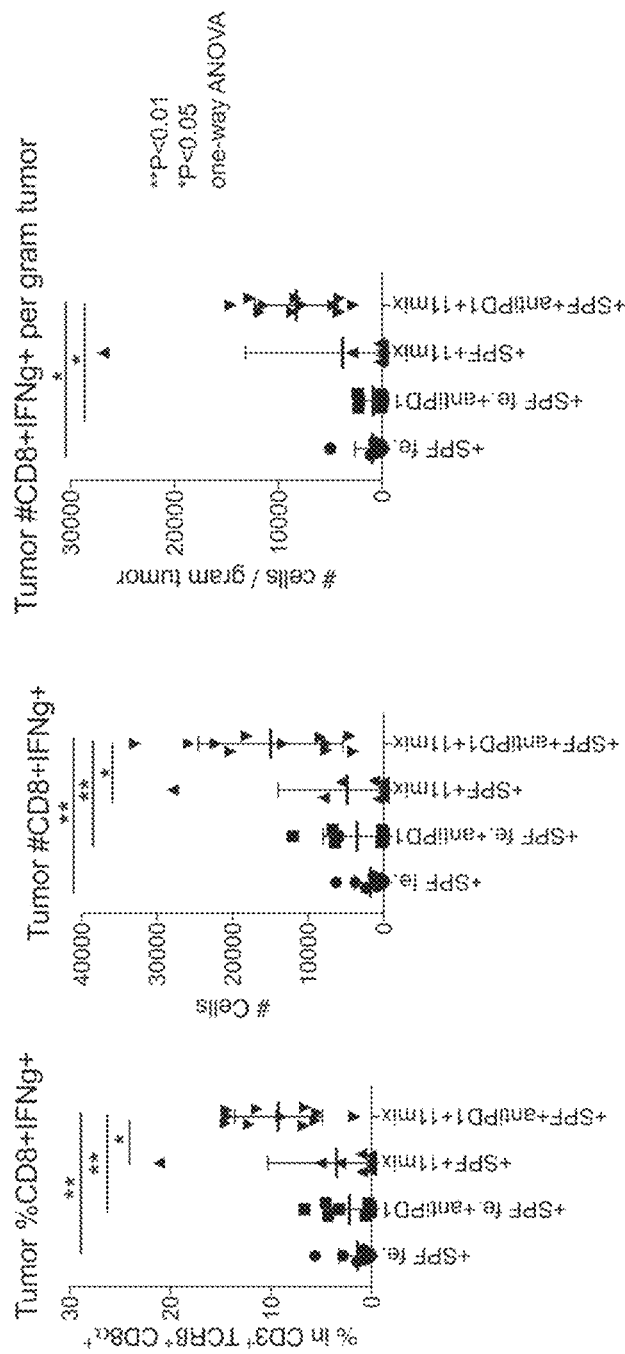
FIGS. 37A-37C show data on lymphocytes isolated from tumor cells. On days 22 and 24, lymphocytes were isolated from tumors. CD3, TCRβ, CD8, and IFNγ were stained with antibodies.
Figure 38:
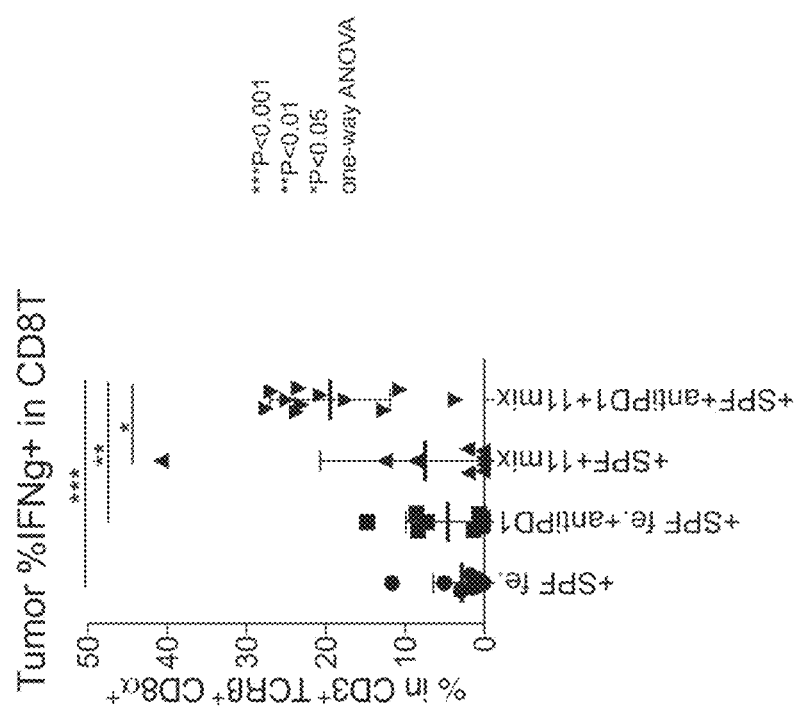
FIG. 38 shows the percentage of IFNγ+ cells in the population of CD8T cells isolated from the tumors.* $P<0.001$, $P<0.01$, * $P<0.05$ (one-way ANOVA).
Figures 39A, 39B, 39C, 39D:
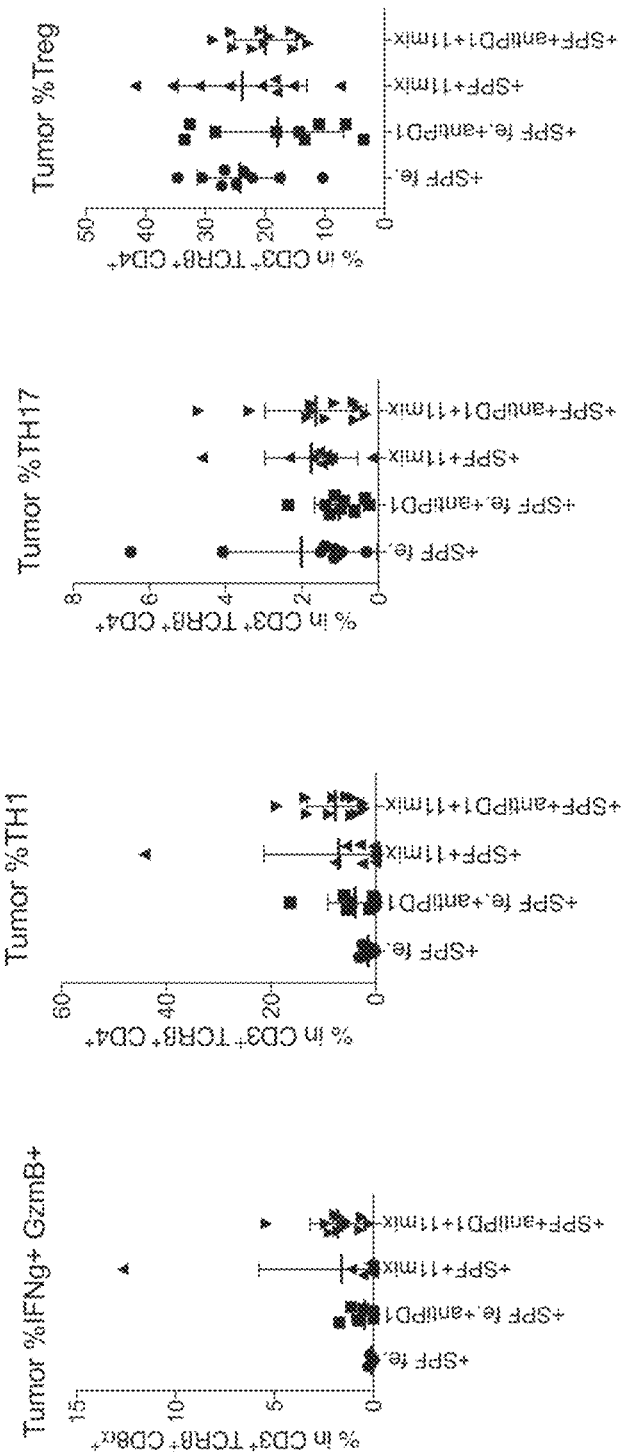
FIGS. 39A-39D show data on lymphocytes isolated from tumor cells. On days 22 and 24, lymphocytes were isolated from tumors. CD3, TCRβ, CD8, IFNγ, GzmB, IL-17, and CD4 were stained with antibodies.

On days 3, 6, and 9, the mice were administered SLC SPF feces from specific-pathogen free (SPF) mice obtained from Japan SLC (SLC SPF feces), an anti-PD1 antibody (arrows on the timelines in FIGS. 34 and 35) and/or the 11-mix (arrows with asterisk on the timelines in FIGS. 34 and 35). The 11-mix was administered to the indicated groups of mice 2 or 3 times per week by gavage. Mice that received the combination of the anti-PD1 antibody and the 11-mix had reduced tumor volume (FIG. 34), tumor area (FIG. 35), and tumor weight (FIG. 36) as compared to the other groups of mice.

Lymphocytes were isolated from tumors obtained from the mice on days 22 and 24 and stained using antibodies to cell markers, including CD3, TCRβ, CD8, CD4, IFNγ, Granzyme, and IL-17. Treatment with the 11-mix and anti-PD1 antibody combination resulted in elevated accumulation of IFNγ+CD8+ T cells in the melanoma tumor. FIGS. 37A-37C and 38. In this experiment, there was no significant difference in the number of IFNγ+GzmB+ cells, Th1 cells, Th17 cells, or Treg cells between the groups of mice. FIGS. 39A-39D.

These results show that treatment with 11-mix in combination with the anti-PD1 antibody systemically activates CD8 T cells in the melanoma.

Example 7: CD8 T-Cell Induction in Specific-Pathogen Free (SPF) Mice

Experimental parameters were evaluated for the induction of CD8 T cells by the 11-mix bacterial cocktail. The animals used in this study were specific pathogen free mice (SPF mice) as compared to germ-free mice.

Figure 40:
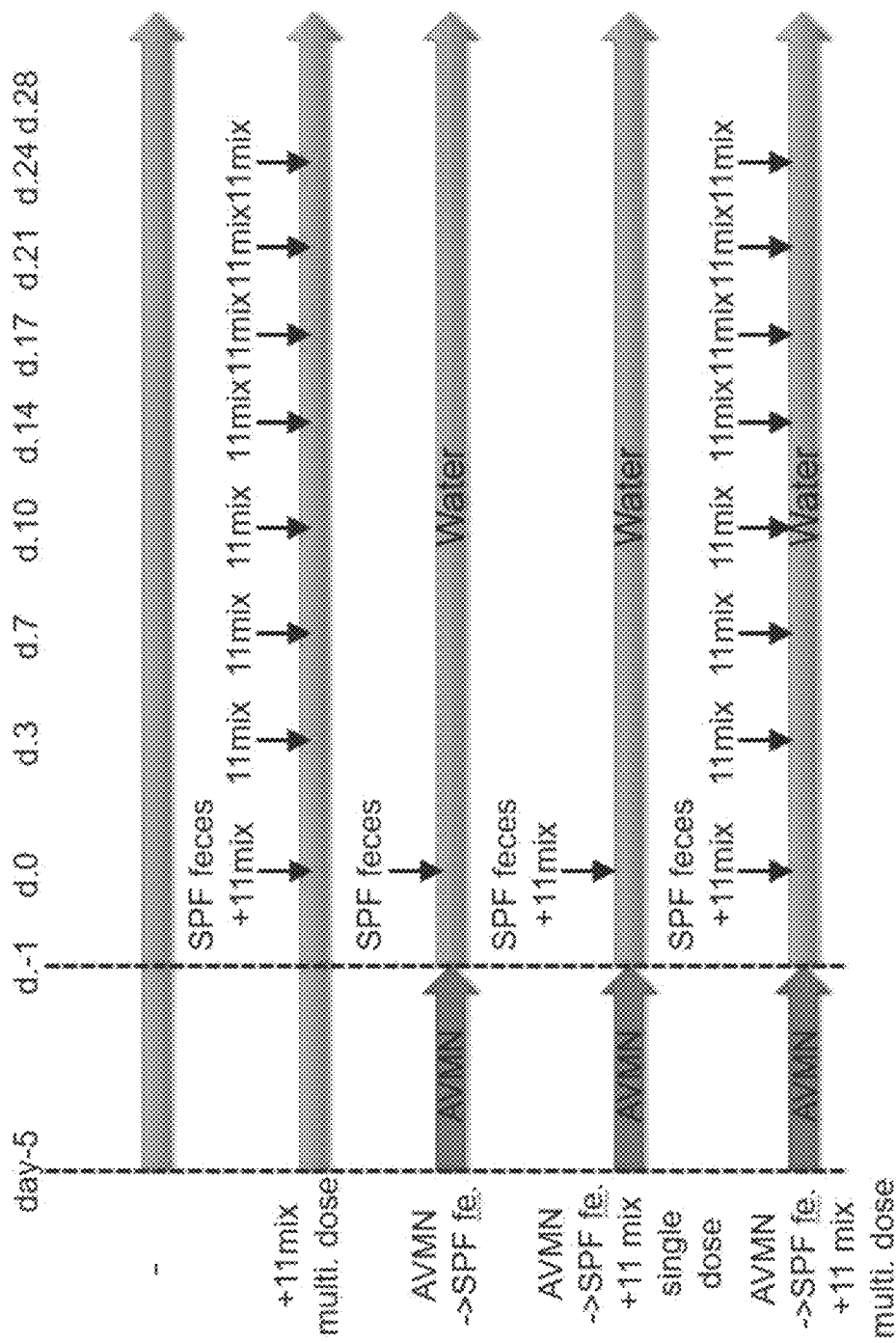
FIG. 40 shows a schematic of the experimental plan described in Example 7 (the dosing study).

As shown in FIG. 40, the mice were grouped in the following treatment groups:
11-mix multi-dose;
AVMN+SPF feces;
AVMN+SPF feces+11-mix single dose; and
AVMN+SPF feces+11-mix multi-dose.

The indicated groups of mice received antibiotics (Ampicillin, Vancomycin, Metronidazole. and Neomycin: "AVMN") in their drinking water from day −5 to day −1. Mice were inoculated with SPF feces with or without the 11-mix on day 0. For groups that received multiple doses of the 11-mix, the bacterial cocktail was also administered in the water on days 3, 7, 10, 14, 17, 21, 24, and 28.

Figure 41C:
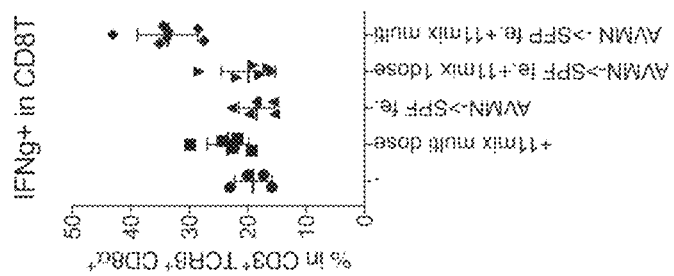
FIGS. 41A-41C show data on lymphocytes isolated from mice in the experiment shown in FIG. 40 (Example 7). CD3, TCRβ, CD8, and IFNγ were stained with antibodies.
Figure 41B:
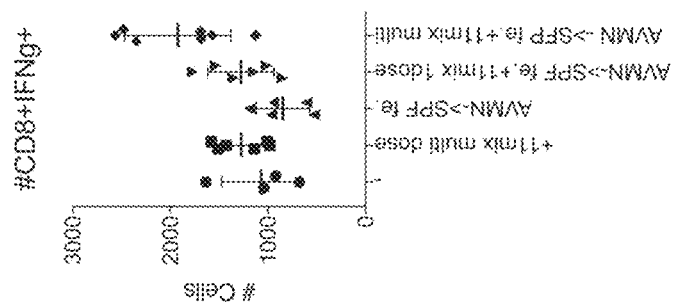
Figure 41A:
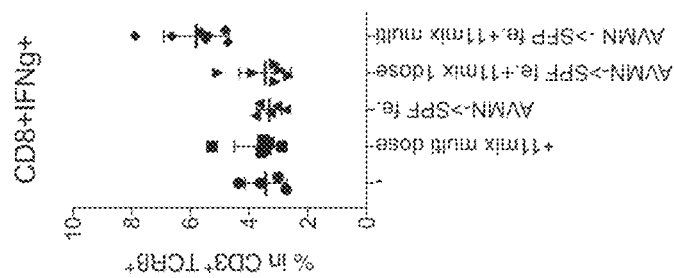
Figure 42C:
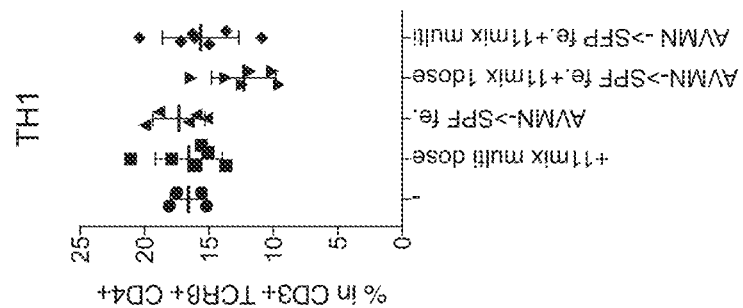
FIGS. 42A-42C show data on lymphocytes isolated from mice from the experiment shown in FIG. 40 (Example 7). CD3, TCRβ, CD8, IFNγ, CD103, IL-17, and CD4 were stained with antibodies.
Figure 42B:
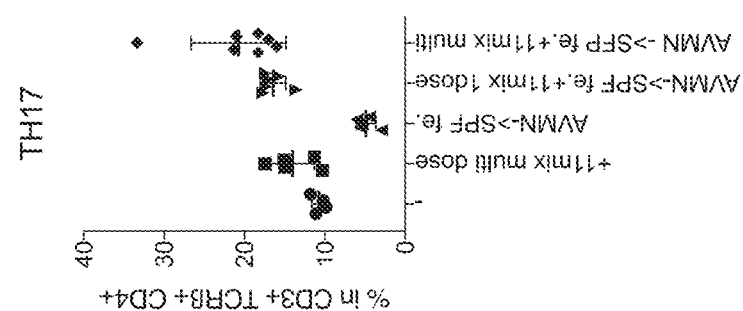
Figure 42A:
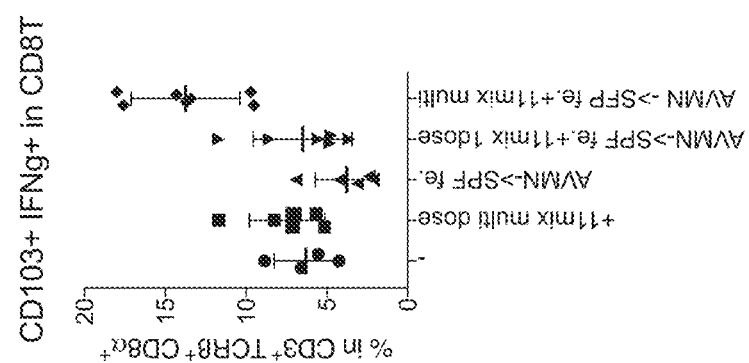

Lymphocytes were isolated from the mice on days 22 and 24 and stained using antibodies to cell markers, including CD3, TCRβ, CD8, CD4, IFNγ, Granzyme, and IL17. Mice that received the antibiotic pretreatment and multiple doses of the 11-mixed showed enhanced levels of IFNγ+CD8+ T cells. FIGS. 41A-41C. The mice that received the antibiotic pretreatment and multiple doses of the 11-mixes also had enhanced levels of CD103+IFNγ+ cells in the CD8T cell population of cells (FIG. 42A) and slightly enhanced levels of Th17 cells (FIG. 42B). There was no significant difference in the number of Th1 cells between the groups of mice. (FIG. 42C). These data show that the 11-mix can induce CD8+ T cells in a complex background: a specific pathogen free mouse (as compared to a germ free mouse).

Example 8: The Role of Transcription Factor BATF3

Figures 43A, 43B, 43C:
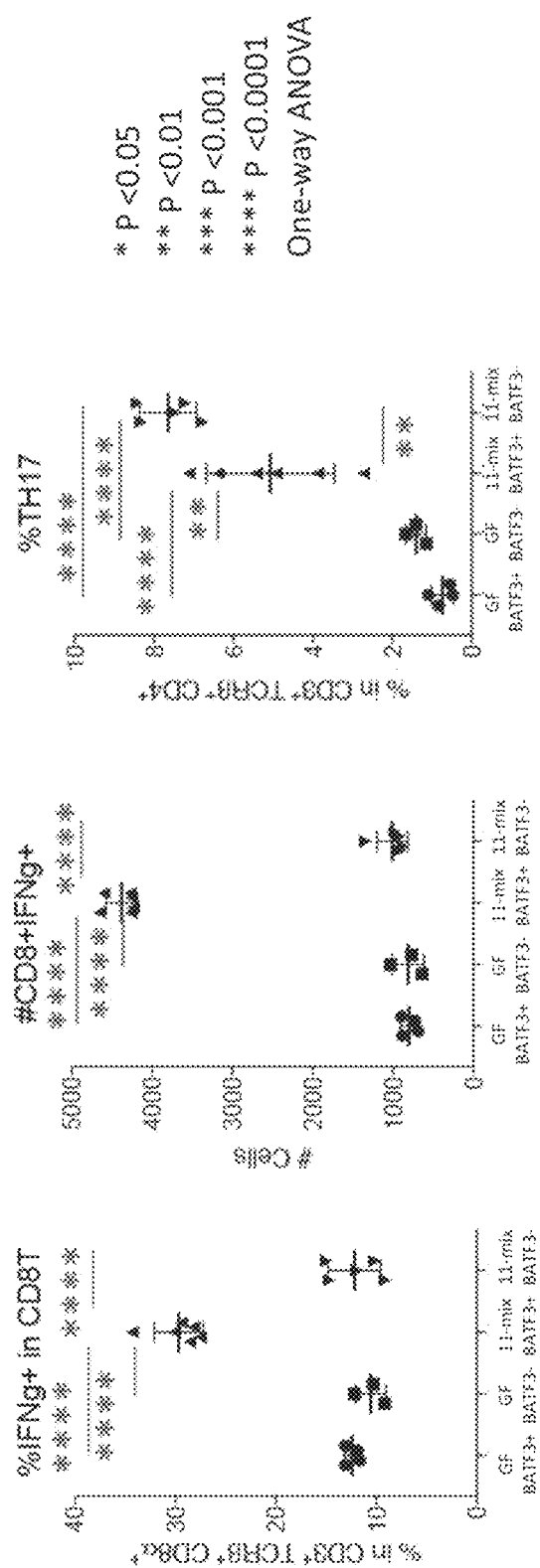
Figure 44B:
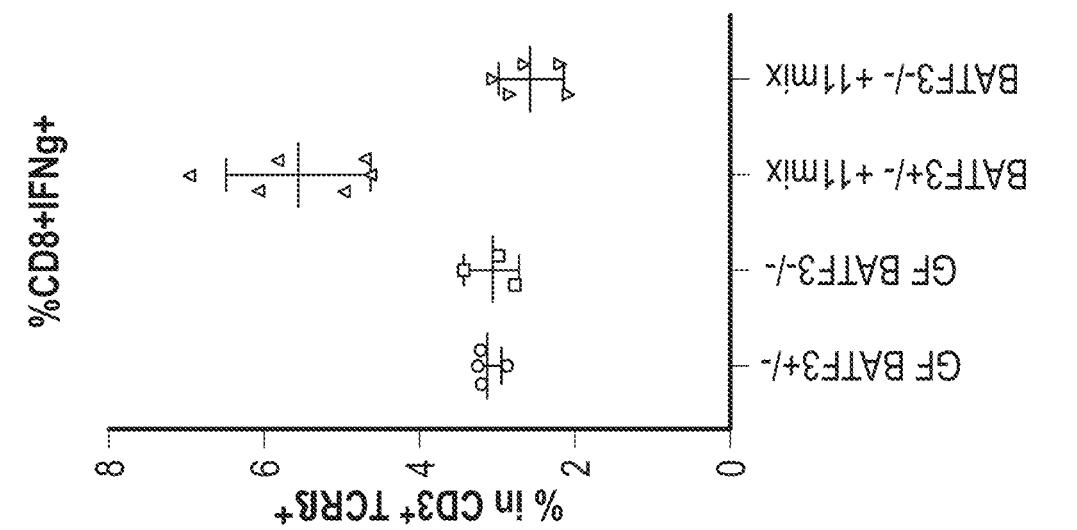
FIGS. 44A-44B shows that BATF3 is required for the 11-mix to induce CD8-T cells, as evidenced by the flow cytometry (FIG. 44A), and the percentage of IFNγ+ in the CD3+ TCRβ+CD8α+(CD8 T cells) population of cells isolated from the indicated mice (FIG. 44B).
Figure 44A:
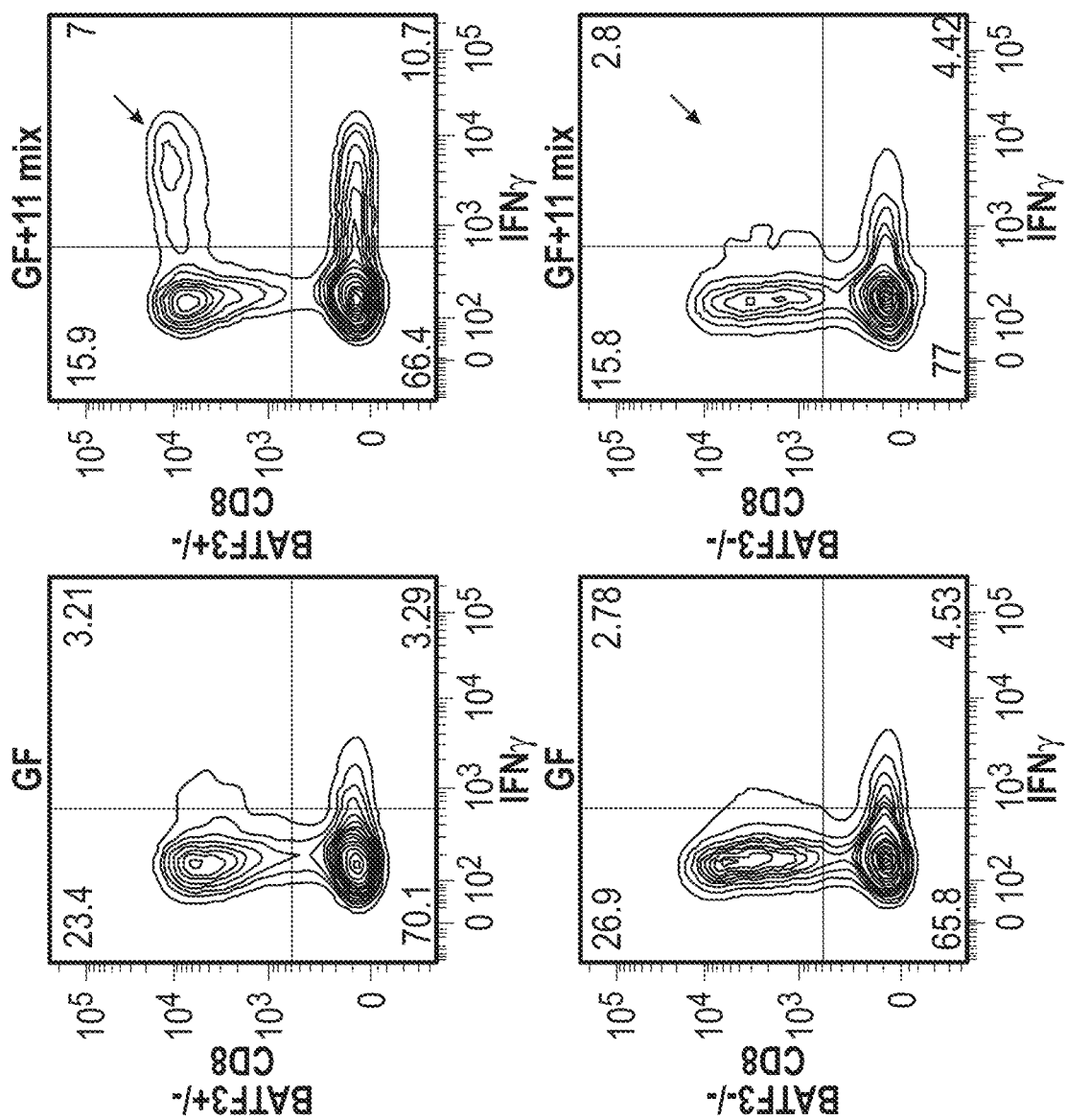

The 11-mix was administered to mice that have the BATF3 transcription factor and mice that do not have the BATF3 transcription factor. Mice that do not have the transcription factor BATF3 are not susceptible to CD8 T cell induction by the 11-mix. (FIGS. 43A and 43B). It is likely that CD103-CD11b dendritic cells are required for stimulation of IFNγ-gamma producing CD8 and Th1 cells. The induction of Th17 cells by the 11-mix cocktail is independent of BAFT3 status. (FIG. 43C). FIGS. 43 and 44 show the results from the experiments of Example 8. The experiments show that BATF3 is required for the 11-mix to induce CD8-T cells. BATF3 is not required to induce Th17.

Example 9: Treatment of *Listeria* Infected Mice

Figure 45:
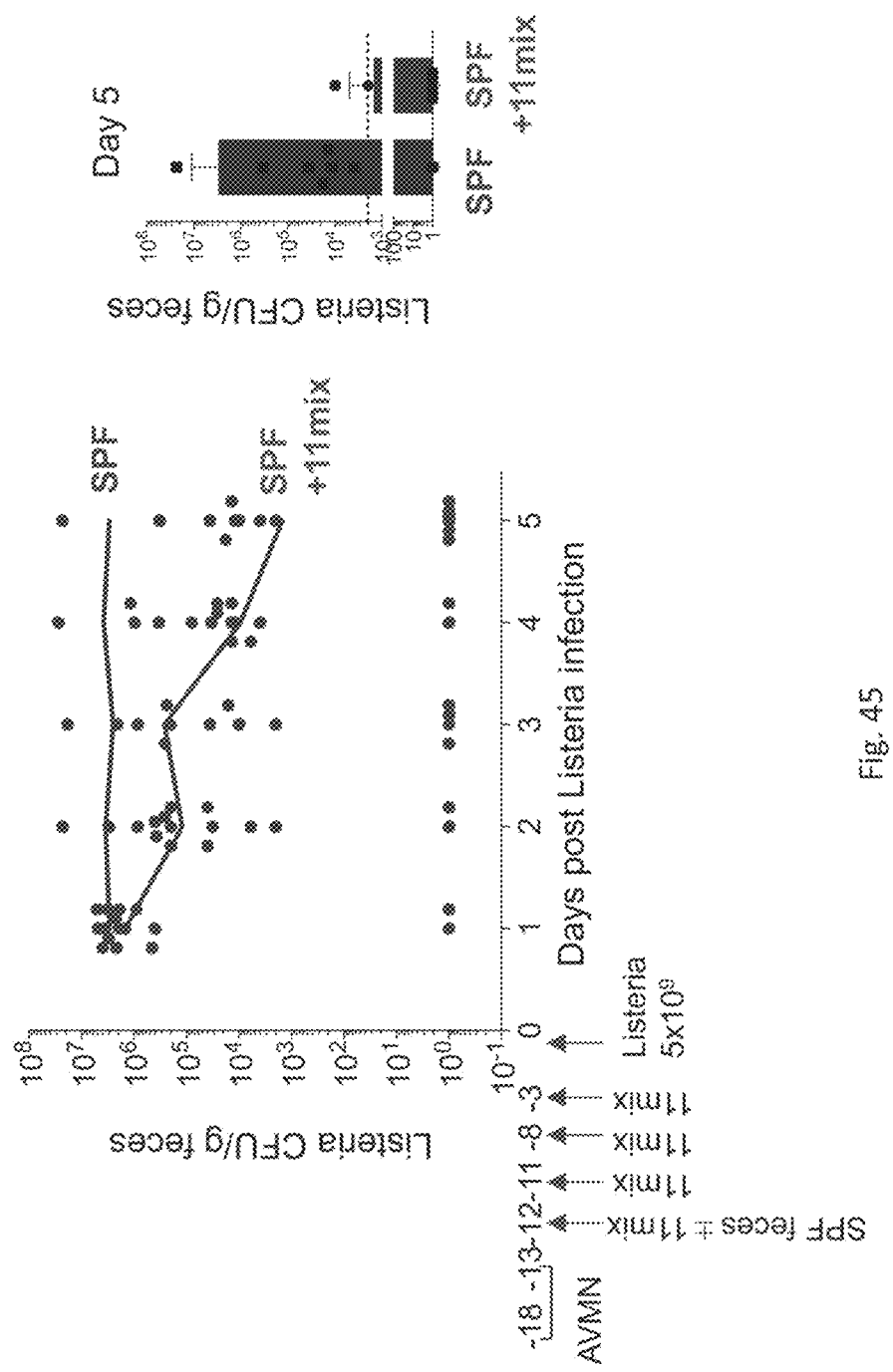
FIGS. 45-46 show the results from the experiments of Example 9. The experiments show that the 11-mix is effective in treating *Listeria* infections.
Figure 46:
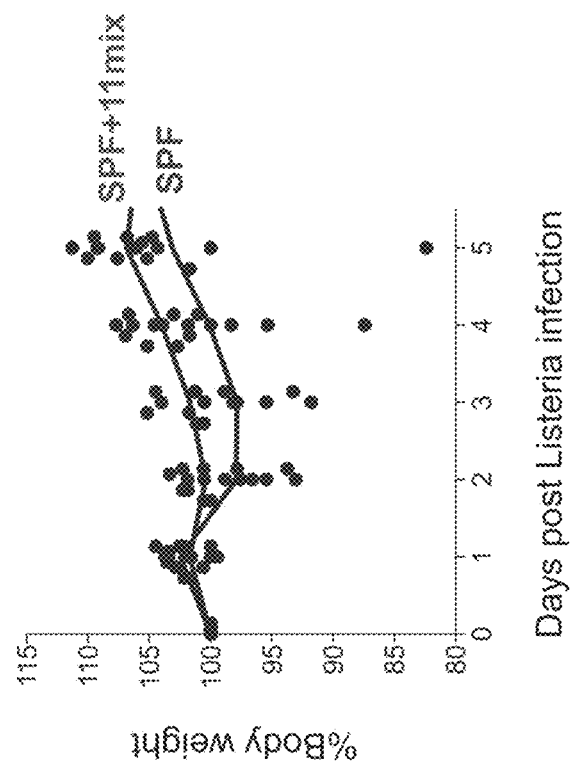

Since IFNγg+CD8+ T cells have been reported to play critical roles in controlling intracellular pathogens, it was evaluated whether oral supplementation with the 11 strain mixture in a multiple dosing regimen could augment host protective immunity against *Listeria monocytogenes* infection. SPF mice were treated with AVMN (ampicillin, vancomycin, metronidazole, neomycin) for 5 days via the drinking water. After one day washout of antibiotics, multiple oral administrations of the 11-mix (4 times) were performed. To reconstitute complex microbiota, fecal microbiota from SPF mice were introduced together with the first administration of 11-mix. The mice were then orally infected with *Listeria monocytogenes* on day 0. Fecal *Listeria* CFU and body weight of mice were determined. Treatment with 11-mix significantly reduced *Listeria monocytogenes* colonization of the gut lumen (FIG. 45) and maintained the body weight of the mice (FIG. 46). Thus, administration of the 11 strain-mixture can provide protective immunity against an intracellar, infectious pathogen.

Example 10: Localization of the CD8 T-Cells Induced by the 11-Mix

Figure 48:
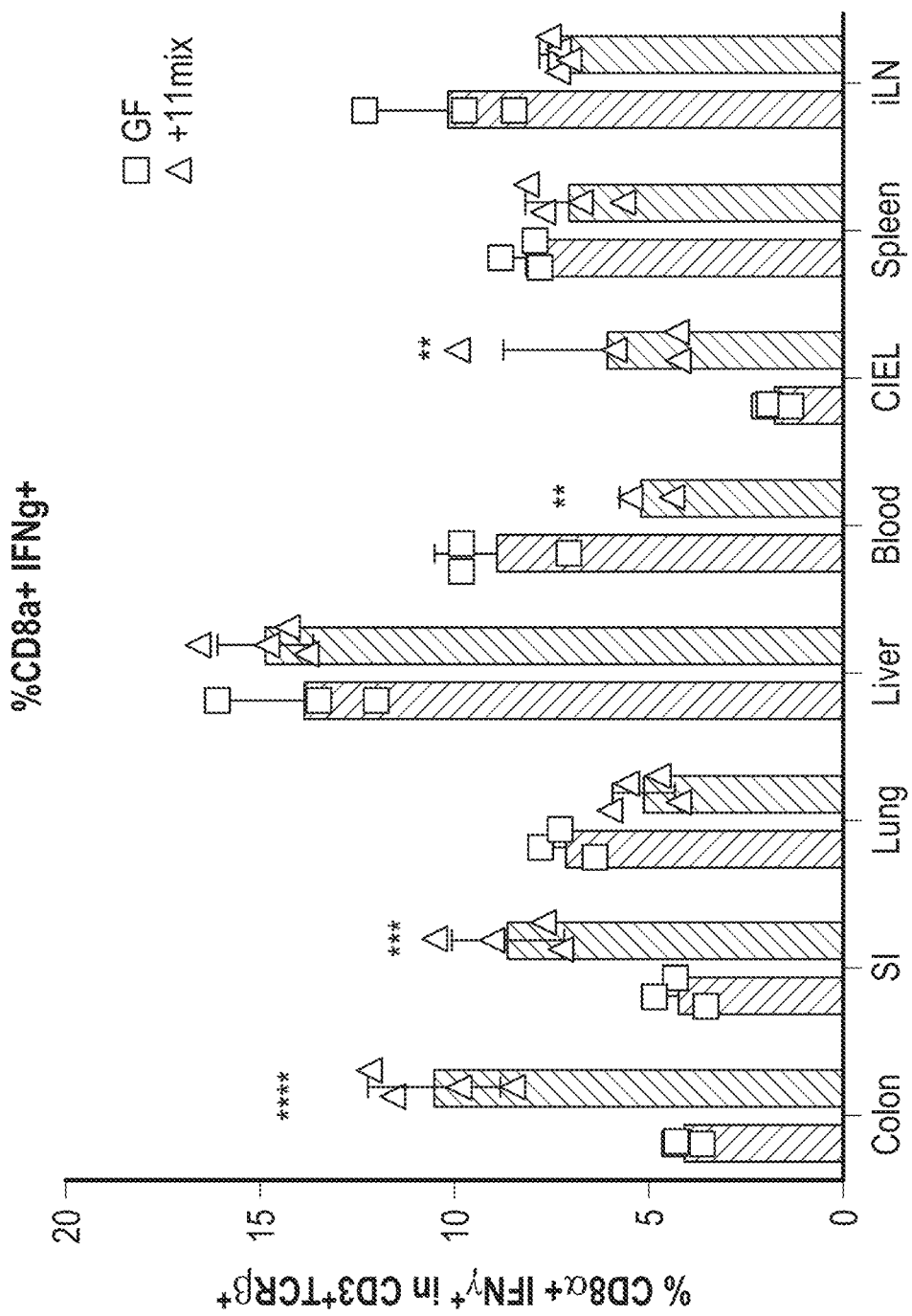
FIG. 48 relates to Example 10 and shows that the CD8 induction effect of the 11-mix in mice that are not otherwise challenged is limited to the intestine/gut compartment. (SI=short intestine, CIEL=colonic intraepithelial lymphocytes, LN=lymph nodes)

The 11-mix was administered to normal healthy mice (i.e., mice that were not otherwise stressed). Various organs and compartments in the mice were investigated for the presence of CD8 positive T-cells. As shown in FIG. 48, the CD8 positive T-cell induction effect of the 11-mix is limited to the intestine/gut (SI=small intestine, CIEL=colonic intra-epithelial lymphocytes, LN=lymph nodes).

Figure 49:
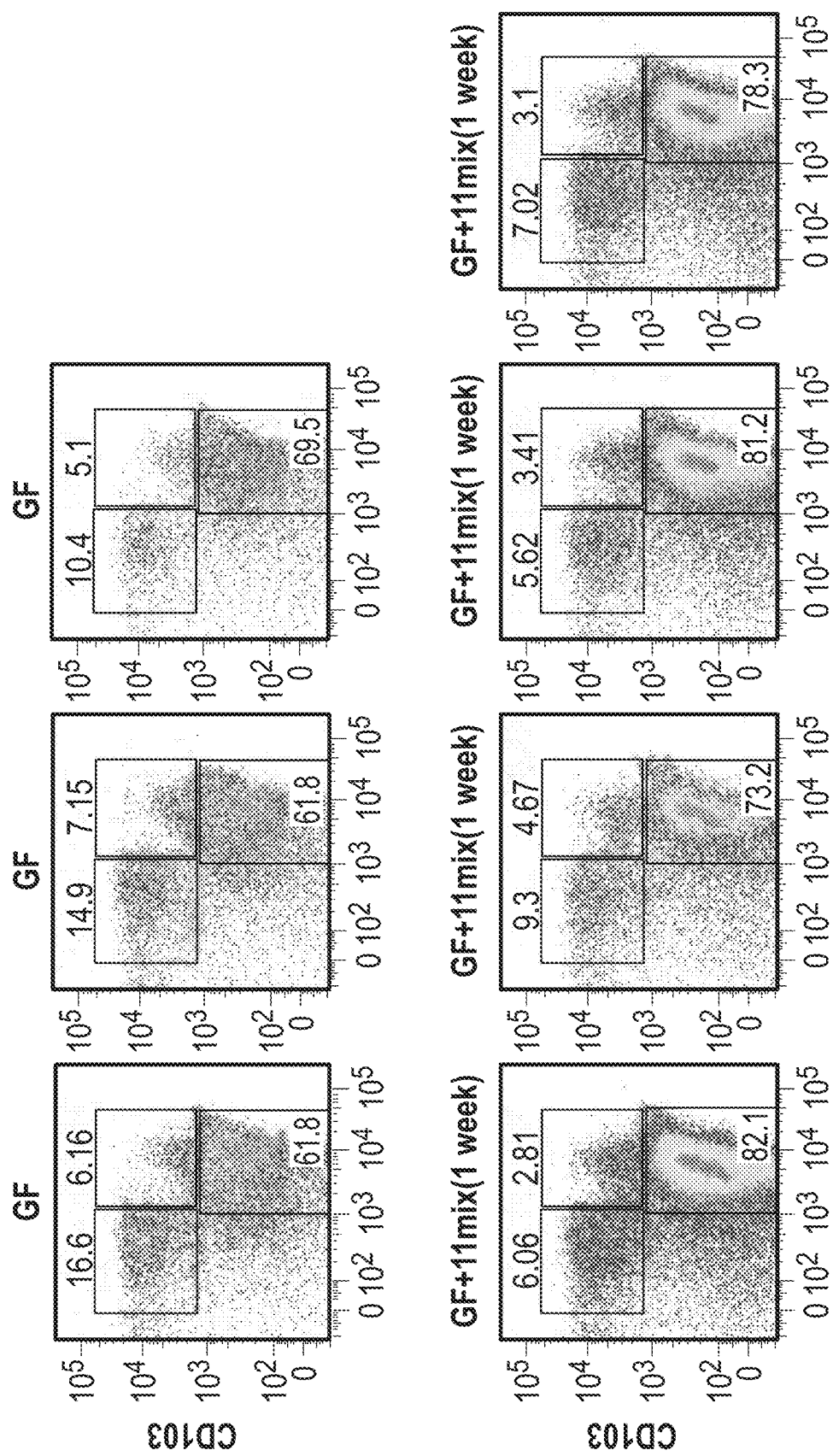
FIG. 49 shows that the frequencies of DC subsets in colonic LP were only slightly changed by the colonization with 11-mix.
Figure 50A:
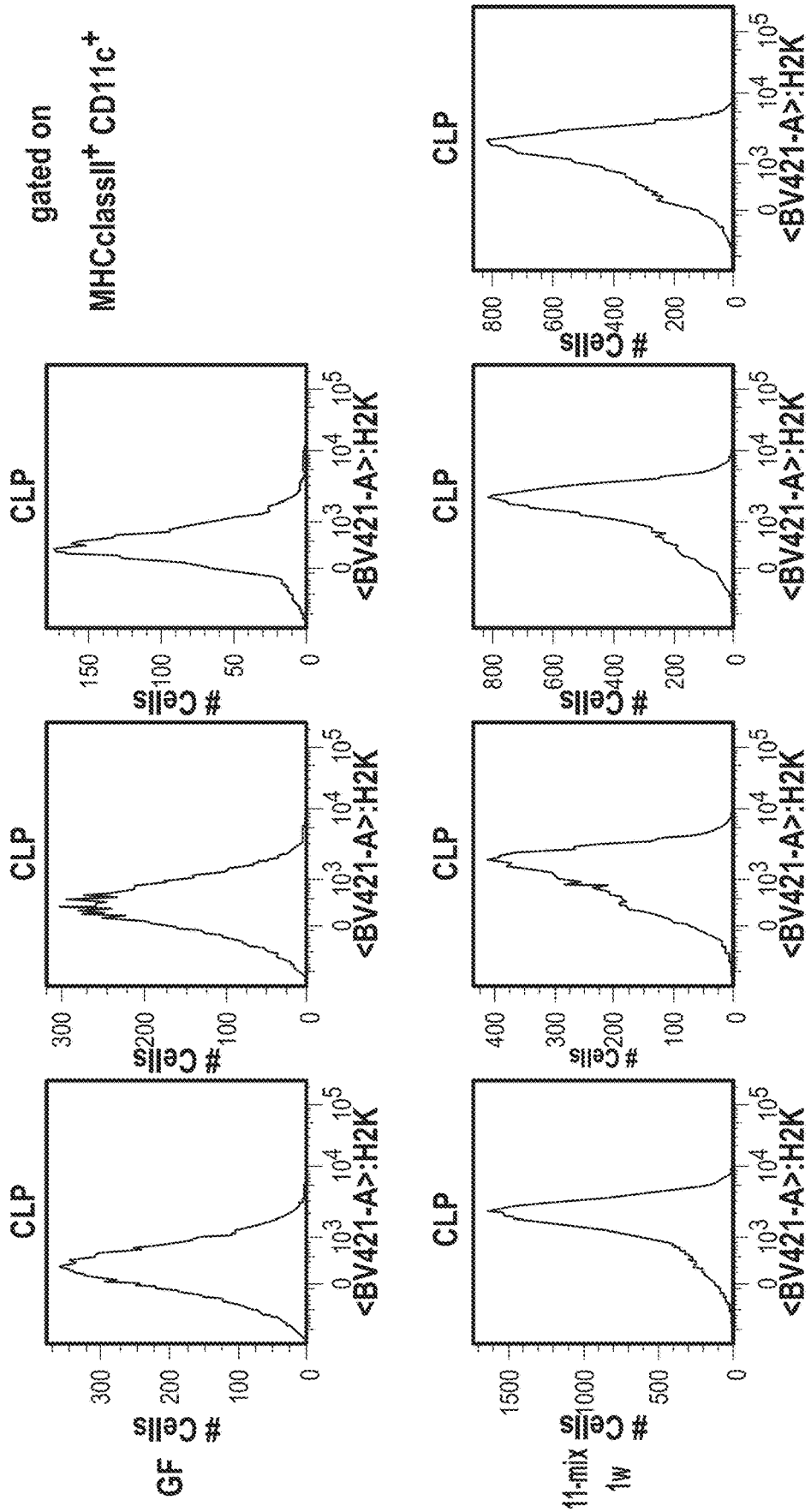
FIGS. 50-52 show that MHC CLP class cells are activated by the administration of the 11-mix, and that the activation is strongest within the first week of activation. There is no activation of the MHC MLN class cells. The individual measurements are shown in FIGS. 50 and 51, while the accumulated data are depicted in FIG. 52.
Figure 50B:
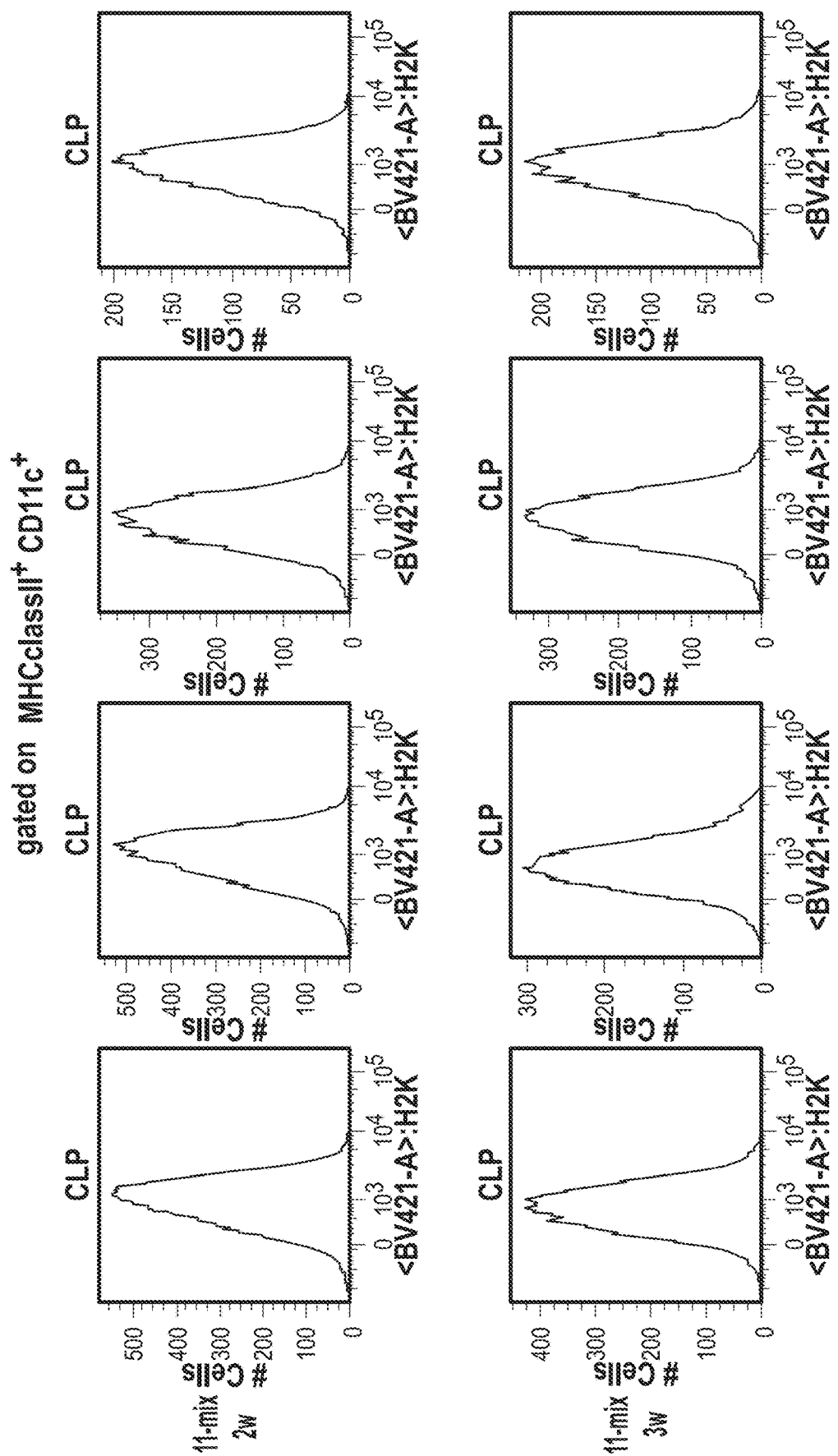
Figure 50C:
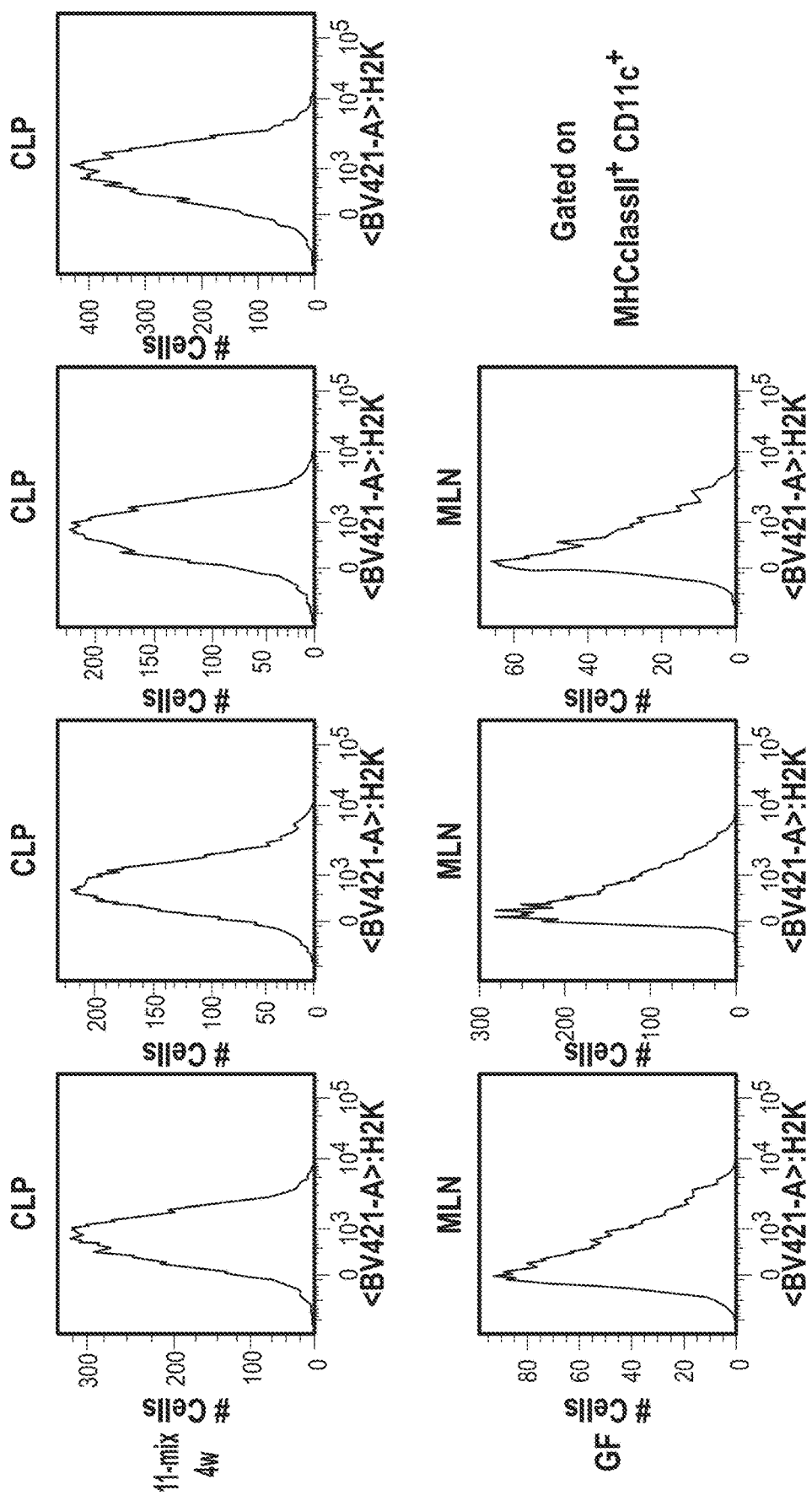
Figure 50D:
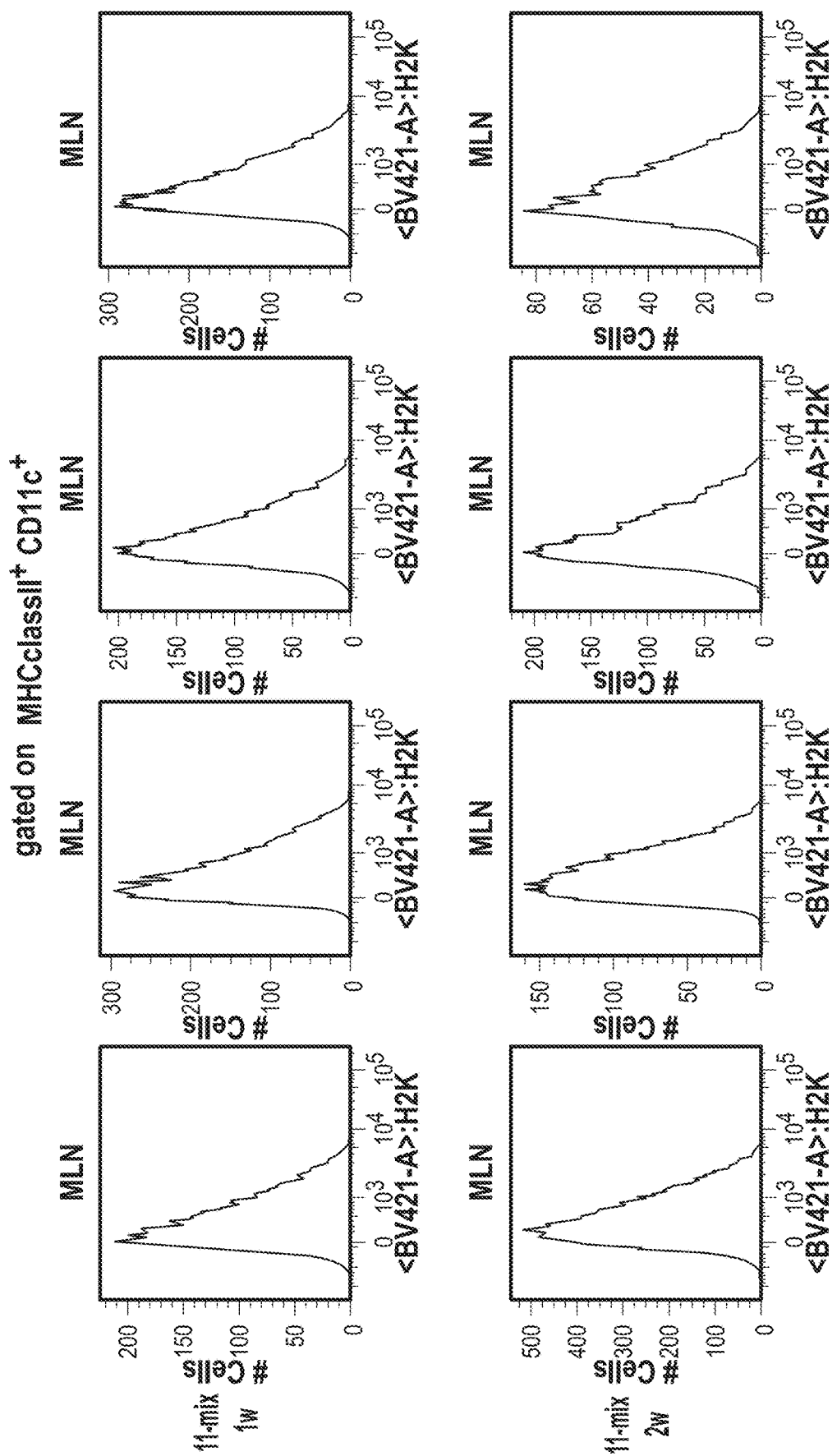
Figure 50E:
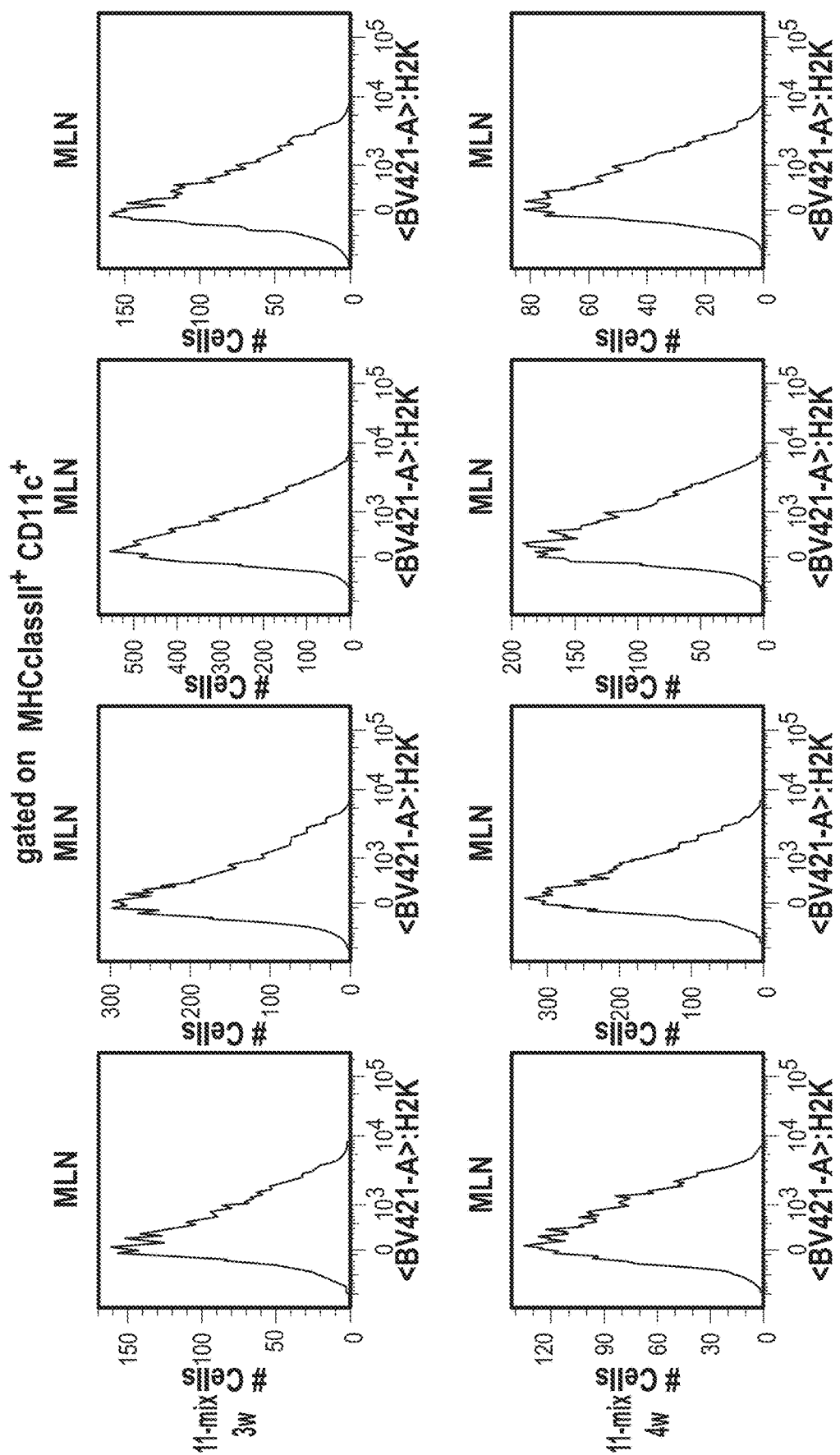
Figure 51A:
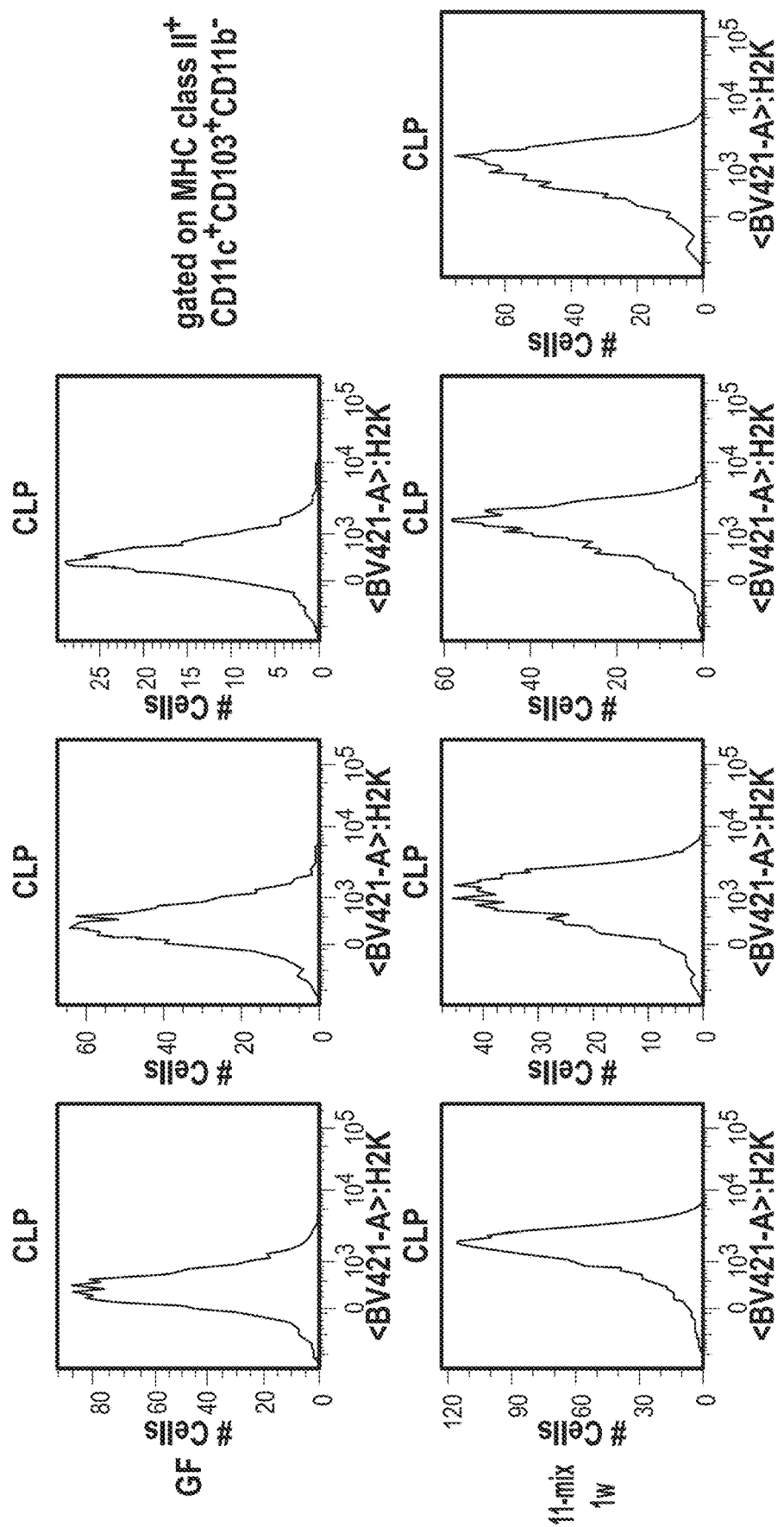
Figure 51B:
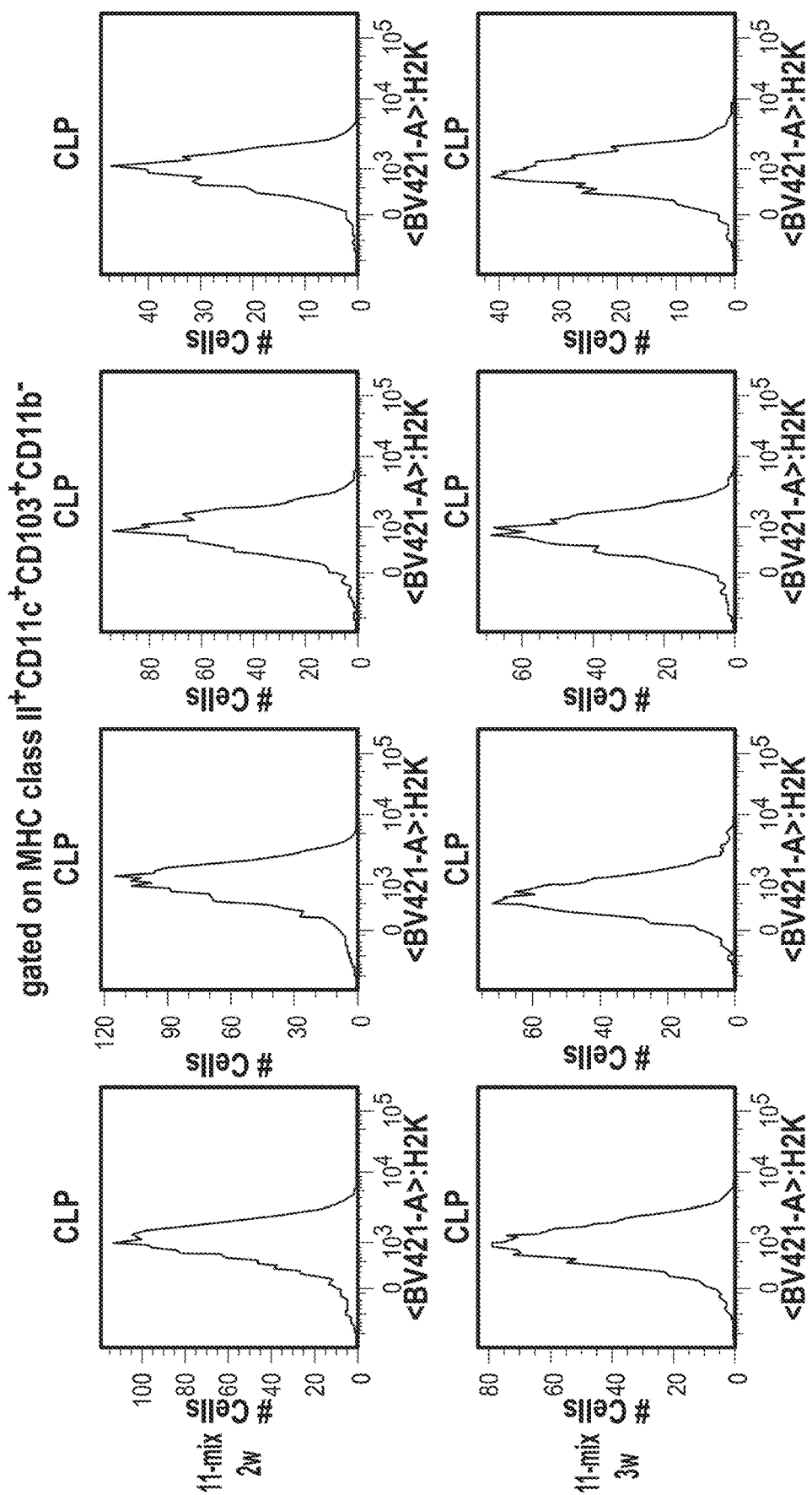
Figure 51C:
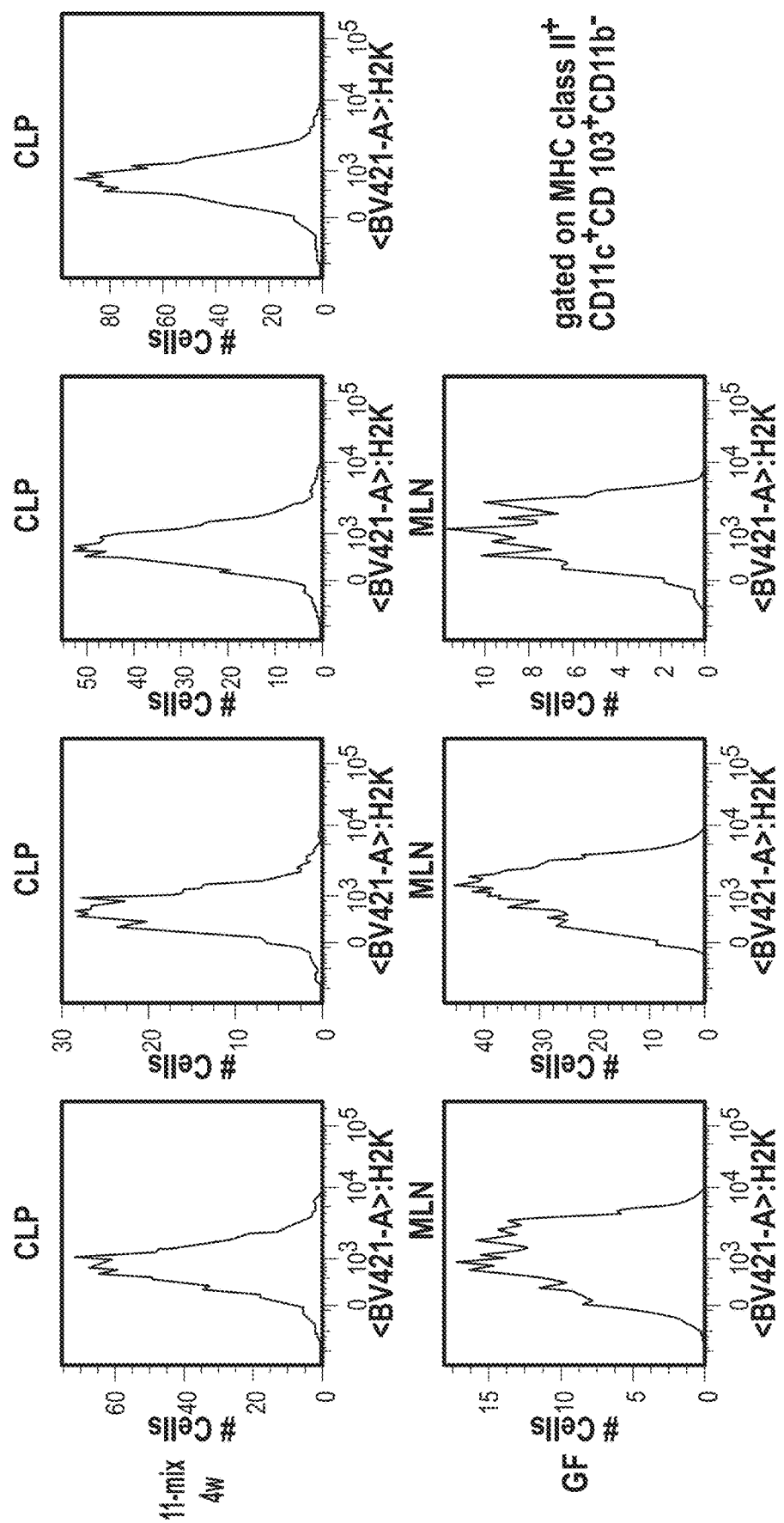
Figure 51D:
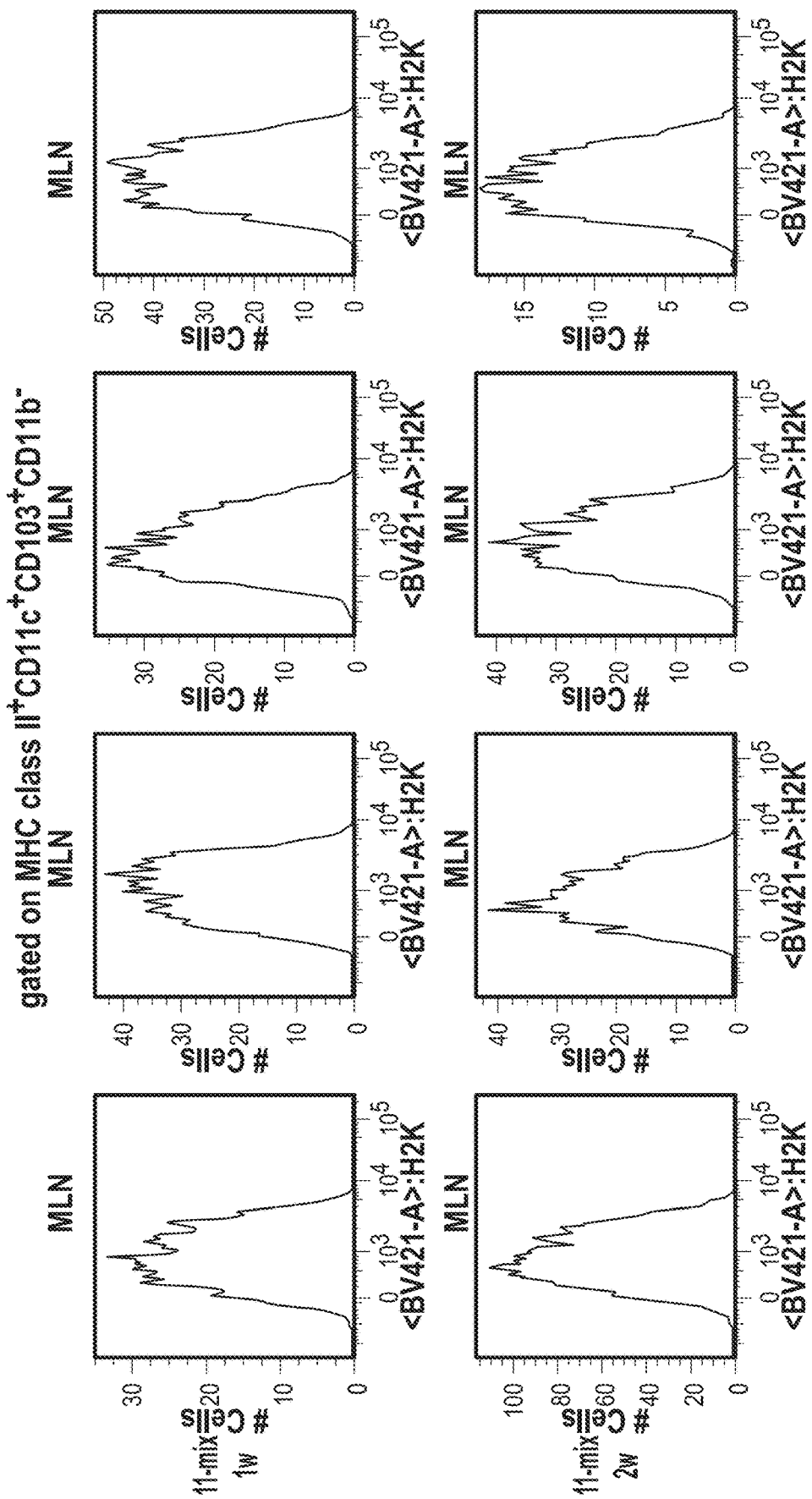
Figure 51E:
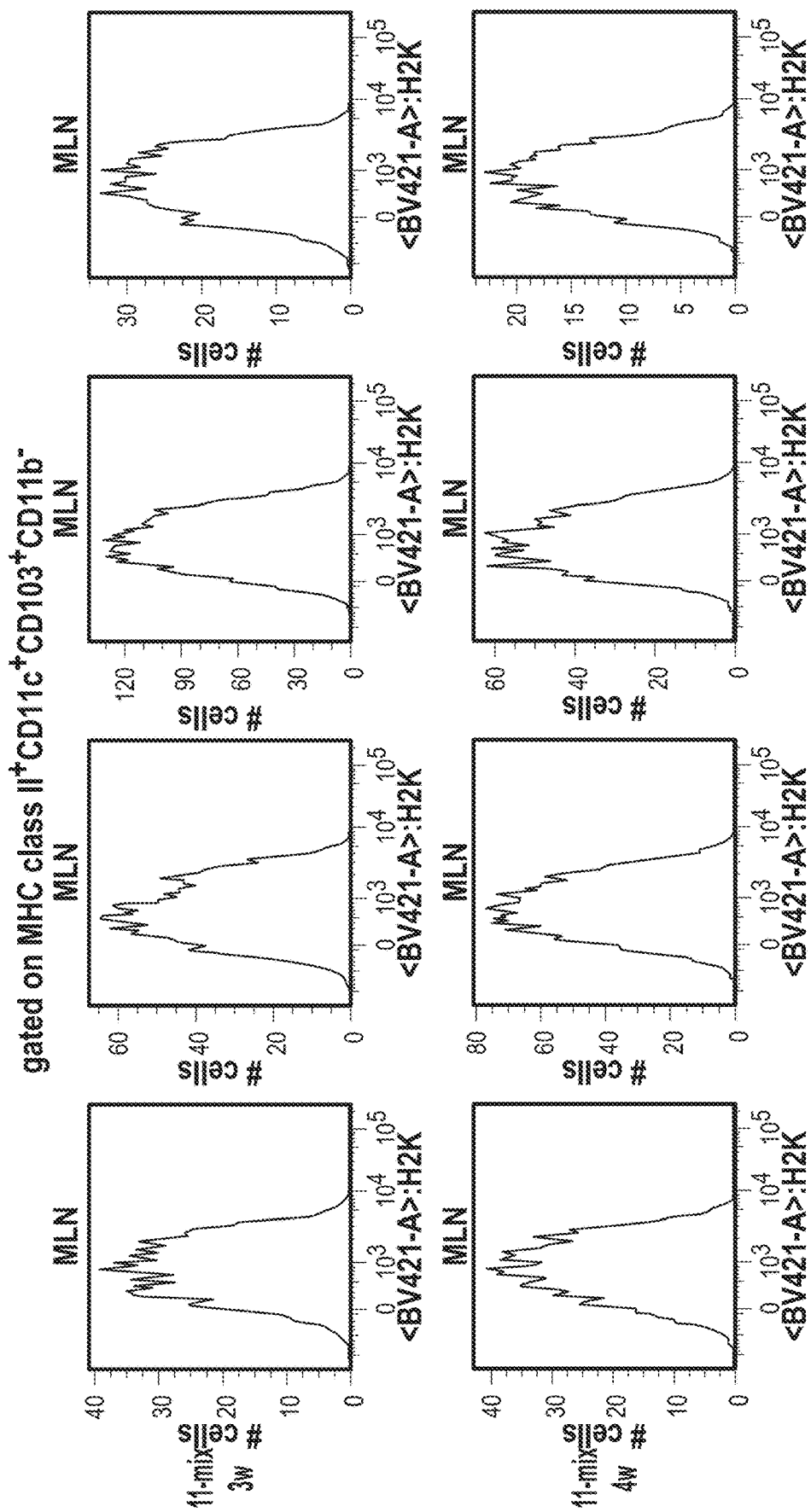
Figure 52:
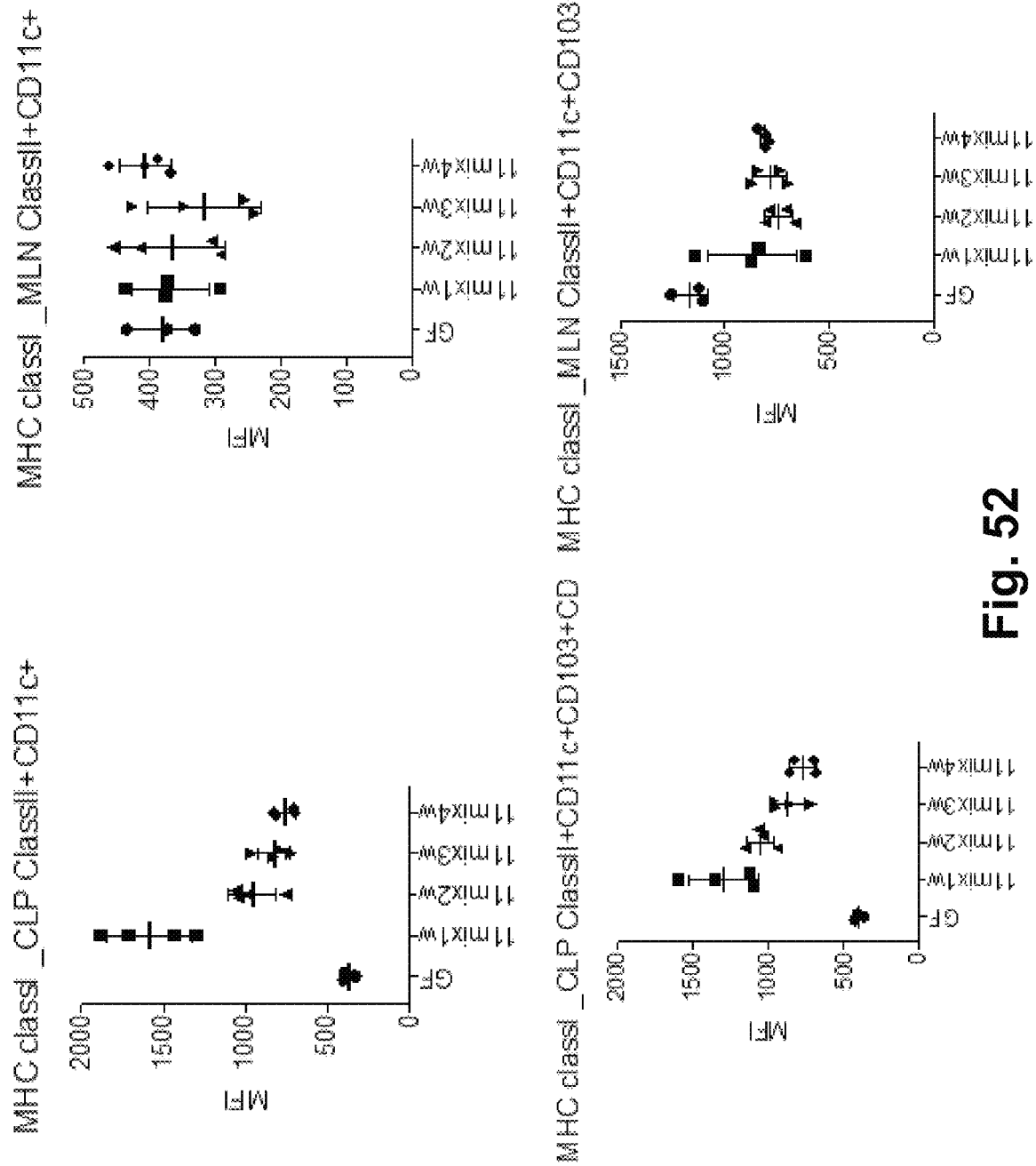
Figure 53A:
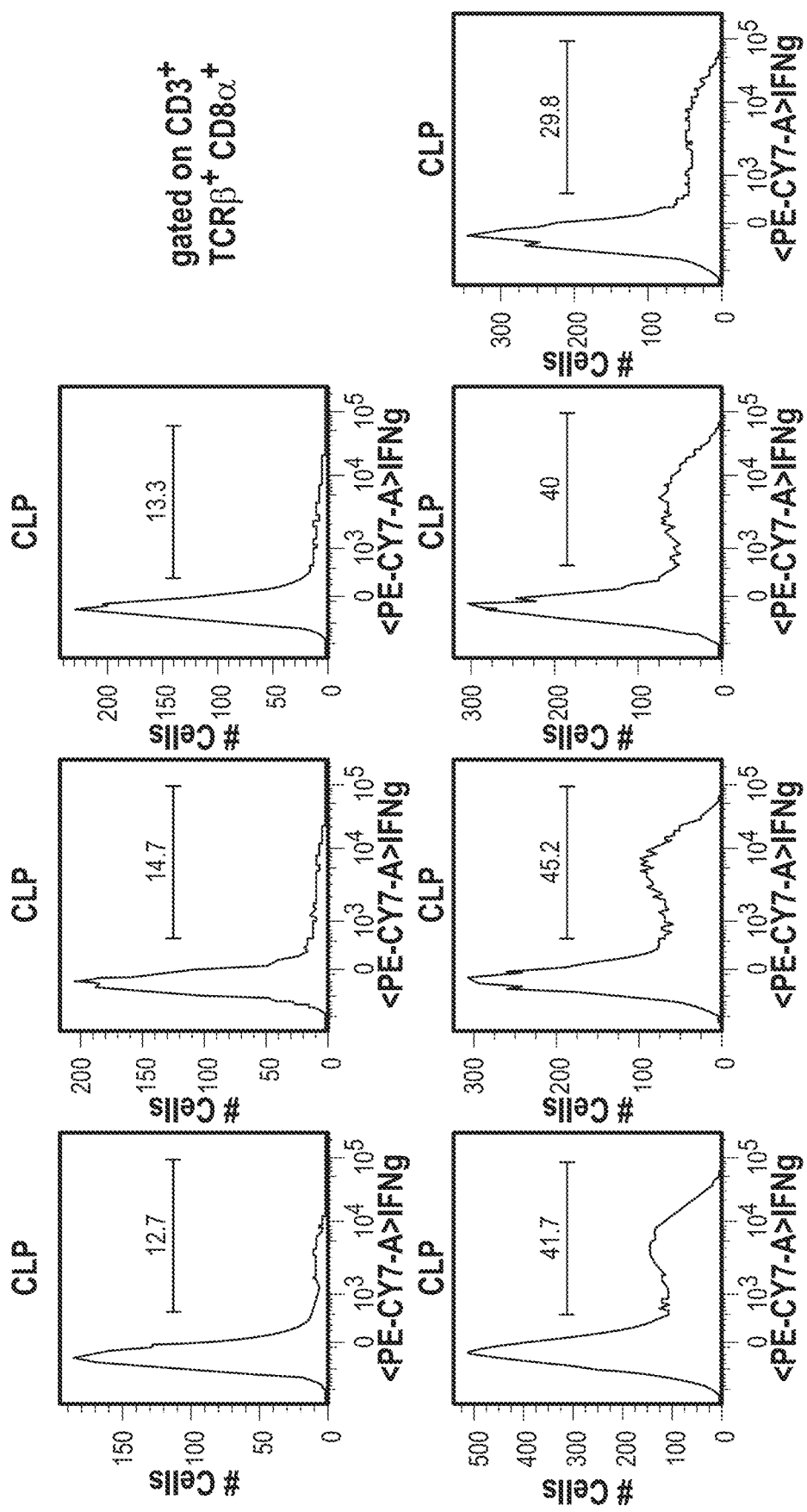
FIGS. 53 and 54 show that MHC CLP class cells are activated by the administration of the 11-mix, while there is no activation of the MHC MLN class cells. The individual measurements are shown in FIG. 53, while the accumulated data are depicted in FIG. 54 expressed as percentage of CD3+ TCDRbet+CD8alpha+ cells.
Figure 53B:
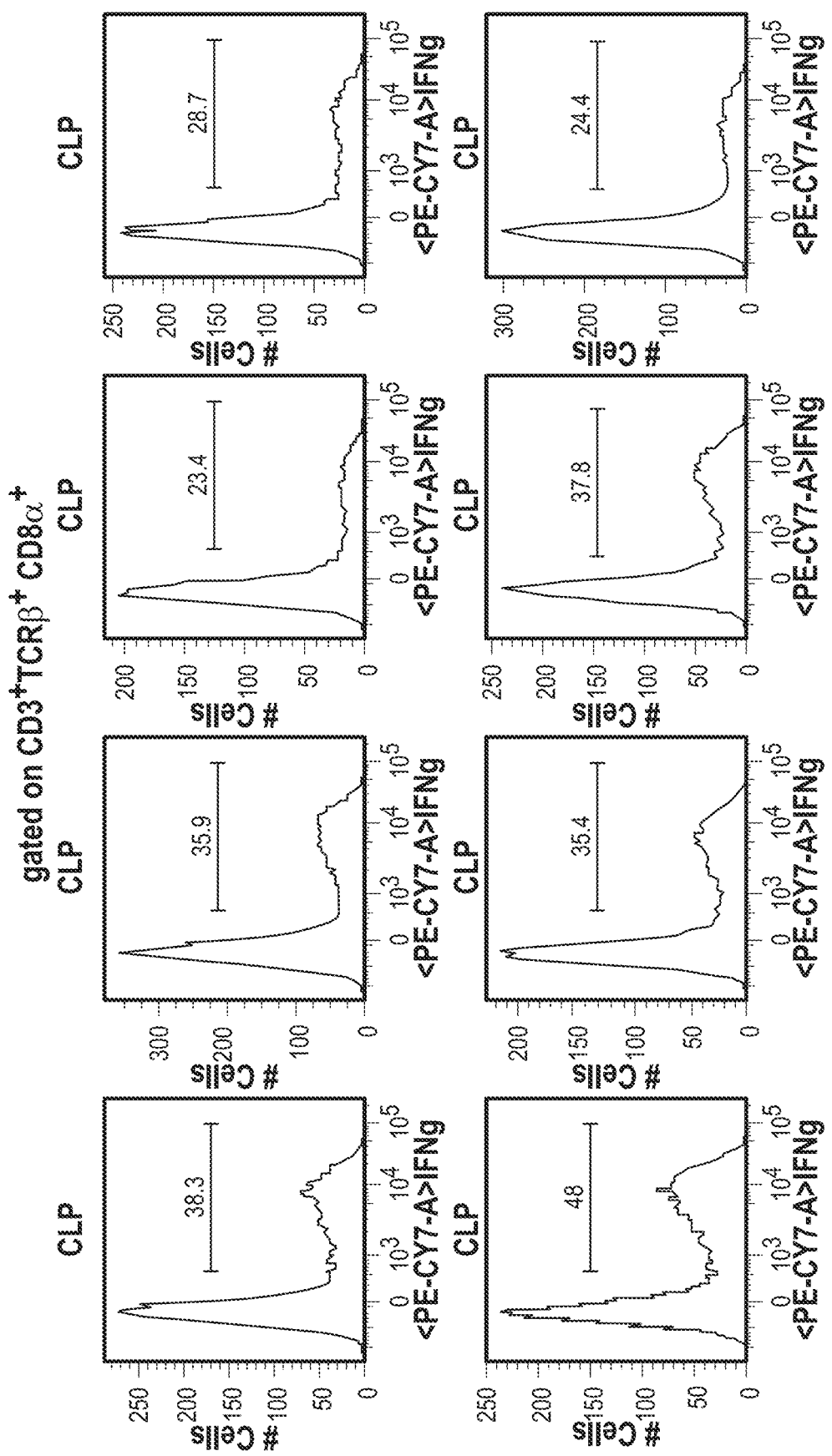
Figure 53C:
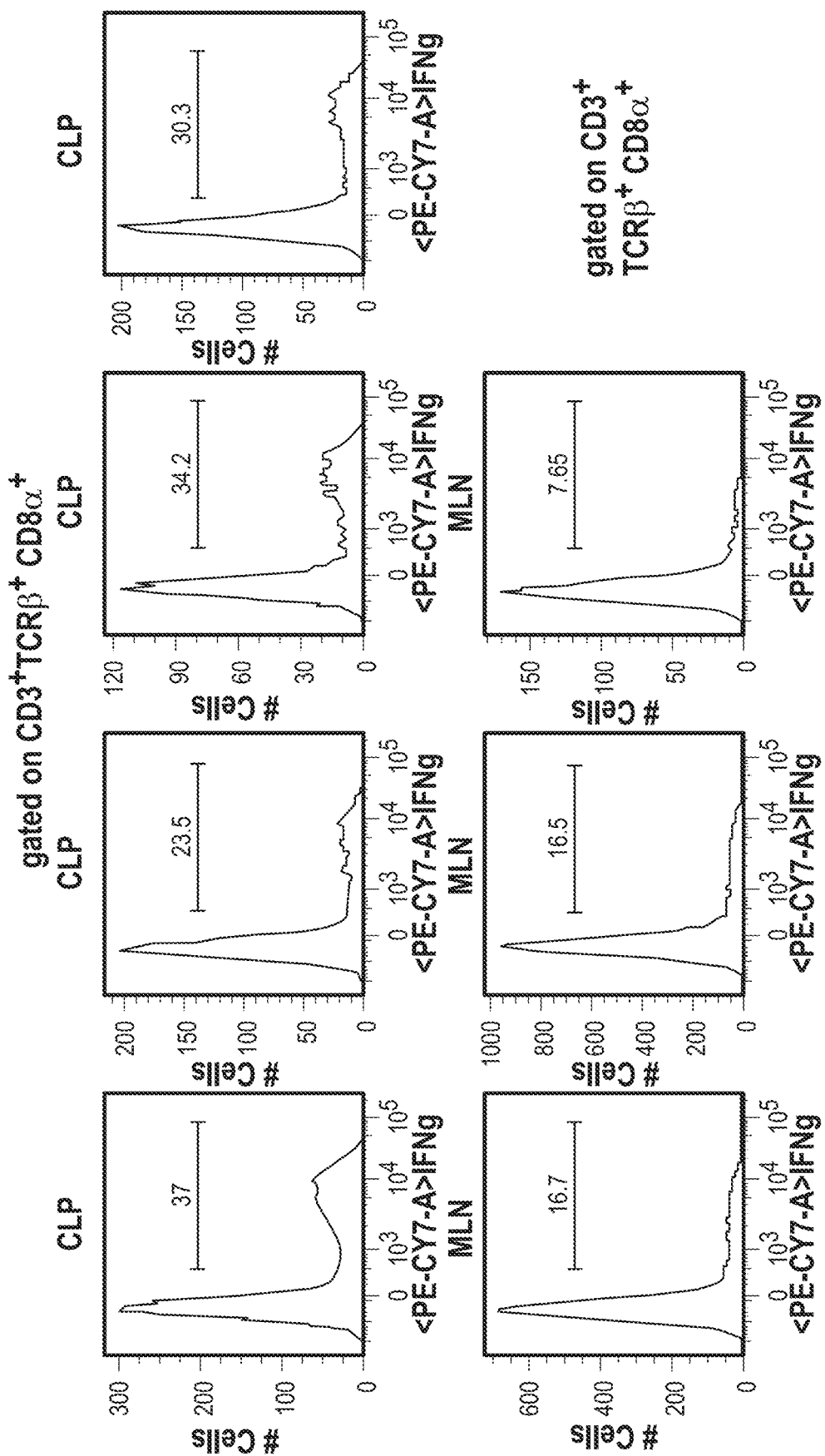
Figure 53D:
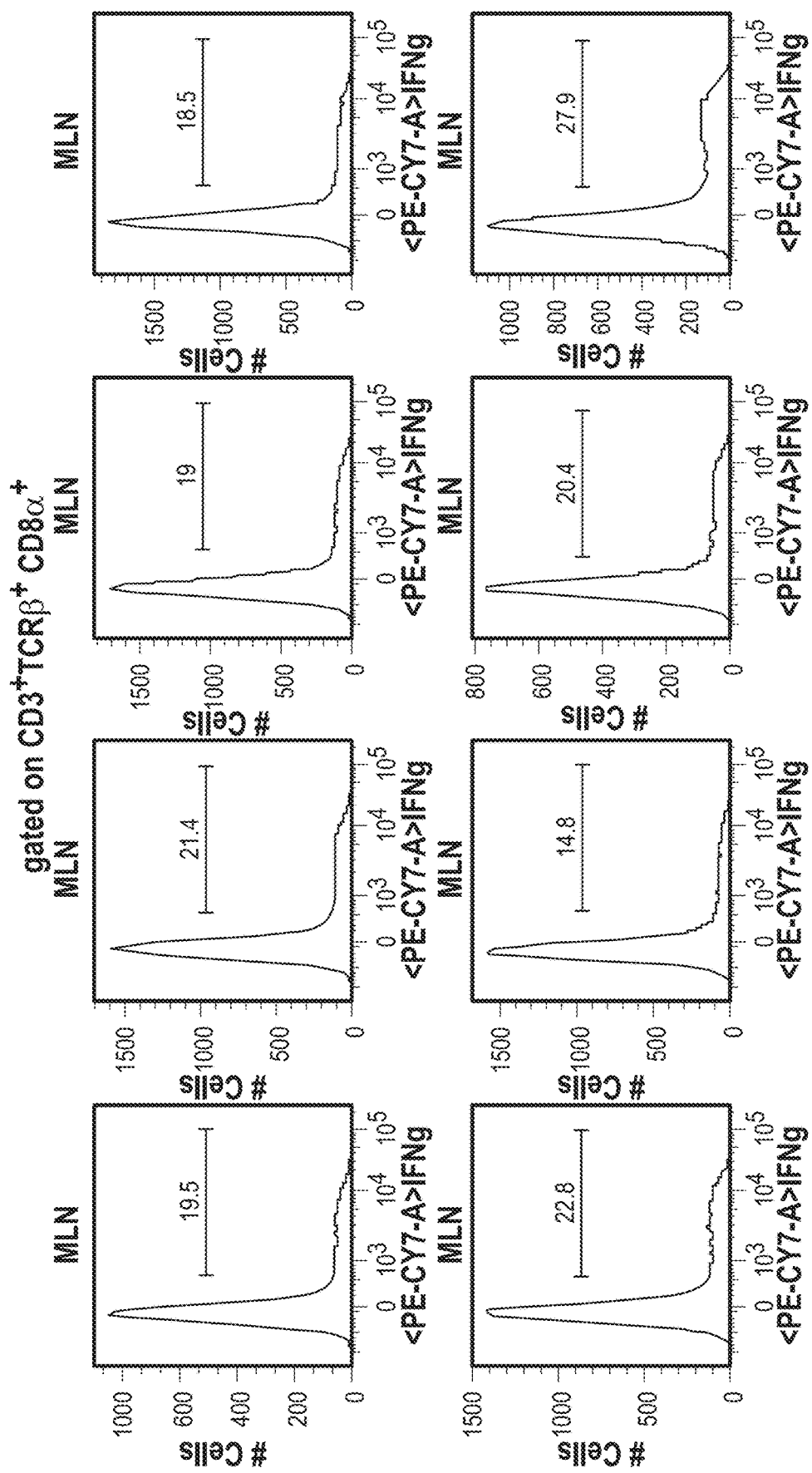
Figure 53E:
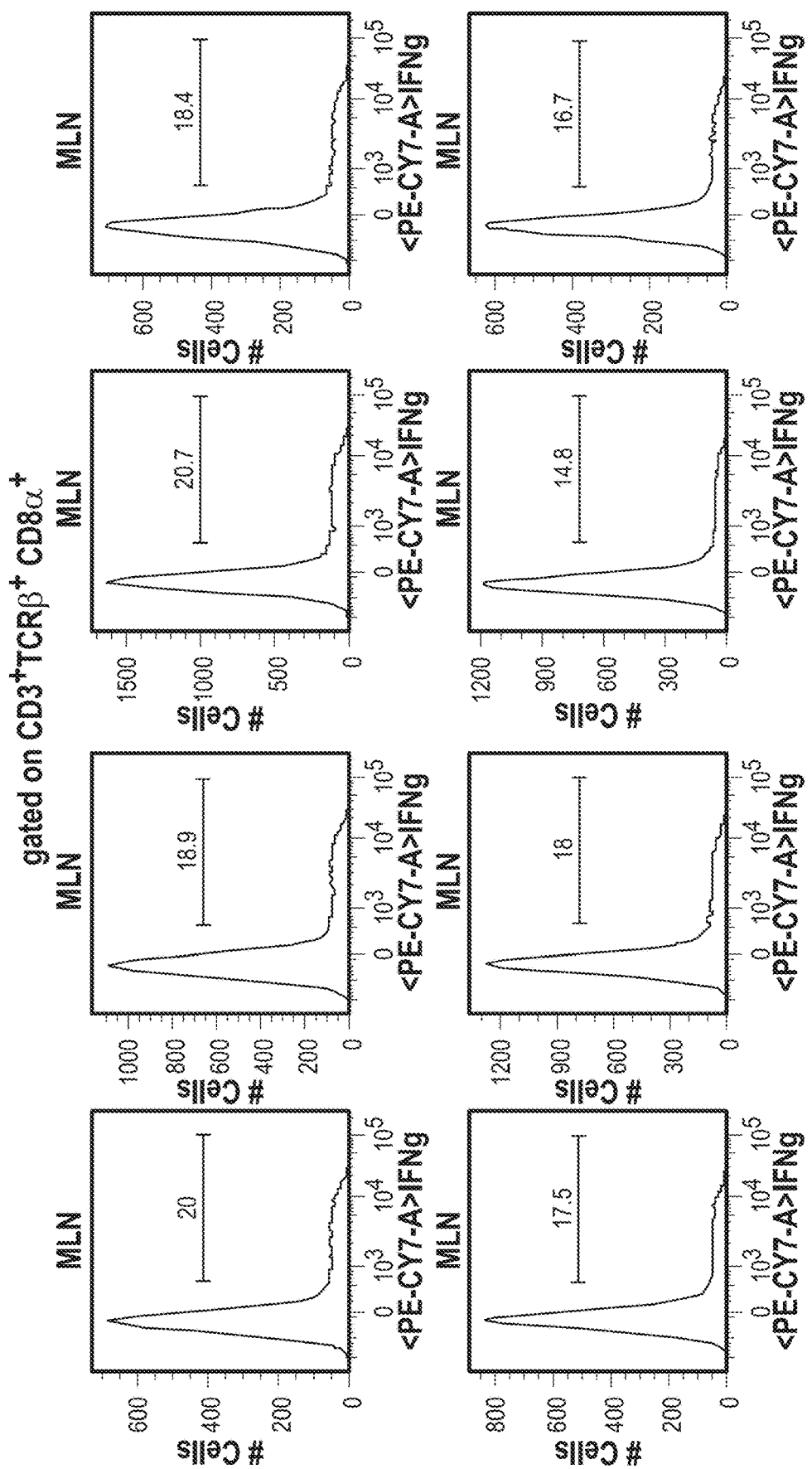
Figure 54:
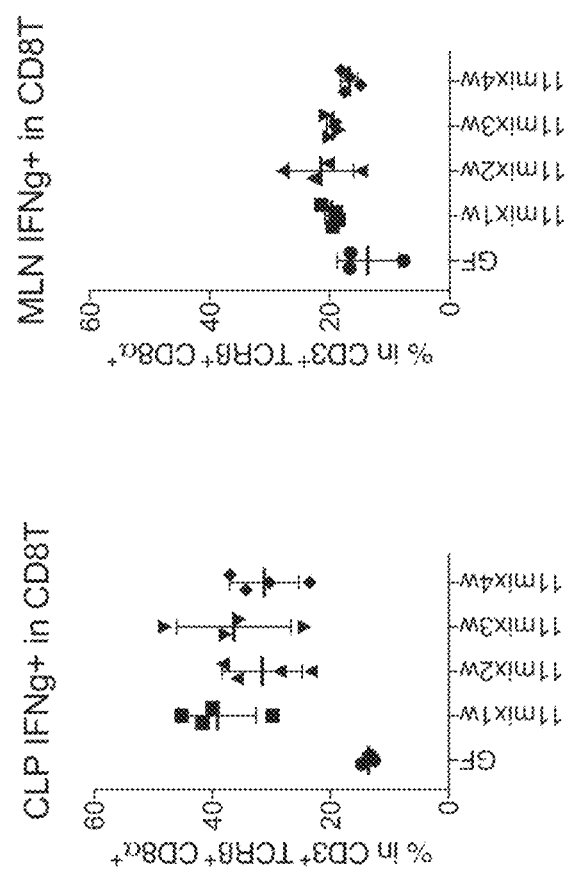

Example 11: Selective and Temporal Activation of Subsets of Lamina Propria Dendritic Cells As CD8 cells can be activated through certain subclasses of dendritic cells, the number and activation state of lamina propria CD11 b– CD103+ dendritic cells was investigated following administration of the 11-mix. As shown in FIG. 49, the administration of the 11-mix did not change the proportion of the lamina propria CDIbCD 103+ dendritic cell subset.

The temporality/kinetics of activation was also investigated. GF mice were colonized with the 11-mix for 1, 2, 3, and 4 weeks. The frequency of colonic LP and MLN dendritic cells (DCs)/macrophage subsets were not affected by the colonization with 11 mix. However, expression of MHC class I on colonic LP DCs (but not MLN DCs), particularly on colonic LP CD103+DC subset (namely, Batf3-dependent DC subset), was significantly enhanced by the colonization with 1 I-mix. Upregulation of MHC class I expression most strongly occurred at 1 week after colonization. (See FIGS. 50-54) Without being limited to a particular mechanism it is likely that induction of the CD8 positive T cells is mostly due to proliferation rather than antigen-specific de novo differentiation.

Figure 55:
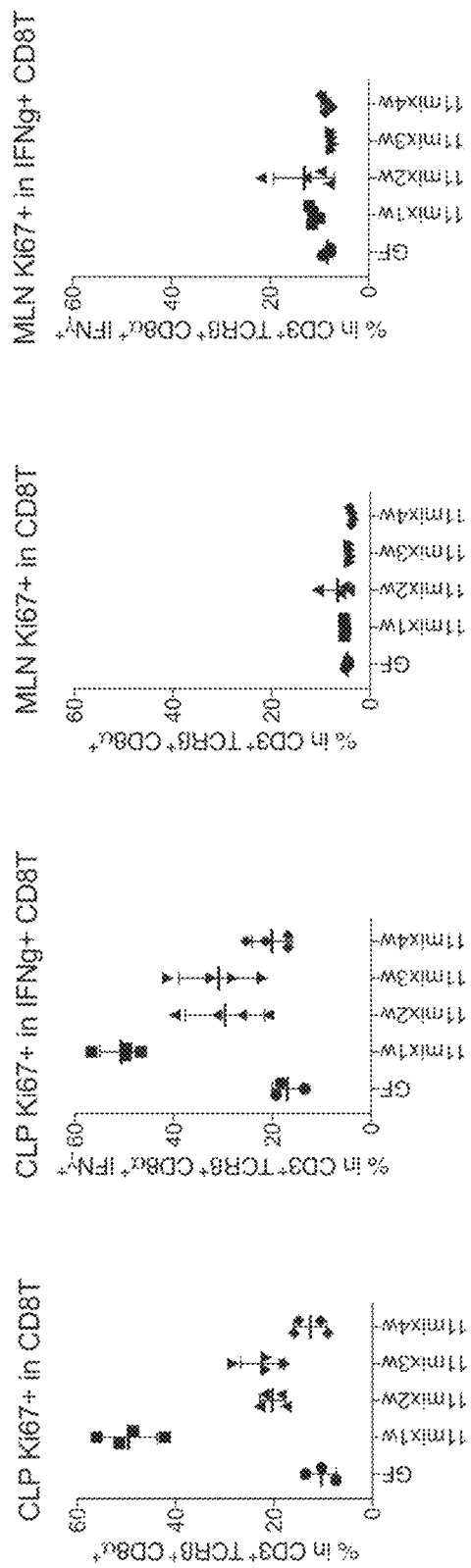
FIG. 55 shows that MHC CLP class cells are activated by the administration of the 11-mix, as evidenced by Ki67 status, while there is no activation of the MHC MLN class cells.
Figure 56A:
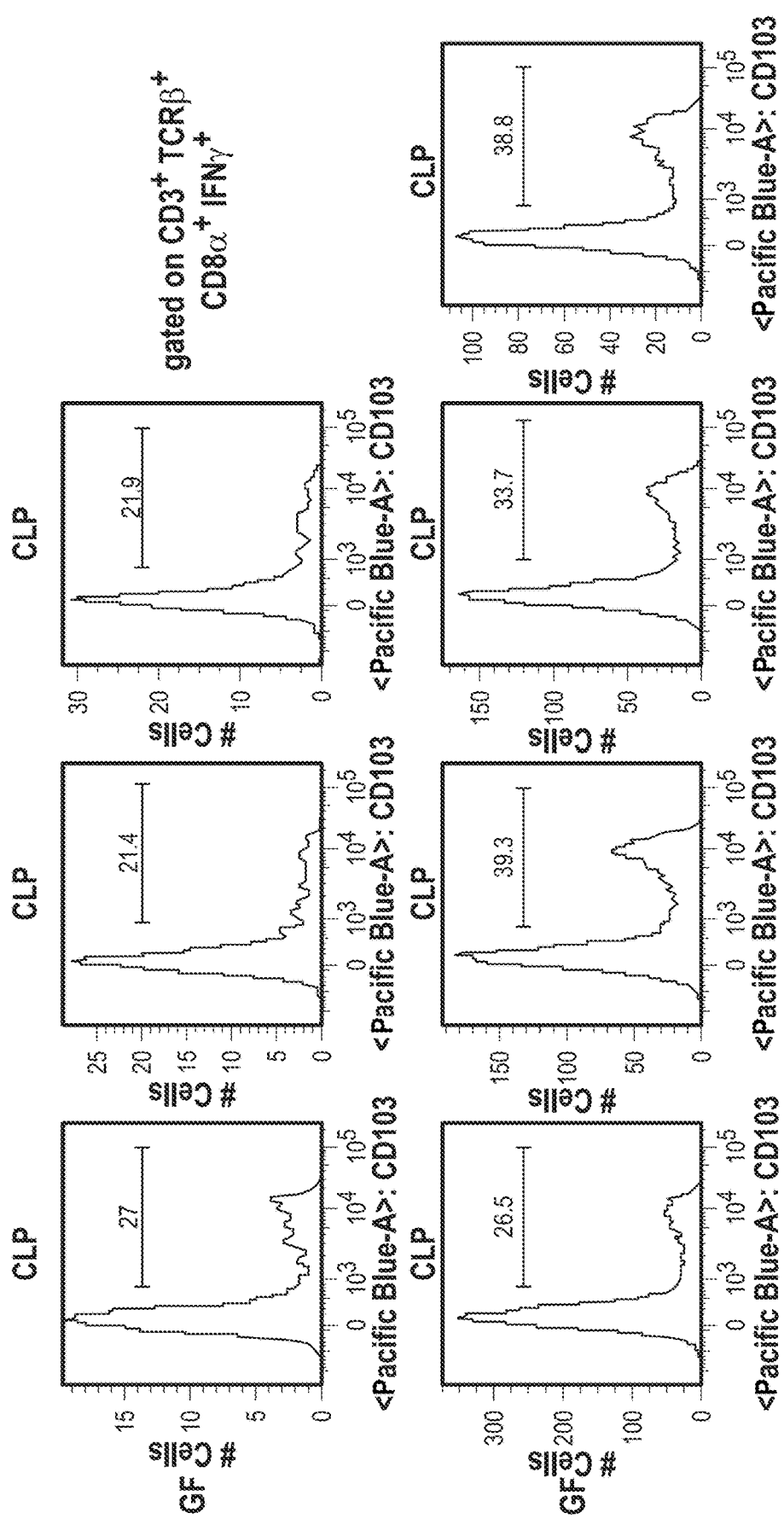
FIGS. 56 and 57 show that MHC CLP class cells are activated by the administration of the 11-mix, as evidenced by CD103+ status, while there is no activation of the MHC MLN class cells. The individual measurements are shown in FIG. 56, while the accumulated data are depicted in FIG. 57 expressed as percentage of CD3+ TCRβeta+CD8alpha+ IFNγgamm+ cells.
Figure 56B:
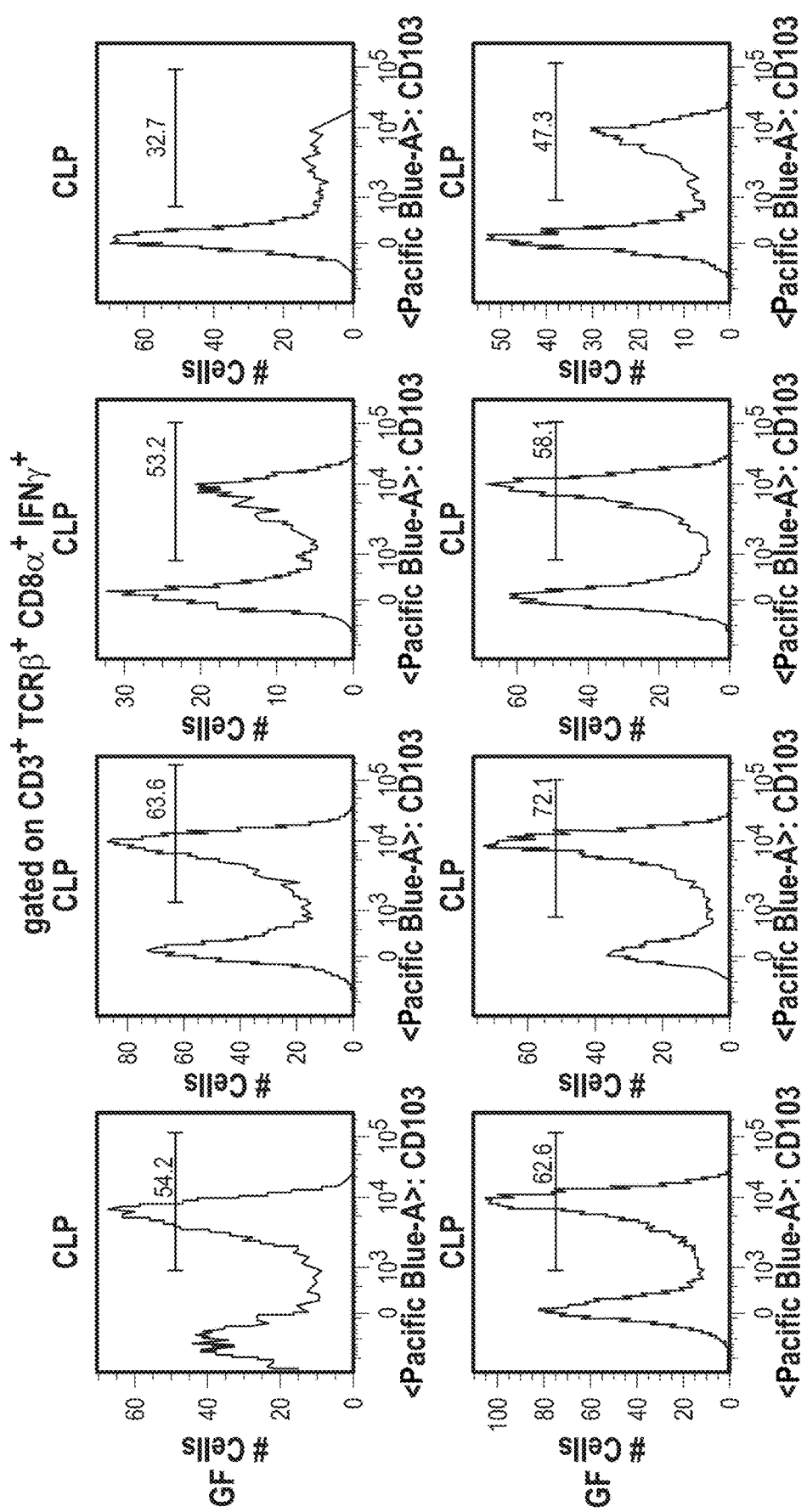
Figure 56C:
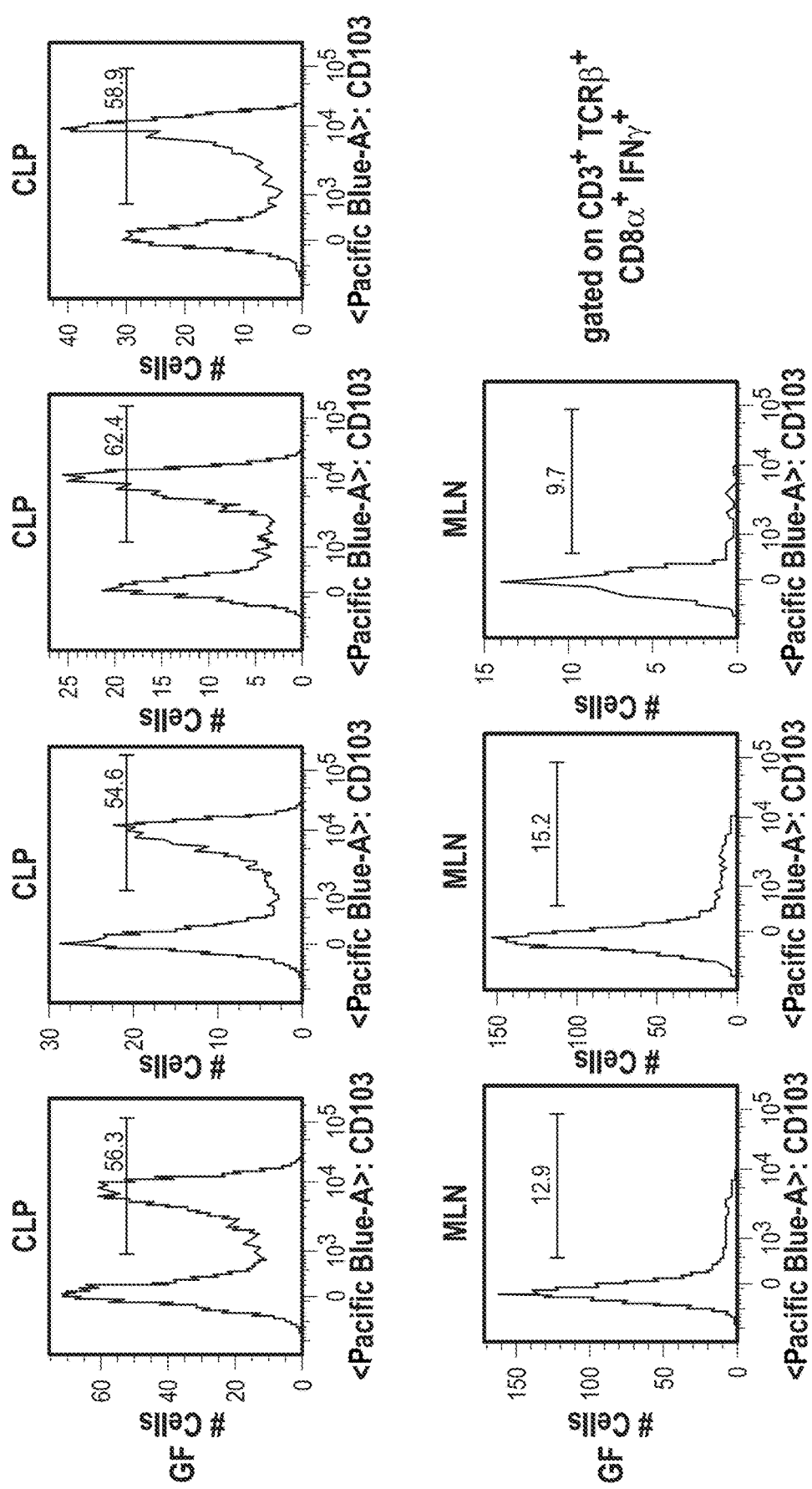
Figure 56D:
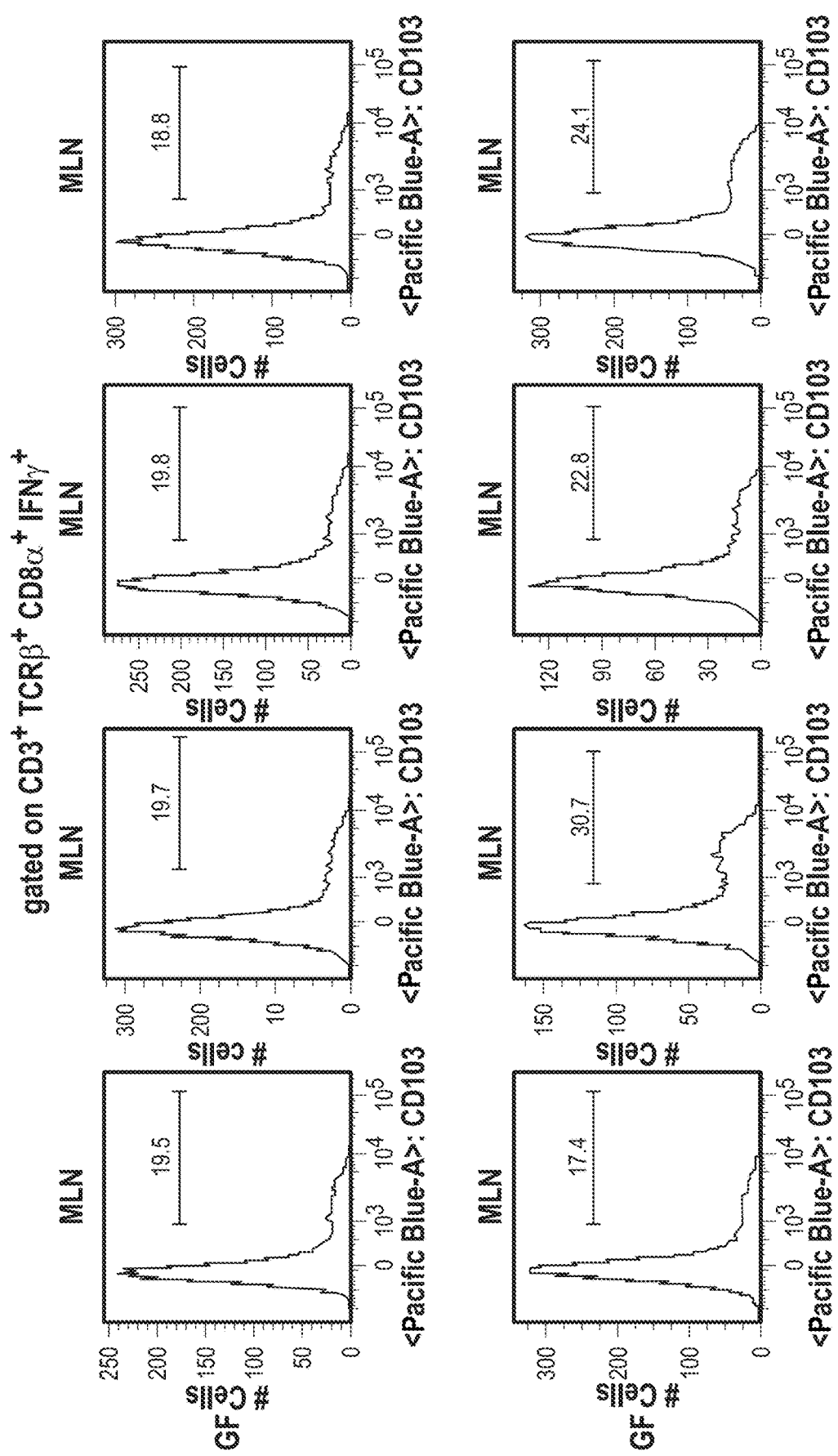
Figure 56E:
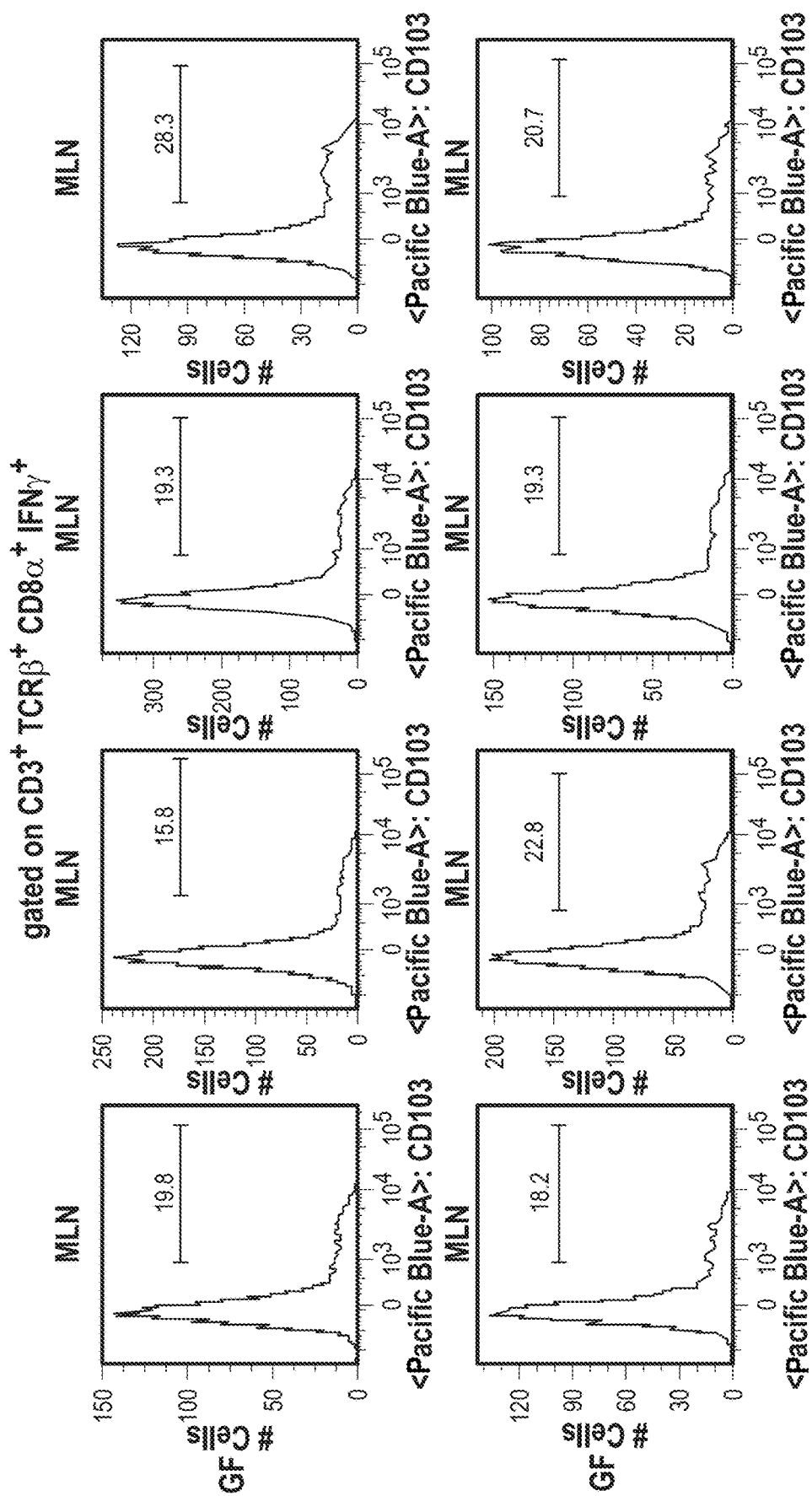
Figure 57:
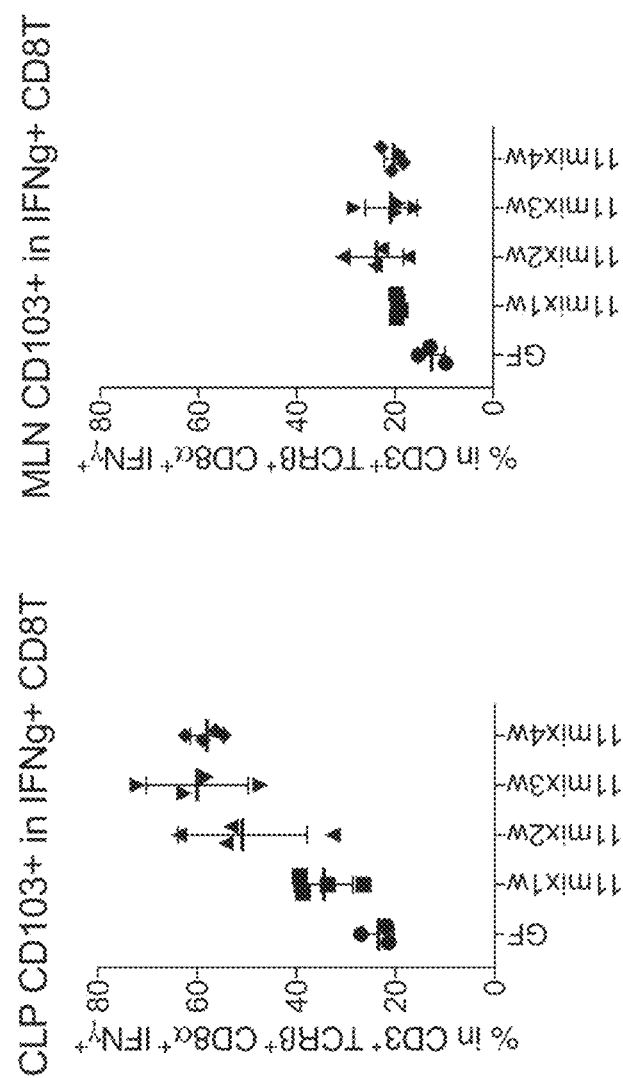

Ki67 staining revealed that expansion of CD8 positive T cells occurred at 1 week, accompanied by increase with IFNγg+CD8+T in the colonic LP (See FIG. 55). CD103 staining revealed that induced IFNγg+CD8+T at 1 week post colonization were mostly CD103 negative, and that CD103+ IFNγg+CD8 T (tissue resident memory phenotype CD8+T) were gradually increased (See FIGS. 56 and 57).

The invention claimed is:

1. A composition comprising a purified bacterial mixture comprising bacterial strains of species *Phascolarctobacterium faecium*, *Fusobacterium ulcerans*, *Subdoligranulum* sp., and *Eubacterium limosum*, wherein the bacterial strains are lyophilized.

2. The composition of claim 1, wherein the composition is a pharmaceutical composition.

3. The composition of claim 2, wherein the pharmaceutical composition comprises a pharmaceutically acceptable excipient.

4. The composition of claim 2, wherein the pharmaceutical composition is formulated for oral administration.

5. The composition of claim 2, wherein the pharmaceutical composition is formulated for delivery to the intestine.

6. The composition of claim 2, wherein the pharmaceutical composition is in the form of a capsule.

7. The composition of claim 2, wherein the pharmaceutical composition further comprises a pH sensitive composition comprising one or more enteric polymers.

8. The composition of claim 1, wherein the composition further comprises an immune checkpoint inhibitor, wherein the immune checkpoint inhibitor is a PD-1 inhibitor, PD-L1 inhibitor, or CTLA-4 inhibitor.

9. The composition of claim 8, wherein the immune checkpoint inhibitor is a PD-1 inhibitor.

10. The composition of claim 8, wherein the immune checkpoint inhibitor is a CTLA-4 inhibitor.

11. A method of treating a disease in a subject, the method comprising administering the composition of claim 1 to the subject in an effective amount to treat the disease.

12. The method of claim 11, wherein the subject has cancer.

13. The method of claim 12, wherein the cancer is carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma.

14. The method of claim 11, further comprising administering one or more anticancer agents.

15. The method of claim 14, wherein the anticancer agent is a cancer immunotherapy agent, further wherein the cancer immunotherapy agent is an immune checkpoint inhibitor, wherein the immune checkpoint inhibitor is a PD-1 inhibitor, PD-L1 inhibitor, or CTLA-4 inhibitor.

16. The method of claim 15, wherein the immune checkpoint inhibitor is a PD-1 inhibitor.

17. The method of claim 15, wherein the immune checkpoint inhibitor is a CTLA-4 inhibitor.

* * * * *

```
                        SEQUENCE LISTING

<160> NUMBER OF SEQ ID NOS: 64

<210> SEQ ID NO 1
<211> LENGTH: 1440
<212> TYPE: DNA
<213> ORGANISM: Phascolarctobacterium faecium

<400> SEQUENCE: 1
gacgaacgct ggcggcgtgc ctaacacatg caagtcgaac ggagaatttt atttcggtag      60
aattcttagt ggcgaacggg tgagtaacgc gtaggcaacc taccctttag acggggacaa     120
cattccgaaa ggagtgctaa taccggatgt gatcatcttg ccgcatggca ggatgaagaa     180
agatggcctc tacaagtaag ctatcgctaa aggatgggcc tgcgtctgat tagctagttg     240
gtagtgtaac ggactaccaa ggcgatgatc agtagccggt ctgagaggat gaacggccac     300
attgggactg agacacggcc caaactccta cgggaggcag cagtggggaa tcttccgcaa     360
tggacgaaag tctgacggag caacgccgcg tgagtgatga aggatttcgg tctgtaaagc     420
tctgttgttt atgacgaacg tgcagtgtgt gaacaatgca ttgcaatgac ggtagtaaac     480
gaggaagcca cggctaacta cgtgccagca gccgcggtaa tacgtaggtg gcgagcgttg     540
tccggaatta ttgggcgtaa agagcatgta ggcggcttaa taagtcgagc gtgaaaatgc     600
ggggctcaac cccgtatggc gctggaaact gttaggcttg agtgcaggag aggaaagggg     660
aattcccagt gtagcggtga aatgcgtaga tattgggagg aacaccagtg gcgaaggcgc     720
ctttctggac tgtgtctgac gctgagatgc gaaagccagg gtagcgaacg ggattagata     780
ccccggtagt cctggccgta aacgatgggt actaggtgta ggaggtatcg accccttctg     840
tgccggagtt aacgcaataa gtacccgcc tggggagtac ggccgcaagg ttgaaactca     900
```

```
aaggaattga cggggggcccg cacaagcggt ggagtatgtg gtttaattcg acgcaacgcg      960
aagaaccttg ccaaggcttg acattgattg aacgctctag agatagagat ttcccttcgg     1020
ggacaagaaa acaggtggtg catggctgtc gtcagctcgt gtcgtgagat gttgggttaa     1080
gtcccgcaac gagcgcaacc cctatcctat gttaccagca agtaaagttg gggactcatg     1140
ggagactgcc agggacaacc tggaggaagg cggggatgac gtcaagtcat catgcccctt     1200
atgtcttggg ctacacacgt actacaatgg tcggaaacag agggaagcga agccgcgagg     1260
cagagcaaac cccagaaacc cgatctcagt tcggatcgca ggctgcaacc cgcctgcgtg     1320
aagtcggaat cgctagtaat cgcaggtcag catactgcgg tgaatacgtt cccgggcctt     1380
gtacacaccg cccgtcacac cacgaaagtt ggtaacaccc gaagccggtg aggtaaccta     1440
```

<210> SEQ ID NO 2
<211> LENGTH: 1392
<212> TYPE: DNA
<213> ORGANISM: Fusobacterium ulcerans

<400> SEQUENCE: 2

```
gatgaacgct gacagaatgc ttaacacatg caagtctact tgatccttcg ggtgaaggtg       60
gcggacgggt gagtaacgcg taaagaactt gccttacaga ctgggacaac atttggaaac      120
gaatgctaat accggatatt atgattgggt cgcatgatct gattatgaaa gctatatgcg      180
ctgtgagaga gctttgcgtc ccattagtta gttggtgagg taacggctca ccaagacgat      240
gatgggtagc cggcctgaga gggtgaacgg ccacaagggg actgagacac ggcccttact      300
cctacgggag gcagcagtgg ggaatattgg acaatggacc aaaagtctga tccagcaatt      360
ctgtgtgcac gaagaagttt ttcggaatgt aaagtgcttt cagttgggaa gaagtcagtg      420
acggtaccaa cagaagaagc gacggctaaa tacgtgccag cagccgcggt aatacgtatg      480
tcgcaagcgt tatccggatt tattgggcgt aaagcgcgtc taggcggctt agtaagtctg      540
atgtgaaaat gcggggctca accccgtatt gcgttggaaa ctgctaaact agagtactgg      600
agaggtaggc ggaactacaa gtgtagaggt gaaattcgta gatatttgta ggaatgccga      660
tggggaagcc agcctactgg acagatactg acgctaaagc gcgaaagcgt gggtagcaaa      720
caggattaga taccctggta gtccacgccg taaacgatga ttactaggtg ttgggggtcg      780
aacctcagcg cccaagctaa cgcgataagt aatccgcctg ggagtacgt acgcaagtat      840 gaaactcaaa ggaattgacg gggacccgca caagcggtgg agcatgtggt ttaattcgac      900
gcaacgcgag gaaccttacc agcgtttgac atcccaagaa gttaacagag atgttttcgt      960
gcctcttcgg aggaacttgg tgacaggtgg tgcatggctg tcgtcagctc gtgtcgtgag     1020
atgttgggtt aagtcccgca acgagcgcaa ccccttcgt atgttaccat cattaagttg     1080
gggactcatg cgagactgcc tgcgatgagc aggaggaagg tggggatgac gtcaagtcat     1140
catgcccctt atacgctggg ctacacacgt gctacaatgg gtagtacaga gagctgcaaa     1200
cctgcgaggg taagctaatc tcataaaact attcttagtt cggattgtac tctgcaactc     1260
gagtacatga agttggaatc gctagtaatc gcaaatcagc tatgttgcgg tgaatacgtt     1320
ctcgggtctt gtacacaccg cccgtcacac cacgagagtt ggttgcacct gaagtaacag     1380
gcctaaccgt aa                                                         1392
```

<210> SEQ ID NO 3
<211> LENGTH: 1443
<212> TYPE: DNA

```
<213> ORGANISM: Bacteroides dorei
<220> FEATURE:
<221> NAME/KEY: misc_feature
<222> LOCATION: (7)..(9)
<223> OTHER INFORMATION: n is a, c, g, or t

<400> SEQUENCE: 3
agtttgnnnt atggctcagg atgaacgcta gctacaggct taacacatgc aagtcgaggg      60
gcagcatggt cttagcttgc taaggctgat ggcgaccggc gcacgggtga gtaacacgta     120
tccaacctgc cgtctactct tggccagcct tctgaaagga agattaatcc aggatgggat     180
catgagttca catgtccgca tgattaaagg tattttccgg tagacgatgg ggatgcgttc     240
cattagatag taggcggggt aacggcccac ctagtcaacg atggataggg gttctgagag     300
gaaggtcccc cacattggaa ctgagacacg gtccaaactc ctacgggagg cagcagtgag     360
gaatattggt caatgggcga tggcctgaac cagccaagta gcgtgaagga tgactgccct     420
atgggttgta aacttctttt ataaaggaat aaagtcgggt atgcataccc gtttgcatgt     480
actttatgaa taaggatcgg ctaactccgt gccagcagcc gcggtaatac ggaggatccg     540
agcgttatcc ggatttattg ggtttaaagg gagcgtagat ggatgtttaa gtcagttgtg     600
aaagtttgcg gctcaaccgt aaaattgcag ttgatactgg atgtcttgag tgcagttgag     660
gcaggcggaa ttcgtggtgt agcggtgaaa tgcttagata tcacgaagaa ctccgattgc     720
gaaggcagcc tgctaagctg caactgacat tgaggctcga aagtgtgggt atcaaacagg     780
attagatacc ctggtagtcc acacggtaaa cgatgaatac tcgctgtttg cgatatacgg     840
caagcggcca agcgaaagcg ttaagtattc cacctgggga gtacgccggc aacggtgaaa     900
ctcaaaggaa ttgacggggg cccgcacaag cggaggaaca tgtggtttaa ttcgatgata     960
cgcgaggaac cttacccggg cttaaattgc actcgaatga tccggaaacg gttcagctag    1020
caatagcgag tgtgaaggtg ctgcatggtt gtcgtcagct cgtgccgtga ggtgtcggct    1080
taagtgccat aacgagcgca acccttgttg tcagttacta acaggtgatg ctgaggactc    1140
tgacaagact gccatcgtaa gatgtgagga aggtggggat gacgtcaaat cagcacggcc    1200
cttacgtccg gggctacaca cgtgttacaa tggggggtac agagggccgc taccacgcga    1260
gtggatgcca atccctaaaa cccctctcag ttcggactgg agtctgcaac ccgactccac    1320
gaagctggat tcgctagtaa tcgcgcatca gccacggcgc ggtgaatacg ttcccgggcc    1380
ttgtacacac cgcccgtcaa gccatgggag ccggggtac ctgaagtgcg taaccgcgag    1440
gat                                                                  1443

<210> SEQ ID NO 4
<211> LENGTH: 1420
<212> TYPE: DNA
<213> ORGANISM: Bacteroides uniformis

<400> SEQUENCE: 4
gatgaacgct agctacaggc ttaacacatg caagtcgagg ggcagcatga acttagcttg      60
ctaagtttga tggcgaccgg cgcacgggtg agtaacacgt atccaacctg ccgatgactc     120
ggggatagcc tttcgaaaga agattaata cccgatggca tagttcttcc gcatggtaga     180
actattaaag aatttcggtc atcgatgggg atgcgttcca ttaggttgtt ggcggggtaa     240
cggcccacca agccttcgat ggatagggt tctgagagga aggtcccca cattggaact     300
gagacacggt ccaaactcct acgggaggca gcagtgagga atattggtca atggacgaga     360
gtctgaacca gccaagtagc gtgaaggatg actgccctat ggttgtaaa cttctttat     420
```

```
acgggaataa agtgaggcac gtgtgccttt ttgtatgtac cgtatgaata aggatcggct    480
aactccgtgc cagcagccgc ggtaatacgg aggatccgag cgttatccgg atttattggg    540
tttaaaggga gcgtaggcgg acgcttaagt cagttgtgaa agtttgcggc tcaaccgtaa    600
aattgcagtt gatactgggt gtcttgagta cagtagaggc aggcggaatt cgtggtgtag    660
cggtgaaatg cttagatatc acgaagaact ccgattgcga aggcagcctg ctggactgta    720
actgacgctg atgctcgaaa gtgtgggtat caaacaggat tagataccct ggtagtccac    780
accagtaaac gatgaatact cgctgtttgc gatatacagt aagcggccaa gcgaaagcgt    840
taagtattcc acctggggag tacgccggca acggtgaaac tcaaaggaat tgacggggc    900 ccgcacaagc ggaggaacat gtggtttaat tcgatgatac gcgaggaacc ttacccgggc    960
ttgaattgca actgaatgat gtggagacat gtcagccgca aggcagttgt gaaggtgctg   1020
catggttgtc gtcagctcgt gccgtgaggt gtcggcttaa gtgccataac gagcgcaacc   1080
cttatcgata gttaccatca ggtgatgctg ggactctgt cgagactgcc gtcgtaagat   1140
gtgaggaagg tggggatgac gtcaaatcag cacggccctt acgtccgggg ctacacacgt   1200
gttacaatgg ggggtacaga aggcagctac acggcgacgt gatgctaatc ccgaaagcct   1260
ctctcagttc ggattggagt ctgcaacccg actccatgaa gctggattcg ctagtaatcg   1320
cgcatcagcc acgcgcggt gaatacgttc ccgggccttg tacacaccgc ccgtcaagcc   1380
atgaaagccg ggggtacctg aagtgcgtaa ccgcaaggag                        1420
```

<210> SEQ ID NO 5
<211> LENGTH: 1410
<212> TYPE: DNA
<213> ORGANISM: Subdoligranulum sp.

<400> SEQUENCE: 5

```
gacgaacgct ggcggcgcgc ctaacacatg caagtcgaac ggagctgttt tctctgaagt     60
tttcggatgg aagagagttc agcttagtgg cgaacgggtg agtaacacgt gagcaacctg    120
cctttcagtg ggggacaaca tttggaaacg aatgctaata ccgcataaga ccacagtgtc    180
gcatggcaca ggggtcaaag gatttatccg ctgaaagatg gctcgcgtc cgattagcta    240 gatggtgagg taacggccca ccatggcgac gatcggtagc cggactgaga ggttgaacgg    300
ccacattggg actgagacac ggcccagact cctacgggag gcagcagtgg ggaatattgc    360
acaatggggg aaaccctgat gcagcgacgc cgcgtgagg aagaaggtct tcggattgta    420
aactcctgtc ccaggggacg ataatgacgg taccctggga ggaagcaccg gctaactacg    480
tgccagcagc cgcggtaaaa cgtagggtgc aagcgttgtc cggaattact gggtgtaaag    540
ggagcgcagg cggattggca agttgggagt gaaatctatg gctcaaccc ataaattgct    600 ttcaaaactg tcagtcttga gtggtgtaga ggtaggcgga attcccggtg tagcggtgga    660
atgcgtagat atcgggagga acaccagtgg cgaaggcggc ctactgggca ctaactgacg    720
ctgaggctcg aaagcatggg tagcaaacag gattagatac cctggtagtc catgccgtaa    780
acgatgatta ctaggtgtgg gaggattgac cccttccgtg ccgcagttaa cacaataagt    840
aatccacctg gggagtacga ccgcaaggtt gaaactcaaa ggaattgacg ggggcccgca    900
caagcagtgg agtatgtggt ttaattcgaa gcaacgcgaa gaaccttacc aggtcttgac    960
atcggatgca tacctaagag attagggaag tccttcggga catccagaca ggtggtgcat   1020
ggttgtcgtc agctcgtgtc gtgagatgtt gggttaagtc cgcaacgag cgcaaccctt   1080
```

| | |
|---|---|
| atcgttagtt actacgcaag aggactctag cgagactgcc gttgacaaaa cggaggaagg | 1140 |
| tggggatgac gtcaaatcat catgcccttt atgacctggg ctacacacgt actacaatgg | 1200 |
| ctattaacag agagaagcga taccgcgagg tggagcaaac ctcacaaaaa tagtctcagt | 1260 |
| tcggatcgca ggctgcaacc cgcctgcgtg aagccggaat tgctagtaat cgcggatcag | 1320 |
| catgccgcgg tgaatacgtt cccgggcctt gtacacaccg cccgtcacac catgagagcc | 1380 |
| gggggacccc gaagtcggta gtctaaccgc | 1410 |

```
<210> SEQ ID NO 6
<211> LENGTH: 1418
<212> TYPE: DNA
<213> ORGANISM: Paraprevotella xylaniphila
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (1411)..(1412)
<223> OTHER INFORMATION: n is a, c, g, or t

<400> SEQUENCE: 6
```

| | |
|---|---|
| gatgaacgct agctacaggc ttaacacatg caagtcgagg ggcagcatga acttagcttg | 60 |
| ctaagtttga tggcgaccgg cgcacgggtg agtaacgcgt atccaacctg ccctttaccc | 120 |
| ggggatagcc ttctgaaaag gaagtttaat acccgatgaa ttcgtttagt cgcatggctn | 180 |
| gatgaataaa gattaattgg taaggatgg ggatgcgtcc cattagcttg ttggcggggt | 240 |
| aacggcccac caaggcgacg atgggtaggg gttctgagag aaggtcccc cacattggaa | 300 |
| ctgagacacg gtccaaactc ctacgggagg cagcagtgag gaatattggt caatgggcgc | 360 |
| gagcctgaac cagccaagta gcgtggagga cgacggccct acgggttgta aactccttt | 420 |
| ataaggggat aaagttggcc atgtatggcc attgcaggt accttatgaa taagcatcgg | 480 |
| ctaattccgt gccagcagcc gcggtaatac ggaagatgcg agcgttatcc ggatttattg | 540 |
| ggtttaaagg gagcgtaggc gggctgtcaa gtcagcggtc aaatggcgcg gctcaaccgc | 600 |
| gttccgccgt tgaaactggc agccttgagt atgcacaggg tacatggaat cgtggtgta | 660 |
| gcggtgaaat gcttagatat cacgaggaac tccgatcgcg caggcattgt accggggcat | 720 |
| tactgacgct gaggctcgaa ggtgcgggta tcaaacagga ttagataccc tggtagtccg | 780 |
| cacagtaaac gatgaatgcc gctgtcggc gacatagtgt cggcggccaa gcgaaagcgt | 840 |
| taagcattcc acctggggag tacgccgca acggtgaaac tcaaaggaat tgacggggc | 900 |
| ccgcacaagc ggaggaacat gtggtttaat tcgatgatac gcgaggaacc ttacccgggc | 960 |
| ttgaatcgca ggtgcatggg ccggagacgg ccctttcctt cgggactcct gcgaaggtgc | 1020 |
| tgcatggttg tcgtcagctc gtgccgtgag gtgtcggctt aagtgccata acgagcgcaa | 1080 |
| cccccctccc cagttgccac cgggtaatgc cgggcacttt ggggacactg ccaccgcaag | 1140 |
| gtgcgaggaa ggtggggatg acgtcaaatc agcacggccc ttacgtccgg ggcgacacac | 1200 |
| gtgttacaat ggggggtaca gagggccgct gcccggtgac ggttggccaa tccctaaaac | 1260 |
| ccctctcagt tcggactgga gtctgcaacc cgactccacg aagctggatt cgctagtaat | 1320 |
| cgcgcatcag ccatggcgcg gtgaatacgt tcccgggcct tgtacacacc gcccgtcaag | 1380 |
| ccatgaaagc cgggggtgcc tgaagtccgt nnccgcga | 1418 |

```
<210> SEQ ID NO 7
<211> LENGTH: 1419
```

<212> TYPE: DNA
<213> ORGANISM: Parabacteroides johnsonii

<400> SEQUENCE: 7

```
gatgaacgct agcgacaggc ttaacacatg caagtcgagg ggcagcatgg taagtagcaa      60
tacttattga tggcgaccgg cgcacgggtg agtaacgcgt atgcaactta cctatcagag     120
ggggatagcc cggcgaaagt cggattaata ctccataaaa caggggttcc gcatgggact     180
atttgttaaa gattcatcgc tgatagatag gcatgcgttc cattaggcag ttggcgggt     240
aacggcccac caaaccgacg atggataggg gttctgagag aaggtcccc cacattggta     300
ctgagacacg gaccaaactc ctacgggagg cagcagtgag gaatattggt caatggccga     360
gaggctgaac cagccaagtc gcgtgaagga tgaaggatct atggtttgta aacttctttt     420
ataggggaat aaagtgtggg acgtgttcca ttttgtatgt accctatgaa taagcatcgg     480
ctaactccgt gccagcagcc gcggtaatac ggaggatgcg agcgttatcc ggatttattg     540
ggtttaaagg gtgcgtaggt ggtaatttaa gtcagcggtg aaagtttgtg gctcaaccat     600
aaaattgccg ttgaaactgg gttacttgag tgtgtttgag gtaggcggaa tgcgtggtgt     660
agcggtgaaa tgcatagata tcacgcagaa ctccaattgc gaaggcagct tactaaacca     720
taactgacac tgaagcacga aagcgtgggt atcaaacagg attagatacc ctggtagtcc     780
acgcagtaaa cgatgattac taggagtttg cgatacacag taagctctac agcgaaagcg     840
ttaagtaatc cacctgggga gtacgccggc aacggtgaaa ctcaaaggaa ttgacggggg     900
cccgcacaag cggaggaaca tgtggtttaa ttcgatgata cgcgaggaac cttacccggg     960
tttgaacgta gtcagaccga ccttgaaaga ggttttctag caatagctga ttacgaggtg    1020
ctgcatggtt gtcgtcagct cgtgccgtga ggtgtcggct taagtgccat aacgagcgca    1080
acccttatca ctagttacta acaggttaag ctgaggactc tggtgagact gccagcgtaa    1140
gctgtgagga aggtggggat gacgtcaaat cagcacggcc cttacatccg ggcgacaca    1200
cgtgttacaa tggcatggac aaagggcagc tacctggcga caggatgcta atctctaaac    1260
catgtctcag ttcggatcgg agtctgcaac tcgactccgt gaagctggat tcgctagtaa    1320
tcgcgcatca gccatggcgc ggtgaatacg ttcccgggcc ttgtacacac cgcccgtcaa    1380
gccatgggag ccggggtac ctgaagtccg taaccgcaa                            1419
```

<210> SEQ ID NO 8
<211> LENGTH: 1414
<212> TYPE: DNA
<213> ORGANISM: Alistipes sp. JC136
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t

<400> SEQUENCE: 8

```
gatgaacgct agcggcaggc ctaacacatg caagtcgagg ggcagcggga ttgaagcttg      60
cttcagttgc cggcgaccgg cgcacgggtg cgtaacgcgt atgcaaccta cccataacag     120
ggggataaca ctgagaaatc ggtactaata tcccataaca tcaagagggg catcccttt     180
ggttgaaaac tccggtggtt atggatggc atgcgttgta ttagctagtt ggtgaggtaa     240
cggctcacca aggcgacgat acatagggg actgagaggt taacccccca cattggtact     300
```

```
gagacacgga ccaaactcct acgggaggca gcagtgagga atattggtca atggacgcaa    360
gtctgaacca gccatgccgc gtgcaggatg acggctctat gagttgtaaa ctgcttttgt    420
acgagggtaa acccggatac gtgtatccgg ctgaaagtat cgtacgaata aggatcggct    480
aactccgtgc cagcagccgc ggtaatacgg aggattcaag cgttatccgg atttattggg    540 tttaagggt gcgtaggcgg tttgataagt tagaggtgaa ataccggtgc ttaacaccgg    600
aactgcctct aatactgttg agctagagag tagttgcggt aggcggaatg tatggtgtag    660
cggtgaaatg cttagagatc atacagaaca ccgattgcng aaggcagctt accaaactat    720
atctgacgtt ngaggcacga aagcgtgggg gagcaaacag gattagatac cctggtagtc    780
cacgcagtaa acgatgataa ctcgctgtcg gcgatacaca gtcggtggct aagcgaaagc    840
gataagttat ccacctgggg agtacgttcg caagaatgaa actcaaagga attgacgggg    900
gcccgcacaa gcggaggaac atgtggttta attcgatgat acgcgaggaa ccttacccgg    960
gcttgaaagt tactgacgat tctggaaaca ggatttccct tcggggcagg aaactaggtg   1020
ctgcatggtt gtcgtcagct cgtgccgtga ggtgtcgggt taagtcccat aacgagcgca   1080 accctaccg ttagttgcca tcaggtcaag ctgggcactc tggcgggact gccggtgtaa   1140
gccgagagga aggtggggat gacgtcaaat cagcacggcc cttacgtccg ggctacaca   1200 cgtgttacaa tggtaggtac agagggcagc tacccagtga tgggatgcga atctcgaaag   1260
cctatctcag ttcggattgg aggctgaaac ccgcctccat gaagttggat tcgctagtaa   1320
tcgcgcatca gccatggcgc ggtgaatacg ttcccgggcc ttgtacacac cgcccgtcaa   1380
gccatggaag ctgggggtgc ctgaagttcg tgac                                1414

<210> SEQ ID NO 9
<211> LENGTH: 1416
<212> TYPE: DNA
<213> ORGANISM: Parabacteroides gordonii
<220> FEATURE:
<221> NAME/KEY: misc_feature
<222> LOCATION: (1408)..(1408)
<223> OTHER INFORMATION: n is a, c, g, or t

<400> SEQUENCE: 9
gatgaacgct agcgacaggc ttaacacatg caagtcgagg ggcagcagga agtagcaata     60
ctttgctggc gaccggcgca cgggtgagta acgcgtatgc aacctaccta tcagaggggg    120
ataacccggc gaaagtcgga ctaataccgc ataaaacagg ggtcccgcat gggaatattt    180
gttaaagatt tattgctgat agatgggcat gcgttccatt agatagttgg tgaggtaacg    240
gctcaccaag tcttcgatgg atagggggttc tgagaggaag gtcccccaca ctggtactga    300
gacacggacc agactcctac gggaggcagc agtgaggaat attggtcaat gggcgagagc    360
ctgaaccagc caagtcgcgt gaaggatgaa ggatctatgg ttcgtaaact tcttttatag    420
gggaataaag tgcaggacgt gtcctgtttt gtatgtaccc tatgaataag gatcggctaa    480
ctccgtgcca gcagccgcgg taatacgag gatccgagcg ttatccggat ttattgggtt    540
taaagggtgc gtaggtggct ttttaagtca gcggtgaaag tttgtggctc aaccataaaa    600
ttgccgttga aactgagggg cttgagtata tttgaggtag gcggaatgcg tggtgtagcg    660
gtgaaatgca tagatatcac gcagaactcc aattgcgaag gcagcttact aaactataac    720
tgacactgaa gcacgaaagc gtgggatca acaggatta gatacctgg tagtccacgc    780 agtaaacgat gattactagg agtttgcgat acacagtaag ctctcagcg aaagcgttaa    840 gtaatccacc tggggagtac gccggcaacg gtgaaactca aaggaattga cggggcccg    900
```

```
cacaagcgga ggaacatgtg gtttaattcg atgatacgcg aggaacctta cccgggtttg    960
aacgtaagtt gaccggagtg gaaacactct ttctagcaat agcaatttac gaggtgctgc   1020
atggttgtcg tcagctcgtg ccgtgaggtg tcggcttaag tgccataacg agcgcaaccc   1080
ttatctttag ttactaacag gtcgagctga ggactctaaa gagactgcca gcgtaagctg   1140
tgaggaaggt ggggatgacg tcaaatcagc acggccctta catccggggc gacacacgtg   1200
ttacaatggt ggggacaaag ggcagctacc tggcgacagg atgctaatct ccaaacccca   1260
tctcagttcg gatcgaagtc tgcaacccga cttcgtgaag ctggattcgc tagtaatcgc   1320
gcatcagcca tggcgcggtg aatacgttcc cgggccttgt acacaccgcc cgtcaagcca   1380
tgggagttgg gggtacctaa agtccgtnac cgcaag                             1416

<210> SEQ ID NO 10
<211> LENGTH: 1419
<212> TYPE: DNA
<213> ORGANISM: Eubacterium limosum

<400> SEQUENCE: 10
gacgaacgct ggcggtatgc ttaacacatg caagtcgaac gagaaggttt tgatggatcc     60
ttcgggtgac attagaactg gaaagtggcg aacgggtgag taacgcgtgg gtaacctgcc    120
ctatggaaag gaatagcctc gggaaactgg gagtaaagcc ttatattatg gttttgtcgc    180
atggcaagat catgaaaact ccggtgccat aggatggacc cgcgtcccat tagctagttg    240
gtgagataac agcccaccaa ggcgacgatg gtaaccggt ctgagagggc gaacggtcac    300
actggaactg agacacggtc cagactccta cgggaggcag cagtggggaa tattgcgcaa    360 tggggggcaac cctgacgcag caataccgcg tgagtgaaga aggttttcgg atcgtaaagc    420
tctgttattg gggaagaaga atgacggtac ccaatgagga agtcccggct aactacgtgc    480
cagcagccgc ggtaatacgt aggggacaag cgttgtccgg aatgactggg cgtaaagggc    540
gcgtaggcgg tctattaagt ctgatgtgaa aggtaccggc tcaaccggtg aagtgcattg    600
gaaactggta gacttgagta ttggagaggc aagtggaatt cctagtgtag cggtgaaatg    660
cgtagatatt aggaggaaca ccagtggcga aggcggcttg ctggacaaat actgacgctg    720
aggtgcgaaa gcgtggggag cgaacaggat tagatacccct ggtagtccac gccgtaaacg    780
atgaatgcta ggtgttgggg aaactcagtg ccgcagttaa cacaataagc attccgcctg    840
gggagtacga ccgcaaggtt gaaactcaaa ggaattgacg ggacccgca caagcagcgg    900 agcatgtggt ttaattcgaa gcaacgcgaa gaaccttacc aggtcttgac atcctctgac    960
gagcctagag ataggaagtt tccttcggga acagagagac aggtggtgca tggttgtcgt   1020
cagctcgtgt cgtgagatgt tgggttaagt cccgcaacga gcgcaacccc tgcctttagt   1080
tgccagcatt aagttgggca ctctagaggg actgccgtag acaatacgga ggaaggtggg   1140
gacgacgtca aatcatcatg ccccttatga cctgggctac acacgtgcta caatggtctg   1200
aacagagggc cgcgaagccg cgaggtgaag caaatccctt aaaacagatc ccagttcgga   1260
ttgcaggctg caactcgcct gcatgaagtt ggagttgcta gtaatcgcgg atcagaatgc   1320
cgcggtgaat gcgttcccgg gtcttgtaca caccgcccgt cacaccacga gagttggcaa   1380 caccgaagc ctgtgagaga accgtaagga ctcagcagt                           1419

<210> SEQ ID NO 11
<211> LENGTH: 1413
<212> TYPE: DNA
```

<213> ORGANISM: Parabacteroides distasonis
<220> FEATURE:
<221> NAME/KEY: misc_feature
<222> LOCATION: (1387)..(1387)
<223> OTHER INFORMATION: n is a, c, g, or t

<400> SEQUENCE: 11

| | | | | | |
|---|---|---|---|---|---|
| gatgaacgct | agcgacaggc | ttaacacatg | caagtcgagg | ggcagcacag | gtagcaatac | 60 |
| cgggtggcga | ccggcgcacg | ggtgagtaac | gcgtatgcaa | cttgcctatc | agaggggat | 120 |
| aacccggcga | aagtcggact | aataccgcat | gaagcagggg | ccccgcatgg | ggatatttgc | 180 |
| taaagattca | tcgctgatag | ataggcatgc | gttccattag | gcagttggcg | gggtaacggc | 240 |
| ccaccaaacc | gacgatggat | aggggttctg | agaggaaggt | cccccacatt | ggtactgaga | 300 |
| cacggaccaa | actcctacgg | gaggcagcag | tgaggaatat | tggtcaatgg | ccgagaggct | 360 |
| gaaccagcca | agtcgcgtga | gggatgaagg | ttctatggat | cgtaaacctc | ttttataagg | 420 |
| gaataaagtg | cgggacgtgt | cccgttttgt | atgtacctta | tgaataagga | tcggctaact | 480 |
| ccgtgccagc | agccgcggta | atacggagga | tccgagcgtt | atccggattt | attgggttta | 540 |
| aaggtgcgt | aggcggcctt | ttaagtcagc | ggtgaaagtc | tgtggctcaa | ccatagaatt | 600 |
| gccgttgaaa | ctgggggct | tgagtatgtt | tgaggcaggc | ggaatgcgtg | gtgtagcggt | 660 |
| gaaatgcata | gatatcacgc | agaaccccga | ttgcgaaggc | agcctgccaa | gccattactg | 720 |
| acgctgatgc | acgaaagcgt | ggggatcaaa | caggattaga | taccctggta | gtccacgcag | 780 |
| taaacgatga | tcactagctg | tttgcgatac | actgtaagcg | gcacagcgaa | agcgttaagt | 840 |
| gatccacctg | gggagtacgc | cggcaacggt | gaaactcaaa | ggaattgacg | ggggcccgca | 900 |
| caagcggagg | aacatgtggt | ttaattcgat | gatacgcgag | gaaccttacc | cgggtttgaa | 960 |
| cgcattcgga | ccgaggtgga | aacaccttt | ctagcaatag | ccgtttgcga | ggtgctgcat | 1020 |
| ggttgtcgtc | agctcgtgcc | gtgaggtgtc | ggcttaagtg | ccataacgag | cgcaaccctt | 1080 |
| gccactagtt | actaacaggt | aaagctgagg | actctggtgg | gactgccagc | gtaagctgcg | 1140 |
| aggaaggcgg | ggatgacgtc | aaatcagcac | ggcccttaca | tccggggcga | cacacgtgtt | 1200 |
| acaatggcgt | ggacaaaggg | aagccacctg | gcgacaggga | gcgaatcccc | aaaccacgtc | 1260 |
| tcagttcgga | tcggagtctg | caacccgact | ccgtgaagct | ggattcgcta | gtaatcgcgc | 1320 |
| atcagccatg | gcgcggtgaa | tacgttcccg | ggccttgtac | acaccgcccg | tcaagccatg | 1380 |
| ggagccnggg | gtacctgaag | tccgtaaccg | cga | | | 1413 |

<210> SEQ ID NO 12
<211> LENGTH: 1406
<212> TYPE: DNA
<213> ORGANISM: Bacteroides cellulosilyticus

<400> SEQUENCE: 12

| | | | | | |
|---|---|---|---|---|---|
| gatgaacgct | agctacaggc | ttaacacatg | caagtcgagg | ggcagcatga | cctagcaata | 60 |
| ggttgatggc | gaccggcgca | cgggtgagta | acacgtatcc | aacctaccgg | ttattccggg | 120 |
| atagcctttc | gaaagaaaga | ttaataccgg | atagtataac | gagaaggcat | ctttttgtta | 180 |
| ttaaagaatt | tcgataaccg | atggggatgc | gttccattag | tttgttggcg | gggtaacggc | 240 |
| ccaccaagac | atcgatggat | aggggttctg | agaggaaggt | cccccacatt | ggaactgaga | 300 |
| cacggtccaa | actcctacgg | gaggcagcag | tgaggaatat | tggtcaatgg | acgagagtct | 360 |
| gaaccagcca | agtagcgtga | aggatgactg | ccctatgggt | tgtaaacttc | ttttatatgg | 420 |
| gaataaagtg | agccacgtgt | ggctttttgt | atgtaccata | cgaataagga | tcggctaact | 480 |

```
ccgtgccagc agccgcggta atacggagga tccgagcgtt atccggattt attgggttta    540
aagggagcgt aggcggacta ttaagtcagc tgtgaaagtt tgcggctcaa ccgtaaaatt    600
gcagttgata ctggtcgtct tgagtgcagt agaggtaggc ggaattcgtg gtgtagcggt    660
gaaatgctta gatatcacga gaactccga ttgcgaaggc agcttactgg actgtaactg     720
acgctgatgc tcgaaagtgt gggtatcaaa caggattaga taccctggta gtccacacag    780
taaacgatga atactcgctg tttgcgatat acagcaagcg ccaagcgaa agcattaagt     840 attccacctg gggagtacgc cggcaacggt gaaactcaaa ggaattgacg ggggcccgca    900
caagcggagg aacatgtggt ttaattcgat gatacgcgag gaaccttacc cgggcttaaa    960
ttgcatctga ataatttgga aacagattag ccgtaaggca gatgtgaagg tgctgcatgg    1020
ttgtcgtcag ctcgtgccgt gaggtgtcgg cttaagtgcc ataacgagcg caacccttat    1080
ctttagttac taacaggtca tgctgaggac tctagagaga ctgccgtcgt aagatgtgag    1140
gaaggtgggg atgacgtcaa atcagcacgg cccttacgtc cggggctaca cacgtgttac    1200 aatgggggt acagaaggca gctacacagc gatgtgatgc taatcccaaa agcctctctc     1260
agttcggatt ggagtctgca acccgactcc atgaagctgg attcgctagt aatcgcgcat    1320
cagccacggc gcggtgaata cgttcccggg ccttgtacac accgcccgtc aagccatgaa    1380
agccgggggt acctgaagtc cgtaac                                         1406

<210> SEQ ID NO 13
<211> LENGTH: 1415
<212> TYPE: DNA
<213> ORGANISM: Bacteroides clarus

<400> SEQUENCE: 13
gatgaacgct agctacaggc ttaacacatg caagtcgagg ggcagcgggg ttgaagcttg     60
cttcaaccgc cggcgaccgg cgcacggggtg agtaacacgt atccaacctg ccgataactc    120
cgggatagcc tttcgaaaga aagattaata ccggatggca tagttttccc gcatggaata    180
actattaaag aatttcggtt atcgatgggg atgcgttcca ttaggcagtt ggcggggtaa    240
cggcccacca aaccgacgat ggatagggt tctgagagga aggtccccca cattggaact    300
gagacacggt ccaaactcct acgggaggca gcagtgagga atattggtca atggacgaga   360
gtctgaacca gccaagtagc gtgaaggatg actgccctat ggttgtaaa cttcttttat    420 acgggaataa agttggccac gtgtggtttt ttgcatgtac cgtatgaata aggatcggct    480
aactccgtgc cagcagccgc ggtaatacg aggatccgag cgttatccgg atttattggg    540
tttaaaggga gcgtaggcgg ggtattaagt cagttgtgaa agtttgcggc tcaaccgtaa    600
aattgcagtt gatactggta tccttgagtg cagcagaggt gggcggaatt cgtggtgtag    660
cggtgaaatg cttagatatc acgaagaact ccgattgcga aggcagctca ctggagtgta    720
actgacgctg atgctcgaaa gtgtgggtat caaacaggat tagataccct ggtagtccac    780
acagtaaacg atgaatactc gctgttggcg atacaatgtc agcggccaag cgaaagcatt    840
aagtattcca cctggggagt acgccggcaa cggtgaaact caaaggaatt gacggggggcc    900 cgcacaagcg gaggaacatg tggtttaatt cgatgatacg cgaggaacct tacccgggct    960
tgaattgcaa ctgactgagc tggaaacagt tctttcttcg acagttgtg aaggtgctgc    1020 atggttgtcg tcagctcgtg ccgtgaggtg tcggcttaag tgccataacg agcgcaaccc    1080
ttatctatag ttaccatcag gtcatgctgg ggactctatg gagactgccg tcgtaagatg    1140
```

-continued

| | |
|---|---|
| tgaggaaggt ggggatgacg tcaaatcagc acggccctta cgtccggggc tacacacgtg | 1200 |
| ttacaatggg gggtacagaa ggcagctaca cggcgacgtg atgctaatcc caaaaacctc | 1260 |
| tctcagttcg gattggagtc tgcaacccga ctccatgaag ctggattcgc tagtaatcgc | 1320 |
| gcatcagcca cggcgcggtg aatacgttcc cgggccttgt acacaccgcc cgtcaagcca | 1380 |
| tgaaagccgg gggtacctga agtacgtaac cgcaa | 1415 |

<210> SEQ ID NO 14
<211> LENGTH: 938
<212> TYPE: DNA
<213> ORGANISM: Anaerostipes sp.
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (899)..(901)
<223> OTHER INFORMATION: n is a, c, g, or t

<400> SEQUENCE: 14

| | |
|---|---|
| gatgaacgct ggcggcgtgc ttaacacatg caagtcgaac gaagcattta ggattgaagt | 60 |
| tttcggatgg atttcctata tgactgagtg gcggacgggt gagtaacgcg tggggaacct | 120 |
| gccctataca gggggataac agctggaaac ggctgctaat accgcataag cgcacagaat | 180 |
| cgcatgattc agtgtgaaaa gcccktggcag tataggatgg tcccgcgtct gattagctgg | 240 |
| ttggtgaggt aacggctcac caaggcgacg atcagtagcc ggcttgagag agtgaacggc | 300 |
| cacattggga ctgagacacg gcccaaactc ctacggagg cagcagtggg gaatattgca | 360 |
| caatgggga acccctgatg cagcgacgcc gcgtgagtga agaagtattt cggtatgtaa | 420 |
| agctctatca gcagggaaga aaacagacgg tacctgacta agaagccccg gctaactacg | 480 |
| tgccagcagc cgcggtaata cgtaggggc aagcgttatc cggaattact gggtgtaaag | 540 |
| ggtgcgtagg tggcatggta agtcagaagt gaaagcccgg ggcttaaccc cgggactgct | 600 |
| tttgaaactg tcatgctgga gtgcaggaga ggtaagcgga attcctagtg tagcggtgaa | 660 |
| atgcgtagat attaggagga acaccagtgg cgaaggcggc ttactggact gtcactgaca | 720 |
| ctgatgcacg aaagcgtggg gagcaaacag gattagatac cctggtagtc cacgccgtaa | 780 |
| acgatgaata ctaggtgtcg gggccgtaga ggcttcggtg ccgcagcaaa cgcagtaagt | 840 |
| attccacctg gggagtacgt tcgcaagaat gaaactcaaa gganttgacg gggaccgcnn | 900 |
| nagcggtgga gcatgtggtt aattcgaagc acgcgaag | 938 |

<210> SEQ ID NO 15
<211> LENGTH: 1406
<212> TYPE: DNA
<213> ORGANISM: Bacteroides salyersiae

<400> SEQUENCE: 15

| | |
|---|---|
| gatgaacgct agctacaggc ttaacacatg caagtcgagg ggcatcaggg tgtagcaata | 60 |
| caccgctggc gaccggcgca cgggtgagta acacgtatcc aacctgccct ttactcgggg | 120 |
| atagcctttc gaaagaaaga ttaatacccg atggtataac atgacctcct ggttttgtta | 180 |
| ttaaagaatt tcggtagagg atggggatgc gttccattag gcagttggcg gggtaacggc | 240 |
| ccaccaaacc ttcgatggat aggggttctg agaggaaggt cccccacatt ggaactgaga | 300 |
| cacggtccaa actcctacgg gaggcagcag tgaggaatat tggtcaatgg gcgagagcct | 360 |
| gaaccagcca agtagcgtga aggatgaccg ccctatgggt tgtaaacttc ttttatatgg | 420 |

```
gaataaagtc tgccacgtgt ggcattttgt atgtaccata tgaataagga tcggctaact      480
ccgtgccagc agccgcggta atacggagga tccgagcgtt atccggattt attgggttta      540
aagggagcgt aggtggacat gtaagtcagt tgtgaaagtt tgcggctcaa ccgtaaaatt      600
gcagttgaaa ctgcgtgtct tgagtacagt agaggtgggc ggaattcgtg gtgtagcggt      660
gaaatgctta gatatcacga gaactccga ttgcgaaggc agctcactgg actgcaactg       720
acactgatgc tcgaaagtgt gggtatcaaa caggattaga taccctggta gtccacacag      780
taaacgatga atactcgctg tttgcgatat acagtaagcg gccaagcgaa agcattaagt      840
attccacctg gggagtacgc cggcaacggt gaaactcaaa ggaattgacg ggggcccgca      900
caagcggagg aacatgtggt ttaattcgat gatacgcgag gaaccttacc cgggcttaaa      960
ttgcaaatga atatgccgga aacggcatag ccgcaaggca tttgtgaagg tgctgcatgg     1020
ttgtcgtcag ctcgtgccgt gaggtgtcgg cttaagtgcc ataacgagcg caacccttat     1080
cttcagttac taacaggtca tgctgaggac tctggagaga ctgccgtcgt aagatgtgag     1140
gaaggtgggg atgacgtcaa atcagcacgg cccttacgtc cggggctaca cacgtgttac     1200 aatgggggt acagaaggcc gctacacagc gatgtgatgc caatccctaa agcccctctc      1260
agttcggatc gaagtctgca acccgacttc gtgaagctgg attcgctagt aatcgcgcat     1320
cagccacggc gcggtgaata cgttcccggg ccttgtacac accgcccgtc aagccatggg    1380
agccgggggt acctgaagta cgtaac                                         1406

<210> SEQ ID NO 16
<211> LENGTH: 1417
<212> TYPE: DNA
<213> ORGANISM: Bacteroides fragilis

<400> SEQUENCE: 16
gatgaacgct agctacaggc ttaacacatg caagtcgagg ggcatcagga agaaagcttg       60 cttttctttgc tggcgaccgg cgcacgggtg agtaacacgt atccaacctg cccttttactc    120 ggggatagcc tttcgaaaga aagattaata cccgatagca taatgattcc gcatggtttc     180
attattaaag gattccggta aaggatgggg atgcgttcca ttaggttgtt ggtgaggtaa     240
cggctcacca agccttcgat ggataggggt tctgagagga aggtccccca cattggaact     300
gagacacggt ccaaactcct acgggaggca gcagtgagga atattggtca atgggcgcta     360
gcctgaacca gccaagtagc gtgaaggatg aaggctctat gggtcgtaaa cttctttat      420 ataagaataa agtgcagtat gtatactgtt ttgtatgtat tatatgaata aggatcggct     480
aactccgtgc cagcagccgc ggtaatacgg aggatccgag cgttatccgg atttattggg     540
tttaaaggga gcgtaggtgg actggtaagt cagttgtgaa agtttgcggc tcaaccgtaa     600
aattgcagtt gatactgtca gtcttgagta cagtagaggt gggcggaatt cgtggtgtag     660
cggtgaaatg cttagatatc acgaagaact ccgattgcga aggcagctca ctggactgca     720
actgacactg atgctcgaaa gtgtgggtat caaacaggat tagataccct ggtagtccac     780
acagtaaacg atgaatactc gctgtttgcg atatacagta agcggccaag cgaaagcatt     840
aagtattcca cctggggagt acgccggcaa cggtgaaact caaaggaatt gacggggccc    900
cgcacaagcg gaggaacatg tggtttaatt cgatgatacg cgaggaacct tacccgggct     960
taaattgcag tggaatgatg tggaaacatg tcagtgagca atcaccgctg tgaaggtgct    1020
gcatggttgt cgtcagctcg tgccgtgagg tgtcggctta agtgccataa cgagcgcaac    1080
```

| | |
|---|---|
| ccttatctttt agttactaac aggttatgct gaggactcta gagagactgc cgtcgtaaga | 1140 |
| tgtgaggaag gtggggatga cgtcaaatca gcacggccct tacgtccggg gctacacacg | 1200 |
| tgttacaatg gggggtacag aaggcagcta acgggtgacc gtatgctaat cccaaaagcc | 1260 |
| tctctcagtt cggatcgaag tctgcaaccc gacttcgtga agctggattc gctagtaatc | 1320 |
| gcgcatcagc cacggcgcgg tgaatacgtt cccgggcctt gtacacaccg cccgtcaagc | 1380 |
| catgggagcc ggggtacct gaagtacgta accgcaa | 1417 |

<210> SEQ ID NO 17
<211> LENGTH: 1407
<212> TYPE: DNA
<213> ORGANISM: Bacteroides uniformis

<400> SEQUENCE: 17

| | |
|---|---|
| gatgaacgct agctacaggc ttaacacatg caagtcgagg ggcatcagga agaaagcttg | 60 |
| ctttctttgc tggcgaccgg cgcacggggtg agtaacacgt atccaacctg ccgatgactc | 120 |
| ggggatagcc tttcgaaaga aagattaata cccgatggta tatctgaaag gcatctttca | 180 |
| gctattaaag aatttcggtc attgatgggg atgcgttcca ttaggttgtt ggcggggtaa | 240 |
| cggcccacca agccatcgat ggatagggggt tctgagagga aggtccccca cattggaact | 300 |
| gagacacggt ccaaactcct acgggaggca gcagtgagga atattggtca atggacgaga | 360 |
| gtctgaacca gccaagtagc gtgaaggatg actgccctat gggttgtaaa cttctttttat | 420 |
| acgggaataa agttaggcac gtgtgccttt ttgtatgtac cgtatgaata aggatcggct | 480 |
| aactccgtgc cagcagccgc ggtaatacga aggatccgag cgttatccgg atttattggg | 540 |
| tttaaaggga gcgtaggcgg atgcttaagt cagttgtgaa agtttgcggc tcaaccgtaa | 600 |
| aattgcagtt gatactgggt gtcttgagta cagtagaggc aggcggaatt cgtggtgtag | 660 |
| cggtgaaatg cttagatatc acgaagaact ccgattgcga aggcagcttg ctggactgta | 720 |
| actgacgctg atgctcgaaa gtgtgggtat caaacaggat tagataccct ggtagtccac | 780 |
| acagtaaacg atgaatactc gctgtttgcg atatacagta gcggccaag cgaaagcgtt | 840 |
| aagtattcca cctggggagt acgccggcaa cggtgaaact caaaggaatt gacggggggcc | 900 |
| cgcacaagcg gaggaacatg tggtttaatt cgatgatacg cgaggaacct tacccgggct | 960 |
| taaattgcaa atgaatgttc tggaaacaga tcagccgcaa ggcatttgtg aaggtgctgc | 1020 |
| atggttgtcg tcagctcgtg ccgtgaggtg tcggcttaag tgccataacg agcgcaaccc | 1080 |
| ttatcgatag ttaccatcag gttatgctgg ggactctgtc gagactgccg tcgtaagatg | 1140 |
| tgaggaaggt ggggatgacg tcaaatcagc acggccctta cgtccggggc tacacacgtg | 1200 |
| ttacaatggg gggtacagaa ggcagctaca cggcgacgtg atgctaatcc ctaaaacctc | 1260 |
| tctcagttcg gattggagtc tgcaacccga ctccatgaag ctggattcgc tagtaatcgc | 1320 |
| gcatcagcca cggcgcggtg aatacgttcc cgggccttgt acacaccgcc cgtcaagcca | 1380 |
| tgaaagccgg gggtacctga agtgcgt | 1407 |

<210> SEQ ID NO 18
<211> LENGTH: 1420
<212> TYPE: DNA
<213> ORGANISM: Bacteroides eggerthii
<220> FEATURE:
<221> NAME/KEY: misc_feature
<222> LOCATION: (220)..(220)
<223> OTHER INFORMATION: n is a, c, g, or t

<400> SEQUENCE: 18

```
gatgaacgct agctacaggc ttaacacatg caagtcgagg ggcagcatga ttgaagcttg      60
cttcaatcga tggcgaccgg cgcacgggtg agtaacacgt atccaacctg ccgataactc     120
ggggatagcc tttcgaaaga aagattaata cccgatagca tagtatttcc gcatggtttc     180
actattaaag aatttcggtt atcgatgggg atgcgttccn ttagatagtt ggcggggtaa     240
cggcccacca agtcaacgat ggataggggt tctgagagga aggtccccca cattggaact     300
gagacacggt ccaaactcct acgggaggca gcagtgagga atattggtca atggacgaga     360
gtctgaacca gccaagtagc gtgaaggatg actgccctat ggttgtaaa  cttctttat      420
acgggaataa agtggagtat gcatactcct ttgtatgtac cgtatgaata aggatcggct     480
aactccgtgc cagcagccgc ggtaatacgg aggatccgag cgttatccgg atttattggg     540
tttaaaggga gcgtaggcgg gtgcttaagt cagttgtgaa agtttgcggc tcaaccgtaa     600
aattgcagtt gatactgggc gccttgagtg cagcataggt aggcggaatt cgtggtgtag     660
cggtgaaatg cttagatatc acgaagaact ccgattgcga aggcagctta ctggactgta     720
actgacgctg atgctcgaaa gtgtgggtat caaacaggat tagataccct ggtagtccac     780
acagtaaacg atgaatactc gctgttggcg atacacagtc agcggccaag cgaaagcatt     840
aagtattcca cctggggagt acgccggcaa cggtgaaact caaaggaatt gacggggggcc    900
cgcacaagcg gaggaacatg tggtttaatt cgatgatacg cgaggaacct acccgggct      960
taaattgcag cggaatgtag tggaaacatt acagccttcg ggccgctgtg aaggtgctgc    1020
atggttgtcg tcagctcgtg ccgtgaggtg tcggcttaag tgccataacg agcgcaaccc    1080
ttatctatag ttactatcag gtcatgctga ggactctatg gagactgccg tcgtaagatg    1140
tgaggaaggt ggggatgacg tcaaatcagc acggccctta cgtccggggc tacacacgtg    1200
ttacaatggg gggtacagaa ggcagctacc tggcgacagg atgctaatcc ctaaaacctc    1260
tctcagttcg gattggagtc tgcaacccga ctccatgaag ctggattcgc tagtaatcgc    1320
gcatcagcca cggcgcggtg aatacgttcc cgggccttgt acacaccgcc cgtcaagcca    1380
tgaaagccgg gggtacctga agtacgtaac cgcaaggagc                          1420
```

<210> SEQ ID NO 19
<211> LENGTH: 1408
<212> TYPE: DNA
<213> ORGANISM: Clostridium sp.

<400> SEQUENCE: 19

```
gatgaacgct ggcggcgtgc ctaatacatg caagtcggac gcaatgcttc ggcattgagt      60
ggcgaacggg tgagtaatac ataagcaacc tgccctgtg  aggggataa  ctgctggaaa     120
cggcagctaa gaccgcatat gcatacatga cgcatgtcga gtatgttaaa tatcccacgg     180
gatagcacag ggatgggctt atgacgcatt agctagctgg tgaggtagag gctcaccagg     240
gcgacgatgc gtagccggcc tgagagggtg acggccaca  ctgggactga gacacggccc     300
agactcctac gggaggcagc agtagggaat tttcggcaat gggcgaaagc ctgaccgagc     360
aacgccgcgt gaaggaagaa gtcattcgtg atgtaaactt ctgttataaa ggaagaacgg     420
cgcctgtagg gaatgacagg cgagtgacgg tactttatga ggaagccacg gctaactacg     480
tgccagcagc cgcggtaata cgtaggtggc gagcgttatc cggaatcatt gggcgtaaag     540
agggagcagg cggcagtgca ggtctgcggt gaaagcccga agctaaactt cggtaagccg     600
tggaaaccgc acagctagag agcatcagag gatcgcggaa ttccatgtgt agcggtgaaa     660
```

```
tgcgtagata tatggaggaa caccagtggc gaaggcggcg gtctggggtg cagctgacgc    720
tcagtcccga aagcgtgggg agcaaatagg attagatacc ctagtagtcc acgccgtaaa    780
cgatgagtgc taagtgttgg gggtcagacc tcagtgctgc agttaacgca ataagcactc    840
cgcctgagta gtacgttcgc aagaatgaaa ctcaaaggaa ttgacggggg cccgcacaag    900
cggtggagca tgtggtttaa ttcgaagcaa cgcgaagaac cttaccaggt cttgacatgg    960
agataaaggc tctggagaca gagagatagg tatatctcac acaggtggtg catggttgtc   1020
gtcagctcgt gtcgtgagat gttgggttaa gtcccgcaac gagcgcaacc cctgttgcca   1080
gttgccagca ttaggttggg gactctggcg agactgcctc tgcaaggagg aggaaggcgg   1140
ggatgacgtc aaatcatcat gccccttatg acctgggcta cacacgtgct acaatggacg   1200
gatcagaggg aggcgaagcc gcgaggtgga gcgaaaccca gaaacccgtt cacagttcgg   1260
actgcagtct gcaactcgac tgcacgaagc tggaatcgct agtaatcgcg aatcagcatg   1320
tcgcggtgaa tacgttctcg ggccttgtac acaccgcccg tcacaccatg agagttggta   1380 acaccccgaag ccggtggccc aaccgcaa                                     1408
```

<210> SEQ ID NO 20
<211> LENGTH: 1413
<212> TYPE: DNA
<213> ORGANISM: Parabacteroides goldsteinii

<400> SEQUENCE: 20

```
gatgaacgct agcgacaggc ttaacacatg caagtcgagg ggcagcacga tgtagcaata     60
cattggtggc gaccggcgca cgggtgagta acgcgtatgc aacctaccta tcagagggga    120
ataacccggc gaaagtcgga ctaataccgc ataaacagg ggttccacat ggaaatattt     180
gttaaagaat tatcgctgat agatgggcat gcgttccatt agatagttgg tgaggtaacg    240
gctcaccaag tccacgatgg ataggggttc tgagaggaag gtcccccaca ctggtactga    300
gacacggacc agactcctac gggaggcagc agtgaggaat attggtcaat gggcgagagc    360
ctgaaccagc caagtcgcgt gaaggatgaa ggatctatgg tttgtaaact tcttttatat    420
gggaataaag tgaggaacgt gttcctttt gtatgtacca tatgaataag catcggctaa    480
ctccgtgcca gcagccgcgg taatacggag gatgcgagcg ttatccggat ttattgggtt    540
taaagggtgc gtaggtggtt aattaagtca gcggtgaaa tttgtggctc aaccataaaa    600
ttgccgttga aactggttga cttgagtata tttgaggtag gcggaatgcg tggtgtagcg    660
gtgaaatgca tagatatcac gcagaactcc gattgcgaag gcagcttact aaactataac    720
tgacactgaa gcacgaaagc gtggggatca acaggatta gatacctgg tagtccacgc    780 agtaaacgat gattactagc tgtttgcgat acacagtaag cggcacagcg aaagcgttaa    840
gtaatccacc tggggagtac gccggcaacg gtgaaactca aaggaattga cggggcccg    900 cacaagcgga ggaacatgtg gtttaattcg atgatacgcg aggaaccta cccgggtttg    960 aacgcatatt gacagctctg gaaacagagt ctctagtaat agcaatttgc gaggtgctgc   1020
atggttgtcg tcagctcgtg ccgtgaggtg tcggcttaag tgccataacg agcgcaaccc   1080
ttatcactag ttactaacag gtcatgctga ggactctagt gagactgcca gcgtaagctg   1140
tgaggaaggt ggggatgacg tcaaatcagc acggcccta catccgggc gacacacgtg    1200 ttacaatggt ggggacaaag gcagctaccg tgtgagcgg atgcaaatct ccaaacccca   1260
tctcagttcg gatcgaagtc tgcaaccga cttcgtgaag ctggattcgc tagtaatcgc    1320
gcatcagcca tggcgcggtg aatacgttcc cgggccttgt acacaccgcc cgtcaagcca    1380
```

```
tgggagttgg gggtacctaa agtccgtaac cgc                                 1413
```

<210> SEQ ID NO 21
<211> LENGTH: 1145
<212> TYPE: DNA
<213> ORGANISM: Bacteroides sp.
<220> FEATURE:
<221> NAME/KEY: misc_feature
<222> LOCATION: (167)..(167)
<223> OTHER INFORMATION: n is a, c, g, or t

<400> SEQUENCE: 21

```
gatgaacgct agctacaggc ttaacacatg caagtcgagg ggcagcattt cagtttgctt      60
gcaaactgga gatggcgacc ggcgcacggg tgagtaacac gtatccaacc tgccgataac     120
tcggggatag cctttcgaaa gaaagattaa tacccgatgg tataatnaga ccgcatggtc     180
ttgttattaa agaatttcgg ttatcgatgg ggatgcgttc cattaggcag ttggtgaggt     240
aacggctcac caaaccttcg atggataggg gttctgagag gaaggtcccc cacattggaa     300
ctgagacacg gtccaaactc ctacgggagg cagcagtgag gaatattggt caatgggcgc     360
aggcctgaac cagccaagta gcgtgaagga tgactgccct atgggttgta aacttctttt     420
atatgggaat aaagttttcc acgtgtggaa ttttgtatgt accatatgaa taaggatcgg     480
ctaactccgt gccagcagcc gcggtaatac ggaggatccg agcgttatcc ggatttattg     540
ggtttaaagg gagcgtaggt ggacagttaa gtcagttgtg aaagtttgcg gctcaaccgt     600
aaaattgcag ttgatactgg ctgtcttgag tacagtagag gtgggcggaa ttcgtggtgt     660
agcggtgaaa tgcttagata tcacgaagaa ctccgattgc gaaggcagct cactggactg     720
caactgacac tgatgctcga agtgtgggt atcaaacagg attagatacc ctggtagtcc     780
acacagtaaa cgatgaatac tcgctgtttg cgatatacag taagcggcca agcgaaagca     840
ttaagtattc cacctgggga gtacgccggc aacggtgaaa ctcaaaggaa ttgacggggg     900
cccgcacaag cggaggaaca tgtggtttaa ttcgatgata cgcgaggaac cttacccggg     960
cttaaattgc atttgaatat attggaaaca gtatagccgt aaggcaaatg tgaaggtgct    1020
gcatggttgt cgtcagctcg tgccgtgagg tgtcggctta agtgccataa cgagcgcaac    1080
ccttatcttt agttactaac aggtcatgct gaggactcta gagagactgc cgtcgtaaga    1140
tgtga                                                                1145
```

<210> SEQ ID NO 22
<211> LENGTH: 965
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:

```
<221> NAME/KEY: misc_feature
<222> LOCATION: (879)..(880)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (927)..(929)
<223> OTHER INFORMATION: n is a, c, g, or t
<220> FEATURE:
<221> NAME/KEY: misc_feature
<222> LOCATION: (937)..(937)
<223> OTHER INFORMATION: n is a, c, g, or t
<220> FEATURE:
<221> NAME/KEY: misc_feature
<222> LOCATION: (939)..(942)
<223> OTHER INFORMATION: n is a, c, g, or t
<220> FEATURE:
<221> NAME/KEY: misc_feature
<222> LOCATION: (953)..(953)
<223> OTHER INFORMATION: n is a, c, g, or t
<220> FEATURE:
<221> NAME/KEY: misc_feature
<222> LOCATION: (956)..(957)
<223> OTHER INFORMATION: n is a, c, g, or t
<220> FEATURE:
<221> NAME/KEY: misc_feature
<222> LOCATION: (959)..(962)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t

<400> SEQUENCE: 22
nnnnnnnnnt gcagtcgaac gaagcgattt gaatgaagtt ttcggatgga tttcaanttg      60
actgagtggc ggacgggtga gtaacgcgtg ggtaacctgc cccatacagg gggataacag     120
ttagaaatga ctgctaatac cgcataagac cacagnnccg catggtgcag gggtaaaaac     180
tccggtggta tgggatggac ccgcgtctga ttagcttgtt ggcggggtaa cggcccacca     240
aggcgacgat cagtagccga cctgagaggg tgaccggcca cattgggact gagacacggc     300
ccaaactcct acgggaggca gcagtgggga atattgcaca atgggggaaa ccctgatgca     360
gcgacgccgc gtgagtgatg aagtatttcg gtatgtaaag ctctatcagc agggaagaaa     420
atgacggtac ctgactaaga agccccggct aactacgtgc cagcagccgc ggtaatacgt     480
aggggggcaag cgttatccgg atttactggg tgtaaaggga gcgtagacgg ctgtgcaagt     540
ctggagtgaa agcccggggc tcaaccccgg gactgctttg gaaactgtac ggctggagtg     600
ctggagaggc aagcggaatt cctagtgtag cggtgaaatg cgtagatatt aggaggaaca     660
ccagtggcga aggcggcttg ctggacagta actgacgttg aggctcgaaa gcgtggggag     720
caaacaggat tagatacccct ggtagtccac gccgtaaacg atgaatgcta ggtgtcgggg     780
agcaaagctc ttcggtgccg ccgcaaacgc aataagcatt ccacctgggg agtacgttcg     840
caagaatgaa actcaaagga nttgacgggg accgcacann ggtggagcat gtggttattc     900
gagcacgcga aancttacca gtcttgnnnc ccctgangnn nngtatgtcg ctnctnngnn     960
nnggn                                                                 965

<210> SEQ ID NO 23
<211> LENGTH: 1457
<212> TYPE: DNA
<213> ORGANISM: Artificial Sequence
<220> FEATURE:
<223> OTHER INFORMATION: Synthetic polynucleotide
```

<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1451)..(1457)
<223> OTHER INFORMATION: n is a, c, g, or t

<400> SEQUENCE: 23

| | | | | | | |
|---|---|---|---|---|---|---|
| agtttgatta | tggctcagga | tgaacgctgg | cggcgtgctt | aacacatgca | agtcgagcga | 60 |
| agcggtttca | atgaagtttt | cggatggatt | tgaaattgac | ttagcggcgg | acgggtgagt | 120 |
| aacgcgtggg | taacctgcct | tacactgggg | gataacagtt | agaaatgact | gctaataccg | 180 |
| cataagcgca | cagggccgca | tggtccggtg | tgaaaaactc | cggtggtgta | agatggaccc | 240 |
| gcgtctgatt | aggtagttgg | cggggtaacg | gcccaccaag | ccgacgatca | gtagccgacc | 300 |
| tgagagggtg | accggccaca | ttgggactga | gacacggccc | aaactcctac | gggaggcagc | 360 |
| agtggggaat | attggacaat | gggcgaaagc | ctgatccagc | gacgccgcgt | gagtgaagaa | 420 |
| gtatttcggt | atgtaaagct | ctatcagcag | ggaagaaaat | gacggtacct | gactaagaag | 480 |
| ccccggctaa | ctacgtgcca | gcagccgcgg | taatacgtag | ggggcaagcg | ttatccggat | 540 |
| ttactgggtg | taagggagc | gtagacggtt | tagcaagtct | gaagtgaaag | cccggggctc | 600 |
| aaccccggta | ctgctttgga | aactgttaga | cttgagtgca | ggagaggtaa | gtggaattcc | 660 |
| tagtgtagcg | gtgaaatgcg | tagatattag | gaggaacacc | agtggcgaag | gcggcttact | 720 |
| ggactgtaac | tgacgttgag | gctcgaaagc | gtggggagca | aacaggatta | gatacctgg | 780 |
| tagtccacgc | cgtaaacgat | gaatactagg | tgtcgggggg | caaagccctt | cggtgccgcc | 840 |
| gcaaacgcaa | taagtattcc | acctggggag | tacgttcgca | agaatgaaac | tcaaaggaat | 900 |
| tgacggggac | ccgcacaagc | ggtggagcat | gtggtttaat | tcgaagcaac | gcgaagaacc | 960 |
| ttaccaagtc | ttgacatccc | actgaaaaca | ctttaaccgg | tgtccctctt | cggagcagtg | 1020 |
| gagacaggtg | gtgcatggtt | gtcgtcagct | cgtgtcgtga | gatgttgggt | taagtcccgc | 1080 |
| aacgagcgca | acccttatcc | ttagtagcca | gcgagtagag | tcgggcactc | tggggagact | 1140 |
| gccagggata | acctggagga | aggtggggat | gacgtcaaat | catcatgccc | cttatgattt | 1200 |
| gggctacaca | cgtgctacaa | tggcgtaaac | aaagggaggc | aaaggagcga | tctggagcaa | 1260 |
| accccaaaaa | taacgtctca | gttcggattg | caggctgcaa | ctcgcctgca | tgaagctgga | 1320 |
| atcgctagta | atcgcgaatc | agaatgtcgc | ggtgaatacg | ttcccgggtc | ttgtacacac | 1380 |
| cgcccgtcac | accatgggag | ttggtaacgc | ccgaagtcag | tgacccaacc | gcaaggaggn | 1440 |
| agctgccgaa | nnnnnnn | | | | | 1457 |

<210> SEQ ID NO 24
<211> LENGTH: 1456
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (1314)..(1315)
<223> OTHER INFORMATION: n is a, c, g, or t
<220> FEATURE:
<221> NAME/KEY: misc_feature
<222> LOCATION: (1358)..(1358)

<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1444)..(1444)
<223> OTHER INFORMATION: n is a, c, g, or t
<220> FEATURE:
<221> NAME/KEY: misc_feature
<222> LOCATION: (1449)..(1450)
<223> OTHER INFORMATION: n is a, c, g, or t
<220> FEATURE:
<221> NAME/KEY: misc_feature
<222> LOCATION: (1452)..(1456)
<223> OTHER INFORMATION: n is a, c, g, or t

<400> SEQUENCE: 24

| | | | | | |
|---|---|---|---|---|---|
| agtttgnnnn | ngctcaggat | gaacgctggc | ggcgtgccta | acacatgcaa | gtcgaacgaa | 60 |
| gcatttcaga | tgaagttttc | ggatggattc | tgagatgact | gagtggcgga | cgggtgagta | 120 |
| acacgtggat | aacctgcctc | acactggggg | acaacagtta | gaaatgactg | ctaataccgc | 180 |
| ataagcgcac | agtaccgcat | ggtacagtgt | gaaaaactcc | ggtggtgtga | gatggatccg | 240 |
| cgtctgatta | gccagttggc | ggggtaacgg | cccaccaaag | cgacgatcag | tagccgacct | 300 |
| gagagggtga | ccggccacat | tgggactgag | acacggccca | aactcctacg | ggaggcagca | 360 |
| gtggggaata | ttgcacaatg | ggcgaaagcc | tgatgcagcg | acgccgcgtg | agtgaagaag | 420 |
| tatttcggta | tgtaaagctc | tatcagcagg | gaagataatg | acggtacctg | actaagaagc | 480 |
| cccggctaac | tacgtgccag | cagccgcggt | aatacgtagg | gggcaagcgt | tatccggatt | 540 |
| tactgggtgt | aaagggagcg | tagacggcat | ggcaagtctg | aagtgaaaac | ccagggctca | 600 |
| accctgggac | tgctttggaa | actgtcaagc | tagagtgcag | gagaggtaag | tggaattcct | 660 |
| agtgtagcgg | tgaaatgcgt | agatattagg | aggaacacca | gtggcgaagg | cggcttactg | 720 |
| gactgtaact | gacgttgagg | ctcgaaagcg | tggggagcaa | acaggattag | ataccctggt | 780 |
| agtccacgcc | gtaaacgatg | agtgctaggt | gttgggggc | aaagcccttc | ggtgccgtcg | 840 |
| caaacgcaat | aagcactcca | cctggggagt | acgttcgcaa | gaatgaaact | caaaggaatt | 900 |
| gacgggggacc | cgcacaagcg | gtggagcatg | tggtttaatt | cgaagcaacg | cgaagaacct | 960 |
| taccaagtct | tgacatcctc | ttgaccggcg | tgtaacggcg | cctttccttc | gggacaagag | 1020 |
| agacaggtgg | tgcatggttg | tcgtcagctc | gtgtcgtgag | atgttgggtt | aagtcccgca | 1080 |
| acgagcgcaa | cccttatcct | tagtagccag | cattaagatg | ggcactctag | ggagactgcc | 1140 |
| agggacaacc | tggaggaagg | tggggatgac | gtcaaatcat | catgcccctt | atgatttggg | 1200 |
| ctacacacgt | gctacaatgg | cgtaaacaaa | gggaagcgac | cctgcgaagg | tgagcaaatc | 1260 |
| tcaaaaataa | cgtcccagtt | cggactgtag | tctgcaaccc | gactacacga | agcnngaatc | 1320 |
| gctagtaatc | gcgaatcaga | atgtcgcggt | gaatacgntc | ccgggtcttg | tacacaccgc | 1380 |
| ccgtcacacc | atgggagtca | gcaacgnccg | aagtcagtga | cccaaccgaa | aggagggagn | 1440 |
| tgcngaagnn | gnnnnn | | | | | 1456 |

<210> SEQ ID NO 25
<211> LENGTH: 1455
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1443)..(1455)
<223> OTHER INFORMATION: n is a, c, g, or t

<400> SEQUENCE: 25

```
agtttgannt tggctcagga tgaacgctgg cggcgtgcct aacacatgca agtcgagcga      60
agcgctgttt tcagaatctt cggaggaaga ggacagtgac tgagcggcgg acgggtgagt     120
aacgcgtggg caacctgcct catacagggg gataacagtt agaaatgact gctaataccg     180
cataagcgca caggaccgca tggtgtagtg tgaaaaactc cggtggtatg agatggaccc     240
gcgtctgatt aggtagttgg tggggtaaag gcctaccaag ccgacgatca gtagccgacc     300
tgagagggtg accggccaca ttgggactga gacacggccc aaactcctac gggaggcagc     360
agtggggaat attgcacaat gggggaaacc ctgatgcagc gacgccgcgt gaaggaagaa     420
gtatttcggt atgtaaactt ctatcagcag gaagaagat gacggtacct gagtaagaag     480
caccggctaa atacgtgcca gcagccgcgg taatacgtat ggtgcaagcg ttatccggat     540
ttactgggtg taaagggagc gtagacggat aggcaagtct ggagtgaaaa cccagggctc     600
aactctggga ctgctttgga aactgcagat ctggagtgcc ggagaggtaa gcggaattcc     660
tagtgtagcg gtgaaatgcg tagatattag gaggaacacc agtggcgaag gcggcttact     720
ggacggtgac tgacgttgag gctcgaaagc gtggggagca acaggatta gataccctgg     780
tagtccacgc cgtaaacgat gactactagg tgtcggtgtg caaagcacat cggtgccgca     840
gcaaacgcaa taagtagtcc acctggggag tacgttcgca agaatgaaac tcaaaggaat     900
tgacggggac ccgcacaagc ggtggagcat gtggtttaat tcgaagcaac gcgaagaacc     960
ttacctggtc ttgacatccg gatgacgggc gagtaatgtc gccgtccctt cggggcatcc    1020
gagacaggtg gtgcatggtt gtcgtcagct cgtgtcgtga gatgttgggt taagtcccgc    1080
aacgagcgca acccttatct tcagtagcca gcatataagg tgggcactct ggagagactg    1140
ccagggagaa cctggaggaa ggtggggatg acgtcaaatc atcatgcccc ttatggccag    1200
ggctacacac gtgctacaat ggcgtaaaca agggaagcg agagggtgac ctgaagcgaa    1260
tcccaaaaat aacgtctcag ttcggattgt agtctgcaac tcgactacat gaagctggaa    1320
tcgctagtaa tcgcggatca gcatgccgcg gtgaatacgt tcccgggtct tgtacacacc    1380
gcccgtcaca ccatgggagt cagtaacgcc cgaagccant gacccaacct tagaggaggg    1440
agnnnnnnnn nnnnn                                                    1455
```

<210> SEQ ID NO 26
<211> LENGTH: 1458
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1439)..(1439)
<223> OTHER INFORMATION: n is a, c, g, or t
<220> FEATURE:

```
<221> NAME/KEY: misc_feature
<222> LOCATION: (1445)..(1449)
<223> OTHER INFORMATION: n is a, c, g, or t
<220> FEATURE:
<221> NAME/KEY: misc_feature
<222> LOCATION: (1452)..(1457)
<223> OTHER INFORMATION: n is a, c, g, or t

<400> SEQUENCE: 26
agtttgatta tggctcagga tgaacgctgg cggcatgcct aatacatgca agtcgaacga      60
agtttcgagg aagcttgctt ccaaagagac ttagtggcga acgggtgagt aacacgtagg     120
taacctgccc atgtgtccgg gataactgct ggaaacggta gctaaaaccg gataggtata     180
cagagcgcat gctcagtata ttaaagcgcc catcaaggcg tgaacatgga tggacctgcg     240
gcgcattagc tagttggtga ggtaacggcc caccaaggcg atgatgcgta gccggcctga     300
gagggtaaac ggccacattg ggactgagac acggcccaaa ctcctacggg aggcagcagt     360
agggaatttt cgtcaatggg ggaaaccctg aacgagcaat gccgcgtgag tgaagaaggt     420
cttcggatcg taaagctctg ttgtaagtga agaacggctc atagaggaaa tgctatggga     480
gtgacggtag cttaccagaa agccacggct aactacgtgc cagcagccgc ggtaatacgt     540
aggtggcaag cgttatccgg aatcattggg cgtaaagggt gcgtaggtgg cgtactaagt     600
ctgtagtaaa aggcaatggc tcaaccattg taagctatgg aaactggtat gctggagtgc     660
agaagagggc gatggaattc catgtgtagc ggtaaaatgc gtagatatat ggaggaacac     720
cagtggcgaa ggcggtcgcc tggtctgtaa ctgacactga ggcacgaaag cgtggggagc     780
aaataggatt agatacccta gtagtccacg ccgtaaacga tgagaactaa gtgttggagg     840
aattcagtgc tgcagttaac gcaataagtt ctccgcctgg ggagtatgca cgcaagtgtg     900
aaactcaaag gaattgacgg gggcccgcac aagcggtgga gtatgtggtt taattcgaag     960
caacgcgaag aaccttacca ggccttgaca tggaaacaaa taccctagag atagggggat    1020
aattatggat cacacaggtg gtgcatggtt gtcgtcagct cgtgtcgtga gatgttgggt    1080
taagtcccgc aacgagcgca acccttgtcg catgttacca gcatcaagtt ggggactcat    1140
gcgagactgc cggtgacaaa ccggaggaag gtggggatga cgtcaaatca tcatgcccct    1200
tatggcctgg gctacacacg tactacaatg gcgaccacaa agagcagcga cacagtgatg    1260
tgaagcgaat ctcataaagg tcgtctcagt tcggattgaa gtctgcaact cgacttcatg    1320
aagtcggaat cgctagtaat cgcagatcag catgctgcgg tgaatacgtt ctcgggcctt    1380
gtacacaccg cccgtcaaac catgggagtc agtaataccc gaagccggtg cataaccnt    1440
aaggnnnnnc cnnnnnna                                                  1458

<210> SEQ ID NO 27
<211> LENGTH: 1217
<212> TYPE: RNA
<213> ORGANISM: Phascolarctobacterium faecium

<400> SEQUENCE: 27
agaggaccgg ccaggacgaa cgcggcggcg gccaacacag caagcgaacg gagaaacgga      60
gaacagggcg aacggggaga acgcgaggca accgcccaga cggggacaac accgaaagga     120
ggcaaaccgg aggacacggc cgcaggcagg agaagaaaga ggcccacaag aagcacgcaa     180
aggagggccg cgcgaagcag ggaggaacgg acaccaaggc gagacagagc cggcgagagg     240
agaacgccca cagggacgag acacggccca aacccacggg aggcagcagg gggaacccgc     300
aaggacgaaa gcgacggagc aacgccgcgg aggagaagga cggcgaaagc cggagacgaa     360
```

```
cggcagggga acaagcagca agacggagaa acgaggaagc cacggcaaca cggccagcag    420
ccgcggaaac gaggggcgag cggccggaaa gggcgaaaga gcagaggcgg caaaagcgag    480
cggaaaagcg gggccaaccc cgaggcgcgg aaacgaggcg aggcaggaga ggaaagggga    540
acccaggagc gggaaagcga gaagggagga acaccagggc gaaggcgccc ggacggcgac    600
gcgagagcga aagccaggga gcgaacggga agaacccccgg agccggccga aacgagggac    660
agggaggagg acgacccccg gccggagaac gcaaaagacc ccgccgggga gacggccgca    720
agggaaacca aaggaagacg ggggcccgca caagcgggga gagggaacga cgcaacgcga    780
agaaccacca aggcgacaga gaacgccaga gaagagcccc cggggacaag aaaacagggg    840
gcaggcgcgc agccggcgga gaggggaagc ccgcaacgag cgcaacccca ccagaccagc    900
aagaaagggg gaccagggag acgccaggga caaccggagg aaggcgggga gacgcaagca    960
cagccccagc gggcacacac gacacaaggc ggaaacagag ggaagcgaag ccgcgaggca   1020
gagcaaaccc cagaaacccg accagcggac gcaggcgcaa cccgccgcgg aagcggaacg   1080
cagaacgcag gcagcaacgc gggaaacgcc cgggccgaca caccgcccgc acaccacgaa   1140
agggaacacc cgaagccggg aggaaccaag gagccagccg caagggggc cgagaggggg   1200 aagcgaacaa ggagccg                                                  1217
```

<210> SEQ ID NO 28
<211> LENGTH: 1104
<212> TYPE: RNA
<213> ORGANISM: Fusobacterium ulcerans

<400> SEQUENCE: 28

```
gccaggagaa cgcgacagaa gcaacacagc aagcacgacc cggggaaggg gcggacgggg     60
agaacgcgaa agaacgccac agacgggaca acaggaaacg aagcaaaccg gaaagagggc    120
gcagacgaag aaagcaagcg cggagagagc gcgcccaaga ggggaggaac ggccaccaag    180
acgagaggga gccggccgag aggggaacgg ccacaagggg acgagacacg gcccacccac    240
gggaggcagc agggggaaag gacaaggacc aaaagcgacc agcaacgggc acgagaagcg    300
gaagaaaggc caggggaaga agcaggacgg accaacagaa gaagcgacgg caaaacggcc    360
agcagccgcg gaaacgagcg caagcgaccg gaagggcgaa agcgcgcagg cggcagaagc    420
gaggaaaagc ggggccaacc ccgagcggga aacgcaaaca gagacggaga ggaggcggaa    480
cacaaggaga gggaaacgag aagaggaagc cgaggggaag ccagccacgg acagaacgac    540
gcaaagcgcg aaagcgggga gcaaacagga agaacccgga gccacgccga aacgagaaca    600 gggggggcg aacccagcgc ccaagcaacg cgaaagaacc gccggggaga cgacgcaaga    660
gaaaccaaag gaagacgggg acccgcacaa gcggggagca gggaacgacg caacgcgagg    720
aaccaccagc ggacacccaa gaagaacaga gagcggcccc ggaggaacgg gacaggggc    780 aggcgcgcag ccggcggaga ggggaagccc gcaacgagcg caaccccga gaccacaaag    840 ggggaccagc gagacgccgc gagagcagga ggaagggggg agacgcaagc acagccccaa    900
cgcgggcaca cacggcacaa gggagacaga gagcgcaaac cgcgagggaa gcaaccaaaa    960
acacagcgga gaccgcaacc gagacagaag ggaacgcaga acgcaaacag caggcgggaa   1020
acgccgggcg acacaccgcc cgcacaccac gagaggggca ccgaagaaca ggccaaccga   1080
aggagggagc cgagggggaa gcga                                          1104
```

<210> SEQ ID NO 29

<211> LENGTH: 1202
<212> TYPE: RNA
<213> ORGANISM: Bacteroides dorei

<400> SEQUENCE: 29

| | | | | |
|---|---|---|---|---|
| aacaagaaga | ggaccggcca | ggagaacgca | gcacaggcaa | cacagcaagc | gaggggcagc | 60 |
| aggcagcgca | aggcgaggcg | accggcgcac | ggggagaaca | cgaccaaccg | ccgcaccggc | 120 |
| cagcccgaaa | ggaagaaacc | aggagggaca | gagcacagcc | gcagaaaagg | accggagacg | 180 |
| aggggagcgc | caagaagagg | cggggaacgg | cccaccagca | acgaggaagg | ggcgagagga | 240 |
| aggcccccac | aggaacgaga | cacggccaaa | cccacgggag | gcagcaggag | gaaaggcaag | 300 |
| ggcgaggccg | aaccagccaa | gagcggaagg | agacgcccag | gggaaaccaa | aaggaaaaag | 360 |
| cgggagcaac | ccggcagaca | gaaaaggacg | gcaacccggc | cagcagccgc | ggaaacggag | 420 |
| gaccgagcga | ccgaaaggga | aagggagcga | gaggagaagc | agggaaaggc | ggccaaccga | 480 |
| aaagcaggaa | cggagcgagg | caggaggcag | gcggaacggg | gagcgggaaa | gcagaacacg | 540 |
| aagaacccga | gcgaaggcag | ccgcaagcgc | aacgacagag | gccgaaaggg | ggacaaacag | 600 |
| gaagaacccg | gagccacacg | gaaacgagaa | accgcggcga | aacggcaagc | ggccaagcga | 660 |
| aagcgaagac | caccggggag | acgccggcaa | cgggaaacca | aaggaagacg | ggggcccgca | 720 |
| caagcggagg | aacagggaac | gagaacgcga | ggaaccaccc | gggcaaagca | ccgaagaccg | 780 |
| gaaacgcag | cagcaaagcg | agggaaggc | gcagggcgca | gccggccgga | gggcggcaag | 840 |
| gccaaacgag | cgcaacccgg | cagacaacag | ggagcgagga | ccgacaagac | gccacgaaga | 900 |
| ggaggaaggg | gggagacgca | aacagcacgg | cccacgccgg | ggcacacacg | gacaagggg | 960 |
| gacagagggc | cgcaccacgc | gagggagcca | acccaaaacc | ccccagcgga | cggagcgcaa | 1020 |
| cccgacccac | gaagcggacg | cagaacgcgc | acagccacgg | cgcgggaaac | gcccgggccg | 1080 |
| acacaccgcc | cgcaagccag | ggagccgggg | gaccgaaggc | gaaccgcgag | gacgcccagg | 1140 |
| gaaaacggga | cggggcaagc | gaacaaggag | ccgaccggaa | gggcggcgga | acaccccgg | 1200 |
| ag | | | | | | 1202 |

<210> SEQ ID NO 30
<211> LENGTH: 1148
<212> TYPE: RNA
<213> ORGANISM: Bacteroides uniformis

<400> SEQUENCE: 30

| | | | | | | |
|---|---|---|---|---|---|---|
| cggccaggag | aacgcagcac | aggcaacaca | gcaagcgagg | ggcagcagaa | cagcgcaagg | 60 |
| aggcgaccgg | cgcacgggga | gaacacgacc | aaccgccgag | accggggaag | cccgaaagaa | 120 |
| agaaaacccg | aggcaagccc | gcaggagaac | aaaagaacgg | cacgaggga | gcgcaagggg | 180 |
| ggcggggaac | ggcccaccaa | gcccgaggaa | ggggcgagag | gaaggccccc | acaggaacga | 240 |
| gacacggcca | aacccacggg | aggcagcagg | aggaaaggca | aggacgagag | cgaaccagcc | 300 |
| aagagcggaa | ggagacgccc | aggggaaacc | aacgggaaaa | aggaggcacg | ggccgagacc | 360 |
| gagaaaagga | cggcaacccg | gccagcagcc | gcggaaacgg | aggaccgagc | gaccggaagg | 420 |
| gaaagggagc | gaggcggacg | caagcaggga | aaggcggcca | accgaaaagc | aggaacgggg | 480 |
| cgagacagag | aggcaggcgg | aacggggagc | gggaaagcag | aacacgaaga | acccgagcga | 540 |
| aggcagcgcg | gacgaacgac | gcgagccgaa | aggggggacaa | acaggaagaa | cccgagccca | 600 |
| cacagaaacg | agaaaccgcg | gcgaaacaga | agcggccaag | cgaaagcgaa | gaccaccggg | 660 |
| gagacgccgg | caacgggaaa | ccaaaggaag | acggggggccc | gcacaagcgg | aggaacaggg | 720 |

```
aacgagaacg cgaggaacca cccgggcgaa gcaacgaaga gggagacagc agccgcaagg        780
cagggaaggg cgcagggcgc agccggccgg agggcggcaa ggccaaacga gcgcaaccca        840
cgaagaccac aggagcgggg accgcgagac gccgcgaaga ggaggaaggg gggagacgca        900
aacagcacgg cccacgccgg ggcacacacg gacaaggggg gacagaaggc agcacacggc        960
gacggagcaa cccaaagccc ccagcggagg agcgcaaccc gacccagaag cggacgcaga       1020
acgcgcacag ccacggcgcg ggaaacgccc gggccgacac accgcccgca agccagaaag       1080
ccgggggacc gaaggcgaac cgcaaggagc gcccagggaa aacgggaggg gcaagcgaac       1140
aaggaacc                                                               1148

<210> SEQ ID NO 31
<211> LENGTH: 1219
<212> TYPE: RNA
<213> ORGANISM: Subdoligranulum sp.

<400> SEQUENCE: 31
agaggaccgg ccaggacgaa cgcggcggcg cgccaacaca gcaagcgaac ggagcgccga         60
agcggaggaa gagagcagca gggcgaacgg ggagaacacg gagcaaccgc ccagggggga       120
caacaggaaa cgaagcaaac cgcaaagacc acaggcgcag gcacaggggc aaaggaaccg       180
cgaaagaggg ccgcgccgaa gcagagggag gaacggccca ccaggcgacg acggagccgg       240
acgagaggga acgccacag ggacgagaca cggcccagac ccacgggagg cagcaggggg        300
aaagcacaag ggggaaaccc gagcagcgac gccgcgggag gaagaaggcc ggagaaaccc       360
gcccagggga cgaaagacgg acccgggagg aagcaccggc aacacggcca gcagccgcgg       420
aaaacgaggg gcaagcggcc ggaaacgggg aaagggagcg caggcggagg caaggggagg       480
aaacagggcc aacccaaaag ccaaaacgca gcgaggggag aggaggcgga acccgggagc       540
ggggaagcga gaacgggagg aacaccaggg cgaaggcggc cacgggcaca acgacgcgag       600
gccgaaagca gggagcaaac aggaagaacc cggagccagc cgaaacgaga acaggggga       660 ggagaccccc cggccgcaga acacaaaaga accaccgggg agacgaccgc aagggaaacc       720
aaaggaagac gggggcccgc acaagcaggg agagggaacg aagcaacgcg aagaaccacc       780
aggcgacacg gagcaaccaa gagaaggaa gcccgggaca ccagacaggg ggcagggcgc       840
agccggcgga gaggggaagc ccgcaacgag cgcaacccac gagacacgca agaggaccag       900
cgagacgccg gacaaaacgg aggaaggggg gagacgcaaa cacagcccag accgggcaca       960
cacgacacaa ggcaaacaga gagaagcgaa ccgcgagggg agcaaaccca caaaaaagcc      1020
agcggacgca ggcgcaaccc gccgcggaag ccggaagcag aacgcggaca gcagccgcgg      1080
gaaacgcccg ggccgacaca ccgcccgcac accagagagc cggggggacc cgaagcggag      1140
caaccgaagg aggacgccgc cgaaggaaaa cgggaggggg aagcgaacaa ggagccgacg      1200
gaagggcggc ggacacccc                                                 1219

<210> SEQ ID NO 32
<211> LENGTH: 1186
<212> TYPE: RNA
<213> ORGANISM: Paraprevotella xylaniphila

<400> SEQUENCE: 32
agaggaccgg ccaggagaac gcagcacagg caacacagca agcgaggggc agcagaacag         60
cgcaaggagg cgaccggcgc acggggagaa cgcgaccaac cgcccacgcg gggaagcccg       120
```

| | |
|---|---|
| aaaggaagaa acccgagaac gagcgcaggc gagaaaaaga acagaaagga ggggagcgcc | 180 |
| caagcgggcg gggaacggcc caccaagcg acgaggagg ggcgagagga aggcccccac | 240 |
| aggaacgaga cacggccaaa cccacgggag gcagcaggag gaaaggcaag ggcgcgagcc | 300 |
| gaaccagcca agagcgggag gacgacggcc cacggggaaa cccaaagggg aaaagggcca | 360 |
| gaggccagca ggaccagaaa agcacggcaa ccggccagca gccgcggaaa cggaagagcg | 420 |
| agcgaccgga agggaaggg agcgaggcgg gcagcaagca gcggcaaagg cgcggccaac | 480 |
| cgcgccgccg gaaacggcag ccgagagcac agggacagga acgggagcg ggaaagcaga | 540 |
| acacgaggaa cccgacgcgc aggcagaccg ggcaacgac gcgaggccga agggcgggac | 600 |
| aaacaggaag aacccggagc cgcacagaaa cgagaagccc gcgcggcgac aaggcggcgg | 660 |
| ccaagcgaaa gcgaagcacc accggggaga cgccggcaac gggaaaccaa aggaagacgg | 720 |
| gggcccgcac aagcggagga cagggaacg agaacgcgag gaaccacccg ggcgaacgca | 780 |
| gggcaggggcc ggagacggcc ccccgggacc cgcgaagggc gcagggcgca gccggccgga | 840 |
| gggcggcaag gccaaacgag cgcaaccccc ccccaggcc acgggaagcc gggcacgggg | 900 |
| acacgccacc gcaagggcga ggaagggggg agacgcaaac agcacggccc acgccggggc | 960 |
| gacacacgga caaggggga cagagggccg cgcccggac ggggcaaacc caaagccccc | 1020 |
| cagcggaccgg agcgcaaccc gacccacgaa gcggacgcag aacgcgcaca gccaggcgcg | 1080 |
| ggaaacgccc gggccgacac accgcccgca agccagaaag ccgggggggcc gaagccggac | 1140 |
| cgcgagggcg gccagggaaa accgggaggg gcaagcgaac aaggaa | 1186 |

<210> SEQ ID NO 33
<211> LENGTH: 1165
<212> TYPE: RNA
<213> ORGANISM: Parabacteroides johnsonii

<400> SEQUENCE: 33

| | |
|---|---|
| agaggaccgg ccaggagaac gcagcgacag gcaacacagc aagcgagggg cagcaggaag | 60 |
| agcaaacaga ggcgaccggc gcacggggag aacgcgagca acaccacaga ggggaaagcc | 120 |
| cggcgaaagc ggaaaaccca aaaacagggg ccgcagggac agaaagacac gcgaagaagg | 180 |
| cagcgccaag gcagggcggg gaacggccca ccaaaccgac gaggaagggg cgagaggaag | 240 |
| gcccccacag gacgagacac ggaccaaacc cacgggaggc agcaggagga aaggcaaggc | 300 |
| cgagaggcga accagccaag cgcggaagga gaaggacagg gaaaccaagg ggaaaagggg | 360 |
| ggacggccag agacccagaa aagcacggca acccggccag cagccgcgga aacggaggag | 420 |
| cgagcgaccg gaagggaaag gggcgagggg aaaagcagcg ggaaaggggc caaccaaaaa | 480 |
| gccggaaacg ggacgagggg aggaggcgga agcggggagc gggaaagcaa gaacacgcag | 540 |
| aacccaagcg aaggcagcac aaaccaaacg acacgaagca cgaaagcggg gacaaacagg | 600 |
| aagaacccgg agccacgcag aaacgagaac aggaggcgaa cacagaagcc acagcgaaag | 660 |
| cgaagaacca ccggggagac gccggcaacg ggaaaccaaa ggaagacggg ggcccgcaca | 720 |
| agcggaggaa cagggaacga gaacgcgagg aaccacccgg ggaacgagca gaccgaccga | 780 |
| aagaggccaa caaagcgaac gagggcgcag ggcgcagccg gccggagggc ggcaaggcca | 840 |
| aacgagcgca acccacacag acaacaggca agcgaggacc gggagacgcc agcgaagcgg | 900 |
| aggaaggggg gagacgcaaa cagcacggcc cacaccgggg cgacacacgg acaaggcagg | 960 |
| acaagggcag gcaccggcga caggagcaac caaaccagcc agcggacgga gcgcaaccga | 1020 |
| cccggaagcg gacgcagaac gcgcacagcc aggcgcggga aacgcccggg ccgacacacc | 1080 |

| | |
|---|---|
| gcccgcaagc cagggagccg ggggaccgaa gccgaaccgc aaggacggcc agggaaaacg | 1140 |
| ggacggggca agcgaacaag gaacc | 1165 |

<210> SEQ ID NO 34
<211> LENGTH: 1181
<212> TYPE: RNA
<213> ORGANISM: Alistipes sp

<400> SEQUENCE: 34

| | |
|---|---|
| agaggaccgg ccaggagaac gcagcggcag gccaacacag caagcgaggg gcagcgggag | 60 |
| aagcgccaac gccggcgacc ggcgcacggg gcgaacgcga gcaaccaccc agaacagggg | 120 |
| gaaacacgag aaaggacaaa cccaaacaca aggggcacc cgggaaaacc cggggcggag | 180 |
| ggcagcggaa gcggggagg aacgccacc aaggcaacga acaaggggga cgagaggaac | 240 |
| cccccacagg acgagacacg gaccaaaccc acgggaggca gcaggaggaa aggcaaggac | 300 |
| gcaagcgaac cagccagccg cggcaggaag acggccagag gaaacgcgac agggaaacca | 360 |
| gaacgcgacg acgaaagaag acgaaaagga ccggcaaccc ggccagcagc cgcggaaacg | 420 |
| gagggccaag cgaccggaag ggaaaggggc gaggcggaga aagagaggga aaaccgggca | 480 |
| acaccggaac gcccaaacga gcagagaaag gcggaggsgg aagagggagc gggaaagcag | 540 |
| agacaacaga acaccgagcg aaggcagcac caagcacgac ggaggcacga aagcggggga | 600 |
| gcaaacagga agaacccgga gccacgcaga aacgagaaac cgcgcggcga acacagcggc | 660 |
| ggcaagcgaa agcgaaagac caccggggag acgcgcaaga agaaaccaaa ggaagacggg | 720 |
| ggcccgcaca agcggaggaa cagggaacga gaacgcgagg aaccacccgg gcgaaagacg | 780 |
| acgacggaaa caggaccccg gggcaggaaa cagggcgcag ggcgcagccg gccggagggc | 840 |
| gggaagccca acgagcgca accccaccga ggccacaggc aagcgggcac cgacgggacg | 900 |
| ccgggaagcc gagaggaagg ggggagacgc aaacagcacg gcccacgccg ggcacacac | 960 |
| ggacaaggag gacagagggc agcacccgcg aagggagcga accgaaagcc accagcggac | 1020 |
| ggaggcgaaa cccgcccggg aagggacgca gaacgcgcac agccaggcgc gggaaacgcc | 1080 |
| cgggccgaca caccgcccgc aagccaggaa gcgggggcc gaagcggacc gcaaggagcg | 1140 |
| accagggcaa aaccgggacg gggcaagcga acaaggagcc g | 1181 |

<210> SEQ ID NO 35
<211> LENGTH: 1157
<212> TYPE: RNA
<213> ORGANISM: Parabacteroides gordonii

<400> SEQUENCE: 35

| | |
|---|---|
| agaggaccgg ccaggagaac gcagcgacag gcaacacagc aagcgagggg cagcaggaag | 60 |
| agcaaacgcg gcgaccggcg cacggggaga acgcgagcaa ccaccacaga gggggaaacc | 120 |
| cggcgaaagc ggacaaaccg caaaaacagg ggcccgcagg gaaagaaaga aagcgaagag | 180 |
| ggcagcgcca agaagggaag gaacggcacc aagcgcgagg aaggggcgag aggaaggccc | 240 |
| ccacacggac gagacacgga ccagacccac gggaggcagc aggaggaaag gcaagggcga | 300 |
| gagccgaacc agccaagcgc ggaaggagaa ggacaggcga aaccaaaggg aaaaggcgg | 360 |
| acggccggag accagaaaag gacggcaacc cggccagcag ccgcggaaac ggaggaccga | 420 |
| gcgaccggaa gggaaggggg cgagggggaaa gcagcggaaa aggggccaac caaaaagccg | 480 |
| gaaacggaac gagaagagga ggcggaagcg gggagcggga aagcaagaac acgcagaacc | 540 |

| | | |
|---|---|---|
| caagcgaagg cagcacaaac aaacgacacg aagcacgaaa gcggggggaca acaggaaga | 600 | |
| acccggagcc acgcagaaac gagaacagga ggcgaacaca gaagccacag cgaaagcgaa | 660 | |
| gaaccaccgg ggagacgccg gcaacgggaa accaaaggaa gacggggggcc cgcacaagcg | 720 | |
| gaggaacagg gaacgagaac gcgaggaacc acccgggggaa cgcaggacag ccgaaagagg | 780 | |
| accagcaaag ccagcgaggg cgcagggcgc agccggccgg agggcggcaa ggccaaacga | 840 | |
| gcgcaaccca cagacaacag gcgcgaggac caaagagacg ccagcgaagc ggaggaaggg | 900 | |
| gggagacgca aacagcacgg cccacaccgg ggcgacacac ggacaagggg ggacaaaggg | 960 | |
| cagcacacag cgaggagcaa cccaaaccccc accagcggac gaagcgcaac ccgaccggaa | 1020 | |
| gcggacgcag aacgcgcaca gccaggcgcg ggaaacgccc gggccgacac accgcccgca | 1080 | |
| agccagggag gggggaccaa agccgaaccg caaggacggc caggaaaacc gagacggggc | 1140 | |
| aagcgaacca aggaacc | 1157 | |

<210> SEQ ID NO 36
<211> LENGTH: 1189
<212> TYPE: RNA
<213> ORGANISM: Eubacterium limosum

<400> SEQUENCE: 36

| | | |
|---|---|---|
| agaggaccgg ccaggacgaa cgcggcggag caacacagca agcgaacgag aagggaggac | 60 | |
| ccggggacaa gaacggaaag ggcgaacggg gagaacgcgg ggaaccgccc aggaaaggaa | 120 | |
| agcccgggaa acgggagaaa gccaaagggc gcaggcaaga cagaaaaccc gggccaagga | 180 | |
| ggacccgcgc ccaagcaggg gagaaacagc ccaccaaggc gacgagggaa ccggcgagag | 240 | |
| ggcgaacggc acacggaacg agacacggcc agacccacgg gaggcagcag gggggaaagcg | 300 | |
| caagggggca acccgacgca gcaaaccgcg gaggaagaag gcggacgaaa gccgagggga | 360 | |
| agaagaagac ggacccaaga ggaagcccgg caacacggcc agcagccgcg gaaacgaggg | 420 | |
| gacaagcggc cggaagacgg gcgaaagggc gcgaggcggc aaagcgagga aaggaccggc | 480 | |
| caaccgggaa ggcaggaaac ggagacgaga ggagaggcaa gggaaccagg agcgggaaag | 540 | |
| cgagaaagga ggaacaccag ggcgaaggcg gcgcggacaa aacgacgcga gggcgaaagc | 600 | |
| gggggagcga acaggaagaa cccggagcca cgccgaaacg agaagcaggg ggggaaacca | 660 | |
| ggccgcagaa cacaaaagca ccgcggggga gacgaccgca aggaaaacca aggaagacg | 720 | |
| gggacccgca caagcagcgg agcagggaac gaagcaacgc gaagaaccac caggcgacac | 780 | |
| ccgacgagcc agagaaggaa gcccgggaac agagagacag ggggcagggc gcagccggcg | 840 | |
| gagaggggaa gcccgcaacg agcgcaaccc cgccaggcca gcaaaggggc accagaggga | 900 | |
| cgccgagaca aacggaggaa gggggggacga cgcaaacaca gccccagacc gggcacacac | 960 | |
| ggcacaaggc gaacagaggg ccgcgaagcc gcgagggaag caaacccaaa acagacccag | 1020 | |
| cggagcaggc gcaaccgccg cagaaggagg cagaacgcg gacagaagcc gcgggaagcg | 1080 | |
| cccgggcgac acaccgcccg cacaccacga gagggcaaca cccgaagccg gagagaaccg | 1140 | |
| caaggaccag cagcgaaggg gggcagaagg gggaagcgaa caaggaacc | 1189 | |

<210> SEQ ID NO 37
<211> LENGTH: 1190
<212> TYPE: RNA
<213> ORGANISM: Parabacteroides distasonis

<400> SEQUENCE: 37

| | | |
|---|---|---|
| agaggaccgg ccaggagaac gcagcgacag gcaacacagc aagcgagggg cagcggggga | 60 | |

```
gcaaacaccg ccggcgaccg gcgcacgggg agaacgcgag caacgccaca gaggggggaaa      120 cccggcgaaa gcggacaaac cgcagaagca gggacccgca gggaaagcaa agacacgcga      180
agaaggcagc gccaaggcag ggcggggaac ggcccaccaa accgacgagg aaggggcgag      240
aggaaggccc ccacaggacg agacacggac caaacccacg ggaggcagca ggaggaaagg      300
caagggcgaa gccgaaccag ccaagcgcgg agggagaagg caggacgaaa cccaaaggga      360
aaaaggcggg acggcccgga gaccagaaaa ggacggcaac ccggccagca gccgcgaaa       420 cggaggaccg agcgaccgga agggaaaggg gcgaggcggc caagcagcgg gaaagcgggc      480
caaccaagaa gccggaaacg gggggcgaga ggaggcaggc ggaagcgggg agcgggaaag      540
caagaacacg cagaaccccg agcgaaggca gccgccaagc caacgacgcg agcacgaaag      600
cgggggacaa acaggaagaa cccggagcca cgcagaaacg agacacagcg gcgaacacga      660
agcggcacag cgaaagcgaa ggaccaccgg ggagacgccg gcaacgggaa accaaaggaa      720
gacgggggcc cgcacaagcg gaggaacagg gaacgagaac gcgaggaacc acccggggaa      780
cgcacggacc gagggggaaac acccagcaaa gccggcgagg gcgcagggcg cagccggccg      840
gagggcggca aggccaaacg agcgcaaccc gccacagaca acaggaggcg aggaccgggg      900
gacgccagcg aagcgcgagg aaggcgggga gacgcaaaca gcacggccca caccggggcg      960
acacacggac aaggcgggac aaagggaggc caccggcgac agggagcgaa ccccaaacca    1020
cgccagcgga cggagcgcaa cccgacccgg aagcggacgc agaacgcgca cagccaggcg    1080
cgggaaacgc ccgggccgac acaccgcccg caagccaggg agccggggga ccgaagccga    1140
accgaaagga cggccaggga aaacgggacg gggcaagcga acaaggaacc                1190

<210> SEQ ID NO 38
<211> LENGTH: 1141
<212> TYPE: RNA
<213> ORGANISM: Bacteroides cellulosilyticus

<400> SEQUENCE: 38
agaggaccgg ccaggagaac gcagcacagg caacacagca agcgagggggc agcagaccag       60 caaagggagg cgaccggcgc acggggagaa cacgaccaac caccggaccg ggaagcccga      120
aagaaagaaa accggaagaa acgagaaggc acgaaaagaa cgaaaccgag gggagcgcca      180
aggggcgggg aacggcccac caagacacga ggaaggggcg agaggaaggc ccccacagga      240
acgagacacg gccaaaccca cgggaggcag caggaggaaa ggcaaggacg agagcgaacc      300
agccaagagc ggaaggagac gcccagggga aaccaaggga aaaaggagcc acggggcgag      360
accaacgaaa aggacggcaa cccggccagc agccgcggaa acggaggacc gagcgaccgg      420
aagggaaagg gagcgaggcg gacaaagcag cggaaaggcg gccaaccgaa aagcaggaac      480
ggcgcgaggc agagaggagg cggaacgggg agcgggaaag cagaacacga agaacccgag      540
cgaaggcagc acggacgaac gacgcgagcc gaaagggggga caaacaggaa gaacccggag      600
ccacacagaa acgagaaacc gcggcgaaac agcaagcggc caagcgaaag caaagaccac      660
cggggagacg ccggcaacgg gaaaccaaag gaagacgggg gcccgcacaa gcggaggaac      720
agggaacgag aacgcgagga accacccggg caaagcacga aaaggaaaca gaagccgcaa      780
ggcagaggaa gggcgcaggg cgcagccggc cggagggcgg caaggccaaa cgagcgcaac      840
ccacagacaa caggcagcga ggaccagaga gacgccgcga agaggaggaa gggggagac       900 gcaaacagca cggcccacgc cggggcacac acggacaagg ggggacagaa ggcagcacac      960
```

```
agcgaggagc aacccaaaag cccccagcgg aggagcgcaa cccgacccag aagcggacgc   1020
agaacgcgca cagccacggc gcgggaaacg cccgggccga cacaccgccc gcaagccaga   1080
aagccggggg accgaagccg aaccgcaagg agcggccagg gaaaacggaa ggggcaagcg   1140
a                                                                 1141
```

<210> SEQ ID NO 39
<211> LENGTH: 1155
<212> TYPE: RNA
<213> ORGANISM: Bacteroides clarus

<400> SEQUENCE: 39

```
gagaacgcag cacaggcaac acagcaagcg aggggcagcg ggggaagcgc caaccgccgg     60
cgaccggcgc acgggagaa cacgaccaac cgccgaaacc cgggaagccc gaaagaaaga    120
aaaccggagg caagcccgca ggaaaacaaa agaacggacg aggggagcgc caaggcaggg    180
cggggaacgg cccaccaaac cgacgaggaa gggggcgagag aaggccccc acaggaacga    240 gacacggcca aacccacggg aggcagcagg aggaaaggca aggacgagag cgaaccagcc    300
aagagcggaa ggagacgccc aggggaaacc aacgggaaaa agagccacgg gggcagaccg    360
agaaaaggac ggcaacccgg ccagcagccg cggaaacgga ggaccgagcg accggaaggg    420
aaagggagcg aggcggggaa agcagggaaa ggcggccaac cgaaaagcag gaacggaccg    480
aggcagcaga gggggcggaa cggggagcgg gaaagcagaa cacgaagaac ccgagcgaag    540
gcagccacgg aggaacgacg cgagccgaaa ggggggacaaa caggaagaac ccggagccac    600
acagaaacga gaaaccgcgg gcgaacaagc agcggccaag cgaaagcaaa gaccaccggg    660
gagacgccgg caacgggaaa ccaaaggaag acgggggccc gcacaagcgg aggaacaggg    720
aacgagaacg cgaggaacca cccgggcgaa gcaacgacgg aaggaaacag cccggacagg    780
gaagggcgca gggcgcagcc ggccggaggg cggcaaggcc aaacgagcgc aacccacgaa    840
gaccacaggc agcggggacc acgagacgcc gcgaagagga ggaagggggg agacgcaaac    900
agcacggccc acgccggggc acacacggac aaggggggac agaaggcagc acacggcgac    960
ggagcaaccc caaaaccccc agcggaggag cgcaacccga cccagaagcg gacgcagaac    1020
gcgcacagcc acggcgcggg aaacgcccgg gccgacacac cgcccgcaag ccagaaagcc    1080
gggggaccga agacgaaccg caaggagcgc cagggaaaac gggaggggca agcgaacaag    1140
gagccgaccg gaagg                                                   1155
```

<210> SEQ ID NO 40
<211> LENGTH: 408
<212> TYPE: RNA
<213> ORGANISM: Anaerostipes caccae

<400> SEQUENCE: 40

```
gaccaagacg agggcggacg gggagaacgc ggggggaaccg cccaacaggg ggaaacagcg     60
gaaacggcgc aaaccgcaaa gcgcacagaa cgcagacagg gaaaagcccg gcagaaggag    120
gcccgcgcga agcgggggag gaacggccac caaggcgacg acagagccgg cgagagagga    180
acggccacag ggacgagaca cggcccaaac ccacgggagg cagcaggggg aaagcacaag    240
ggggaaaccc gagcagcgac gccgcggagg aagaagacgg agaaagccac agcagggaag    300
aaaacagacg gaccgacaag aagccccggc aacacggcca gcagccgcgg aaacgagggg    360
gcaagcgacc ggaaacgggg aaaggggcga ggggcaggaa gcagaagg                 408
```

```
<210> SEQ ID NO 41
<211> LENGTH: 1111
<212> TYPE: RNA
<213> ORGANISM: Bacteroides salyersiae

<400> SEQUENCE: 41
aggagaacgc agcacaggca acacagcaag cgaggggcac aggggagcaa acaccgcggc    60
gaccggcgca cggggagaac acgaccaacc gcccaccggg gaagcccgaa agaaagaaaa   120
cccgaggcaa acagacccccg ggaaaagaac ggagaggagg ggagcgccaa ggcagggcgg   180
ggaacggccc accaaacccg aggaagggc gagaggaagg cccccacagg aacgagacac   240
ggccaaaccc acgggaggca gcaggaggaa aggcaagggc gagagccgaa ccagccaaga   300
gcggaaggag accgcccagg ggaaaccaag ggaaaaaggg gccacggggc agagaccaag   360
aaaaggacgg caacccggcc agcagccgcg gaaacgagg accgagcgac cggaagggaa   420
agggagcgag gggacagaag cagggaaagg cggccaaccg aaaagcagga aacgcggcga   480
gacagagagg gggcggaacg gggagcggga aagcagaaca cgaagaaccc gagcgaaggc   540
agccacggac gcaacgacac gagccgaaag ggggacaaac aggaagaacc cggagccaca   600
cagaaacgag aaaccgcggc gaaacagaag cggccaagcg aaagcaaaga ccaccggggga   660
gacgccggca acgggaaacc aaaggaagac gggggcccgc acaagcggag gaacagggaa   720
cgagaacgcg aggaaccacc cgggcaaagc aaagaaagcc ggaaacggca agccgcaagg   780
caggaagggc gcagggcgca gccggccgga gggcggcaag gccaaacgag cgcaacccac   840
cagacaacag gcagcgagga ccggagagac gccgcgaaga ggaggaaggg gggagacgca   900
aacagcacgg cccacgccgg ggcacacacg gacaaggggg gacagaaggc cgcacacagc   960
gaggagccaa cccaaagccc cccagcggac gaagcgcaac ccgaccggaa gcggacgcag  1020
aacgcgcaca gccacggcgc gggaaacgcc cgggccgaca caccgcccgc aagccaggga  1080
gccggggggac cgaagacgaa ccgcaaggag c                                1111

<210> SEQ ID NO 42
<211> LENGTH: 1146
<212> TYPE: RNA
<213> ORGANISM: Bacteroides fragilis
<220> FEATURE:
<221> NAME/KEY: misc_feature
<222> LOCATION: (205)..(205)
<223> OTHER INFORMATION: n is a, c, g, or u

<400> SEQUENCE: 42
agaggaccgg ccaggagaac gcagcacagg caacacagca agcgaggggc acaggaagaa    60
agcgccgcgg cgaccggcgc acggggagaa cacgaccaac cgcccaccgg ggaagcccga   120
aagaaagaaa acccgaagca aagaccgcag gcaaaaagga ccggaaagga ggggagcgcc   180
aagggggggag gaacggccac caagnccgag gaaggggcga gaggaaggcc cccacaggaa   240
cgagacacgg ccaaacccac gggaggcagc aggaggaaag gcaagggcgc agccgaacca   300
gccaagagcg gaaggagaag gccagggcga aaccaaaaga aaaggcaga gaacggagaa   360
agaaaaggac ggcaacccgg ccagcagccg cggaaacgga ggaccgagcg accggaaggg   420
aaagggagcg aggggacgga agcagggaaa ggcggccaac cgaaaagcag gaacgcagcg   480
agacagagag ggggcggaac ggggagcggg aaagcagaac acgaagaacc cgagcgaagg   540
cagccacgga cgcaacgaca cgagccgaaa ggggacaaac aggaagaac ccggagccac   600
acagaaacga gaaccgcgg cgaaacagaa gcggccaagc gaaagcaaag accaccgggg   660
```

| | |
|---|---|
| agacgccggc aacgggaaac caaaggaaga cggggggcccg cacaagcgga ggaacaggga | 720 |
| acgagaacgc gaggaaccac ccgggcaaag cagggaagag ggaaacagca ggagcaacac | 780 |
| cgcggaaggg cgcagggcgc agccggccgg agggcggcaa ggccaaacga gcgcaaccca | 840 |
| cagacaacag gagcgaggac cagagagacg ccgcgaagag gaggaagggg ggagacgcaa | 900 |
| acagcacggc ccacgccggg gcacacacgg acaagggggg acagaaggca gcagcgggga | 960 |
| ccgagcaacc caaaagcccc cagcggacga agcgcaaccc gaccggaagc ggacgcagaa | 1020 |
| cgcgcacagc cacggcgcgg gaaacgcccg ggccgacaca ccgcccgcaa gccagggagc | 1080 |
| cgggggaccg aagacgaacc gcaaggacgc cagggaaaac gggacggggc aagcgaacaa | 1140 |
| ggaacc | 1146 |

<210> SEQ ID NO 43
<211> LENGTH: 1150
<212> TYPE: RNA
<213> ORGANISM: Bacteroides uniformis

<400> SEQUENCE: 43

| | |
|---|---|
| agaggaccgg ccaggagaac gcagcacagg caacacagca agcgaggggc acaggaagaa | 60 |
| agcgccgcgg cgaccggcgc acggggagaa cacgaccaac cgccgagacc ggggaagccc | 120 |
| gaaagaaaga aaacccgagg aacgaaaggc accagcaaaa gaacggcaga ggggagcgcc | 180 |
| aaggggggcgc ggaacggccc accaagccac gaggaagggg cgagaggaag gcccccacag | 240 |
| gaacgagaca cggccaaacc cacgggaggc agcaggagga aaggcaagga cgagagcgaa | 300 |
| ccagccaaga gcgaaggag acgcccaggg gaaaccaacg ggaaaaagag gcacgggccg | 360 |
| agaccgagaa aaggacggca acccggccag cagccgcgga aacggaggac cgagcgaccg | 420 |
| gaagggaaag ggagcgaggc ggagcaagca gggaaaggcg gccaaccgaa aagcaggaac | 480 |
| ggggcgagac agagaggcag gcggaacggg gagcgggaaa gcagaacacg aagaacccga | 540 |
| gcgaaggcag cgcggacgaa cgacgcgagc cgaaaggggg acaaacagga agaacccgga | 600 |
| gccacacaga aacgagaaac cgcggcgaaa cagaagcggc caagcgaaag cgaagaccac | 660 |
| cggggagacg ccggcaacgg gaaaccaaag gaagacgggg gcccgcacaa gcggaggaac | 720 |
| agggaacgag aacgcgagga accacccggg caaagcaaag aagcggaaac agacagccgc | 780 |
| aaggcaggaa gggcgcaggg cgcagccggc cggagggcgg caaggccaaa cgagcgcaac | 840 |
| ccacgaagac cacaggagcg gggaccgcga gacgccgcga agaggaggaa gggggggagac | 900 |
| gcaaacagca cggcccacgc cggggcacac acggacaagg ggggacagaa ggcagcacac | 960 |
| gggacggagc aacccaaaac ccccagcgga ggagcgcaac ccgacccaga agcggacgca | 1020 |
| gaacgcgcac agccacggcg cgggaaacgc ccggccgac acaccgcccg caagccagaa | 1080 |
| agccgggga ccgaaggcga accgcgagga gcgcccaggg aaaacgggag gggcaagcga | 1140 |
| acaaggaacc | 1150 |

<210> SEQ ID NO 44
<211> LENGTH: 1154
<212> TYPE: RNA
<213> ORGANISM: Bacteroides eggerthii

<400> SEQUENCE: 44

| | |
|---|---|
| agaggaccgg ccaggagaac gcagcacagg caacacagca agcgaggggc agcagagaag | 60 |
| cgccaacgag gcgaccggcg cacggggaga acacgaccaa ccgccgaaac cggggaagcc | 120 |
| cgaaagaaag aaaacccgaa gaagccgcag gcacaaaaga acggacgagg ggagcgccaa | 180 |

| | |
|---|---|
| gaagggcggg gaacggccca ccaagcaacg aggaaggggc gagaggaagg cccccacagg | 240 |
| aacgagacac ggccaaaccc acgggaggca gcaggaggaa aggcaaggac gagagcgaac | 300 |
| cagccaagag cggaaggaga cgcccagggg aaaccaacgg gaaaaaggga gagcaacccg | 360 |
| agaccgagaa aaggacggca acccggccag cagccgcgga acggaggac cgagcgaccg | 420 |
| gaagggaaag ggagcgaggc ggggcaagca gggaaaggcg gccaaccgaa aagcaggaac | 480 |
| gggcgccgag gcagcaagga ggcggaacgg ggagcgggaa agcagaacac gaagaacccg | 540 |
| agcgaaggca gcacggacga acgacgcgag ccgaaagggg gacaaacagg aagaacccgg | 600 |
| agccacacag aaacgagaaa ccgcgggcga acacagcagc ggccaagcga aagcaaagac | 660 |
| caccggggag acgccggcaa cgggaaacca aggaagacg ggggcccgca caagcggagg | 720 |
| aacagggaac gagaacgcga ggaaccaccc gggcaaagca gcggaagagg gaaacaacag | 780 |
| cccgggccgc ggaagggcgc agggcgcagc cggccggagg gcggcaaggc caaacgagcg | 840 |
| caacccacaa gacacaggca gcgaggacca ggagacgccg cgaagaggag gaagggggga | 900 |
| gacgcaaaca gcacggccca cgccggggca cacacggaca agggggggaca gaaggcagca | 960 |
| ccggcgacag gagcaacccg aaaaccccca gcggaggagc gcaacccgac ccagaagcgg | 1020 |
| acgcagaacg cgcacagcca cggcgcggga aacgcccggg ccgacacacc gcccgcaagc | 1080 |
| cagaaagccg ggggaccgaa gacgaaccgc aaggagcgcc agggaaaacg ggaggggcaa | 1140 |
| gcgaacaagg aacc | 1154 |

<210> SEQ ID NO 45
<211> LENGTH: 1162
<212> TYPE: RNA
<213> ORGANISM: Clostridium sp.

<400> SEQUENCE: 45

| | |
|---|---|
| acagcaagcg gacgcaagcc ggcagagggc gaacggggag aagacaaagc aaccgcccccg | 60 |
| gaggggaaa cgcggaaacg gcagcaagac cgcaaggcaa gaggacgcag cgacagaaaa | 120 |
| cccacgggaa gcacaggag ggcagacgca agccagcggg aggaacggcc accagggcga | 180 |
| cgagcgagcc ggccgagagg gggacggcca cacgggacga gacacggccc agacccacgg | 240 |
| gaggcagcag agggaacggc aagggcgaaa gccgaccgag caacgccgcg gaaggaagaa | 300 |
| gcacggagaa accgagaagg aagaacggca gaggagggaa gccaggcgga cggaccagag | 360 |
| gaagccacgg caacacggcc agcagccgcg gaaacgaggg gcgagcgacc ggaacagggc | 420 |
| gaaagaggga gcaggcggca ggcaggcgcg ggaaagaccg gagcaaaccg gaagccggga | 480 |
| aaccgcacag cagagagcac agaggacgcg gaaccaggag cgggaaagcg agaaaggagg | 540 |
| aacaccaggg cgaaggcggc ggcggggggca gcgacgccag cccgaaagcg ggggagcaaa | 600 |
| aggaagaacc cagagccacg ccgaaacgag aggcaagggg gggcagaccc agcggagaa | 660 |
| cgcaaaagca cccgccgaga gacgcgcaag aagaaaccaa aggaagacgg gggcccgcac | 720 |
| aagcggggag cagggaacga agcaacgcga agaaccacca ggcgacagga gaaaaggccc | 780 |
| ggagacaggg agaagaaacc acacagggggg cagggcgcag ccggcggaga ggggaagccc | 840 |
| gcaacgagcg caacccccggc caggccagca aggggggacc ggcgagacgc ccgcaaggag | 900 |
| gaggaaggcg gggagacgca aacacagccc cagaccgggc acacacggca caaggacgga | 960 |
| cagagggagg cgaagccgcg aggggagcga aacccagaaa cccgcacagc ggacgcagcg | 1020 |
| caaccgacgc acgaagcgga acgcagaacg cgaacagcag cgcgggaaac gccgggccga | 1080 |

```
cacaccgccc gcacaccaga gagggaacac ccgaagccgg ggcccaaccg caaggaggga    1140
gcgcaagggg gacgagaggg gg                                             1162

<210> SEQ ID NO 46
<211> LENGTH: 1153
<212> TYPE: RNA
<213> ORGANISM: Parabacteroides goldsteinii

<400> SEQUENCE: 46
ggccaggaga acgcagcgac aggcaacaca gcaagcgagg ggcagcacga gagcaaacag      60
gggcgaccgg cgcacgggga gaacgcgagc aaccaccaca gagggaaaaa cccggcgaaa     120
gcggacaaac cgcaaaaaca ggggccacag gaaaagaaag aaacgcgaag agggcagcgc     180
caagaagggg aggaacggcc accaagccac gaggaagggg cgagaggaag gcccccacac     240
ggacgagaca cggaccagac ccacggggagg cagcaggagg aaaggcaagg gcgagagccg     300
aaccagccaa gcgcggaagg agaaggacag ggaaaccaag ggaaaaagga ggaacggccg     360
agaccaagaa aagcacggca acccggccag cagccgcgga acggaggag cgagcgaccg      420 gaagggaaag gggcgagggg aaaagcagcg ggaaagggc aaccaaaaa gccggaaacg       480 ggacgagaag aggaggcgga agcggggagc gggaaagcaa gaacacgcag aacccgagcg     540
aaggcagcac aaacaaacga cacgaagcac gaaagcgggg gacaaacagg aagaacccgg     600
agccacgcag aaacgagaac agcggcgaac acagaagcgg cacagcgaaa gcgaagaacc     660
accggggaga cgccggcaac gggaaaccaa aggaagacgg gggcccgcac aagcggagga     720
acagggaacg agaacgcgag gaaccacccg gggaacgcaa gacagccgga aacagagcca     780
gaaagcaagc gagggcgcag ggcgcagccg gccggagggc ggcaaggcca acgagcgca     840 acccacacag caacaggca gcgaggacca ggagacgcca gcgaagcgga ggaagggggg     900
agacgcaaac agcacggccc acaccggggc gacacacgga caagggggga caaagggcag    960 caccggggagc ggagcaaccc aaaccccacca gcggacgaag cgcaacccga ccggaagcgg    1020
acgcagaacg cgcacagcca ggcgcgggaa acgcccgggc cgacacaccg cccgcaagcc    1080
agggaggggg gaccaaagcc gaaccgcaag gacggccagg gaaaaccgag acggggcaag    1140
cgaacaagga acc                                                       1153

<210> SEQ ID NO 47
<211> LENGTH: 1125
<212> TYPE: RNA
<213> ORGANISM: Bacteroides thetaiotaomicron

<400> SEQUENCE: 47
caggagaacg cagcacaggc aacacagcaa gcgaggggca gcacaggcgc aaacggagag      60
gcgaccggcg cacgggaga acacgaccaa ccgccgaaac cggggaagcc cgaaagaaag     120
aaaacccgag gaaacagacc gcaggcgaaa agaacggacg aggggagcgc caaggcaggg     180
gaggaacggc caccaaaccc gaggaagggg cgagaggaag gcccccacag gaacgagaca     240
cggccaaacc cacggggaggc agcaggagga aaggcaaggg cgcaggccga accagccaag     300
agcgaaggga gacgcccagg ggaaaccaag ggaaaaagcc acggggaaga gaccaagaaa     360
aggacggcaa cccggccagc agccgcgaaa acggaggacc gagcgaccgg aagggaaagg     420
gagcgagggg acagaagcag ggaaaggcgc ccaaccgaaa agcaggaacg gcgcgagaca    480 gagaggggc ggaacgggga gcgggaaagc agaacacgaa gaacccgagc gaaggcagcc     540
acggacgcaa cgacacgagc cgaaaggggg acaaacagga agaacccgga gccacacaga    600
```

```
aacgagaaac cgcggcgaaa cagaagcggc caagcgaaag caaagaccac cggggagacg      660
ccggcaacgg gaaaccaaag gaagacgggg gcccgcacaa gcggaggaac agggaacgag      720
aacgcgagga accacccggg caaagcagaa aaggaaacag aagccgaagg caaaggaagg      780
gcgcagggcg cagccggccg gagggcggca aggccaaacg agcgcaaccc acagacaaca      840
ggcagcgagg accagagaga cgccgcgaag aggaggaagg ggggagacgc aaacagcacg      900
gcccacgccg gggcacacac ggacaagggg ggacagaagg cagcaccggg acaggagcaa      960
cccaaaagcc cccagcggac gaagcgcaac ccgaccggaa gcggacgcag aacgcgcaca     1020
gccaggcgcg ggaaacgccc gggccgacac accgcccgca agccagaaag ccgggggacc     1080
gaagacgaac cgcaaggagc gccagggaaa acggaagggg caagc                     1125
```

<210> SEQ ID NO 48
<211> LENGTH: 420
<212> TYPE: RNA
<213> ORGANISM: Lachnospiraceae bacterium

<400> SEQUENCE: 48

```
gacgagcggc ggacggggag aacgcgggga accgcccaac aggggggaaac agggaaacgg       60 cgcaaaccgc aaagcgcaca gaccgcagga ccgggaaaaa cccggggaga gaggacccgc      120
gcgaagcagg gggggaacgg ccaccaaggc gacgacagag ccgaccgaga ggggaccggc      180
cacagggacg agacacggcc caaacccacg ggaggcagca gggggaaagc acaaggggga      240
aacccgagca gcgacgccgc ggagcgagaa gacggagaaa gccacagcag ggaagaaaag      300
acggaccgac aagaagcccc ggcaacacgg ccagcagccg cggaaacgag ggggcaagcg      360
accggaacgg ggaaagggag cgagacggca ggcaagccag aggaaagccc ggggccaacc      420
```

<210> SEQ ID NO 49
<211> LENGTH: 1203
<212> TYPE: RNA
<213> ORGANISM: Clostridium hathewayi
<220> FEATURE:
<221> NAME/KEY: misc_feature
<222> LOCATION: (150)..(150)
<223> OTHER INFORMATION: n is a, c, g, or u
<220> FEATURE:
<221> NAME/KEY: misc_feature
<222> LOCATION: (166)..(166)
<223> OTHER INFORMATION: n is a, c, g, or u
<220> FEATURE:
<221> NAME/KEY: misc_feature
<222> LOCATION: (193)..(193)
<223> OTHER INFORMATION: n is a, c, g, or u
<220> FEATURE:
<221> NAME/KEY: misc_feature
<222> LOCATION: (791)..(791)
<223> OTHER INFORMATION: n is a, c, g, or u

<400> SEQUENCE: 49

```
ccaggagaac gcggcggcgg caacacagca agcgagcgaa gcgcaagaa gcggaggaga        60 aagacagcgg cggacgggga gaacgcgggg aaccgccaca cggggggaaac agagaaagac     120 gcaaaccgca aagcgcacag gccgcaggn cggggaaaaa cccggnggga agaggacccg      180
cgcgaaggag ggnggggaac ggcccaccaa gccgacgaca gagccgaccg agaggggacc     240
ggccacaggg acgagacacg gcccaaaccc acgggaggca gcgggggaa aggacaaggg      300 cgaaagccga ccagcgacgc cgcggaggaa gaagacggag aaagccacag cagggaagaa     360
aagacggacc gacaagaagc cccggcaaca cggccagcag ccgcggaaac gagggggcaa     420
```

```
gcgaccggaa cggggaaagg gagcgagacg gagcaagcga aggaaagccc ggggccaacc      480
ccggacgcgg aaacgagacg aggcaggaga ggaagggaac caggagcggg aaagcgagaa      540
aggaggaaca ccagggcgaa ggcggcacgg acgaacgacg gaggccgaaa gcgggggagc      600
aaacaggaag aacccggagc cacgccgaaa cgagaaacag gcgggggggc aaagccccgg      660
gccgccgcaa acgcaaaaga ccaccgggga gacgcgcaag aagaaaccaa aggaagacgg      720
ggacccgcac aagcggggag cagggaacga agcaacgcga agaaccacca agcgacaccc      780
acgaaaacac naaccggacc cccggagcag ggagacaggg ggcagggcgc agccggcgga      840
gaggggaagc ccgcaacgag cgcaacccac cagagccagc gagagagcgg gcaccggggga     900 gacgccaggg aaaccggagg aagggggagg acgcaaacac agccccagag ggcacacacg      960
gcacaaggcg aaacaaaggg aggcaaagga gcgacggagc aaaccccaaa aaaacgccag     1020
cggagcaggc gcaaccgccg cagaagcgga acgcagaacg cgaacagaag cgcgggaaac     1080
gcccgggcga cacaccgccc gcacaccagg gagggaacgc ccgaagcagg acccaaccga     1140
aaggagggag cgccgaaggc gggacgaaac ggggggaagcg aacaaggagc cgacggaagg     1200
gcg                                                                   1203

<210> SEQ ID NO 50
<211> LENGTH: 1177
<212> TYPE: RNA
<213> ORGANISM: Clostridium lavalense
<220> FEATURE:
<221> NAME/KEY: misc_feature
<222> LOCATION: (887)..(887)
<223> OTHER INFORMATION: n is a, c, g, or u

<400> SEQUENCE: 50
gccaggagaa cgcggcggcg gccaacacag caagcgaacg aagcayagag aagcggagga       60
cgagagacga gggcggacgg ggagaacacg ggaaaccgcc cacacggggg acaacagaga      120
aagacgcaaa ccgcaaagcg cacagaccgc aggacaggga aaaacccggg gggagaggac      180
cgcgcgaagc cagggcgggg aacggcccac caaagcgacg acagagccga ccgagagggg      240
accggccaca gggacgagac acggcccaaa cccacgggag gcagcagggg gaaagcacaa      300
gggcgaaagc cgagcagcga cgccgcggag gaagaagacg gagaaagcca cagcagggaa      360
gaaagacgga ccgacaagaa gccccggcaa cacggccagc agccgcggaa acgagggggc      420
aagcgaccgg aacggggaaa gggagcgaga cggcaggcaa gcgaaggaaa cccagggcc      480 aacccgggac gcggaaacgc aagcagaggc aggagaggaa gggaaccagg agcgggaaag     540
cgagaaagga ggaacaccag ggcgaaggcg gcacggacga acgacggagg ccgaaagcgg      600
gggagcaaac aggaagaacc cggagccacg ccgaaacgag aggcaggggg ggggcaaagc      660
cccgggccgc gcaaacgcaa aagcacccac cggggagacg cgcaagaaga accaaagga      720 agacggggac ccgcacaagc ggggagcagg gaacgaagca acgcgaagaa ccaccaagcg      780
acacccgacc ggcggaacgg cgcccccggg acaagagaga caggggggcag ggcgcagccg      840 gcggagaggg gaagcccgca acgagcgcaa cccaccagag ccagcanrag agggcaccag      900
ggagacgcca gggacaaccg gaggaagggg ggagacgcaa acacagcccc agagggcaca      960
cacggcacaa ggcgaaacaa agggaagcga cccgcgaagg gagcaaacca aaaaaacgcc     1020
cagcggacga gcgcaacccg acacacgaag cggaacgcag aacgcgaaca gaagcgcggg     1080
aaacgcccgg gcgacacacc gcccgcacac caggagcag caacgcccga agcaggaccc     1140
aaccgcaaga gagggagcgc cgaaggcggg gcaggaa                              1177
```

<210> SEQ ID NO 51
<211> LENGTH: 1204
<212> TYPE: RNA
<213> ORGANISM: Ruminococcus sp

<400> SEQUENCE: 51

```
gaacgcggcg gcggccaaca cagcaagcga gcgaagcgcg cagaaccgga ggaagaggac      60
aggacgagcg gcgacgggg agaacgcggg gcaaccgccc aacaggggga aacagagaaa     120
gacgcaaacc gcaaagcgca caggaccgca gggagggaaa aacccgggga gagaggaccc     180
gcgcgaagga ggggggggaaa ggccaccaag ccgacgacag agccgaccga gaggggaccg     240
gccacaggga cgagacacgg cccaaaccca cgggaggcag caggggaaa gcacaagggg     300
gaaacccgag cagcgacgcc gcggaaggaa gaagacggga aaaccacagc agggaagaag     360
agacggaccg agaagaagca ccggcaaaac ggccagcagc cgcggaaacg agggcaagcg     420
accggaacgg ggaaagggag cgagacgaaa ggcaagcgga ggaaaaccca gggccaaccc     480
gggacgcgga acgcagacg gaggccggag aggaagcgga accaggagcg ggaaagcgag     540
aaaggaggaa caccagggcg aaggcggcac ggacgggacg acggaggccg aaagcggggg     600
agcaaacagg aagaacccgg agccacgccg aaacgagaca cagggcgggg caaagcacac     660
gggccgcagc aaacgcaaaa gagccaccgg ggagacgcgc aagaagaaac caaaggaaga     720
cggggacccg cacaagcggg gagcagggaa cgaagcaacg cgaagaacca ccggcgacac     780
cggagacggg cgagaagcgc cgccccgggg caccgagaca ggggcaggg cgcagccggc     840
ggagagggga agcccgcaac gagcgcaacc caccagagcc agcaaaaggg ggcaccggag     900
agacgccagg gagaaccgga ggaagggggg agacgcaaac acagcccag gccagggcac     960
acacggcaca aggcgaaaca aagggaagcg agaggggacc ggagcgaacc caaaaaacg    1020
ccagcggaga gcgcaaccga cacagaagcg gaacgcagaa cgcggacagc agccgcggga    1080
aacgcccggg cgacacaccg cccgcacacc agggagcaga acgcccgaag ccaggaccca    1140
accagaggag ggagcgcgaa ggcgggacgg aaacggggga agcgaacaag gagccgacgg    1200
aagg                                                                1204
```

<210> SEQ ID NO 52
<211> LENGTH: 1170
<212> TYPE: RNA
<213> ORGANISM: Clostridium innocuum

<400> SEQUENCE: 52

```
gaccggccag gagaacgcgg cggcagccaa acagcaagcg aacgaagcga ggaagcgccc      60
aaagagacag ggcgaacggg gagaacacga ggaaccgccc aggccgggaa acgcggaaac     120
ggagcaaaac cggaaggaac agagcgcagc cagaaaaagc gcccacaagg cggaacagga     180
ggaccgcggc gcaagcaggg gaggaacggc ccaccaaggc gagagcgagc cggccgagag     240
ggaaacggcc acagggacga gacacggccc aaacccacgg gaggcagcag agggaacgca     300
aggggggaaac ccgaacgagc aagccgcgga ggaagaaggc cggacgaaag ccggaaggaa     360
gaacggccaa gaggaaagca gggaggacgg agcaccagaa agccacggca acacggccag     420
cagccgcgga aacgagggc aagcgaccgg aacagggcga aggggcgag gggcgacaag     480
cgagaaaagg caaggccaac cagaagcagg aaacggagcg gaggcagaag agggcgagga     540
accaggagcg gaaaagcgag aaaggaggaa caccagggcg aaggcggcgc cggcgaacga     600
```

```
cacgaggcac gaaagcgggg gagcaaaagg aagaacccag agccacgccg aaacgagaga    660
acaaggggag gaacaggcgc agaacgcaaa agcccgccgg ggagagcacg caagggaaac    720
caaaggaaga cggggggcccg cacaagcggg gagagggaac gaagcaacgc gaagaaccac   780
caggccgaca ggaaacaaaa cccagagaag ggggaaaagg acacacaggg ggcagggcgc    840
agccggcgga gaggggaagc ccgcaacgag cgcaacccgc gcagaccagc acaagggga    900 ccagcgagac gccgggacaa accggaggaa ggggggagac gcaaacacag ccccaggccg    960
ggcacacacg acacaaggcg accacaaaga gcagcgacac aggaggaagc gaaccaaaag   1020
gcgccagcgg agaagcgcaa ccgaccagaa gcggaacgca gaacgcagac agcagcgcgg   1080
gaaacgccgg gccgacacac cgcccgcaaa ccagggagca gaaacccgaa gccggggcaa   1140
accgaaggag gagccgcgaa ggaggaccga                                    1170
```

<210> SEQ ID NO 53
<211> LENGTH: 8
<212> TYPE: PRT
<213> ORGANISM: Artificial Sequence
<220> FEATURE:
<223> OTHER INFORMATION: Synthetic polynucleotide

<400> SEQUENCE: 53

Lys Ser Pro Trp Phe Thr Thr Leu
1               5

<210> SEQ ID NO 54
<211> LENGTH: 1161
<212> TYPE: RNA
<213> ORGANISM: Artificial Sequence
<220> FEATURE:
<223> OTHER INFORMATION: Synthetic polynucleotide

<400> SEQUENCE: 54

```
cgaagaggac cggccaggag aacgcgacag aagcaacaca gcaagcacga cccggggaag     60
gggcggacgg ggagaacgcg aaagaacgcc acagacggga caacaggaaa cgaagcaaac    120
cggaaagagg gcgcagacga agaaagcaag cgcggagaga gcgcgcccaa gaggggagga    180
acggccacca agacgagagg gagccggccg agaggggaac ggccacaagg ggacgagaca    240
cggcccaccc acgggaggca gcaggggaa aggacaagga ccaaaagcga ccagcaacgg    300
gcacgaagaa gcgaagaaa ggccagggga agaagcagga cggaccaaca gaagaagcga    360
cggcaaaacg gccagcagcc gcggaaacga gcgcaagcga ccggaagggc gaaagcgcgc    420
aggcggcaga agcgaggaaa agcggggcca acccccgagcg ggaaacgcaa acagagacgg    480
agaggaggcg gaacacaagg agagggaaac gagaagagga agccgagggg aagccagcca    540
cggacagaac gacgcaaagc gcgaaagcgg ggagcaaaca ggaagaaccc ggagccacgc    600
cgaaacgaga acaggggggg gcgaacccag cgcccaagca acgcgaaaga accgccgggg    660
agacgacgca agagaaacca aggaagacg gggacccgca caagcgggga gcagggaacg    720
acgcaacgcg aggaaccacc agcggacacc caagaagaac agagagcggc cccggaggaa    780
cgggacaggg ggcaggcgcg cagccggcgg agagggaaag cccgcaacga gcgcaacccc    840
cgagaccaca aaggggggacc agcgagacgc cgcgagagca ggaggaaggg gggagacgca    900
agcacagccc caacgcgggc acacacggca aagggagac agagagcgca aaccgcgagg    960
gaagcaacca aaaacacagc ggagaccgca accgagacag aagggaacgc agaacgcaaa   1020
cagcaggcgg gaaacgccgg gcgacacacc gcccgcacac cacgagaggg gcaccgaaga   1080
```

```
acaggccaac cgaaggaggg agccgagggg gaagcgaggg ggaagcgaac aaggaccgac    1140
gggaacggcg gaggacaccc c                                             1161

<210> SEQ ID NO 55
<211> LENGTH: 1190
<212> TYPE: RNA
<213> ORGANISM: Artificial Sequence
<220> FEATURE:
<223> OTHER INFORMATION: Synthetic polynucleotide

<400> SEQUENCE: 55
cgaagaggac cggccaggag aacgcagcga caggcaacac agcaagcgag gggcacagga      60
agagcaaaca gaggcgaccg gcgcacgggg agaacgcgag caacaccaca gagggggaag     120
cccggcgaaa gcggaaaacc caaaaacagg ggccgcaggg acagaaagac acgcgaagaa     180
ggcagcgcca aggcagggcg gggaacggcc caccaaaccg acgaggaagg ggcgagagga     240
aggcccccac aggacgagac acggaccaaa cccacgggag gcagcaggag gaaaggcaag     300
gccgagaggc gaaccagcca agcgcggaag gagaaggaca gggaaaccaa ggggaaaaag     360
ggggacggcc agagacccag aaaagcacgg caacccggcc agcagccgcg gaaacggagg     420
agcgagcgac cggaagggaa aggggcgagg ggaaaagcag cgggaaaggg gccaaccaaa     480
aagccggaaa cgggacgagg ggaggaggcg gaagcgggga gcgggaaagc aagaacacgc     540
agaacccaag cgaaggcagc acaaaccaaa cgacacgaag cacgaaagcg gggacaaaca     600
ggaagaaccc ggagccacgc agaaacgaga acaggaggcg aacacagaag ccacagcgaa     660
agcgaagaac caccggggag acgccggcaa cgggaaacca aggaagacg ggggcccgca      720 caagcggagg aacagggaac gagaacgcga ggaaccaccc ggggaacgag cagaccgacc     780
gaaagaggca gcaaagcgaa cgagggcgca gggcgcagcc ggccggaggg cggcaaggcc     840
aaacgagcgc aacccacaca gacaacagga agcgaggacc gggagacgcc agcgaagcgg     900
aggaaggggg gagacgcaaa cagcacggcc cacaccgggg cgacacacgg acaaggcagg     960
acaaagggca gcaccggcga caggagcaac caaaccagcc agcggacgga gcgcaaccga    1020
cccggaagcg gacgcagaac gcgcacagcc aggcgcggga aacgcccggg ccgacacacc    1080
gcccgcaagc cagggagccg ggggaccgaa gccgaaccgc aaggacggcc agggaaaacg    1140
ggacggggca agcgaacaag gagccgaccg gaagggcggc ggaacacccc                1190

<210> SEQ ID NO 56
<211> LENGTH: 1061
<212> TYPE: RNA
<213> ORGANISM: Artificial Sequence
<220> FEATURE:
<223> OTHER INFORMATION: Synthetic polynucleotide

<400> SEQUENCE: 56
aaaaagaaag gaaaggaggg gagcgcccaa gcgggcgggg aacggcccac caaggcgacg      60
agggaggggc gagaggaagg cccccacagg aacgagacac ggccaaaccc acggaggca     120 gcaggaggaa aggcaagggc gcgagccgaa ccagccaaga gcgggaggac gacggcccac     180
ggggaaaccc aaagggaaa agggccagag gccagcagga ccagaaaagc acggcaaccg     240
gccagcagcc gcggaaacgg aagagcgagc gaccggaagg gaaagggagc gaggcgggca     300
gcaagcagcg gcaaaggcgc ggccaaccgc gccgccggaa acgcagccga gagcacagg     360 gacaggaacg gggagcggga aagcagaaca cgaggaaccc gacgcgcagg cagaccgggg     420
caacgacgcg aggccgaagg gcgggacaaa caggaagaac ccggagccgc acagaaacga     480
```

```
gaagcccgcg cggcgacaag gcggcggcca agcgaaagcg aagcaccacc ggggagacgc      540
cggcaacggg aaaccaaagg aagacggggg cccgcacaag cggaggaaca gggaacgaga      600
acgcgaggaa ccacccgggc gaacgcaggg cagggccgga gacggccccc cgggacccgc      660
gaagggcgca gggcgcagcc ggccggaggg cggcaaggcc aaacgagcgc aaccccccc      720 ccaggccacc gggaagccgg gcacggggac acgccaccgc aagggcgagg aaggggggag      780
acgcaaacag cacggcccac gccggggcga cacacggaca agggggggaca gagggccgcg      840 cccgggacgg ggccaaccca aaaccccccca gcggacggag cgcaacccga cccacgaagc      900
ggacgcagaa cgcgcacagc caggcgcggg aaacgcccgg gccgcacacac cgcccgcaag      960 ccagaaagcc gggggggccga agccggaccg cgagggcggc cagggaaaac cgggaggggc     1020
aagcgaacaa ggagccgacc ggaagggcgg cggaacaccc c                         1061

<210> SEQ ID NO 57
<211> LENGTH: 1219
<212> TYPE: RNA
<213> ORGANISM: Artificial Sequence
<220> FEATURE:
<223> OTHER INFORMATION: Synthetic polynucleotide

<400> SEQUENCE: 57
cgaagaggac cggccaggag aacgcagcga caggcaacac agcaagcgag gggcagcaca       60
ggagcaaacc gggggcgacc ggcgcacggg gagaacgcga gcaacgccac agaggggaa      120 acccggcgaa agcggacaaa ccgcagaagc agggggcccg caggggaagc aaagacacgc      180
gaagaaggca gcgccaaggc agggcgggga acggcccacc aaaccgacga ggaaggggcg      240
agaggaaggc ccccacagga cgagacacgg accaaaccca cggggaggcag caggaggaaa      300 ggcaaggccg agaggcgaac cagccaagcg cggagggaga aggcaggacg aaacccaaag      360
ggaaaaaggc gggacggccc ggagaccaga aaaggacggc aacccggcca gcagccgcgg      420
aaacggagga ccgagcgacc ggaagggaaa ggggcgaggc ggccaagcag cgggaaagcg      480
ggccaaccaa gaagccggaa acgggggcg agaggaggca ggcggaagcg gggagcggga      540
aagcaagaac acgcagaacc ccgagcgaag gcagccgcca agccaacgac gcgagcacga      600
aagcggggga caaacaggaa gaacccggag ccacgcagaa acgagacaca gcggcgaaca      660
cgaagcggca cagcgaaagc gaaggaccac cggggagacg ccggcaacgg gaaaccaaag      720
gaagacgggg gcccgcacaa gcggaggaac agggaacgag aacgcgagga accacccggg      780
gaacgcacgg accgagggga aacacccagc aaagccggcg agggcgcagg gcgcagccgg      840
ccggagggcg gcaaggccaa acgagcgcaa cccgccacag acaacaggaa agcgaggacc      900
gggggacgcc agcgaagcgc gaggaaggcg gggagacgca aacagcacgg cccacaccgg      960
ggcgacacac ggacaaggcg ggacaaaggg aagccaccgg cgacagggag cgaacccccaa     1020 accacgccag cggacggagc gcaacccgac ccggaagcgg acgcagaacg cgcacagcca     1080
ggcgcgggaa acgcccgggc cgacacaccg cccgcaagcc agggagccgg gggaccgaag     1140
ccgaaccgcg aggacggcca gggaaaacgg gacggggcaa gcgaacaagg agccgaccgg     1200
aagggcggcg gaacacccc                                                 1219

<210> SEQ ID NO 58
<211> LENGTH: 1205
<212> TYPE: RNA
<213> ORGANISM: Artificial Sequence
<220> FEATURE:
```

<223> OTHER INFORMATION: Synthetic polynucleotide

<400> SEQUENCE: 58

| | | | | | | |
|---|---|---|---|---|---|---|
| aggagaggac | cggccaggag | aacgcagcgg | caggccaaca | cagcaagcga | ggggcagcgg | 60 |
| gagaagcgcc | aggccggcga | ccggcgcacg | gggcgaacgc | gagcaaccac | ccaaacaggg | 120 |
| ggaaacacga | gaaacggaca | aacccaaaca | caagaggggc | acccgggaaa | acccggggag | 180 |
| gagggcagcg | gaagcagggg | aggaacggcc | accaaggcga | cgaacaaggg | ggacgagagg | 240 |
| aaccccccac | aggacgagac | acggaccaaa | cccacgggag | gcagcaggag | gaaaggcaag | 300 |
| gacgcaagcg | aaccagccag | ccgcggcagg | agacggccag | aggaaacgcg | acgagggaaa | 360 |
| cccggaacgg | accggcgaaa | gacgacgaaa | aggacggcaa | cccggccagc | agccgcggaa | 420 |
| acggaggaca | agcgaccgga | agggaaaggg | gcgaggcggg | aaagagaggg | aaaaccgggc | 480 |
| aacaccggaa | cgcccaaacg | gagcagagag | aggcggaggc | ggaagaggga | gcgggaaagc | 540 |
| agagacaaca | gaacaccgag | cgaaggcagc | accaaacaac | gacggaggca | cgaaagcggg | 600 |
| ggagcaaaca | ggaagaaccc | ggagccacgc | agaaacgaga | accgcgcgg | cgaacacagc | 660 |
| ggggcaagcg | aaagcgaaag | accaccgggg | agacgcgcaa | gaagaaacca | aggaagacg | 720 |
| ggggcccgca | caagcggagg | aacagggaac | gagaacgcga | ggaaccaccc | gggcgaaaga | 780 |
| cgacgacgga | aacaggaccc | cggggcagga | aacagggcgc | agggcgcagc | cggccggagg | 840 |
| gcgggaagcc | caaacgagcg | caaccccacc | gaggccacag | gcaagcgggc | accggcggga | 900 |
| cgccgggaag | ccgagaggaa | gggggagac | gcaaacagca | cggcccacgc | cggggcacac | 960 |
| acggacaagg | aggacagagg | gcagcaccca | ggagggagcg | aaccgaaagc | caccagcgga | 1020 |
| ggaggcgaaa | cccgccccag | aagggacgca | gaacgcgcac | agccaggcgc | gggaaacgcc | 1080 |
| cgggccgaca | caccgcccgc | aagccaggaa | gcgggggggcc | gaagcggacc | gcaaggagcg | 1140 |
| accagggcaa | aaccgggacg | gggcaagcga | acaaggagcc | gaccggaagg | gcggcggaac | 1200 |
| acccc | | | | | | 1205 |

<210> SEQ ID NO 59
<211> LENGTH: 1213
<212> TYPE: RNA
<213> ORGANISM: Artificial Sequence
<220> FEATURE:
<223> OTHER INFORMATION: Synthetic polynucleotide

<400> SEQUENCE: 59

| | | | | | | |
|---|---|---|---|---|---|---|
| agagaggacc | ggccaggacg | aacgcggcgg | agcaacacag | caagcgaacg | agaagggagg | 60 |
| acccggggaa | cagaacggaa | agggcgaacg | gggagaacgc | ggggaaccgc | ccaggaaagg | 120 |
| aaagcccggg | aaacgggaga | aagccaaagg | gcgcaggcaa | gacagaaaac | ccgggccaag | 180 |
| gaggacccgc | gcccaagcag | gggagaaaca | gcccaccaag | gcgacgaggg | aaccggcgag | 240 |
| agggcgaacg | gcacacggaa | cgagacacgc | ccagacccac | gggaggcagc | aggggggaaag | 300 |
| cgcaaggggg | caacccgacg | cagcaaaccg | cggaggaaga | aggcggacga | aagccgaggg | 360 |
| gaagaagaag | acggacccaa | gaggaagccc | ggcaacacgg | ccagcagccg | cggaaacgag | 420 |
| gggacaagcg | gccggaagac | gggcgaaagg | gcgcgaggcg | gcaaagcgag | gaaaggaccg | 480 |
| gccaaccggg | aaggcaggaa | acggagacga | gaggagaggc | aagggaacca | ggagcgggaa | 540 |
| agcgagaaag | gaggaacacc | agggcgaagg | cggcgcggac | aaaacgacgc | gagggcgaaa | 600 |
| gcgggggagc | gaacaggaag | aacccggagc | cacgccgaaa | cgagaagcag | gggggaaac | 660 |
| caggccgcag | aacacaaaag | caccgccggg | gagacgaccg | caagggaaac | caaaggaaga | 720 |

```
cggggacccg cacaagcagc ggagcaggga acgaagcaac gcgaagaacc accaggcgac    780
acccgacgag ccagagaagg aagcccggga acagagagac aggggggcagg gcgcagccgg    840 cggagagggg aagcccgcaa cgagcgcaac cccgccaggc cagcaaaggg gcaccagagg    900
gacgccgaga caaacggagg aagggggggac gacgcaaaca cagccccaga ccgggcacac    960
acggcacaag gcgaacagag ggccgcgaag ccgcgaggga agcaaaccca aaacagaccc   1020
agcggagcag gcgcaaccgc cgcagaaggg aggcagaacg cggacagaag ccgcgggaag   1080
cgcccgggcg acacaccgcc cgcacaccac gagagggcaa cacccgaagc cggagagaac   1140
cgaaggacca gcagcgaagg ggggcagaag ggggaagcga acaaggagcc gacggaaggg   1200
cggcggacac ccc                                                      1213

<210> SEQ ID NO 60
<211> LENGTH: 1193
<212> TYPE: RNA
<213> ORGANISM: Artificial Sequence
<220> FEATURE:
<223> OTHER INFORMATION: Synthetic polynucleotide

<400> SEQUENCE: 60
agaagaggac cggccaggag aacgcagcac aggcaacaca gcaagcgagg ggcagcaggc     60
agcgcaaggc gaggcgaccg gcgcacgggg agaacgcgac caaccgccgc accggccagc    120
ccgaaaggaa gaaaccagga gggacagagc acagccgcag aaaaggaccg gagacgaggg    180
gagcgccaag aagaggcggg gaacggccca ccagcaacga ggaaggggcg agaggaaggc    240
ccccacagga acgagacacg gccaaaccca cgggaggcag caggaggaaa ggcaagggcg    300
aggccgaacc agccaagagc ggaaggagac gcccagggga aaccaaaagg aaaaagcggg    360
agcaacccgg cagacagaaa aggacggcaa cccggccagc agccgcggaa acggaggacc    420
gagcgaccgg aagggaaagg gagcgagagg agaagcaggg aaaggcggcc aaccgaaaag    480
caggaacgga gcgaggcagg aggcaggcgg aacgggagc gggaaagcag aacacgaaga     540
acccgagcga aggcagccgc aagcgcaacg acagaggccg aaaggggggac aaacaggaag    600 aacccggagc cacacggaaa cgagaaaccg cggcgaaacg gcaagcggcc aagcgaaagc    660
gaagaccacc ggggagacgc cggcaacggg aaaccaaagg aagacggggg cccgcacaag    720
cggaggaaca gggaacgaga acgcgaggaa ccacccgggc aaagcaccga agaccggaaa    780
cggcagcagc aaagcgaggg aagggcgcag ggcgcagccg gccggagggc ggcaaggcca    840
aacgagcgca acccggcaga caacaggag cgaggaccga caagacgcca cgaagaggag     900
gaagggggga gacgcaaaca gcacggccca cgccggggca cacacggaca agggggggaca    960 gagggccgca ccacgcgagg gagccaaccc aaaacccccc agcggacgga gcgcaacccg   1020
acccacgaag cggacgcaga acgcgcacag ccacggcgcg ggaaacgccc gggccgacac   1080
accgccgcca agccagggag ccgggggacc gaaggcgaac cgcgaggacg cccagggaaa   1140
acgggacggg gcaagcgaac aaggagccga ccggaagggc ggcggaacac ccc          1193

<210> SEQ ID NO 61
<211> LENGTH: 1191
<212> TYPE: RNA
<213> ORGANISM: Artificial Sequence
<220> FEATURE:
<223> OTHER INFORMATION: Synthetic polynucleotide

<400> SEQUENCE: 61
```

| | |
|---|---:|
| cgaagaggac cggccaggag aacgcagcga caggcaacac agcaagcgag gggcagcagg | 60 |
| aagagcaaac gcggcgaccg gcgcacgggg agaacgcgag caaccaccac agaggggaa | 120 |
| acccggcgaa agcggacaaa ccgcaaaaac aggggcccgc agggaaagaa agaagcgaag | 180 |
| agggcagcgc caagaagggg aggaacggcc accaagccga ggaaggggcg agaggaaggc | 240 |
| ccccacacgg acgagacacg gaccagaccc acgggaggca gcaggaggaa aggcaagggc | 300 |
| gagagccgaa ccagccaagc gcggaaggag aaggacaggc gaaaccaagg ggaaaaaggc | 360 |
| aggacggccg gagacccaga aaaggacggc aacccggcca gcagccgcgg aaacggagga | 420 |
| ccgagcgacc ggaagggaaa ggggcgaggg gcaagcagcg ggaaagggc caaccaaaaa | 480 |
| gccggaaacg gaggggcgaga agaggaggcg gaagcgggga gcgggaaagc aagaacacgc | 540 |
| agaacccaag cgaaggcagc acaaacaaac gacacgaagc acgaaagcgg gggacaaaca | 600 |
| ggaagaaccc ggagccacgc agaaacgaga acaggaggcg aacacagaag ccacagcgaa | 660 |
| agcgaagaac caccggggag acgccggcaa cgggaaacca aggaagacg ggggcccgca | 720 |
| caagcggagg aacaggaac gagaacgcga ggaaccaccc ggggaacgaa ggaccggagg | 780 |
| gaaacacccca gcaaagcaaa cgagggcgca gggcgcagcc ggccggaggg cggcaaggcc | 840 |
| aaacgagcgc aacccacaga caacaggcga gcgaggacca agagacgcc agcgaagcgg | 900 |
| aggaagggggg gagacgcaaa cagcacggcc cacaccgggg cgacacacgg acaaggggg | 960 |
| acaagggca gcaccggcga caggagcaac ccaaaccca ccagcggacg aagcgcaacc | 1020 |
| cgaccggaag cggacgcaga acgcgcacag ccaggcgcgg gaaacgcccg ggccgacaca | 1080 |
| ccgccccgcaa gccagggagg ggggaccaaa gccgaaccgc aaggacggcc agggaaaacc | 1140 |
| gagacgggggc aagcgaacaa ggagccgacc ggaagggcgg cggaacaccc c | 1191 |

<210> SEQ ID NO 62
<211> LENGTH: 1224
<212> TYPE: RNA
<213> ORGANISM: Artificial Sequence
<220> FEATURE:
<223> OTHER INFORMATION: Synthetic polynucleotide

<400> SEQUENCE: 62

| | |
|---|---:|
| aagaagagga ccggccagga cgaacgcggc ggcgcgccaa cacagcaagc gaacggagcg | 60 |
| ccgaagcgga ggaagagagc agcagggcga acggggagaa cacggagcaa ccgcccaggg | 120 |
| gggacaacag gaaacgaagc aaaccgcaaa gaccacaggc gcaggcacag gggcaaagga | 180 |
| accgcgaaag agggccgcgc cgaagcagag ggaggaacgg cccaccaggc gacgacggag | 240 |
| ccggacgaga gggaacggcc acagggacga gacacggccc agacccacgg gaggcagcag | 300 |
| ggggaaagca caaggggggaa acccgagcag cgacgccgcg ggaggaagaa ggccggagaa | 360 |
| acccgcccag gggacgaaag acggacccgg gaggaagcac cggcaacacg ccagcagcc | 420 |
| gcggaaaacg aggggcaagc ggccggaaac ggggaaaggg agcgcaggcg gaggcaaggg | 480 |
| gaggaaacag ggccaaccca aaagccaaaa cgcagcgagg ggagaggagg cggaacccgg | 540 |
| gagcggggaa gcgagaacgg gaggaacacc agggcgaagg cggccacggg cacaacgacg | 600 |
| cgaggccgaa agcaggagc aaacaggaag aacccggagc cagccgaaac gagaacaggg | 660 |
| gggaggagac cccccggccg cagaacacaa agaaccaccc ggggagacga ccgcaaggga | 720 |
| aaccaaagga agacgggggc cgcacaagc agggagaggg aacgaagcaa cgcgaagaac | 780 |
| caccaggcga cacggagcaa ccaagagaag ggaagcccgg acaccagac aggggcagg | 840 |
| gcgcagccgg cggagagggg aagcccgcaa cgagcgcaac ccacgagaca cgcaagagga | 900 |

```
ccagcgagac gccggacaaa acggaggaag gggggagacg caaacacagc ccagaccggg    960
cacacacgac acaaggcaaa cagagagaag cgaaccgcga ggggagcaaa cccacaaaaa   1020
agccagcgga cgcaggcgca acccgccgcg gaagccggaa gcagaacgcg acagcagcc   1080 gcgggaaacg cccgggccga cacaccgccc gcacaccaga gagccggggg gacccgaagc   1140
ggagcaaccg caaggaggac gccgccgaag gaaaacggga gggggaagcg aacaaggagc   1200
cgacggaagg gcggcggaca cccc                                          1224
```

<210> SEQ ID NO 63
<211> LENGTH: 1186
<212> TYPE: RNA
<213> ORGANISM: Artificial Sequence
<220> FEATURE:
<223> OTHER INFORMATION: Synthetic polynucleotide

<400> SEQUENCE: 63

```
agaagaggac cggccaggag aacgcagcac aggcaacaca gcaagcgagg ggcagcagaa     60
cagcgcaagg aggcgaccgg cgcacgggga gaacacgacc aaccgccgag accggggaag    120
cccgaaagaa agaaaacccg aggcaagccc gcagggaaac aaaagaacgg cacgagggga    180
gcgccaaggg ggcggggaac ggcccaccaa gcccgaggaa ggggcgagag aaggcccccc    240
acaggaacga gacacggcca aacccacggg aggcagcagg aggaaaggca aggacgagag    300
cgaaccagcc aagagcggaa ggagacgccc aggggaaacc aacgggaaaa aggaggcacg    360
ggccgagacc gagaaaagga cggcaacccg ccagcagcc gcggaaacgg aggaccgagc    420
gaccggaagg gaaagggagc gaggcggacg caagcaggga aaggcggcca accgaaaagc    480
aggaacgggg cgagacagag aggcaggcgg aacgggagc gggaaagcag aacacgaaga    540
acccgagcga aggcagccgc ggacgaacga cgcgagccga aaggggggaca aacaggaaga    600 acccggagcc acacagaaac gagaaaccgc ggcgaaacag aagcggccaa gcgaaagcga    660
agaccaccgg ggagacgccg gcaacgggaa accaaaggaa gacgggggcc cgcacaagcg    720
gaggaacagg gaacgagaac gcgaggaacc acccgggcga agcaacgaag agggagacag    780
cagccgcaag gcagggaagg gcgcaggcgg cagccgccg gagggcggca aggccaaacg    840
agcgcaaccc acgaagacca cagggagcgg ggaccgcgag acgccgcgaa gaggaggaag    900
gggggagacg caaacagcac ggcccacgcc ggggcacaca cggacaaggg gggacagaag    960
gcagcacacg gcgacggagc aacccgaaag cccccagcgg aggagcgcaa cccgacccag   1020
aagcggacga gaacgcgca cagccacggc gcgggaaacg cccgggccga cacaccgccc   1080
gcaagccaga aagccggggg accgaaggcg aaccgcaagg agcgcccagg gaaaacggga   1140
ggggcaagcg aacaaggagc cgaccggaag ggcggcggaa caccccc                 1186
```

<210> SEQ ID NO 64
<211> LENGTH: 1241
<212> TYPE: RNA
<213> ORGANISM: Artificial Sequence
<220> FEATURE:
<223> OTHER INFORMATION: Synthetic polynucleotide

<400> SEQUENCE: 64

```
aggagaggac cggccaggac gaacgcggcg gcggccaaca cagcaagcga acggagaaac     60
ggagaacagg gcgaacgggg agaacgcgag gcaaccaccc agacggggac aacaccgaaa    120
ggaggcaaac cggaggacac gccgcaggca ggagaagaaa gaggcccaca agaagcacgc    180
```

```
aaaggagggc cgcgcgaagc agggaggaac ggacaccaag gcgagacaga gccggcgaga      240
ggagaacggc cacagggacg agacacggcc caaacccacg ggaggcagca gggggaaccc      300
gcaaggacga aagcgacgga gcaacgccgc ggaggagaag gacggcgaaa gccggagacg      360
aacggcaggg gaacaagcag caagacggag aaacgaggaa gccacggcaa cacggccagc      420
agccgcggaa acgaggggcg agcggccgga aagggcgaaa gagcagaggc ggcaaaagcg      480
agcggaaaag cggggccaac cccgaggcgc ggaaacgagg cgaggcagga gaggaaaggg      540
gaacccagga gcgggaaagc gagaagggag gaacaccagg gcgaaggcgc ccggacggcg      600
acgcgagagc gaaagccagg gagcgaacgg gaagaacccc ggagccggcc gaaacgaggg      660
acagggagga ggacgacccc cggccggaga acgcaaaaga ccccgccggg gagacggccg      720
caagggaaac caaaggaaga cggggcccg cacaagcggg gagagggaac gacgcaacgc       780
gaagaaccac caaggcgaca gagaacgcca gagaagagac cccggggaca agaaaacagg      840
gggcaggcgc gcagccggcg gagagggaa gcccgcaacg agcgcaaccc caccagacca       900
gcaagaaagg gggaccaggg agacgccagg gacaaccgga ggaaggcggg gagacgcaag      960
cacagcccca gcgggcacac acgacacaag gcggaaacag agggaagcga agccgcgagg     1020
cagagcaaac cccagaaacc cgaccagcgg acgcaggcgc aacccgccgc ggaagcggaa     1080
cgcagaacgc aggcagcaac gcgggaaacg cccgggccga cacaccgccc gcacaccacg     1140
aaagggaaca cccgaagccg ggaggaacca aggagccagc cgcaaggggg gccgagaggg     1200
ggaagcgaac aaggagccga cggaagggcg gcggacaccc c                         1241
```

UNITED STATES PATENT AND TRADEMARK OFFICE
CERTIFICATE OF CORRECTION

PATENT NO. : 11,167,018 B2
APPLICATION NO. : 16/472937
DATED : November 9, 2021
INVENTOR(S) : Kenya Honda et al.

It is certified that error appears in the above-identified patent and that said Letters Patent is hereby corrected as shown below:

In the Claims

Claim 1, beginning at Column 253, Line 34, should read:
1. A composition comprising a purified bacterial mixture comprising bacterial strains of species *Phascolarctobacterium faecium*, *Fusobacterium ulcerans*, *Subdoligranulum* sp., and *Eubacterium limosum*, wherein the bacterial strains are lyophilized.

Signed and Sealed this
Eighth Day of March, 2022

Drew Hirshfeld
*Performing the Functions and Duties of the
Under Secretary of Commerce for Intellectual Property and
Director of the United States Patent and Trademark Office*